United States Patent
Smith et al.

(10) Patent No.: US 9,708,308 B2
(45) Date of Patent: Jul. 18, 2017

(54) FACTOR IXA INHIBITORS

(71) Applicants: Merck Sharp & Dohme Corp., Rahway, NJ (US); Mochida Pharmaceutical Co., Ltd., Tokyo (JP)

(72) Inventors: Cameron James Smith, Lawrenceville, NJ (US); John Qiang Tan, Westfield, NJ (US); Ting Zhang, Princeton Junction, NJ (US); James Balkovec, Martinsville, NJ (US); William John Greenlee, Teaneck, NJ (US); Liangqin Guo, Edison, NJ (US); Yi-Heng Chen, Whippany, NJ (US); Yili Chen, Hillsborough, NJ (US); Jiayi Xu, Edison, NJ (US); Samuel Chackalamannil, Califon, NJ (US); Tomokazu Hirabayashi, Shizuoka Prefecture (JP); Hiroshi Nagasue, Shizuoka Prefecture (JP); Kouki Ogawa, Shizuoka Prefecture (JP)

(73) Assignees: Merck Sharp Dohme Corp., Rahway, NJ (US); Mochida Pharmacuetical Co., Ltd., Tokyo (JP)

( * ) Notice: Subject to any disclaimer, the term of this patent is extended or adjusted under 35 U.S.C. 154(b) by 0 days.

(21) Appl. No.: 14/652,237

(22) PCT Filed: Dec. 16, 2013

(86) PCT No.: PCT/US2013/075233
§ 371 (c)(1),
(2) Date: Jun. 15, 2015

(87) PCT Pub. No.: WO2014/120346
PCT Pub. Date: Aug. 7, 2014

(65) Prior Publication Data
US 2015/0322056 A1    Nov. 12, 2015

Related U.S. Application Data

(60) Provisional application No. 61/739,266, filed on Dec. 19, 2012.

(51) Int. Cl.
C07D 471/04    (2006.01)
C07D 413/14    (2006.01)
(Continued)

(52) U.S. Cl.
CPC ......... C07D 413/14 (2013.01); C07D 417/14 (2013.01); C07D 471/04 (2013.01); C07D 487/04 (2013.01); C07D 498/04 (2013.01)

(58) Field of Classification Search
CPC .................................................. C07D 413/14
See application file for complete search history.

(56) References Cited

U.S. PATENT DOCUMENTS

2004/0220206 A1    11/2004    Smallheer et al.
2005/0228000 A1    10/2005    Smallheer et al.
(Continued)

FOREIGN PATENT DOCUMENTS

WO    WO2011025565 A1    3/2011
WO    WO2014099694        6/2014
WO    WO2014099695 A1    6/2014

OTHER PUBLICATIONS

Extended European Search Report for 13873301.9, mailed May 10, 2016, 6 pages.
(Continued)

Primary Examiner — Shawquia Jackson
(74) Attorney, Agent, or Firm — Nicole M. Beeler; Catherine D. Fitch

(57) ABSTRACT

The present invention provides a compound of Formula (I)

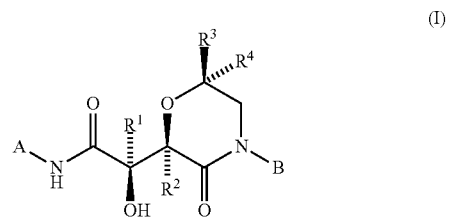

wherein
$R^1$ is H or $C_{1-6}$ alkyl, $R^2$, is H or $C_{1-6}$ alkyl or $CH_2OH$, $R^3$ is H or $C_{1-6}$ alkyl, and $R^4$ is H or $C_{1-6}$ alkyl, provided that when $R^1$, $R^2$, and $R^3$ are H, $R^4$ is $C_{1-6}$ alkyl, and when $R^1$, $R^2$, and $R^4$ are H, then $R^3$ is $C_{1-6}$ alkyl, and when $R^1$, $R^3$, and $R^4$ are H, $R^2$ is $C_{1-6}$ alkyl or —$CH_2OH$, and when $R^2$, $R^3$, and $R^4$ are H, then $R^1$ is $C_{1-6}$ alkyl;

A is
1) a 9-10 membered bicyclic heterocycle having 1-3 heteroatoms independently selected from N, S and O, which 9-10 membered bicyclic heterocycle is unsubstituted or substituted with $R^5$ and unsubstituted or substituted with $R^6$ and unsubstituted or substituted with $NH_2$, or
2) a 6-9 membered monocyclic or bicyclic carbocyclic ring system unsubstituted or substituted with $R^5$, unsubstituted or substituted with $R^6$, and unsubstituted or substituted with —$CH_2NH_2$; and B is
1) a 5- or 6-membered monocyclic heterocycle having 1 or 2 heteroatoms independently selected from N, S or O, which is unsubstituted or substituted on a carbon or nitrogen atom with $R^7$, unsubstituted or substituted on a carbon or nitrogen atom with $R^8$, and unsubstituted or substituted on a carbon or nitrogen atom with $R^9$, or
2) an 8- or 9-membered fused bicyclic heterocycle having 1, 2 or 3 nitrogen atoms which is unsubstituted or
(Continued)

substituted on a carbon or nitrogen atom with $R^7$, and unsubstituted or substituted on a carbon or nitrogen atom with $R^8$;

and pharmaceutical compositions comprising one or more said compounds, and methods for using said compounds for treating or preventing thromboses.

16 Claims, No Drawings

(51) Int. Cl.
*C07D 417/14* (2006.01)
*C07D 487/04* (2006.01)
*C07D 498/04* (2006.01)

(56) References Cited

U.S. PATENT DOCUMENTS

| | | |
|---|---|---|
| 2006/0293336 A1 | 12/2006 | Sutton et al. |
| 2008/0279845 A1 | 11/2008 | Conley et al. |
| 2009/0181983 A1 | 7/2009 | Corte |
| 2011/0059958 A1 | 3/2011 | Nishida et al. |
| 2011/0065682 A1 | 3/2011 | Clasby et al. |
| 2011/0135650 A1 | 6/2011 | Chackalamannil et al. |

OTHER PUBLICATIONS

International Search Report and Written Opinion for PCT/US13/75233 mailed on Apr. 21, 2014, 11 pages.

FACTOR IXA INHIBITORS

CROSS REFERENCE TO RELATED APPLICATIONS

This application is a U.S. National Phase application under 35 U.S.C. §371 of PCT Application No. PCT/US13/75233 filed Dec. 16, 2013, which claims priority from U.S. Provisional Application Ser. No. 61/739,266, filed Dec. 19, 2012.

BACKGROUND OF THE INVENTION

Factor IXa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commences after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. Clotting factor IX can be activated by means of the intrinsic pathway and the extrinsic pathway. The activation of factor IXa is thus a central point of intersection between the two pathways of activation of clotting. Factor IXa has an important role in blood clotting. Defects in factor IXa lead to hemophilia B, while increased concentrations of factor IXa in the blood lead to a significantly increased risk of thrombosis formation (Weltermann A, et al., J Thromb Haemost. 2003; 1:28-32). The regulation of factor IXa activity can reduce thrombus formation in animal models (Feuerstein G Z, et al., Thromb Haemost. 1999; 82: 1443-1445). Vijayku-mar et al., *Bioorganic & Medicinal Chemistry Letters* (2006), 16 (10), 2796-2799, discloses hydroxy pyrazole based factor IXa inhibitors.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor IXa inhibitors and may have therapeutic value in, for example, preventing coronary artery disease. The invention includes compounds of formula I:

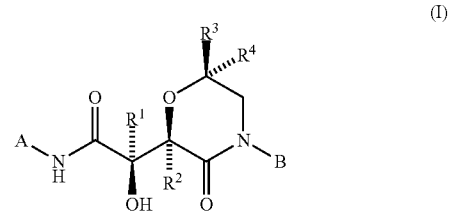

and pharmaceutically acceptable salts thereof, wherein
$R^1$ is H or $C_{1-6}$ alkyl, $R^2$, is H or $C_{1-6}$ alkyl or $CH_2OH$, $R^3$ is H or $C_{1-6}$ alkyl, and $R^4$ is H or $C_{1-6}$ alkyl,
provided that when $R^1$, $R^2$, and $R^3$ are H, $R^4$ is $C_{1-6}$ alkyl, and when $R^1$, $R^2$, and $R^4$ are H, then $R^3$ is $C_{1-6}$ alkyl, and when $R^1$, $R^3$, and $R^4$ are H, $R^2$ is $C_{1-6}$ alkyl or —$CH_2OH$, and when $R^2$, $R^3$, and $R^4$ are H, then $R^1$ is $C_{1-6}$ alkyl;

A is
1) a 9-10 membered bicyclic heterocycle having 1-3 heteroatoms independently selected from N, S and O, which 9-10 membered bicyclic heterocycle is unsubstituted or substituted with $R^5$, unsubstituted or substituted with $R^6$, and unsubstituted or substituted with $NH_2$, or
2) a 6-9 membered monocyclic or bicyclic carbocyclic ring system unsubstituted or substituted with $R^5$, unsubstituted or substituted with $R^6$, and unsubstituted or substituted with —$CH_2NH_2$;

$R^5$ is halogen;
$R^6$ is $C_{1-6}$alkyl;

B is
1) a 5- or 6-membered monocyclic heterocycle having 1 or 2 heteroatoms independently selected from N, S or O, which is unsubstituted or substituted on a carbon or nitrogen atom with $R^7$, unsubstituted or substituted on a carbon or nitrogen atom with $R^8$, and unsubstituted or substituted on a carbon or nitrogen atom with $R^9$, or
2) an 8- or 9-membered fused bicyclic heterocycle having 1, 2 or 3 nitrogen atoms which is unsubstituted or substituted on a carbon or nitrogen atom with $R^7$, and unsubstituted or substituted on a carbon or nitrogen atom with $R^8$;

$R^7$ is $CF_3$, $C_{1-6}$alkyl, $C_{1-6}$alkanol, $C_{3-8}$carbocycle, aryl,

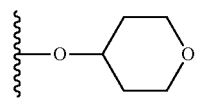

or a 5- or 6-membered heterocycle having 1 or 2 nitrogen atoms and zero or 1 oxygen atom, which heterocycle or $C_{3-8}$carbocycle or aryl is unsubstituted or mono-, di-, tri- or tetra-substituted with a group independently selected from $R^{10}$, $R^{11}$, $R^{12}$, $R^{13}$, and $R^{15}$;

$R^8$ is $C_{1-6}$alkyl;
$R^9$ is halogen;
$R^{10}$ is $CF_3$, CN, $C(O)NH_2$, $OCD_3$, $OC_{1-6}$alkyl, $OCH(CH_2Cl)(CH_2OH)$, $-OC_{3-8}$cycloalkyl, or

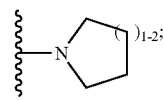

$R^{11}$ is halogen, $C_{1-6}$alkyl, $CF_3$, $CHF_2$, CN, or COOH;
$R^{12}$ is $CF_3$, COOH, $C(O)OC_{1-6}$alkyl, CN, halogen, $OCF_3$, =O, or $SO_2C_{1-6}$alkyl;
$R^{13}$ is $C_{1-6}$alkyl, $C(O)OC_{1-6}$alkyl, CN, $CF_3$, $OC_{1-6}$alkyl, $N(C_{1-6}alkyl)_2$, $OC_{1-6}$alkyl, or $OCHF_2$; and
$R^{15}$ is halogen, $CF_3$, $CHF_2$, $C_{1-6}$alkyl, CN, or COOH.

One embodiment of the invention includes compounds of the formula I

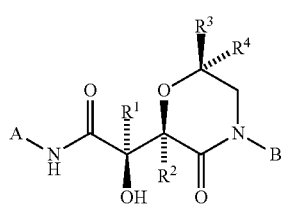

and pharmaceutically acceptable salts thereof, wherein
$R^1$ is H or $C_{1-6}$ alkyl, $R^2$, is H or $C_{1-6}$ alkyl or $CH_2OH$, $R^3$ is H or $C_{1-6}$ alkyl, and $R^4$ is H or $C_{1-6}$ alkyl,
provided that when $R^1$, $R^2$, and $R^3$ are H, $R^4$ is $C_{1-6}$ alkyl, and when $R^1$, $R^2$, and $R^4$ are H, then $R^3$ is $C_{1-6}$ alkyl, and when $R^1$, $R^3$, and $R^4$ are H, $R^2$ is $C_{1-6}$ alkyl or $-CH_2OH$, and when $R^2$, $R^3$, and $R^4$ are H, then $R^1$ is $C_{1-6}$ alkyl;

A is

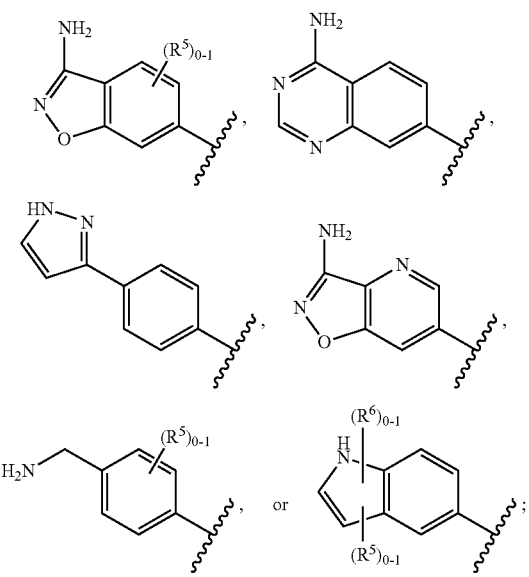

$R^5$ is halogen;
$R^6$ is $C_{1-6}$alkyl;
B is

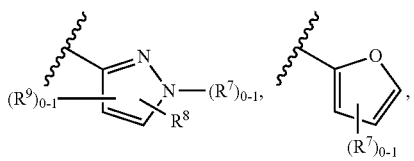

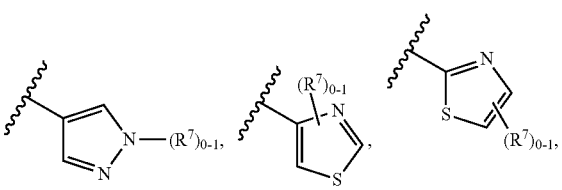

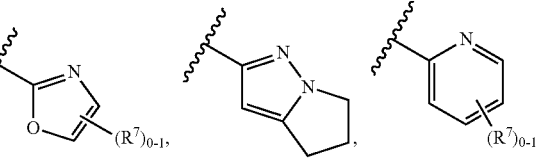

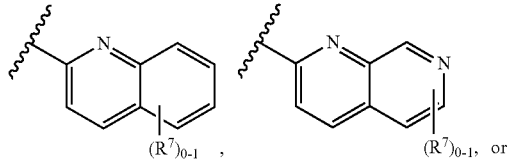

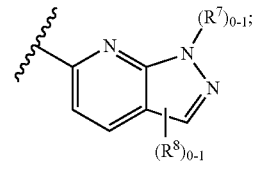

$R^7$ is $CF_3$, $C_{1-6}$alkyl, $C_{1-6}$alkanol or $C_{3-8}$carbocycle,

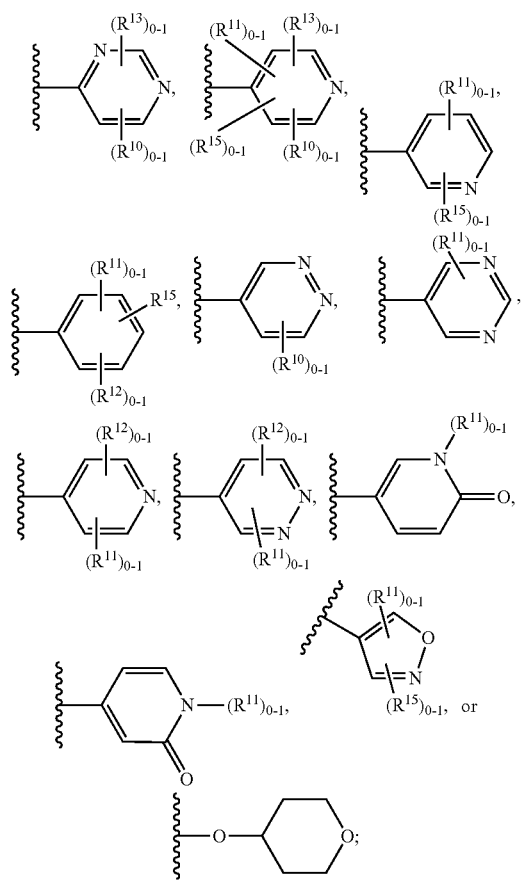

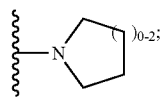

$R^8$ is $C_{1-6}$alkyl;
$R^9$ is halogen;
$R^{10}$ is $CF_3$, $CN$, $C(O)NH_2$, $OD_3$, $OC_{1-6}$alkyl, $OCH(CH_2Cl)(CH_2OH)$, $-OC_{3-8}$cycloalkyl, or

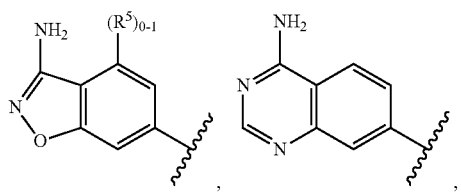

$R^{11}$ is halogen, $C_{1-6}$alkyl, $CF_3$, $CHF_2$, $CN$, or $COOH$;
$R^{12}$ is $CF_3$, $COOH$, $C(O)OC_{1-6}$alkyl, $CN$, halogen, $OCF_3$, $=O$, or $SO_2C_{1-6}$alkyl;
$R^{13}$ is $C_{1-6}$alkyl, $C(O)OC_{1-6}$alkyl, $CN$, $CF_3$, $OC_{1-6}$alkyl, $N(C_{1-6}$alkyl$)_2$, $OC_{1-6}$alkyl, or $OCHF_2$; and
$R^{15}$ is halogen, $CF_3$, $CHF_2$, $C_{1-6}$alkyl, $CN$, or $COOH$.

In one embodiment of the invention, A is

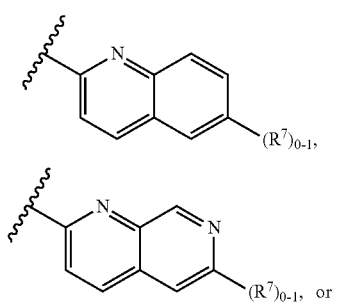

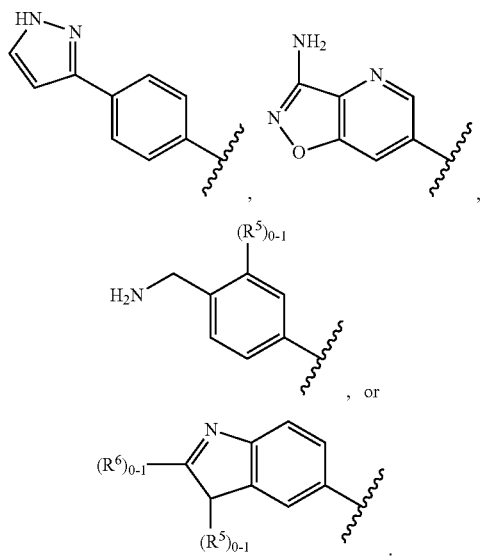

In another embodiment of the invention, B is

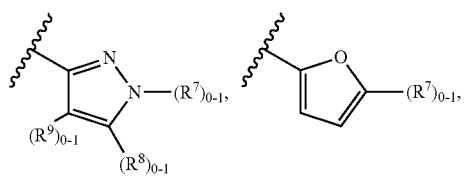

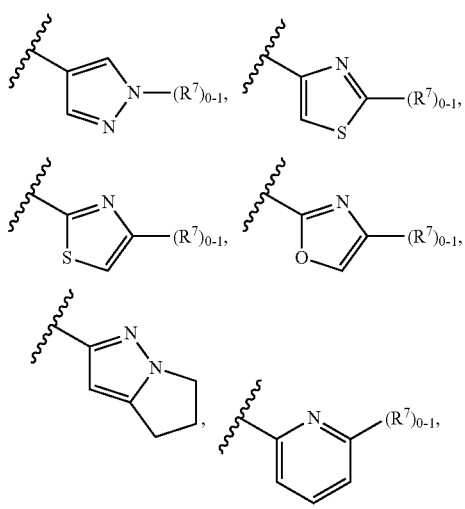

-continued

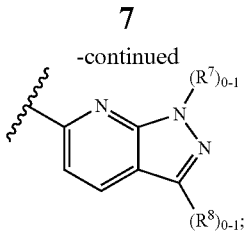

In another embodiment of the invention, R⁷ is hydrogen, CF₃, CH₃, C(CH₃)₂OH, cyclopropyl,

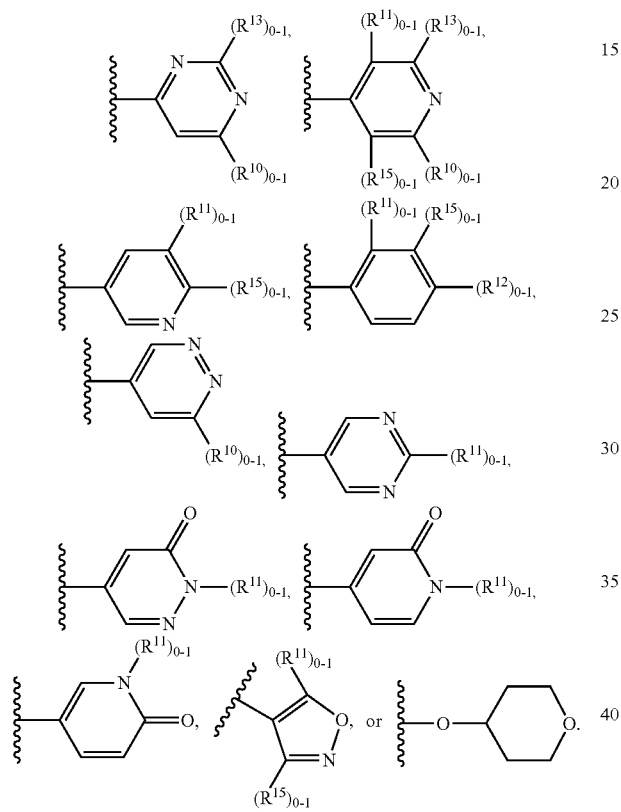

In another embodiment of the invention,
R⁵ is Cl, or F;
R⁶ is CH₃;
R⁸ is CH₃;
R⁹ is F;
R¹⁰ is CF₃, CN, C(O)NH₂, OCH₂CH₃, OD₃, OCH₃, OC(CH₃)₃, OCH(CH₃)₂, OCH(CH₂Cl)(CH₂OH),

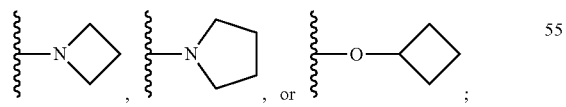

R¹¹ is F, Cl, Br, CH₃, CF₃, CHF₂, CN, COOH;
R¹² is CF₃, COOH, C(O)OCH₃, CN, F, Cl, OCF₃, SO₂CH₃;
R¹³ is CH₃, C(O)OCH₃, CN, CF₃, OCH₃, N(CH₃)₂, OCH₂CH₃, OCH(CH₃)₂, OCHF₂;
R¹⁵ is F, Cl, Br, CF₃, CHF₂, CH₃, CN, COOH.
In another embodiment of the invention,
R¹ is H or CH₃, R² is H, CH₃, CH₂CH₃, or CH₂OH, R³ is H or CH₃, and R⁴ is H or CH₃,
provided that at least one of the group of R¹, R², R³, and R⁴ is CH₃ or,
when R¹, R³ and R⁴ are H, then R² is CH₃, CH₂CH₃, or CH₂OH;

A is

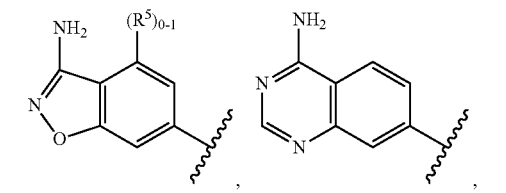

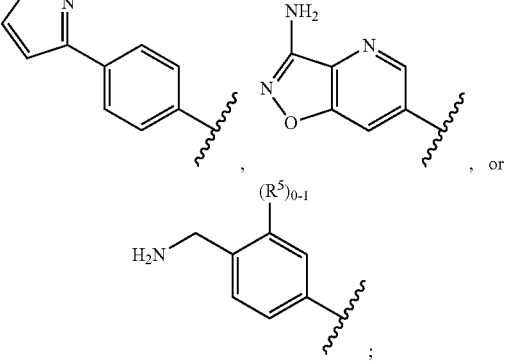

R⁵ is Cl, or F;
R⁶ is CH₃;
B is

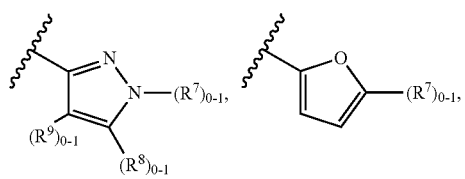

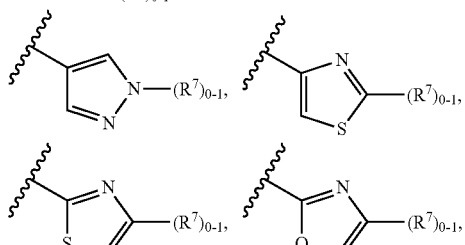

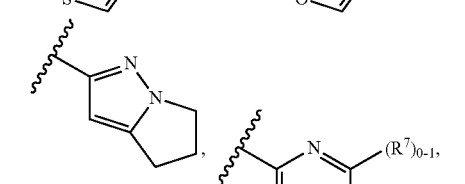

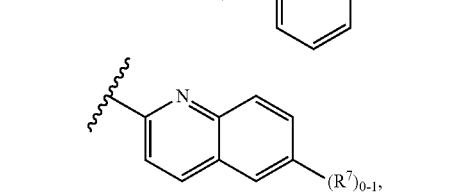

-continued

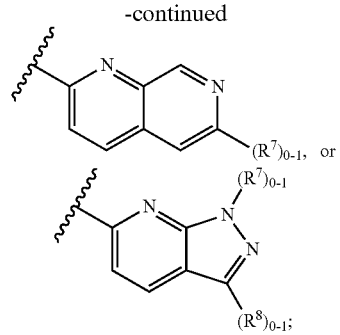

$R^7$ is $CF_3$, $CH_3$, $C(CH_3)_2OH$, cyclopropyl,

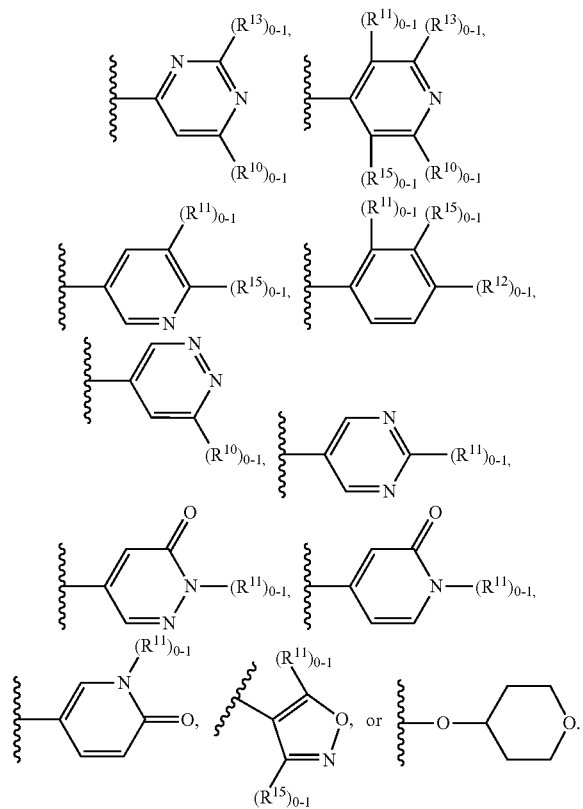

$R^8$ is $CH_3$;
$R^9$ is F;
$R^{10}$ is $CF_3$, CN, $C(O)NH_2$, $OCH_2CH_3$, $OCD_3$, $OCH_3$, $OC(CH_3)_3$, $OCH(CH_3)_2$, $OCH(CH_2Cl)(CH_2OH)$

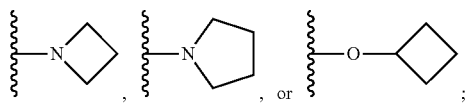

$R^{11}$ is F, Cl, Br, $CH_3$, $CF_3$, $CHF_2$, CN, COOH;
$R^{12}$ is $CF_3$, COOH, $C(O)OCH_3$, CN, F, Cl, $OCF_3$, $SO_2CH_3$;
$R^{13}$ is $CH_3$, $C(O)OCH_3$, CN, $CF_3$, $OCH_3$, $N(CH_3)_2$, $OCH_2CH_3$, $OCH(CH_3)_2$, $OCHF_2$; and
$R^{15}$ is F, Cl, Br, $CF_3$, $CHF_2$, $CH_3$, CN, COOH.

In another embodiment,
$R^1$ is H or $CH_3$, $R^2$ is H, $CH_3$, $CH_2CH_3$, or $CH_2OH$, $R^3$ is H or $CH_3$, and $R^4$ is H or $CH_3$,
provided that when $R^1$, $R^2$, and $R^3$ are H, then $R^4$ is $CH_3$, and when $R^1$, $R^2$, and $R^4$ are H, then $R^3$ is $CH_3$, and when $R^1$, $R^3$, and $R^4$ are H, $R^2$ is $CH_3$, $CH_2CH_3$ or —$CH_2OH$, and when $R^2$, $R^3$, and $R^4$ are H, then $R^1$ is $CH_3$.

In another embodiment, $R^1$ and $R^2$ are H, and $R^3$ and $R^4$ are $CH_3$.

In another embodiment, $R^1$, $R^2$ and $R^3$ are H, and $R^4$ is $CH_3$.

In another embodiment, $R^2$, $R^3$ and $R^4$ are H, and $R^1$ is $CH_3$.

In another embodiment, $R^1$, $R^3$ and $R^4$ are H, and $R^2$ is $CH_3$.

In another embodiment, $R^1$ and $R^2$ are $CH_3$, and $R^3$ and $R^4$ are H.

In another embodiment, $R^1$, $R^3$ and $R^4$ are H, and $R^2$ is $CH_2OH$.

In another embodiment, $R^1$, $R^3$ and $R^4$ are H, and $R^2$ is $CH_2CH_3$.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Reference to the compounds of this invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.

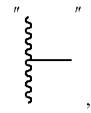

ethyl may be represented by "Et" or CH₂CH₃, propyl may be represented by "Pr" or CH₂CH₂CH₃, butyl may be represented by "Bu" or CH₂CH₂CH₂CH₃, etc. "C$_{1-4}$ alkyl" (or "C$_1$-C$_4$ alkyl") for example, means linear or branched chain alkyl groups, including all isomers, having the specified number of carbon atoms. For example, the structures

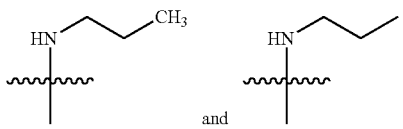

and have equivalent meanings. C$_{1-4}$ alkyl includes n-, iso-, sec- and t-butyl, n- and isopropyl, ethyl and methyl. If no number is specified, 1-4 carbon atoms are intended for linear or branched alkyl groups.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —C$_{1-6}$alkyl esters and —C$_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

When any variable occurs more than one time in any constituent or in formula I, its definition on each occurrence is independent of its definition at every other occurrence. Also, combinations of substituents and/or variables are permissible only if such combinations result in stable compounds.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted herein, alkyl groups may be unsubstituted, or substituted with 1 to 3 substituents on any one or more carbon atoms, with halogen, C$_1$-C$_{20}$ alkyl, CF$_3$, NH$_2$, —NH(C$_1$-C$_6$ alkyl), —N(C$_1$-C$_6$ alkyl)$_2$, NO$_2$, oxo, CN, N$_3$, —OH, —O(C$_1$-C$_6$ alkyl), C$_3$-C$_{10}$ cycloalkyl, C$_2$-C$_6$ alkenyl, C$_2$-C$_6$ alkynyl, (C$_1$-C$_6$ alkyl)S(O)$_{0-2}$—, HS(O)$_{0-2}$—, (C$_1$-C$_6$ alkyl)S(O)$_{0-2}$(C$_1$-C$_6$ alkyl)-, HS(O)$_{0-2}$(C$_1$-C$_6$ alkyl)-, (C$_0$-C$_6$ alkyl)C(O)NH—, H$_2$N—C(NH)—, —O(C$_1$-C$_6$ alkyl)CF$_3$, HC(O)—, (C$_1$-C$_6$ alkyl)C(O)—, HOC(O)—, (C$_1$-C$_6$ alkyl)OC(O)—, HO(C$_1$-C$_6$ alkyl)-, (C$_1$-C$_6$ alkyl)O(C$_1$-C$_6$ alkyl)-, (C$_1$-C$_6$ alkyl)C(O)$_{1-2}$(C$_1$-C$_6$ alkyl)-, HC(O)$_{1-2}$(C$_1$-C$_6$ alkyl)-, (C$_1$-C$_6$ alkyl)C(O)$_{1-2}$—, HOC(O)NH—, (C$_1$-C$_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted, the term "halogen" means fluorine, chlorine, bromine or iodine.

Except where noted, the term "aryl" refers to a stable 6- to 10-membered mono- or bicyclic ring system such as phenyl, or naphthyl. The aryl ring can be unsubstituted or substituted with one or more of C$_{1-4}$ alkyl, hydroxyl, alkoxy, halogen, or amino.

Except where noted, the term "heterocycle" refers to a stable 4- to 7-membered mono- or bicyclic- or stable 7- to 12-membered bicyclic or stable 12- to 14-membered heteroatom-containing ring system unsubstituted or substituted with C$_{1-4}$ alkyl or halogen, any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocycle is fused to a benzene ring. Especially useful are rings containing one oxygen or sulfur, one to four nitrogen atoms, or one oxygen or sulfur combined with one or two nitrogen atoms. The heterocycle may be attached at any heteroatom or carbon atom which results in the creation of a stable structure. Examples of such heterocycles include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyridyl N-oxide, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

Except where noted herein, the term "heteroaryl" refers to a monocyclic unsaturated heterocycle having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring system having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) or a tricyclic unsaturated ring system having a specified number of atom members (e.g., 12-, 13- or 14-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, and isoxazolyl.

The term "saturated heterocycle" refers to a saturated monocyclic 5- to 8-membered ring having 1-4 heteroatoms selected from N, O and S, or a 7- to 12-membered saturated or partially saturated bicyclic ring system having 1-6 heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Except where noted herein, the term "carbocycle" (and variations thereof such as "carbocyclic" or "carbocyclyl") as used herein, unless otherwise indicated, refers to a $C_3$ to $C_8$ monocyclic saturated or unsaturated ring, e.g., $C_{3-8}$ carbocycle. The carbocycle may be attached to the rest of the molecule at any carbon atom which results in a stable compound. Saturated carbocyclic rings are also referred to as "cycloalkyl" rings, e.g., cyclopropyl, cyclobutyl, etc.

Except where noted herein, aryl groups and carbocycle groups may be unsubstituted, or substituted on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, $HS(O)_{0-2}$—, $(C_1$-$C_6$ alkyl)$S(O)_{0-2}$—, $(C_1$-$C_6$ alkyl)$S(O)_{0-2}(C_1$-$C_6$ alkyl)-, $HS(O)_{0-2}(C_1$-$C_6$ alkyl)-, $(C_1$-$C_6$ alkyl)$S(O)_{0-2}$—, $(C_1$-$C_6$ alkyl)$C(O)NH$—, $HC(O)NH$—, $H_2N$—$C(NH)$—, —$O(C_1$-$C_6$ alkyl)$CF_3$, $(C_1$-$C_6$ alkyl)$C(O)$—, $HC(O)$—, $(C_1$-$C_6$ alkyl)$OC(O)$—, $HOC(O)$—, $(C_1$-$C_6$ alkyl)$O(C_1$-$C_6$ alkyl)-, $HO(C_1$-$C_6$ alkyl)-, $(C_1$-$C_6$ alkyl)$C(O)_{1-2}(C_1$-$C_6$ alkyl)-, $(C_1$-$C_6$ alkyl)$C(O)_{1-2}$—, $HC(O)_{1-2}(C_1$-$C_6$ alkyl)-, $(C_1$-$C_6$ alkyl)$OC(O)NH$—, $HOC(O)NH$—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted herein, heteroaryl and heterocyclic rings may be unsubstituted, or substituted on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, $(C_1$-$C_6$ alkyl)$S(O)_{0-2}$—, $HS(O)_{0-2}$—, $(C_1$-$C_6$ alkyl)$S(O)_{0-2}(C_1$-$C_6$ alkyl)-, $HS(O)_{0-2}(C_1$-$C_6$ alkyl)-, $(C_1$-$C_6$ alkyl)$S(O)_{0-2}$—, $(C_1$-$C_6$ alkyl)$C(O)NH$—, $HC(O)NH$—, $H_2N$—$C(NH)$—, —$O(C_1$-$C_6$ alkyl)$CF_3$, $HC(O)$—, $(C_1$-$C_6$ alkyl)$C(O)$—, $(C_1$-$C_6$ alkyl)$OC(O)$—, $HOC(O)$—, $(C_1$-$C_6$ alkyl)$O(C_1$-$C_6$ alkyl)-, $HO(C_1$-$C_6$ alkyl)-, $(C_1$-$C_6$ alkyl)$O$—, $(C_1$-$C_6$ alkyl)$C(O)_{1-2}(C_1$-$C_6$ alkyl)-, $HC(O)_{1-2}(C_1$-$C_6$ alkyl)-, $(C_1$-$C_6$ alkyl)$C(O)_{1-2}$, $(C_1$-$C_6$ alkyl)$OC(O)NH$—, $HOC(O)NH$—, silyl groups (including trimethylsilyl, tetramethylsilyl, or supersilyl groups such as tri(trimethylsilyl)silyl or a silicon group connected to tert butyl groups), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —$C(O)C_{1-6}$ alkyl, —$C(O)NHC_1$-$C_6$ alkyl, —$C(O)NH_2$, —$C_1$-$C_6$ alkyl$C(O)NH_2$, —$C_1$-$C_6$ alkyl$OC(O)NH_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound.

Except where noted herein, structures containing substituent variables such as variable "R" below:

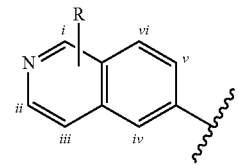

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Also except where noted herein, structures containing substituent variables defined to include R as shown below

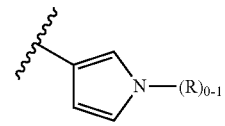

represent rings which have either an R substituent attached to the nitrogen atom (where the subscript value is "1") or else hydrogen attached to the nitrogen atom (where the subscript value is "0").

The invention also includes derivatives of the compound of Formula I, acting as prodrugs. Prodrugs, following administration to the patient, are converted in the body by normal metabolic or chemical processes, such as through hydrolysis in the blood, to the compound of Formula 1. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Factor IXa inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the Factor IXa inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor IXa inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor IXa inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor IXa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The effectiveness of compounds of the present invention to inhibit the coagulation factors XIa, VIIa, IXa, Xa, plasma kallikrein or thrombin, can be determined using a relevant purified serine protease, respectively, and an appropriate synthetic substrate.

Methods for Making the Compounds of Present Invention
General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention. It should be noted that, when compounds of the present invention synthesized has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme.

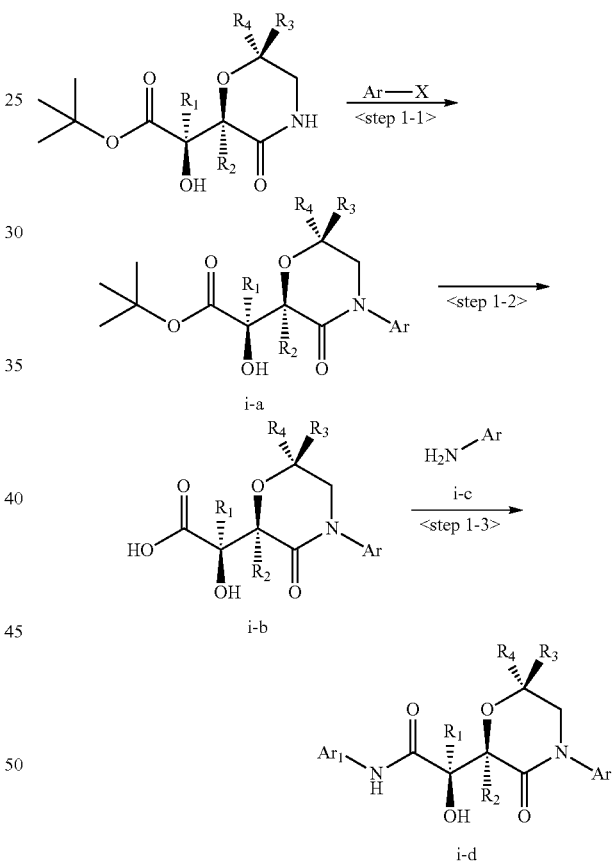

<Step 1-1>

A compound represented by formula (i-a) can be produced by allowing a key intermediate compound represented by formula (key intermediate) to react with a compound represented by Ar—X (aryl halide or heteroaryl halide, wherein X represents halogen atom) by a process known as Goldberg reaction which are similar to that described in published documents, for example, *JACS*, 2002, 124, 7421 in the presence of a base such as potassium phosphate, cesium carbonate, potassium tert-butoxide, sodium hydride, lithium hydroxide, sodium hydroxide, potassium hydroxide, lithium carbonate, sodium carbonate, or potassium carbonate in the presence of 1,2-diamine ligand such as trans-1,2-cyclohexanediamine, trans-N,N'-dimethylcyclohexane-1,2-diamine, or ethylene diamine, and in the presence of catalytic amount of cupper iodide using a solvent which is inactive to the reaction, such as an ethereal solvent, e.g., diethyl ether, tetrahydrofuran, 1,2-dimethoxyethane, 1,4-dioxane, polar solvents such as N,N-dimethylformamide, and dimethyl sulfoxide; or an aromatic hydrocarbon solvent, e.g., toluene or benzene or a mixed solvent thereof at a temperature in the range of room temperature to the solvent-reflux temperature.

<Step 1-2>

A compound represented by formula (i-b) can be produced from a compound represented by formula (i-a) by a well-known or similar process that described in published documents, for example, Jikken Kagaku Koza (Experimental Chemistry Series), 4th edition, 22, Organic synthesis IV, Acids, amino acids, and peptides, pp. 1-43, 1992, Maruzen Co., Ltd., in the presence of inorganic or organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid with water or without water and a solvent which is inactive to the reaction, such as methanol, ethanol, 2-propanol, N,N-dimethylformamide, dioxane, or tetrahydrofuran, or a mixed solvent thereof at a temperature in the range of 0° C. to the solvent-reflux temperature.

<Step 1-3>

A compound represented by formula (i-d) can be produced by allowing a compound represented by formula (i-b) to react with a compound represented by formula (i-c) (Ar is aryl or heteroaryl) by a well-known or a process similar to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl or EDC HCl), benzotriazol-1-yloxy tris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), or 4-(4,6-dimethoxy-1,3,5-triazin-2-yl)-4-methylmorpholinium chloride, in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or pyridine at a temperature in the range of 0° C. to the solvent-reflux temperature. When a compound represented by formula (i-b) is converted to an acid halide, a compound represented by formula (i-c) can be similarly produced by conducting a reaction by a process similar to that described in, for example, Organic synthesis IV, Acids, amino acids, and peptides, pp. 144-146, 1992, Maruzen Co., Ltd., in the presence of a base such as triethylamine or pyridine in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, or a polar solvent, e.g., N,N-dimethylformamide at a temperature in the range of 0° C. to the solvent-reflux temperature.

Scheme 2

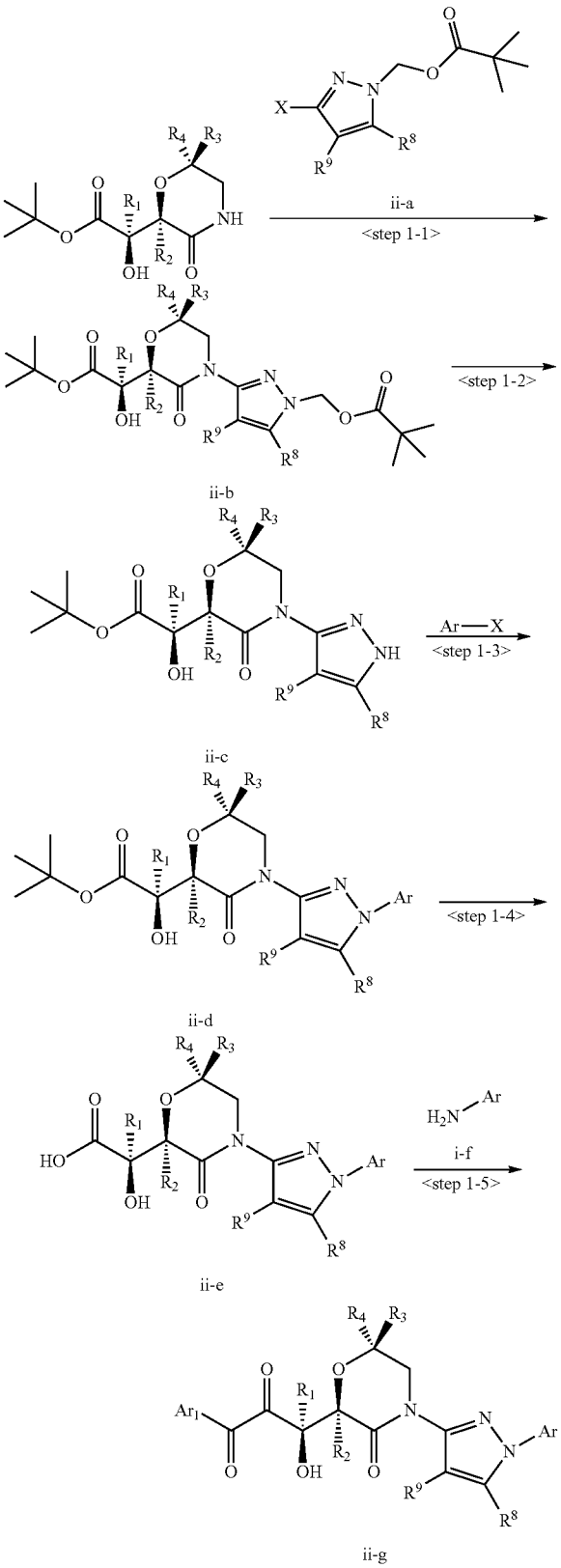

X = halogen; Ar = aryl or heteroaryl

<Step 2-1>
A compound represented by formula (ii-b) can be produced by the similar process as that used in <Step 1-1> of (Reaction Scheme 1) using a compound represented by formula (key intermediate) with a compound represented by formula (ii-a).
<Step 2-2>
A compound represented by formula (ii-c) can be produced by conducting a reaction using a compound represented by formula (ii-b) by a process similar to that described in published documents, for example, Greene, T. W., et. al., *Protective Groups in Organic Synthesis* (2007), 4th Ed., in the presence of ammonia, sodium methoxide, potassium methoxide, lithium hydroxide, sodium hydroxide, potassium hydroxide, lithium carbonate, sodium carbonate, or potassium carbonate using a solvent which is inactive to the reaction, such as an alcoholic solvent, e.g., methanol, ethanol, or 2-propanol, tert-butanol, or a polar solvent, e.g., N,N-dimethylformamide, dimethyl sulfoxide, ethyl acetate, or acetonitrile, or a mixed solvent thereof at a temperature in the range of 0° C. to the solvent-reflux temperature.
<Step 2-3>
A compound represented by formula (ii-d) can be produced by the similar process as that used in <Step 1-1> of (Reaction Scheme 1) using a compound represented by formula (ii-c) with a compound represented by Ar—X (aryl halide or heteroaryl halide, wherein X represents halogen atom)
<Step 2-4>
A compound represented by formula (ii-e) can be produced by the similar process as that used in <Step 1-2> of (Reaction Scheme 1) using a compound represented by formula (ii-d)
<Step 2-5>
A compound represented by formula (ii-g) can be produced by the similar process as that used in <Step 1-3> of (Reaction Scheme 1) using a compound represented by formula (ii-e) with a compound represented by formula (ii-f).

EXAMPLES

The present invention will now be described in more detail using examples, but the present invention is not limited to the examples.

Acronyms and abbreviations are as follows: acetic acid (AcOH); 4-dimethylaminopyridine (DMAP); 1,2-dimethoxyethane (DME); dimethylsulfoxide (DMSO); dimethylformamide (DMF); ethanol (EtOH); ethyl acetate (EtOAc); lithium diisopropylamide (LDA); acetonitrile (MeCN); methanol (MeOH); phenyl (Ph); tetrabutylammonium fluoride (TBAF); tetrahydrofuran (THF); trifluoroacetic acid (TFA); catalyst (cat.); anhydrous (anh.); concentrated (conc.); saturated (sat.); room temperature (RT). Celite is Celite® (Fluka) diatomite which is diatomaceous earth.

Other abbreviations are: DPPF—1,1'-bis diphenylphosphino ferrocene; $Pd_2(dba)_3$—tris(dibenzylideneacetone)dipalladium(0); DIAD—diisopropyl azodicarboxylate; MTBE—methyl tert butyl ether; RBF—round bottom flask; CAN—ceric ammonium nitrate; HOAt—1-hydroxy-7-azabenzotriazole; NMP—N-methylpyrrolidine; PTLC—preparative thin-layer chromatography; DIEA—diisopropylethylamine; and DMA—N,N-dimethylacetamide.

The measurement of nuclear magnetic resonance (NMR) spectrum was performed using a JEOL JNM-ECX300 FT-NMR (manufactured by JEOL Ltd.), a JEOL JNM-ECX400 FT-NMR (manufactured by JEOL Ltd.), or a Varian Unity INOVA AS500 or AS600 FT-NMR (manufactured by Varian).

Liquid chromatography-mass spectrometry (LC-MS) was performed using a Waters FractionLynx MS system (manufactured by Waters Corporation) or a Waters Micromass ZQ Mass Spectromer/Agilent 1100 system. A SunFire Column™ (4.6 mm×5 cm, 5 micron) (manufactured by Waters Corporation) was used as an analytical column. A SunFire Column™ (19 mm×5 cm, 5 micron) (manufactured by Waters Corporation) was used as a preparative column. Methanol or MeCN and 0.05% aqueous acetic acid solution or 0.05% aqueous trifluoroacetic acid solution were used as the mobile phase. The analysis was performed under the following gradient conditions: Methanol or MeCN: 0.05% aqueous acetic acid solution or 0.05% aqueous trifluoroacetic acid solution=1:9 (0 min), 10:0 (5 min), and 10:0 (6 min). Liquid chromatography-mass spectrometry (UPLC-MS) was also performed using a ACQUITY UPLC+MS system (manufactured by Waters Corporation). A CAPCELL Pak® C18 MGIII-H (2.0 mm×5 cm, 3 micron) (manufactured by Shiseido Co., Ltd.) was used as an analytical column. Methanol and 0.05% aqueous trifluoroacetic acid solution were used as the mobile phase. The analysis was performed under the following gradient conditions: Methanol: 0.05% aqueous trifluoroacetic acid solution=5:95 (0 min), 95:5 (1 min), 95:5 (1.6 min), and 5:95 (2 min). The solvent systems are described as the followings: A indicates LCMS system and mobile phase is 0.05% aq. AcOH, B indicates LCMS system and mobile phase is 0.05% aq. TFA, C indicates UPLC-MS system and mobile phase is 0.05% aq. TFA.

Intermediate 1

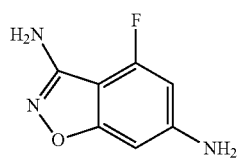 [SMILES: Nc1cc(F)c2c(N)noc2c1]

4-Fluorobenzo[d]isoxazole-3,6-diamine

To a solution of 4-amino-2,6-difluorobenzonitrile (1.0 g) in DMF (32 mL)-water (32 mL) were added acetohydroxamic acid (2.92 g) and $K_2CO_3$ (10.8 g). The reaction mixture was stirred for 19 h at 70° C. After cooling to room temperature, it was diluted with $H_2O$ and extracted with EtOAc. The extract was washed with $H_2O$ and brine, dried over $Na_2SO_4$, filtered and concentrated in vacuo. The residue was purified by silica gel flash chromatography (eluent: Hexane:EtOAc=75:25~50:50) to give a sticky solid. The sticky solid was triturated with $H_2O$ to give compound 4-fluorobenzo[d]isoxazole-3,6-diamine as a colorless solid. LCMS 168 (M+H)$^+$. $^1$H NMR (300 MHz, DMSO-$d_6$): δ 6.25-6.16 (2H, m), 5.93 (2H, s), 5.84 (2H, s).

Intermediate 2

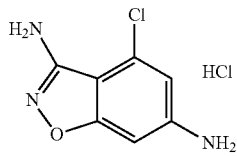

4-Chlorobenzo[d]isoxazole-3,6-diamine hydrochloride

Step A: tert-Butyl (3-chloro-4-cyano-5-fluorophenyl)carbamate

To a solution of 4-amino-2-chloro-6-fluorobenzonitrile (29.3 g, WO2009/003077) in THF (500 mL) were added di-tert-butyl dicarbonate (87.8 g) and DMAP (4.2 g) at room temperature. The reaction mixture was stirred for 17 h at 70° C. After cooling to room temperature, it was diluted with $H_2O$ and extracted with EtOAc (5 times). The combined extracts were washed with brine, dried over $Na_2SO_4$, filtered and concentrated in vacuo. The residue was purified by silica gel flash chromatography (eluent:Hexane:EtOAc=100: 0~80:20) to give a mixture of compound 4-fluorobenzo[d]isoxazole-3,6-diamine and diBoc compound. LCMS 306 (M+Na)$^+$. H NMR (300 MHz, $CDCl_3$): δ 7.38-7.30 (2H, m), 7.18-7.16 (1H, m), 7.01 (1H, dd, J=9, 2 Hz), 6.83 (1H, s), 1.52 (9H, s), 1.47 (18H, s).

Step B: tert-Butyl (3-amino-4-chlorobenzo[d]isoxazol-6-yl)carbamate

To a solution of crude 4-fluorobenzo[d]isoxazole-3,6-diamine (6.0 g) in DMF (60 mL)-water (60 mL) were added acetohydroxamic acid (4.21 g) and $K_2CO_3$ (15.5 g). The reaction mixture was stirred for 4 h at 70° C. After cooling to room temperature, it was diluted with $H_2O$ and extracted with EtOAc (3 times). The extract was washed with $H_2O$ and brine, dried over $Na_2SO_4$, filtered and concentrated in vacuo. The residue was purified by silica gel flash chromatography (eluent:Hexane:EtOAc=90:10~50:50) to give compound tert-butyl (3-amino-4-chlorobenzo[d]isoxazol-6-yl)carbamate as a colorless solid. LCMS 306 (M+Na)$^+$. $^1$H NMR (300 MHz, $CDCl_3$): δ 7.45 (1H, d, J=2 Hz), 7.23-7.21 (1H, m), 6.70 (1H, s), 4.70 (2H, s), 1.53 (9H, s).

Step C: 4-Chlorobenzo[d]isoxazole-3,6-diamine hydrochloride

A solution of compound tert-butyl (3-amino-4-chlorobenzo[d]isoxazol-6-yl)carbamate (2.65 g) in 4M HCl-dioxane (50 mL) was stirred for overnight at room temperature. The organic solvent was evaporated under reduced pressure to afford the desired compound 4-chlorobenzo[d]isoxazole-3,6-diamine hydrochloride as a pale yellow solid. LCMS 184 (M+H)$^+$. $^1$H NMR (300 MHz, DMSO-$d_6$): δ 6.52-6.49 (1H, m), 6.36-6.34 (1H, m).

Intermediate 3

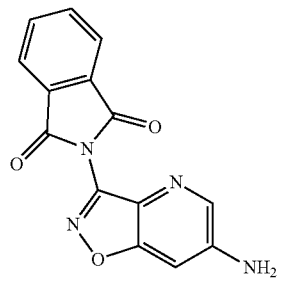 [SMILES: Nc1cnc2c(N3C(=O)c4ccccc4C3=O)noc2c1]

2-(6-Aminoisoxazolo[4,5-b]pyridin-3-yl)isoindoline-1,3-dione

Step A: 3-Fluoro-5-nitropicolinonitrile

A solution of tetrabutylammonium nitrate (11.14 g, 36.6 mmol) and trifluoroacetic anhydride (5.16 mL, 36.6 mmol) in dry $CH_2Cl_2$ (43.2 mL) was added via cannula to a stirred solution of 2-cyano-3-fluoropyridine (3.4376 g, 28.2 mmol) in dry $CH_2Cl_2$ (86 mL) at 0° C. under $N_2$. The reaction was warmed to room temperature and stirred for 3 days. The reaction was quenched with satd aq. $NaHCO_3$ and extracted with $CH_2Cl_2$ (3×). The combined extracts were dried ($Na_2SO_4$) and concentrated in vacuo to give the crude product. This was purified by flash chromatography (Isco Combiflash Rf, RediSep Silica 80 g, 60 mL/min, loaded using solid loading cartridge after dissolving in $CH_2Cl_2$, 100% hexanes for 3 min, gradient to 50% EtOAc in hexanes over 24 min, isocratic at 50% EtOAc in hexanes for 23 min) to afford in order of elution desired product 3-fluoro-5-nitropicolinonitrile, a as colorless solid. LCMS calc.=168.02. found=168.02 (M+H)$^+$. $^1$H NMR (500 MHz, $CHCl_3$-d): δ 9.36 (d, J=2.1 Hz, 1H); 8.44 (dd, J=7.4, 2.1 Hz, 1H).

Step B: 5-Amino-3-fluoropicolinonitrile

Iron (0.643 g, 11.51 mmol) was added to a stirred solution of 3-fluoro-5-nitropicolinonitrile (0.3846 g, 2.302 mmol) in EtOAc (2.06 mL) and Acetic acid (2.06 mL) and the mixture was heated at 65° C. under a reflux condenser for 2 h. The mixture was filtered through a Teflon filter and the eluant was concentrated in vacuo. The residue was partitioned between EtOAc and satd aq. $NaHCO_3$. The aqueous layer was separated and further extracted with EtOAc (2×). The combined organic extracts were dried ($Na_2SO_4$) and concentrated in vacuo to give the product 5-amino-3-fluoropicolinonitrile, as a light brown solid. LCMS calc.=138.05. found=138.10 (M+H)$^+$. $^1$H NMR (500 MHz, $CH_3OH$-$d_4$): δ 7.83 (d, J=2.1 Hz, 1H); 6.77 (dd, J=11.7, 2.2 Hz, 1H).

Step C: Di-tert-butyl (6-cyano-5-fluoropyridin-3-yl) imidodicarbonate and tert-butyl (6-cyano-5-fluoropyridin-3-yl)carbamate To a stirred solution of 5-amino-3-fluoropicolinonitrile (0.2256 g, 1.645 mmol) and di-tert-butyl dicarbonate (0.395 g, 1.810 mmol) in dry $CH_2Cl_2$ (11.75 mL) at 25° C. under $N_2$, was added pyridine (0.146 mL, 1.810 mmol) followed by a solution of 4-dimethylaminopyridine (0.020 g, 0.165 mmol) in CH$_2$Cl$_2$ (4.70 mL). The mixture was stirred at room temperature for 20 min. The mixture was diluted with water, the aqueous layer was separated and extracted with CH$_2$Cl$_2$ (×2), the combined extracts were dried (Na$_2$SO$_4$) and concentrated in vacuo to give the crude product. This was purified by flash chromatography (Isco Combiflash Rf, RediSep Silica 24 g, 35 mL/min, loaded using solid loading cartridge after dissolving in CH$_2$Cl$_2$, 100% hexanes for 2 min, gradient to 50% EtOAc in hexanes over 10 min, isocratic at 50% EtOAc in hexanes for 1 min, gradient to 100% EtOAc over 15 min, hold comp. for 2 min) to afford in order of elution di-tert-butyl (6-cyano-5-fluoropyridin-3-yl)imidodicarbonate and tert-butyl (6-cyano-5-fluoropyridin-3-yl)carbamate. di-tert-butyl (6-cyano-5-fluoropyridin-3-yl)imidodicarbonate: LCMS calc.=338.15. found=338.08 (M+H)$^+$. $^1$H NMR (600 MHz, CHCl$_3$-d): δ 8.35 (s, 1H); 7.48 (dd, J=8.9, 2.0 Hz, 1H); 1.45 (s, 18H). tert-butyl (6-cyano-5-fluoropyridin-3-yl)carbamate: LCMS calc.=238.10. found=238.09 (M+H)$^+$.

Step D: tert-Butyl (3-aminoisoxazolo[4,5-b]pyridin-6-yl)carbamate

Potassium carbonate (1.413 g, 10.23 mmol) and acetohydroxamic acid (0.384 g, 5.11 mmol) were added successively to a stirred solution of di-tert-butyl (6-cyano-5-fluoropyridin-3-yl)imidodicarbonate (0.2875 g, 0.852 mmol) in DMF (7.75 mL) and water (0.775 mL) and the reaction was stirred at 55° C. for 1 h. The reaction mixture was diluted with EtOAc, washed with satd aq. NH$_4$Cl, dried (Na$_2$SO$_4$) and concentrated in vacuo to give the crude product. This was purified by flash chromatography (Isco Combiflash Rf, RediSep Silica 40 g, 40 mL/min, loaded using solid loading cartridge after dissolving in CH$_2$Cl$_2$, 100% hexanes for 2 min, gradient to 100% EtOAc in hexanes over 13 min, isocratic at 100% EtOAc for 15 min) to afford desired product tert-butyl (3-aminoisoxazolo[4,5-b]pyridin-6-yl)carbamate, as a colorless solid. LCMS calc.=251.11. found=251.21 (M+H)$^+$. $^1$H NMR (600 MHz, CH$_3$OH-d$_4$): δ 8.40 (s, 1H); 8.14 (s, 1H); 1.52 (s, 9H).

Step E: tert-Butyl (3-(1,3-dioxoisoindolin-2-yl)isoxazolo[4,5-b]pyridin-6-yl)carbamate To a solution of tert-butyl (3-aminoisoxazolo[4,5-b]pyridin-6-yl)carbamate (0.2914 g, 1.164 mmol) in CH$_2$Cl$_2$ (11.64 mL) at 0° C., was added phthaloyl chloride (0.252 mL, 1.747 mmol), followed by triethylamine (0.649 mL, 4.66 mmol). The mixture was warmed to room temperature and stirred overnight. The mixture was diluted with EtOAc and washed with water. The organic layer was dried (Na$_2$SO$_4$), and concentrated in vacuo to give the crude product. This was purified by flash chromatography (Isco 40 g, Si, ~40 mL/min, 100% hexanes for 2 min, gradient to 50% EtOAc in hexanes over 13 min, hold comp. for 16 min, switch to 100% EtOAc for 10 min) to afford in order of elution tert-butyl (3-(1,3-dioxoisoindolin-2-yl)isoxazolo[4,5-b]pyridin-6-yl)carbamate, as a colorless solid. LCMS calc.=381.12. found=381.09 (M+H)$^+$. $^1$H NMR (600 MHz, CHCl$_3$-d): δ 8.59 (s, 1H); 8.41 (s, 1H); 8.07-8.04 (m, 2H); 7.89 (dd, J=5.6, 3.1 Hz, 2H); 7.03 (s, 1H); 1.61-1.56 (m, 9H).

Step F: 2-(6-Aminoisoxazolo[4,5-b]pyridin-3-yl)isoindoline-1,3-dione

4N HCl in 1,4-dioxane (14.0 mL, 55.8 mmol) was added to a stirred solution of tert-butyl (3-(1,3-dioxoisoindolin-2-yl)isoxazolo[4,5-b]pyridin-6-yl)carbamate (0.3540 g, 0.931 mmol) in dry 1,4-Dioxane (14.0 mL) at room temperature and the resulting mixture was stirred at 25° C. for 24 h. After this time a precipitate appeared. The mixture was concentrated in vacuo and the residue was suspended in EtOAc. Satd aq. NaHCO$_3$ was added and the mixture was stirred until a clear organic layer persisted. The organic layer was dried (Na$_2$SO$_4$) and concentrated in vacuo to give the product 2-(6-aminoisoxazolo[4,5-b]pyridin-3-yl)isoindoline-1,3-dione, as a light brown solid. LCMS calc.=281.07. found=281.08 (M+H)$^+$. $^1$H NMR (600 MHz, DMSO-d$_6$): δ 8.16 (d, J=2.1 Hz, 1H); 8.07 (dd, J=5.7, 3.1 Hz, 2H); 7.99 (dd, J=5.6, 3.1 Hz, 2H); 7.09 (d, J=2.1 Hz, 1H); 6.49 (s, 2H).

Intermediate 4

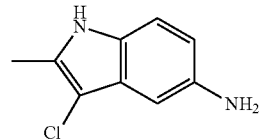

3-Chloro-2-methyl-1H-indol-5-amine

To 2-methyl-1H-indol-5-amine (200 mg, 1.368 mmol) in DMF (4.5 mL) was added N-chlorosuccinimide (183 mg, 1.368 mmol). The reaction was stirred at 25° C. overnight before diluting with water and EtOAc. The phases were separated and the aqueous layer was extracted with EtOAc. The combined organic layers were dried over MgSO$_4$, filtered and concentrated in vacuo. The crude mixture was purified by flash chromatography (ISCO, 0-100% EtOAc in hexanes) to afford 3-chloro-2-methyl-1H-indol-5-amine, as a white solid. LCMS calc.=181.05. found=181.05 (M+H)$^+$. $^1$H NMR (500 MHz, acetone-d$_6$): δ 9.84 (s, 1H); 7.05 (d, J=8.5 Hz, 1H); 6.68 (d, J=2.1 Hz, 1H); 6.57 (dd, J=8.5, 2.1 Hz, 1H); 4.23 (s, 2H); 2.34 (s, 3H).

Intermediate 5

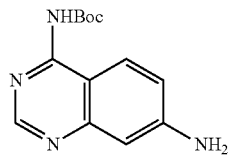 [SMILES: CC(C)(C)OC(=O)Nc1ncnc2cc(N)ccc12]

tert-Butyl (7-aminoquinazolin-4-yl) Carbamate

Step A: 7-nitroquinazolin-4(3H)-one

A mixture of 2-amino-4-nitrobenzoic acid (5.0 g, 82 mmol) and formamide (8 mL, 201.5 mmol) in a microwave reaction vessel was heated in a microwave reactor at 150° C. for 1 h. The resulting slurry was cooled to room temperature, stirred with aqueous NaHCO$_3$, filtered and the solid was washed with water and Et$_2$O then vacuum dried to provide 7-nitroquinazolin-4(3H)-one as a dark brown solid. LCMS calc.=192.03. found=192.16 (M+H)$^+$.

Step B: 4-Chloro-7-nitroquinazoline

To a solution of 7-nitroquinazolin-4(3H)-one (9.14 g, 47.8 mmol) thionyl chloride (90 mL) was added DMF (2 mL) and the mixture was heated at reflux overnight. The reaction mixture was cooled to room temperature, and evaporated to dryness to provide 4-chloro-7-nitroquinazoline. LCMS calc.=210.01. found=210.06 (M+H)$^+$.

Step C: 7-Nitroquinazolin-4-amine

A mixture of 4-chloro-7-nitroquinazoline (10.02 g, 47.8 mmol) in of 7N NH$_3$ in MeOH (100 mL), was stirred overnight at room temperature. The solvents were removed and the solid mass was suspended in water, filtered and rinsed with water followed by Et$_2$O. The solid was vacuum dried to afford 7-nitroquinazolin-4-amine. LCMS calc.=191.05. found=191.15 (M+H)$^+$.

Step D: tert-Butyl (7-nitroquinazolin-4-yl) carbamate

To a suspension of 7-nitroquinazolin-4-amine (7.71 g, 40.5 mmol) in THF (100 mL) at room temperature was added di-tert-butyldicarbonate (18.83 mL, 81 mmol), followed by a 1M solution of LiHMDS in THF (68.9 mL, 68.9 mmol). The resultant clear solution was stirred for 10 min, quenched with aqueous NH$_4$Cl and extracted with EtOAc (3×). The combined organic layers were washed with brine, dried over Na$_2$SO$_4$, filtered and concentrated, then purified by flash chromatography (ISCO, 40 g column eluting with 0-50% EtOAc in hexanes over 30 min) to afford tert-butyl (7-nitroquinazolin-4-yl) carbamate. LCMS calc.=235.10. found=235.11 (M+H−57)$^+$.

Step E: tert-Butyl (7-aminoquinazolin-4-yl) carbamate

To a solution of tert-butyl (7-nitroquinazolin-4-yl) carbamate (0.36 g, 1.24 mmol) in THF:MeOH, (1:1, 9 mL), was added Pd/C (92 mg, 0.087 mmol). The reaction mixture was stirred at room temperature overnight under a hydrogen atmosphere (via balloon). The reaction mixture was filtered through a Celite pad and concentrated to afford tert-butyl (7-aminoquinazolin-4-yl) carbamate. LCMS calc.=260.13. found=205.15 (M+H−57)$^+$.

Intermediate 6

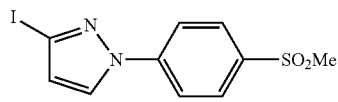 [SMILES: CS(=O)(=O)c1ccc(-n2ccc(I)n2)cc1]

3-Iodo-1-(4-(methylsulfonyl)phenyl)-1H-pyrazole

To a solution of 3-iodopyrazole (0.7 g, 3.61 mmol) in DMSO (18.0 mL) was added sodium hydride (60% disp. in oil, 0.173 g, 4.33 mmol) and the resulting mixture was stirred for 0.5 h before adding 4-methylsulfoylfluorobenzene (0.629 g, 3.61 mmol). The reaction mixture was stirred at 90° C. for 3 h. The reaction was quenched by the addition of water and extracted with EtOAc. The combined organic extracts were washed with water and brine, dried over MgSO$_4$ and concentrated in vacuo. The crude mixture was purified by flash chromatography (ISCO, 40 g, 0-60% EtOAc in hexanes) to afford 3-iodo-1-(4-(methylsulfonyl)phenyl)-1H-pyrazole, as a white solid. LCMS calc.=348.94. found=348.92 (M+H)$^+$. $^1$H NMR (500 MHz, CDCl$_3$): δ 8.03 (dd, J=8.7, 1.7 Hz, 2H); 7.89 (dd, J=8.7, 1.7 Hz, 2H); 7.84 (d, J=2.6 Hz, 1H); 6.69 (d, J=2.6 Hz, 1H); 3.09 (s, 3H).

Intermediate 7

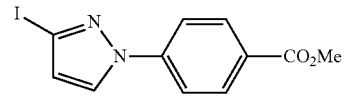 [SMILES: COC(=O)c1ccc(-n2ccc(I)n2)cc1]

Methyl 4-(3-iodo-1H-pyrazol-1-yl)benzoate

To a solution of 3-iodopyrazole (0.7 g, 3.61 mmol) in DMSO (18.0 mL) was added sodium hydride (60% disp. in oil (0.173 g, 4.33 mmol), and the resulting mixture was stirred for 0.5 h before adding methyl 4-fluoro benzoate (0.556 g, 3.61 mmol). The reaction mixture was stirred at 90° C. overnight. The reaction was quenched by the addition of water and extracted with EtOAc. The combined organic extracts were washed with water and brine, dried over MgSO$_4$ and concentrated in vacuo. The crude mixture was purified by flash chromatography (ISCO, 40 g, 0-20% EtOAc in hexanes) to afford methyl 4-(3-iodo-1H-pyrazol-1-yl)benzoate, as a white solid. LCMS calc.=328.97. found=328.96 (M+H)$^+$. $^1$H NMR (500 MHz, CDCl$_3$): δ 8.12 (m, 2H); 7.81 (d, J=2.4 Hz, 1H); 7.76 (m, 2H); 6.65 (m, 1H); 3.94 (s, 3H).

Intermediate 8

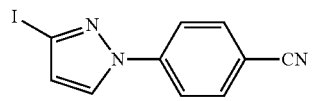 [SMILES: N#Cc1ccc(-n2ccc(I)n2)cc1]

4-(3-Iodo-1H-pyrazol-1-yl)benzonitrile

To 3-iodo-1H-pyrazole (801 mg, 4.13 mmol) in DMSO (10 mL) at 0° C., was added sodium hydride (60% in mineral oil, 198 mg, 4.95 mmol). The reaction was warmed to 25° C. and stirred for 60 min before methyl 4-fluorobenzonitrile (500 mg, 4.13 mmol) was added. The reaction mixture was stirred at 90° C. for 4.5 h before quenching by the addition of water. The reaction mixture was extracted with EtOAc. The combined organic extracts were dried over MgSO$_4$ and concentrated in vacuo. The crude mixture was purified by flash chromatography (ISCO Combiflash, 0-30% EtOAc in hexanes) to afford 4-(3-iodo-1H-pyrazol-1-yl)benzonitrile, as a pale yellow crystalline solid. LCMS calc.=295.96. found=295.90 (M+H)$^+$. $^1$H NMR (500 MHz, CDCl3): δ 7.83 (m, 3H); 7.78 (d, J=8.5 Hz, 2H), 6.71 (d, J=2.6 Hz, 1H).

Intermediate 9

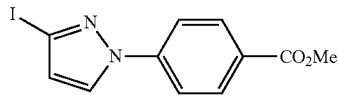 [SMILES: COC(=O)c1ccc(-n2ccc(I)n2)cc1]

Methyl 4-(3-iodo-1H-pyrazol-1-yl)benzoate

To 3-iodo-1H-pyrazole (629 mg, 3.24 mmol) in DMSO (10 mL) at 0° C., was added sodium hydride (60% in mineral oil, 156 mg, 3.89 mmol). The reaction was warmed to 25° C. and stirred for 60 min before methyl 4-fluorobenzoate (500 mg, 4.13 mmol) was added. The reaction mixture was stirred at 90° C. for 4.5 h before quenching by the addition of water. The reaction mixture was extracted with EtOAc. The combined organic extracts were dried over MgSO$_4$ and concentrated in vacuo. The crude mixture was purified by flash chromatography (ISCO Combiflash, 0-30% EtOAc in hexanes) to afford methyl 4-(3-iodo-1H-pyrazol-1-yl)benzoate, as a white solid. LCMS calc.=328.97. found=328.88 (M+H)$^+$. $^1$H NMR (500 MHz, CDCl$_3$): δ 8.15 (d, J=8.5 Hz, 2H); 7.84 (d, J=2.5 Hz, 1H); 7.77 (d, J=8.5 Hz, 2H); 6.69 (d, J=2.5 Hz, 1H); 3.96 (s, 3H).

Intermediate 10

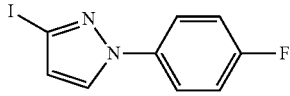 [SMILES: Fc1ccc(-n2ccc(I)n2)cc1]

1-(4-Fluorophenyl)-3-iodo-1H-pyrazole

A mixture of 3-iodo-1H-pyrazole (1 g, 5.16 mmol), (4-fluorophenyl)boronic acid (0.866 g, 6.19 mmol) and [Cu(Cl)(OH)(Me$_2$NCH$_2$CH$_2$NMe$_2$)]$_2$ (0.479 g, 1.031 mmol) in CH$_2$Cl$_2$ (20.6 mL) was sealed and stirred at 25° C. under an atmosphere of oxygen (balloon) overnight. The reaction was filtered over Celite to remove insoluble solids and the filter was washed well with CH$_2$Cl$_2$. The filtrate was concentrated in vacuo and purified by flash chromatography (ISCO Combiflash, 40 g silica gel column, 0-10% EtOAc in hexanes) to afford 1-(4-fluorophenyl)-3-iodo-1H-pyrazole, as white solid. LCMS calc.=288.96. found=288.86 (M+H)$^+$.

Intermediate 11

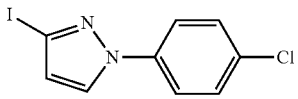 [SMILES: Clc1ccc(-n2ccc(I)n2)cc1]

1-(4-Chlorophenyl)-3-iodo-1H-pyrazole

To 3-iodo-1H-pyrazole (743 mg, 3.83 mmol) in DMSO (10 mL) at 0° C., was added sodium hydride (60% in mineral oil, 184 mg, 4.60 mmol). The reaction was warmed to 25° C. and stirred for 60 min before 1-chloro-4-fluorobenzene (500 mg, 4.13 mmol) was added. The reaction mixture was stirred at 90° C. for 2 days before quenching by the addition of water. The reaction mixture was extracted with EtOAc. The combined organic extracts were dried over MgSO$_4$ and concentrated in vacuo. The crude mixture was purified by flash chromatography (ISCO Combiflash, 0-20% EtOAc in hexanes) to give product, as a white solid. LCMS calc.=304.93. found=304.92 (M+H)$^+$. $^1$H NMR (500 MHz, CDCl$_3$): δ 7.73 (d, J=2.5 Hz, 1H); 7.64-7.61 (m, 2H); 7.46-7.43 (m, 2H); 6.66 (d, J=2.5 Hz, 1H).

Intermediate 12

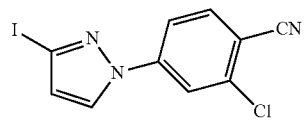 [SMILES: N#Cc1ccc(-n2ccc(I)n2)cc1Cl]

2-Chloro-4-(3-iodo-1H-pyrazol-1-yl)benzonitrile

To a solution of 3-iodo-1H-pyrazole (702 mg, 3.62 mmol) in anhydrous DMSO (10 mL) was added NaH (183 mg, 4.58 mmol) at 0° C. The mixture was stirred for 30 min at 0° C., followed by the addition of 2-chloro-4-fluorobenzonitrile (534 mg, 3.43 mmol) in DMSO (1 mL). The resulting mixture was stirred at 90° C. overnight. The mixture was cooled to room temperature, quenched with water (20 mL) and extracted with EtOAc (3×60 mL). The organic layer was collected and dried over Na$_2$SO$_4$. The solvent was removed in vacuo to give the crude product. This was purified by flash chromatography (Combiflash ISCO, 24 g, Biotage Si column, ~60 mL/min, 100% hexanes for 5 min, gradient to 100% EtOAc in hexanes over 15 min) to afford 2-chloro-4-(3-iodo-1H-pyrazol-1-yl)benzonitrile. LCMS calc.=329.93. found=330.06 (M+H)$^+$. $^1$H NMR (500 MHz, CD$_3$OD): δ 8.30 (d, J=2.7 Hz, 1H); 8.13 (s, 1H); 7.92 (s, 2H); 6.77 (d, J=2.7 Hz, 1H).

Intermediate 13

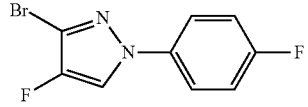

3-Bromo-4-fluoro-1-(4-fluorophenyl)-1H-pyrazole

Cu-TMEDA catalyst (197 mg, 0.424 mmol) and 4-fluorophenylboronic acid (1187 mg, 8.49 mmol) were added sequentially to a solution of 3-bromo-4-fluoro-1H-pyrazole (700 mg, 4.24 mmol) in CH$_2$Cl$_2$ (20 mL) at room temperature. The reaction mixture was stirring under O$_2$ balloon for two days. Removed all the solvent and purified by preparative HPLC (sunfire column), eluting with MeCN+0.1% TFA/Water+0.1% TFA, 10% to 80%, to give 3-bromo-4-fluoro-1-(4-fluorophenyl)-1H-pyrazole. LCMS calc.=260.97. found=260.81 (M+H)$^+$. $^1$H NMR (600 MHz, CDCl$_3$): δ 7.68 (d, 1H); 7.60 (dd, 2H); 7.20 (d, 2H).

Intermediate 14

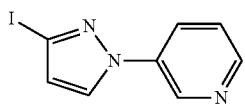

3-(3-Iodo-1H-pyrazol-1-yl)pyridine

To a solution of 3-iodopyrazole (1.00 g, 5.16 mmol) in DMSO (15.1 mL) was added sodium hydride (60% in oil, 0.247 g, 6.19 mmol), and stirred for 0.5 h before 3-fluoropyridine (0.443 mL, 5.16 mmol) was added. The reaction mixture was stirred at 90° C. overnight. This was quenched by the addition of water and extracted with EtOAc. The combined organic extracts were washed with water and brine, dried over MgSO$_4$ and concentrated in vacuo. The crude mixture was purified by flash chromatography (ISCO Combiflash, 40 g, 0-50% EtOAc in hexanes) to give 3-(3-iodo-1H-pyrazol-1-yl)pyridine, as a white solid. LCMS calc.=271.96. found=271.85 (M+H)$^+$. $^1$H NMR (500 MHz, CDCl$_3$): δ 8.93 (d, J=2.5 Hz, 1H); 8.57 (dd, J=4.7, 1.1 Hz, 1H); 8.04 (d, J=8.4 Hz, 1H); 7.79 (d, J=2.5 Hz, 1H); 7.41 (dd, J=8.3, 4.8 Hz, 1H); 6.68 (d, J=2.4 Hz, 1H).

Intermediate 15

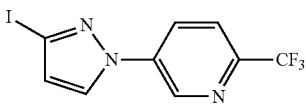

5-(3-Iodo-1H-pyrazol-1-yl)-2-(trifluoromethyl)pyridine

To a solution of 3-iodopyrazole (0.588 g, 3.03 mmol) in DMSO (15.0 mL) was added sodium hydride (60% in oil, 0.145 g, 3.64 mmol) and stirred for 0.5 h before 5-fluoro-2-(trifluoromethyl)pyridines added. The reaction mixture was stirred at 90° C. overnight. The reaction was quenched by the addition of water and extracted with EtOAc. The combined organic extracts were washed with water and brine, dried over MgSO$_4$ and concentrated in vacuo. The crude mixture was purified by passing through the silica gel funnel with CH$_2$Cl$_2$ to give 5-(3-iodo-1H-pyrazol-1-yl)-2-(trifluoromethyl)pyridine, as a yellow solid. LCMS calc.=339.95. found=339.89 (M+H)$^+$. $^1$H NMR (500 MHz, CDCl$_3$): δ 9.03 (d, J=2.3 Hz, 1H); 8.24 (dd, J=8.4, 2.1 Hz, 1H); 7.86 (d, J=2.5 Hz, 1H); 7.80 (d, J=8.5 Hz, 1H); 6.73 (d, J=2.6 Hz, 1H).

Intermediate 16

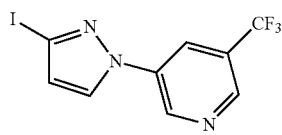 [SMILES: FC(F)(F)c1cncc(-n2ccc(I)n2)c1]

3-(3-Iodo-1H-pyrazol-1-yl)-5-(trifluoromethyl)pyridine

To a solution of 3-iodopyrazole (0.70 g, 3.61 mmol), in DMSO (15.0 mL) was added sodium hydride (60% in oil, 0.159 g, 3.97 mmol), and stirred for 0.5 h before 3-fluoro-5-trifluoromethylpyridine (0.596 g, 3.61 mmol) was added. The reaction mixture was stirred at 90° C. overnight. This was quenched by the addition of water and extracted with EtOAc. The combined organic extracts were washed with water and brine, dried over MgSO$_4$ and concentrated in vacuo. The crude mixture was purified by flash chromatography (ISCO Combiflash, 40 g, 0-20% EtOAc in hexanes) to give 3-(3-iodo-1H-pyrazol-1-yl)-5-(trifluoromethyl)pyridine, as a white solid. LCMS calc.=339.95. found=339.86 (M+H)$^+$. $^1$H NMR (500 MHz, CDCl$_3$): δ 9.12 (br s, 1H); 8.83 (br s, 1H); 8.32 (br s, 1H); 7.85 (br s, 1H); 6.73 (d, J=1.7 Hz, 1H).

Intermediate 17

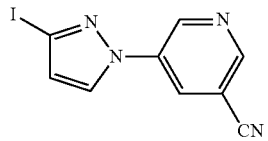 [SMILES: N#Cc1cncc(-n2ccc(I)n2)c1]

5-(3-Iodo-1H-pyrazol-1-yl)nicotinonitrile

To 3-iodo-1H-pyrazole (500 mg, 2.58 mmol) in DMSO (2.6 mL) at 0° C., was added sodium hydride (60% in mineral oil, 113 mg, 2.84 mmol). The reaction was warmed to 25° C. and stirred for 60 min before 5-fluoronicotinonitrile (315 mg, 2.58 mmol) was added. The reaction mixture was stirred at 85° C. for 5 h before quenched by the addition of water. The reaction mixture was extracted with EtOAc. The combined organic extracts were dried over MgSO$_4$ and concentrated in vacuo. The crude mixture was purified by flash chromatography (ISCO Combiflash, 0-50% EtOAc in hexanes) to afford 5-(3-iodo-1H-pyrazol-1-yl)nicotinonitrile, as a white solid. LCMS calc.=296.96. found=296.88 (M+H)$^+$.

Intermediate 18

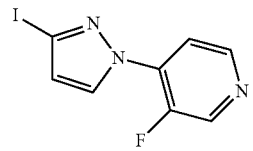 [SMILES: Fc1cnccc1-n1ccc(I)n1]

3-Fluoro-4-(3-iodo-1H-pyrazol-1-yl)pyridine

To a solution of 3-iodopyrazole (0.70 g, 3.61 mmol) in DMSO (15.1 mL) was added sodium hydride (60% in oil, 0.159 g, 3.97 mmol) and stirred for 0.5 h before 3,4-difluoro pyridine (0.415 g, 3.61 mmol) was added. The reaction mixture was stirred at 90° C. for 2.5 h. The reaction was quenched by the addition of water and extracted with EtOAc. The combined organic extracts were washed with water and brine, dried over MgSO₄ and concentrated in vacuo. The crude mixture was purified by flash chromatography (ISCO Combiflash, 40 g, 0-20% EtOAc in hexanes) to give 3-fluoro-4-(3-iodo-1H-pyrazol-1-yl)pyridine, as a white solid. LCMS calc.=289.95. found=289.92 (M+H)⁺. ¹H NMR (500 MHz, CDCl₃): δ 8.61 (d, J=3.8 Hz, 1H); 8.48 (d, J=5.4 Hz, 1H); 8.02 (d, J=2.4 Hz, 1H); 8.00 (d, J=5.4 Hz, 1H); 6.70 (d, J=2.5 Hz, 1H).

Intermediate 19

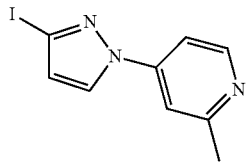

4-(3-Iodo-1H-pyrazol-1-yl)-2-methylpyridine

To a stirred solution of 4-fluoro-2-methylpyridine (1 g, 9.0 mmol) and 3-iodo-1H-pyrazole (1.76 g, 9.1 mmol) in DMSO was added NaH (60% in oil, 0.45 g, 11.25 mmol) in portion at 0° C. The mixture was stirred at room temperature for 30 min or until bubbling ceased, then warmed to 90° C. and stirred at 90° C. for 4 h. The reaction mixture was cooled to room temperature, partitioned between EtOAc and water. The aqueous was extracted with EtOAc three times. The organic phases were combined, dried over Na₂SO₄ and concentrated in vacuo to give the crude product. This was purified by flash chromatography (Isco CombiFlash, 120 g Silica gel column, 0-100% EtOAc in hexanes) to afford 4-(3-iodo-1H-pyrazol-1-yl)-2-methylpyridine. LCMS calc.=285.98. found=285.92 (M+H)⁺. ¹H NMR (500 MHz, CDCl₃): δ 8.57 (br s, 1H); 7.87 (br s, 1H); 7.56 (br s, 1H); 7.35 (br s, 1H); 6.71 (br s, 1H); 2.66 (s, 3H).

Intermediate 20

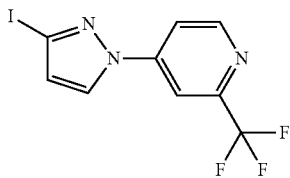 [SMILES: FC(F)(F)c1cc(-n2ccc(I)n2)ccn1]

4-(3-Iodo-1H-pyrazol-1-yl)-2-(trifluoromethyl)pyridine

To a solution of 3-iodopyrazole (0.70 g, 3.61 mmol), in DMSO (18.0 mL) was added sodium hydride (60% disp. in oil, 0.173 g, 4.33 mmol), and the resulting mixture was stirred for 0.5 h before adding 4-fluoro-2-trifluoromethyl pyridine (0.596 g, 3.61 mmol). The reaction mixture was stirred at 90° C. for 3 h. The reaction was quenched by the addition of water and extracted with EtOAc. The combined organic extracts were washed with water and brine, dried over MgSO₄ and concentrated in vacuo. The crude mixture was purified by flash chromatography (ISCO, 40 g, 0-50% EtOAc in hexanes) to afford 4-(3-iodo-1H-pyrazol-1-yl)-2-(trifluoromethyl)pyridine, as a white solid. LCMS calc.=339.95. found=339.93 (M+H)⁺. ¹H NMR (500 MHz, CDCl₃): δ 8.77 (d, J=5.3 Hz, 1H); 8.03 (d, J=3.8 Hz, 1H); 7.91 (d, J=2.6 Hz, 1H); 7.77 (d, J=5.4 Hz, 1H); 6.74 (d, J=2.5 Hz, 1H).

Intermediate 21

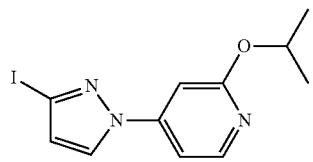 [SMILES: CC(C)Oc1cc(-n2ccc(I)n2)ccn1]

4-(3-Iodo-1H-pyrazol-1-yl)-2-isopropoxypyridine

To a solution of 3-iodopyrazole (0.30 g, 1.547 mmol) in DMSO (7.73 mL) was added sodium hydride (60% in oil, 0.068 g, 1.701 mmol). The resulting mixture was stirred for 0.5 h before 4-bromo-2-isopropoxypyridine (0.334 g, 1.547 mmol) was added. The reaction mixture was stirred at 80° C. overnight. The reaction was quenched by the addition of water and extracted with EtOAc. The combined organic extracts were washed with water and brine, dried over MgSO₄ and concentrated in vacuo. The crude mixture was purified by flash chromatography (ISCO Combiflash, 24 g, 0-10% EtOAc in hexanes) to give 4-(3-iodo-1H-pyrazol-1-yl)-2-isopropoxypyridine, as a white solid. LCMS calc.=330.00. found=329.91. (M+H)⁺. ¹H NMR (500 MHz, CDCl₃): δ 8.17 (d, J=5.7 Hz, 1H); 7.78 (d, J=2.6 Hz, 1H); 7.20 (dd, J=5.7, 1.9 Hz, 1H); 6.93 (d, J=1.9 Hz, 1H); 6.64 (d, J=2.5 Hz, 1H); 5.34 (m, 1H); 1.36 (d, J=6.2 Hz, 6H).

Intermediate 22

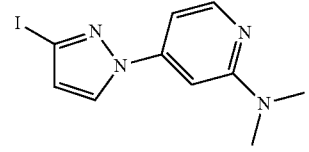

4-(3-Iodo-1H-pyrazol-1-yl)-N,N-dimethylpyridin-2-amine

To a suspension of 3-iodo-1H-pyrazole (100 mg, 0.516 mmol) and N,N-dimethyl-4-(4,4,5,5-tetramethyl-1,3,2-dioxaborolan-2-yl)pyridin-2-amine (192 mg, 0.773 mmol), Na₂CO₃ (109 mg, 1.031 mmol) in anhydrous dichloroethane (4 mL) added a suspension of Cu(OAc)₂ (94 mg, 0.516 mmol) and 2,2'-bipyridine (81 mg, 0.516 mmol) in dichloroethane (4 mL). The reaction was stirred at 70° C. under N₂ overnight. The mixture was filtered through the Celite and washed with EtOAc (5 mL×3), the filtrate was collected and removed in vacuo to give the crude product. This was purified by flash chromatography (ISCO Combiflash, 10 g, Biotage Si column, ~30 mL/min, 100% hexanes 5 min, gradient to 100% EtOAc in hexanes 15 min) to afford 4-(3-iodo-1H-pyrazol-1-yl)-N,N-dimethylpyridin-2-amine. LCMS calc.=315.01. found=315.10 (M+H)⁺.

Intermediate 23

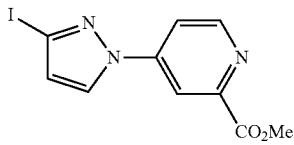 [SMILES: COC(=O)c1cc(-n2ccc(I)n2)ccn1]

Methyl 4-(3-iodo-1H-pyrazol-1-yl)picolinate

To 3-iodo-1H-pyrazole (625 mg, 3.22 mmol) in DMSO (15 mL) at 0° C., was added sodium hydride (60% in mineral oil, 155 mg, 3.87 mmol). The reaction was stirred for 30 min before methyl 4-fluoropicolinate (500 mg, 3.22 mmol) was added and the reaction was stirred at 90° C. for 4.5 h. The reaction mixture was quenched by the addition of water and the mixture was extracted with EtOAc. The combined organic extracts were dried over MgSO$_4$ and concentrated in vacuo. The crude mixture was purified by flash chromatography (ISCO Combiflash, 0-100% EtOAc in hexanes) to afford methyl 4-(3-iodo-1H-pyrazol-1-yl)picolinate, as a colorless solid. LCMS calc.=329.97. found=329.88 (M+H)$^+$.

Intermediate 24

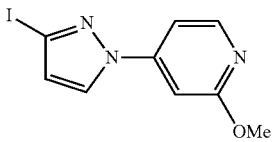 [SMILES: COc1cc(-n2ccc(I)n2)ccn1]

4-(3-Iodo-1H-pyrazol-1-yl)-2-methoxypyridine

To 3-iodo-1H-pyrazole (763 mg, 3.93 mmol) in DMSO (15 mL) at 0° C., was added sodium hydride (60% in mineral oil, 189 mg, 4.72 mmol). The reaction was warmed to 25° C. and stirred for 60 min before 4-fluoro-2-methoxypyridine (500 mg, 3.93 mmol) was added. The reaction mixture was stirred at 90° C. for 4.5 h before quenching by the addition of water. The reaction mixture was extracted with EtOAc. The combined organic extracts were dried over MgSO$_4$ and concentrated in vacuo. The crude mixture was purified by flash chromatography (ISCO Combiflash, 0-30% EtOAc in hexanes) to afford 4-(3-iodo-1H-pyrazol-1-yl)-2-methoxypyridine, as a white solid. LCMS calc.=301.97. found=302.02 (M+H)$^+$.

Intermediate 25

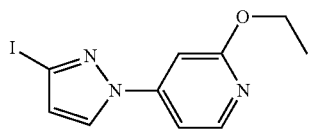

2-Ethoxy-4-(3-iodo-1H-pyrazol-1-yl)pyridine

Anhydrous DMF was added to a mixture of 4-bromo-2-ethoxypyridine (312 mg, 1.55 mmol), 3-iodo-1H-pyrazole (300 mg, 1.55 mmol) and K$_2$CO$_3$ (641 mg, 4.64 mmol). The mixture was stirred at 25° C. overnight. The reaction mixture was then quenched with water and extracted with EtOAc. The organic layer was dried (Na$_2$SO$_4$) and concentrated in vacuo to give the crude product. This was purified by flash chromatography (Isco Combiflash Rf, RediSep Silica 24 g 0-100% EtOAc in hexanes) to afford 2-ethoxy-4-(3-iodo-1H-pyrazol-1-yl)pyridine. LCMS calc.=314.99. found=315.90 (M+H)$^+$.

Intermediate 26

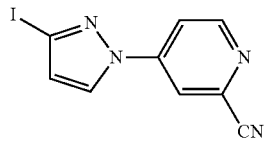 [SMILES: N#Cc1cc(-n2ccc(I)n2)ccn1]

4-(3-Iodo-1H-pyrazol-1-yl)picolinonitrile

Step A: Methyl 4-(3-iodo-1H-pyrazol-1-yl)picolinate

To 3-iodo-1H-pyrazole (625 mg, 3.22 mmol) in DMSO (15.1 mL) was added sodium hydride (155 mg, 3.87 mmol), at 0° C. After stirring for 30 min, methyl 4-fluoropicolinate (500 mg, 3.22 mmol) was added. The reaction mixture was stirred at 90° C. for 4.5 h before quenching by the addition of water. The mixture was extracted with EtOAc (3×). The combined organic extracts were dried over MgSO$_4$ and concentrated in vacuo. The crude mixture was purified by flash chromatography (ISCO, 0-100% EtOAc in hexanes) to afford methyl 4-(3-iodo-1H-pyrazol-1-yl)picolinate, as a colorless solid. LCMS calc.=329.97. found=329.88 (M+H)$^+$.

Step B: 4-(3-Iodo-1H-pyrazol-1-yl)picolinic acid

To methyl 4-(3-iodo-1H-pyrazol-1-yl)picolinate (250 mg, 0.76 mmol) in THF (7.6 mL) was added aq. LiOH (1 M, 3.8 mL). The reaction was stirred at 25° C. for 2 h. The THF was removed by a stream of N$_2$. The aqueous layer was acidified with 2 N TFA in DMSO and directly purified by reversed phase HPLC (C-18, 20%-85% MeCN in water) to afford 4-(3-iodo-1H-pyrazol-1-yl)picolinic acid, as a white solid. LCMS calc.=315.95. found=315.87 (M+H)$^+$.

Step C: 4-(3-Iodo-1H-pyrazol-1-yl)picolinamide

To 4-(3-iodo-1H-pyrazol-1-yl)picolinic acid (160 mg, 0.51 mmol), EDC (292 mg, 1.52 mmol), HOBt (233 mg, 1.52 mmol) and NH$_4$Cl (136 mg, 2.54 mmol) in DMF (5 mL) was added triethylamine (354 uL, 2.54 mmol). The reaction was stirred at 25° C. overnight. The solids were removed by filtration and the DMF was removed in vacuo. The crude product was purified by flash chromatography (ISCO, 0-100% EtOAc in hexanes) to afford 4-(3-Iodo-1H-pyrazol-1-yl)picolinamide. LCMS calc.=314.97. found=314.84 (M+H)$^+$.

Step D: 4-(3-Iodo-1H-pyrazol-1-yl)picolinonitrile

To 4-(3-iodo-1H-pyrazol-1-yl)picolinamide (120 mg, 0.405 mmol) dissolved in THF was added pyridine (309 μl, 3.82 mmol) and trifluoroacetic anhydride (270 μl, 1.910 mmol). The reaction was stirred at 25° C. for 3 h. It was concentrated in vacuo and purified by flash chromatography (ISCO, 0-100% EtOAc in hexanes) to afford 4-(3-iodo-1H-pyrazol-1-yl)picolinonitrile, as a white solid. LCMS calc.=296.96. found=296.87 (M+H)+. 1H NMR (500 MHz, CDCl3): δ 8.77 (d, J=5.6 Hz, 1H); 8.08 (d, J=2.2 Hz, 1H); 7.89 (d, J=2.7 Hz, 1H); 7.81 (dd, J=5.6, 2.2 Hz, 1H); 6.78 (d, J=2.7 Hz, 1H).

Intermediate 27

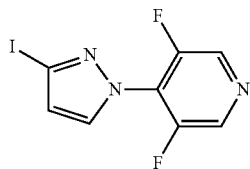 [SMILES: Fc1cncc(F)c1-n1ccc(I)n1]

3,5-Difluoro-4-(3-iodo-1H-pyrazol-1-yl)pyridine

To a solution of 3-iodopyrazole (0.70 g, 3.61 mmol), in DMSO (15.1 mL) was added sodium hydride (60% in oil, 0.159 g, 3.97 mmol) and stirred for 0.5 h before 3,4,5-trifluoropyridine (0.48 g, 3.61 mmol) was added. The reaction mixture was stirred at 90° C. for 3 h. This was quenched by the addition of water and extracted with EtOAc. The combined organic extracts were washed with water and brine, dried over MgSO4 and concentrated in vacuo. The crude mixture was purified by flash chromatography (ISCO Combiflash, 40 g, 0-30% EtOAc in hexanes) to give 3,5-difluoro-4-(3-iodo-1H-pyrazol-1-yl)pyridine, as a white solid. LCMS calc.=307.94. found=307.92 (M+H)+. 1H NMR (500 MHz, CDCl3): δ 8.53 (s, 2H); 7.65 (dd, J=3.9, 2.3 Hz, 1H); 6.72 (d, J=2.5 Hz, 1H).

Intermediate 28

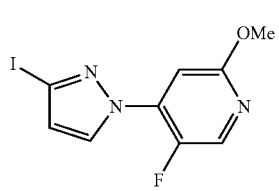

5-Fluoro-4-(3-iodo-1H-pyrazol-1-yl)-2-methoxypyridine

To a solution of 3-iodopyrazole (0.20 g, 1.031 mmol), in DMSO (5.20 mL) was added sodium hydride (60% in oil, 0.045 g, 1.134 mmol) and stirred for 0.5 h before 4-bromo-5-fluoro-2-methoxypyridine (0.212 g, 1.031 mmol) was added. The reaction mixture was stirred at 80° C. for 4 h. This was quenched by the addition of water and extracted with EtOAc. The combined organic extracts were washed with water and brine, dried over MgSO4 and concentrated in vacuo. The crude mixture was purified by flash chromatography (ISCO Combiflash, 12 g, 0-20% EtOAc in hexanes) to give 5-fluoro-4-(3-iodo-1H-pyrazol-1-yl)-2-methoxypyridine, as a white solid. LCMS calc.=319.96. found=320.05 (M+H)+. 1H NMR (500 MHz, CDCl3): δ 8.13 (d, J=2.8 Hz, 1H); 7.97 (d, J=1.7 Hz, 1H); 7.37 (m, 1H); 6.67 (d, J=2.6 Hz, 1H); 3.94 (t, J=1.2 Hz, 3H).

Intermediate 29

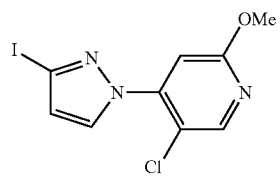 [SMILES: COc1cc(-n2ccc(I)n2)c(Cl)cn1]

5-Chloro-4-(3-iodo-1H-pyrazol-1-yl)-2-methoxypyridine

A solution of 3-iodo-1H-pyrazole (0.3 g, 1.547 mmol), 5-chloro-2-methoxypyridine-4-boronic acid (0.377 g, 2.011 mmol), DMAP (0.756 g, 6.19 mmol), copper(II)acetate (0.281 g, 1.547 mmol), and cesium carbonate (1.26 g, 3.87 mmol) in 1,4-dioxane (7.73 mL) was heated at 80° C. overnight. The reaction was allowed to warm to room temperature and filtered. The filtrate was diluted with EtOAc and water, and the separated aq. layer was extracted with EtOAc. The combined organics were dried over MgSO4, filtered and concentrated. The residue was purified with flash chromatography (ISCO Combiflash, 24 g, 0-10% EtOAc in hexanes) to give 5-chloro-4-(3-iodo-1H-pyrazol-1-yl)-2-methoxypyridine, as a white solid. LCMS calc.=335.93. found=335.82 (M+H)+. 1H NMR (500 MHz, CDCl3): δ 8.25 (s, 1H); 8.01 (d, J=2.6 Hz, 1H); 7.14 (s, 1H); 6.66 (d, J=2.5 Hz, 1H); 3.96 (s, 3H).

Intermediate 30

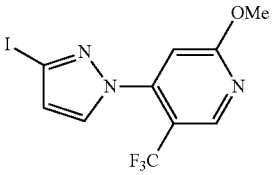 [SMILES: COc1cc(-n2ccc(I)n2)c(C(F)(F)F)cn1]

4-(3-Iodo-1H-pyrazol-1-yl)-2-methoxy-5-(trifluoromethyl)pyridine

To a solution of 3-iodopyrazole (0.30 g, 1.547 mmol), in DMSO (7.73 mL) was added sodium hydride (60% in oil, 0.068 g, 1.701 mmol) and stirred for 0.5 h before 4-iodo-5-trifluoromethyl-2-methoxypyridine (0.469 g, 1.547 mmol) was added. The reaction mixture was stirred at 80° C. for 4 h. The reaction was quenched by the addition of water and extracted with EtOAc. The combined organic extracts were washed with water and brine, dried over MgSO4 and concentrated in vacuo. The crude mixture was purified by flash chromatography (ISCO Combiflash, 24 g, 0-20% EtOAc in hexanes) to give 4-(3-iodo-1H-pyrazol-1-yl)-2-methoxy-5-(trifluoromethyl)pyridine, as a white solid. LCMS calc.=369.96. found=369.83 (M+H)+. 1H NMR (500 MHz, CDCl3): δ 8.58 (s, 1H); 7.63 (s, 1H); 7.01 (d, J=2.8 Hz, 1H); 6.65 (d, J=2.6 Hz, 1H); 4.03 (d, J=3.3 Hz, 3H).

Intermediate 31

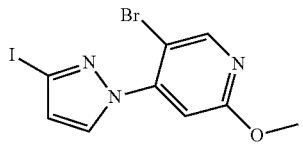

5-Bromo-4-(3-iodo-1H-pyrazol-1-yl)-2-methoxypyridine

To a solution of 4-(3-iodo-1H-pyrazol-1-yl)-2-methoxypyridine (100 mg, 0.332 mmol) in CHCl3 (2 mL) was added N-bromosuccinimide (65 mg, 6.03 mmol). The mixture was stirred at 80° C. overnight. The mixture was cooled to room temperature, quenched with water (10 mL) and extracted with EtOAc (40 mL×3). The organic layer was collected and dried over Na2SO4. The solvent was removed in vacuo to give the crude product. This was purified by flash chromatography (ISCO Combiflash, 10 g, Biotage Si column, ~30 mL/min, 100% hexanes 5 min, gradient to 100% EtOAc in hexanes 15 min) to afford 5-bromo-4-(3-iodo-1H-pyrazol-1-yl)-2-methoxypyridine. LCMS calc.=381.89. found=381.81 (M+H)+. 1H NMR (500 MHz, CDCl3): δ 8.4 (d, J=2.1 Hz, 1H); 8.0 (s, 1H); 7.01 (d, 2.1 Hz, 1H); 6.62 (s, 1H); 3.99 (s, 3H).

Intermediate 32

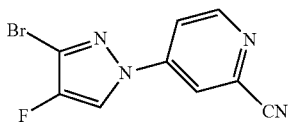 [SMILES: N#Cc1cc(-n2cc(F)c(Br)n2)ccn1]

4-(3-Bromo-4-fluoro-1H-pyrazol-1-yl)picolinonitrile 3-bromo-4-fluoro-1H-pyrazole (100 mg, 0.606 mmol), K3PO4 (232 mg, 1.091 mmol), CuI (34.6 mg, 0.182 mmol) and (1R,2R)—N,N2-dimethylcyclohexane-1,2-diamine (43.1 mg, 0.303 mmol) were added successively to a solution of 4-bromopicolinonitrile (222 mg, 1.212 mmol) in toluene (3 mL) at 25° C. and the reaction was stirred at 90° C. under N2 overnight. After the mixture was filtered and washed with EtOAc (10 mL×3), the filtrate was collected and removed in vacuo to give the crude product. This was purified by flash chromatography (ISCO Combiflash, 12 g, Biotage Si column, ~30 mL/min, 100% hexanes 5 min, gradient to 100% EtOAc in hexanes 15 min) to afford 4-(3-bromo-4-fluoro-1H-pyrazol-1-yl)picolinonitrile. LCMS calc.=268.97 (M+H). found=268.86 (M+H)+.

Intermediate 33

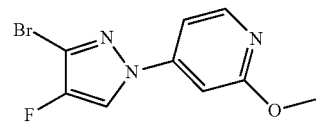

4-(3-Bromo-4-fluoro-1H-pyrazol-1-yl)-2-methoxypyridine

To a solution of 3-bromo-4-fluoro-1H-pyrazole (300 mg, 1.819 mmol) in anhydrous DMSO (4 mL) was added NaH (80 mg, 2.0 mmol) at 0° C. The mixture was stirred for 30 min at 0° C., followed by the addition of 4-chloro-2-methoxypyridine (261 mg, 1.819 mmol) in DMSO (1 mL). The resulting mixture was stirred at 90° C. overnight. The mixture was cooled to room temperature, quenched with water (10 mL) and extracted with EtOAc (40 mL×3). The organic layer was collected and dried over Na2SO4. The solvent was removed in vacuo to give the crude product. This was purified by flash chromatography (ISCO Combiflash, 10 g, Biotage Si column, ~30 mL/min, 100% hexanes 5 min, gradient to 100% EtOAc in hexanes 15 min) to afford 4-(3-bromo-4-fluoro-1H-pyrazol-1-yl)-2-methoxypyridine. LCMS calc.=273.98. found=273.95 (M+H)+.

Intermediate 34

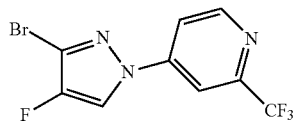 [SMILES: Fc1cn(-c2ccnc(C(F)(F)F)c2)nc1Br]

4-(3-Bromo-4-fluoro-1H-pyrazol-1-yl)-2-(trifluoromethyl)pyridine

To a solution of 3-bromo-4-fluoro-1H-pyrazole (250 mg, 1.515 mmol) in anhydrous DMSO (4 mL) was added NaH (66.7 mg, 1.667 mmol) at 0° C. The mixture was stirred for 30 min at 0° C., followed by the addition of 4-fluoro-2-(trifluoromethyl)pyridine (250 mg, 1.515 mmol) in DMSO (1 mL). The resulting mixture was stirred at 90° C. overnight. The mixture was cooled to room temperature, quenched with water (10 mL) and extracted EtOAc (40 mL×3). The organic layer was collected and dried over Na2SO4. The solvent was removed in vacuo to give the crude product. This was purified by flash chromatography (ISCO Combiflash, 10 g, Biotage Si column, ~30 mL/min, 100% hexanes 5 min, gradient to 100% EtOAc in hexanes 15 min) to afford 4-(3-bromo-4-fluoro-1H-pyrazol-1-yl)-2-(trifluoromethyl)pyridine. LCMS calc.=311.96. found=311.89 (M+H)+.

Intermediate 35

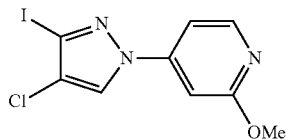 [SMILES: COc1cc(-n2cc(Cl)c(I)n2)ccn1]

4-(4-Chloro-3-iodo-1H-pyrazol-1-yl)-2-methoxypyridine

N-Chlorosuccinimide (244 mg, 1.83 mmol) was added to 4-(3-iodo-1H-pyrazol-1-yl)-2-methoxypyridine (500 mg, 1.66 mmol) in acetic acid (10 mL). The reaction was heated at 90° C. for 6 h. The acetic acid was azeotropically removed with heptane. The crude mixture was purified by flash chromatography (ISCO Combiflash, 0-30% EtOAc in hexanes) to afford 4-(4-chloro-3-iodo-1H-pyrazol-1-yl)-2-methoxypyridine, as a white solid. LCMS calc.=335.93. found=335.92 (M+H)$^+$.

Intermediate 36

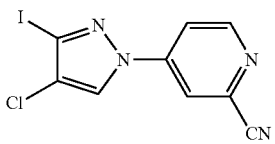

4-(4-Chloro-3-iodo-1H-pyrazol-1-yl)picolinonitrile

N-Chlorosuccinimide (149 mg, 1.11 mmol) was added to 4-(3-iodo-1H-pyrazol-1-yl)picolinonitrile (300 mg, 1.01 mmol) in acetic acid (10 mL). The reaction was heated at 90° C. for 6 h. The acetic acid was azeotropically removed with heptane. The crude mixture was purified by flash chromatography (ISCO Combiflash, 0-30% EtOAc in hexanes) to afford 4-(4-chloro-3-iodo-1H-pyrazol-1-yl)picolinonitrile, as a white solid. LCMS calc.=330.92. found=330.92 (M+H)$^+$. $^1$H NMR (500 MHz, CD$_3$CN): δ 8.76 (d, J=5.6 Hz, 1H); 8.34 (s, 1H); 8.17 (d, J=2.2 Hz, 1H); 7.90 (dd, J=5.5, 2.3 Hz, 1H).

Intermediate 37

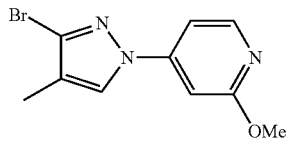

4-(3-Bromo-4-methyl-1H-pyrazol-1-yl)-2-methoxypyridine

To 3-bromo-4-methyl-1H-pyrazole (200 mg, 1.24 mmol) in DMSO (1.2 mL) at 0° C., was added sodium hydride (60% in mineral oil, 55 mg, 1.37 mmol). The reaction was warmed to 25° C. and stirred for 60 min before 4-chloro-2-methoxypyridine (178 mg, 1.24 mmol) was added. The reaction mixture was stirred at 85° C. overnight. The reaction mixture was quenched by the addition of water and was extracted with EtOAc. The combined organic extracts were dried over MgSO$_4$ and concentrated in vacuo. The crude mixture was purified by flash chromatography (ISCO Combiflash, 0-30% EtOAc in hexanes) to afford 4-(3-bromo-4-methyl-1H-pyrazol-1-yl)-2-methoxypyridine, as a white solid. LCMS calc.=268.00. found=267.99 (M+H)$^+$. $^1$H NMR (500 MHz, CDCl$_3$): δ 8.16 (d, J=5.8 Hz, 1H); 7.69 (s, 1H); 7.23-7.15 (m, 1H); 6.95 (s, 1H); 3.96 (s, 3H); 2.08 (s, 3H).

Intermediate 38

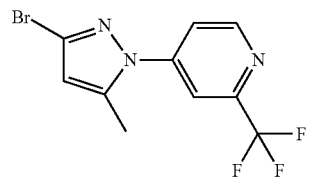 [SMILES: Cc1cc(Br)nn1-c1ccnc(C(F)(F)F)c1]

4-(3-Bromo-5-methyl-1H-pyrazol-1-yl)-2-(trifluoromethyl)pyridine

To a solution of 3-bromo-5-methyl-1H-pyrazole (0.40 g, 2.484 mmol) in DMSO (15.1 mL) was added sodium hydride (60% in oil, 0.119 g, 2.98 mmol), and stirred for 0.5 h before 4-fluoro-2-trifluoromethyl pyridine (0.41 g, 2.484 mmol) was added. The reaction mixture was stirred at 90° C. for 2.5 h. The reaction was quenched by the addition of water and extracted with EtOAc. The combined organic extracts were washed with water and brine, dried over MgSO$_4$ and concentrated in vacuo. The crude mixture was purified by flash chromatography (ISCO Combiflash, 40 g, 0-20% EtOAc in hexanes) to give 4-(3-bromo-5-methyl-1H-pyrazol-1-yl)-2-(trifluoromethyl)pyridine, as a white solid. LCMS calc.=307.98. found=307.88 (M+H)$^+$. $^1$H NMR (500 MHz, CDCl$_3$): δ 8.81 (d, J=4.2 Hz, 1H); 7.93 (d, J=2.0 Hz, 1H); 7.65 (d, J=2.7 Hz, 1H); 6.33 (s, 1H); 2.54 (s, 3H).

Intermediate 39

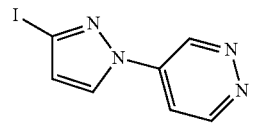 [SMILES: Ic1ccn(-c2ccnnc2)n1]

4-(3-Iodo-1H-pyrazol-1-yl)pyridazine

To the stirred solution of 4-iodopyridazine (1000 mg, 4.85 mmol) and 3-iodo-1H-pyrazole (951 mg, 4.90 mmol) in DMSO was added NaH (60% in oil, 233 mg, 5.83 mmol) in portion at 0° C. The mixture was stirred at room temperature for 30 min or until bubbling ceased, then warmed up to 50° C. and stirred at 50° C. overnight. The reaction mixture was cooled to room temperature, partitioned between EtOAc and water. The aqueous was extracted with EtOAc for three times. The organic phases were combined, dried over Na$_2$SO$_4$ and concentrated in vacuo to give the crude product. This was purified by flash chromatography (Isco Combi-Flash, 80 g Silica gel column, 0-100% EtOAc in hexanes) to afford 4-(3-iodo-1H-pyrazol-1-yl)pyridazine. LCMS calc.=272.96. found=272.96 (M+H)$^+$. $^1$H NMR (500 MHz, CDCl$_3$): δ 9.64 (d, J=3.0 Hz, 1H); 9.27 (d, J=6.0 Hz, 1H); 7.95 (d, J=2.5 Hz, 1H); 7.81 (dd, J=2.5 Hz, J=5.5 Hz, 1H); 6.79 (d, J=2.5 Hz, 1H).

Intermediate 40

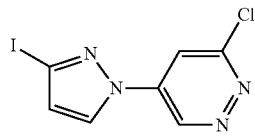 [SMILES: Clc1cc(-n2ccc(I)n2)cnn1]

3-Chloro-5-(3-iodo-1H-pyrazol-1-yl)pyridazine

To a solution of 3-iodopyrazole (500 mg, 2.58 mmol) and 3,5-dichloropyridazine (384 mg, 2.58 mmol) in anhydrous DMF (5 mL) at room temperature was added potassium tert-butoxide (289 mg, 2.58 mmol) in one portion. It was heated at 100° C. for 1 h. It was cooled to room temperature, diluted with EtOAc (50 mL), washed with satd aq. NaHCO$_3$ (10 mL) and water (100 mL). The aqueous layer was separated and extracted with EtOAc (3×50 mL). The combined organic layers were washed with water (100 mL), brine (100 mL), dried over Na$_2$SO$_4$, filtered and concentrated. The residue was purified by flash chromatography (ISCO Combiflash, Gold 40 g, 0-60% EtOAc in hexanes) to give 3-chloro-5-(3-iodo-1H-pyrazol-1-yl)pyridazine, as a white solid. LCMS calc.=306.92. found=306.96 (M+H)$^+$. $^1$H NMR (500 MHz, CHCl$_3$-d): δ 9.54 (d, J=2.3 Hz, 1H); 7.94 (d, J=2.7 Hz, 1H); 7.90 (d, J=2.3 Hz, 1H); 6.81 (d, J=2.7 Hz, 1H).

Intermediate 41

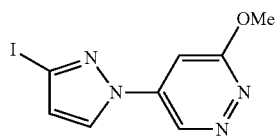

5-(3-Iodo-1H-pyrazol-1-yl)-3-methoxypyridazine

To a suspension of 3-chloro-5-(3-iodo-1H-pyrazol-1-yl)pyridazine (400 mg, 1.305 mmol) in MeOH (1 mL) was added triflic acid (300 μl, 3.38 mmol). The mixture was stirred at 50° C. for 6 h. It became a slight yellow solution. TEA (0.5 mL) was added and the mixture was concentrated and purified by flash chromatography (ISCO Combiflash, 40 g, 0-60% EtOAc in hexane) to give 5-(3-iodo-1H-pyrazol-1-yl)-3-methoxypyridazine. LCMS calc.=302.97. found=302.88 (M+H)$^+$.

Intermediate 42

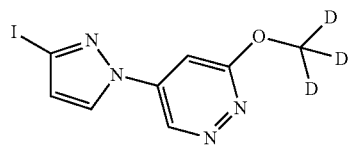 [SMILES: [2H]C([2H])([2H])Oc1cc(-n2ccc(I)n2)cnn1]

5-(3-Iodo-1H-pyrazol-1-yl)-3-methoxy(d3) pyridazine

To the stirred suspension of 3-chloro-5-(3-iodo-1H-pyrazol-1-yl)pyridazine (200 mg, 0.653 mmol) in CD$_3$OD (2.5 mL) was added trifluoromethanesulfonic acid (255 mg, 1.7 mmol) at room temperature. The mixture was stirred at 50° C. for 10 h, cooled to room temperature, neutralized with triethylamine (0.273 mL, 1.96 mmol), concentrated in vacuo and then purified by flash chromatography (Isco Combi-Flash, 40 g Silica gel column, 0-60% EtOAc in hexanes) to afford 5-(3-iodo-1H-pyrazol-1-yl)-3-methoxy(d3) pyridazine. LCMS calc.=305.99. found=305.91 (M+H)$^+$. $^1$H NMR (500 MHz, CDCl$_3$): δ 9.30 (d, J=2.0 Hz, 1H); 7.88 (d, J=2.5 Hz, 1H); 7.23 (d, J=2.0 Hz, 1H); 6.75 (d, J=2.5 Hz, 1H).

Intermediate 43

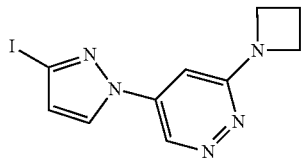 [SMILES: Ic1ccn(-c2cnnc(N3CCC3)c2)n1]

3-(Azetidin-1-yl)-5-(3-iodo-1H-pyrazol-1-yl) pyridazine

Step A:
3-Chloro-5-(3-iodo-1H-pyrazol-1-yl)pyridazine

To a stirred solution of 3,5-dichloropyridazine (1000 mg, 6.71 mmol) and 3-iodo-1H-pyrazole (1302 mg, 6.71 mmol) in DMSO was added NaH (60% in oil, 201 mg, 8.39 mmol) in one portion at 0° C. The mixture was stirred at room temperature overnight. The reaction mixture was partitioned between EtOAc and water. The aqueous layer was extracted with EtOAc three times. The organic phases were combined, dried over Na$_2$SO$_4$ and concentrated in vacuo to give the crude product. To this crude material was added CH$_2$Cl$_2$ (10 mL) and white solid formed. The solid was collected and washed with CH$_2$Cl$_2$ to afford 3-chloro-5-(3-iodo-1H-pyrazol-1-yl)pyridazine, as an off-white solid. The filtrate was concentrated in vacuo and purified by flash chromatography (Isco CombiFlash, 80 g Silica gel column, 0-60% EtOAc in hexanes) to afford additional 3-chloro-5-(3-iodo-1H-pyrazol-1-yl)pyridazine. LCMS calc.=306.92. found=306.89 (M+H)$^+$. $^1$H NMR (500 MHz, CDCl$_3$): δ 9.54 (d, J=2.5 Hz, 1H); 7.93 (d, J=3.0 Hz, 1H); 7.89 (d, J=2.5 Hz, 1H); 6.80 (d, J=3.0 Hz, 1H).

Step B: 3-(Azetidin-1-yl)-5-(3-iodo-1H-pyrazol-1-yl)pyridazine

A mixture of 3-chloro-5-(3-iodo-1H-pyrazol-1-yl)pyridazine (500 mg, 1.63 mmol) and azetidine (466 mg, 8.16 mmol) in 1,4-dioxane (5 mL) was stirred at 60° C. for 6 h. The mixture was cooled to room temperature, diluted with EtOAc, and washed with satd. NaHCO₃. The organic phase was separated, dried over Na₂SO₄, filtered and concentrated in vacuo to give 3-(azetidin-1-yl)-5-(3-iodo-1H-pyrazol-1-yl)pyridazine as light-yellow solid in quantitative yield. LCMS calc.=328.01. found=327.91 (M+H)⁺.

Intermediate 44

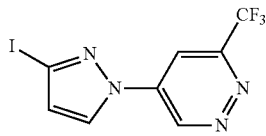 [SMILES: FC(F)(F)c1cc(-n2ccc(I)n2)cnn1]

5-(3-Iodo-1H-pyrazol-1-yl)-3-(trifluoromethyl)pyridazine

Step A: 5-Chloro-3-iodopyridazine

A solution of pyridine (0.72 mL, 8.90 mmol), 5-chloropyridazin-3(2H)-one (1 g, 7.66 mmol) in MeCN (7 mL) was cooled to 0° C. and trifluoromethanesulfonic anhydride (2.4 g, 8.51 mmol) was added dropwise over 2 min. It was stirred for 30 min at room temperature, then charged with sodium iodide (5.74 g, 38.3 mmol) in one portion. Triflic acid (0.75 mL, 8.45 mmol) was added dropwise and the mixture was stirred for 1 h. It was quenched with water (10 mL) and 10 M NaOH (~1.5 mL) and 1 M NaOH (3 mL) were added to adjust pH to 10. 10% Aqueous Na₂CO₃ (10 mL), and saturated aqueous sodium thiosulfate (30 mL) were added and the mixture was extracted with EtOAc (2×50 mL). The combined organic layers were washed with brine, dried over Na₂SO₄, filtered and concentrated. The residue was purified twice by flash chromatography (ISCO Combiflash, 40 g, 0-40% EtOAc in hexanes, then Gold 40 g, 0-40% EtOAc in hexanes) to give 5-chloro-3-iodopyridazine. LCMS calc.=240.90. found=240.92 (M+H)⁺.

Step B: 5-Chloro-3-(trifluoromethyl)pyridazine

Cuprous iodide (0.77 g, 4.04 mmol) and potassium fluoride (0.24 g, 4.13 mmol) were thoroughly mixed and flame-heated under gentle shaking and at reduced pressure for 30 min until a greenish color appeared. 5-Chloro-3-iodopyridazine (0.88 g, 3.66 mmol), anhydrous DMF (2 mL), N-methyl-2-pyrrolidinone (2 mL) and (trifluoromethyl)trimethylsilane (0.57 g, 4.01 mmol) were added and the slurry was stirred vigorously for 16 h at room temperature. It was quenched with satd aq. NH₄Cl (20 mL) and EtOAc (20 mL). The mixture was filtered through Celite and separated. The aqueous layer was extracted with EtOAc (2×30 mL). The combined organic layers were filtered and washed with satd aq. NaHCO₃ and brine, dried over Na₂SO₄, filtered and concentrated. The residue was purified by flash chromatography (ISCO Combiflash, Gold 40 g, 0-30% EtOAc in hexanes) to give 5-chloro-3-(trifluoromethyl)pyridazine, as the desired product. ¹H NMR (500 MHz, CDCl₃): δ 9.41 (d, J=2.3 Hz, 1H); 7.90 (d, J=2.3 Hz, 1H).

Step C: 5-(3-Iodo-1H-pyrazol-1-yl)-3-(trifluoromethyl)pyridazine

To 3-iodopyrazole (124 mg, 0.641 mmol) in DMF (2 mL) was added potassium tert-butoxide (53 mg, 0.472 mmol) at 0° C. The mixture was stirred at room temperature for 15 min. It was transferred into a solution of 5-chloro-3-(trifluoromethyl)pyridazine (78 mg, 0.427 mmol) in DMF (2 mL) at 0° C. It was warmed to room temperature, stirring for 30 min. It was diluted with EtOAc (20 mL), washed with water (3×20 mL), the combined aqueous layers were extracted with EtOAc (30 mL), the combined organic layers were washed with brine (30 mL), dried over Na₂SO₄, filtered and concentrated. The residue was purified by flash chromatography (ISCO Combiflash, 12 g, 0-100% EtOAc in hexanes) to give a mixture of 3-iodopyrazole and the desired product (1:2, 180 mg). It was dissolved in anhydrous CH₂Cl₂ (2 mL) and added a little bit of DMAP and of di-tert-butyl dicarbonate (~100 mg). It was stirred at room temperature for 10 min and purified by flash chromatography (ISCO Combiflash, 0-40% EtOAc in hexanes) to give 5-(3-iodo-1H-pyrazol-1-yl)-3-(trifluoromethyl)pyridazine, as white solid. LCMS calc.=340.95. found=340.84 (M+H)⁺. ¹H NMR (500 MHz, CHCl₃-d): δ 9.78 (d, J=2.5 Hz, 1H); 8.17 (d, J=2.5 Hz, 1H); 8.04 (d, J=2.7 Hz, 1H); 6.84 (d, J=2.7 Hz, 1H).

Intermediate 45

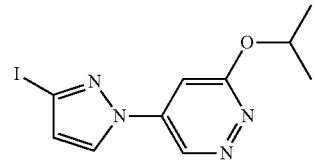 [SMILES: CC(C)Oc1cc(-n2ccc(I)n2)cnn1]

5-(3-Iodo-1H-pyrazol-1-yl)-3-isopropoxypyridazine

Step A: 5-Chloro-3-isopropoxypyridazine

A mixture of 5-chloropyridazin-3(2H)-one (250 mg, 1.915 mmol), silver acetate (384 mg, 2.298 mmol), 2-bromopropane (0.270 mL, 2.87 mmol) and toluene (4 mL) was heated at 80° C. for 16 h. It was purified directly by flash chromatography (ISCO Combiflash, 24 g, 0-30% EtOAc in hexanes) to give 5-chloro-3-isopropoxypyridazine, as a colorless oil. LCMS calc.=173.05. found=173.08 (M+H)⁺. ¹H NMR (500 MHz, CDCl₃): δ 8.78 (d, J=2.0 Hz, 1H); 6.95 (d, J=2.0 Hz, 1H); 5.64-5.54 (m, 1H); 1.42 (d, J=6.2 Hz, 6H).

Step B: 5-(3-Iodo-1H-pyrazol-1-yl)-3-isopropoxypyridazine

To a solution of 3-iodopyrazole (270 mg, 1.390 mmol) in anhydrous DMF (2 mL) at 0° C. was added potassium tert-butoxide (143 mg, 1.275 mmol). It was stirred at room temperature for 10 min, and then 5-chloro-3-isopropoxypyridazine (200 mg, 1.159 mmol) was added neat. The mixture was stirred at room temperature for 15 min. It was heated at 100° C. for 1 h. It was cooled to room temperature, diluted with EtOAc (20 mL), washed with water (3×20 mL). The combined aqueous layers were extracted with EtOAc (30 mL), washed with brine (20 mL), dried over Na$_2$SO$_4$, filtered and concentrated. The residue was purified by flash chromatography (ISCO Combiflash, 12 g, 0-50% EtOAc in hexanes) to give the titled product, as a white solid. LCMS calc.=331.01. found=330.88 (M+H)$^+$.

Intermediate 46

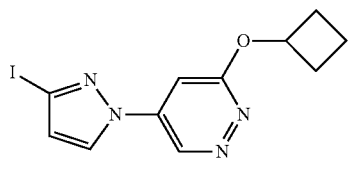 [SMILES: Ic1ccn(-c2cnnc(OC3CCC3)c2)n1]

3-Cyclobutoxy-5-(3-iodo-1H-pyrazol-1-yl)pyridazine

To a solution of potassium tert-butoxide (0.732 g, 6.53 mmol) in THF (20 mL) was added cyclobutanol (0.565 g, 7.83 mmol) at room temperature. The solution was stirred for 5 min and transferred to a solution of 3-chloro-5-(3-iodo-1H-pyrazol-1-yl)pyridazine (2 g, 6.53 mmol) in THF (20 mL) then stirred at room temperature for 16 h. It was diluted with EtOAc (50 mL), washed with 10% aqueous solution of Na$_2$CO$_3$ (2×25 mL), water (2×20 mL) and brine (20 mL). It was dried over Na$_2$SO$_4$, filtered and concentrated. The residue was purified by flash chromatography (ISCO Combiflash, 80 g, 0-30% EtOAc in hexanes) to give a white solid (0.53 g) which was a mixture of the desired product and two by-products. A solution of the white solids in CH$_2$Cl$_2$ (2 mL) was treated with di-tert-butyl-di-carbonate (0.2 g) and catalytic amount of DMAP for 15 min at room temperature. The reaction mixture was directly purified by flash chromatography (ISCO Combiflash, 40 g, 0-30% EtOAc in hexanes) to give 3-cyclobutoxy-5-(3-iodo-1H-pyrazol-1-yl)pyridazine. LCMS calc.=343.01. found=342.86 (M+H)$^+$. $^1$H NMR (500 MHz, DMSO-d$_6$): δ 9.48 (d, J=2.2 Hz, 1H); 8.66 (d, J=2.7 Hz, 1H); 7.63 (d, J=2.2 Hz, 1H); 6.93 (d, J=2.6 Hz, 1H); 5.80-5.73 (m, 1H); 4.98-4.91 (m, 3H); 4.60 (ddd, J=23.7, 7.6, 5.0 Hz, 3H).

Intermediate 47

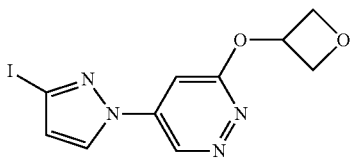 [SMILES: Ic1ccn(-c2cnnc(OC3COC3)c2)n1]

5-(3-Iodo-1H-pyrazol-1-yl)-3-(oxetan-3-yloxy)pyridazine

To a solution of potassium tert-butoxide (1.450 g, 12.92 mmol) in THF (40 mL) was added oxetan-3-ol (1.131 g, 15.27 mmol) at room temperature. The solution was stirred for 5 min. It was transferred to a solution of 3-chloro-5-(3-iodo-1H-pyrazol-1-yl)pyridazine (3.6 g, 11.75 mmol) in THF (20 mL), stirring at room temperature for 16 h. It was diluted with EtOAc (50 mL), washed with 10% aqueous solution of Na$_2$CO$_3$ (2×25 mL), water (2×20 mL) and brine (20 mL). It was dried over Na$_2$SO$_4$, filtered and concentrated. The residue was purified by flash chromatography (ISCO Combiflash, 80 g, 0-30% EtOAc in hexanes) to give 5-(3-iodo-1H-pyrazol-1-yl)-3-(oxetan-3-yloxy)pyridazine. LCMS calc.=344.98. found=344.88 (M+H)$^+$.

Intermediate 48

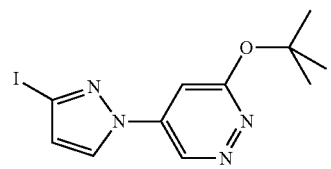 [SMILES: CC(C)(C)Oc1cc(-n2ccc(I)n2)cnn1]

3-(tert-Butoxy)-5-(3-iodo-1H-pyrazol-1-yl)pyridazine

Step A: 3-(tert-Butoxy)-5-chloropyridazine

A mixture of 5-chloropyridazine-3(2H)-one (1 g, 7.66 mmol), silver acetate (1.534 g, 9.19 mmol), 2-bromo-2-methylpropane (1.301 mL, 11.49 mmol) and toluene (15.32 mL) was heated at 80° C. overnight. This mixture was filtered and the filtrate was concentrated. The residue was purified by flash chromatography (ISCO Combiflash, 24 g, 0-30% EtOAc in hexane) to give 3-(tert-butoxy)-5-chloropyridazine, as a white solid. LCMS calc.=187.06. found=187.07 (M+H)$^+$. $^1$H NMR (500 MHz, CDCl$_3$): δ 8.74 (d, J=2.0 Hz, 1H); 6.90 (d, J=2.0 Hz, 1H); 1.66 (s, 9H).

Step B: 3-(tert-Butoxy)-5-(3-iodo-1H-pyrazol-1-yl)pyridazine

To a solution of 3-iodopyrazole (0.208 g, 1.072 mmol) in DMF (5.36 mL) was added potassium tert-butoxide (0.132 g, 1.179 mmol) and then stirred at room temperature for 10 min. 3-(tert-Butoxy)-5-chloropyridazine (0.2 g, 1.072 mmol) was added, then stirred at 100° C. for 1 h, and cooled to room temperature. EtOAc and water were added and the organic was washed with water and brine, dried over MgSO$_4$, filtered and concentrated. The residue was purified by flash chromatography (ISCO Combiflash, 24 g, 0-30% EtOAc in hexanes) to give 3-(tert-Butoxy)-5-(3-iodo-1H-pyrazol-1-yl)pyridazine, as a white solid. LCMS calc.=288.95. found=288.87 (M+H-tert-Bu)+. $^1$H NMR (500 MHz, CDCl$_3$): δ 9.22 (d, J=2.2 Hz, 1H); 7.83 (d, J=2.5 Hz, 1H); 7.09 (d, J=2.3 Hz, 1H); 6.70 (d, J=2.5 Hz, 1H); 1.69 (s, 9H).

Intermediate 49

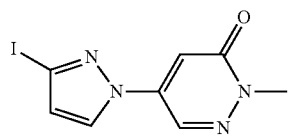

5-(3-Iodo-1H-pyrazol-1-yl)-2-methylpyridazin-3(2H)-one

Step A: 5-Chloro-2-methylpyridazin-3(2H)-one

A solution of 5-chloropyridazin-3(2H)-one (1 g, 7.66 mmol) in $CH_2Cl_2$ (20 mL) and MeOH (4.00 mL) was cooled to 0° C., trimethylsilyldiazomethane (8 mL, 16.00 mmol) was added and the resulting mixture was stirred for 1 h. The reaction mixture was warmed to room temperature and stirred for 64 h. It was quenched with acetic acid (1 mL) and concentrated under reduced pressure. The residue was purified by flash chromatography (ISCO Combiflash, Gold 40 g, 0-50% EtOAc in hexanes) to give 5-chloro-2-methylpyridazin-3(2H)-one, as a white solid. LCMS calc.=145.02. found=145.00 (M+H)+. $^1$H NMR (500 MHz, $CDCl_3$): δ 7.72 (d, J=2.4 Hz, 1H); 6.97 (d, J=2.4 Hz, 1H); 3.76 (s, 3H).

Step B: 5-(3-Iodo-1H-pyrazol-1-yl)-2-methylpyridazin-3(2H)-one

To a clean dry flask was added sodium hydride (200 mg, 5.00 mmol) and anhydrous NMP (10 mL). The mixture was cooled to 0° C. 3-Iodopyrazole (959 mg, 4.95 mmol) was added to the mixture in one portion. The mixture was stirred for 10 min at room temperature, then 5-chloro-2-methylpyridazin-3(2H)-one (650 mg, 4.50 mmol) was added in one portion. The mixture was stirred at 100° C. for 2 h. The reaction mixture was cooled to room temperature, water (100 mL) was added, and the resulting mixture was extracted with EtOAc (100 mL). The organic layer was washed with water (3×50 mL) and the combined aqueous layers were extracted with EtOAc (2×100 mL). The combined organic layers were washed with brine (100 mL), dried over $Na_2SO_4$, filtered and concentrated under reduced pressure. The residue was purified by flash chromatography (ISCO Combiflash, 40 g, 0-100% EtOAc in hexanes) to give 5-(3-iodo-1H-pyrazol-1-yl)-2-methylpyridazin-3(2H)-one, as a white solid. LCMS calc.=302.97. found=302.95 (M+H)+. $^1$H NMR (500 MHz, $CDCl_3$): δ 8.47 (d, J=2.6 Hz, 1H); 7.79-7.74 (d, J=2.6 Hz, 1H); 6.93 (d, J=2.6 Hz, 1H); 6.74 (d, J=2.6 Hz, 1H); 3.84 (s, 3H).

Intermediate 50

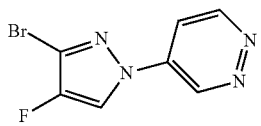 [SMILES: Fc1cn(-c2ccnnc2)nc1Br]

4-(3-Bromo-4-fluoro-1H-pyrazol-1-yl)pyridazine

To a solution of 3-bromo-4-fluoro-1H-pyrazole (497 mg, 3.01 mmol) in anhydrous DMSO (6 mL) was added NaH (241 mg, 6.03 mmol) at 0° C. The mixture was stirred for 30 min at 0° C., followed by the addition of 4-chloropyridazine (451 mg, 3.01 mmol) in DMSO (2 mL). The resulting mixture was stirred at 60° C. overnight. The mixture was cooled to room temperature, quenched with water (10 mL) and extracted EtOAc (40 mL×3). The organic layer was collected and dried over $Na_2SO_4$. The solvent was removed in vacuo to give the crude product. This was purified by flash chromatography (ISCO Combiflash, 24 g, Biotage Si column, ~60 mL/min, 100% hexanes 5 min, gradient to 100% EtOAc in hexanes 15 min) to afford 4-(3-bromo-4-fluoro-1H-pyrazol-1-yl)pyridazine. LCMS calc.=244.97. found=244.91 (M+H)+.

Intermediate 51

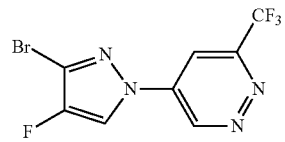 [SMILES: Fc1cn(-c2cnnc(C(F)(F)F)c2)nc1Br]

5-(3-Bromo-4-fluoro-1H-pyrazol-1-yl)-3-(trifluoromethyl)pyridazine

Anhydrous DMF (0.3 mL) was added to a mixture of potassium tert-butoxide (17.8 mg, 0.159 mmol) and 3-bromo-4-fluoro-1H-pyrazole (28.8 mg, 0.175 mmol). The resulting mixture was stirred for 15 min at 25° C. in a screw-cap sealed vial. A solution of 5-chloro-3-(trifluoromethyl)pyridazine (29 mg, 0.159 mmol) in anhydrous DMF (0.3 mL) was added, and the resulting mixture was stirred for 1.5 h at 25° C. The reaction mixture was cooled to 0° C., and acidified by small drops of formic acid until pH 3. The mixture was diluted with DMSO and purified by semi-preparative reverse-phase HPLC (YMC C18, gradient from 20% MeCN in water-0.1% formic acid to 90% MeCN in water-0.1% formic acid) to afford 5-(3-bromo-4-fluoro-1H-pyrazol-1-yl)-3-(trifluoromethyl)pyridazine, as a white solid. LCMS calc.=312.95. found=312.90 (M+H)+.

Intermediate 52

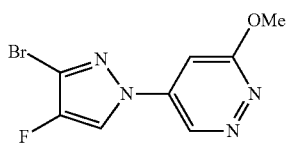

5-(3-Bromo-4-fluoro-1H-pyrazol-1-yl)-3-methoxypyridazine

Step A: 5-(3-Bromo-4-fluoro-1H-pyrazol-1-yl)-3-chloropyridazine

To a solution of 3-bromo-4-fluoro-1H-pyrazole (548 mg, 3.32 mmol) in anhydrous DMF (3 mL) at 0° C. was added potassium tert-butoxide (339 mg, 3.02 mmol). The resulting mixture was stirred for 10 min at 0° C. in a screw-cap sealed vial, and transferred into a solution of 3,5-dichloropyridazine (450 mg, 3.02 mmol) in anhydrous DMF (3 mL) in a screw-cap sealed vial. The reaction mixture was stirred for 15 min at 25° C., diluted with EtOAc (100 mL), and washed with water (100 mL). The aqueous layer was separated and extracted with EtOAc (3×50 mL). The combined organic layers were washed with water (100 mL) and concentrated in vacuo. The residue was dissolved in 10% MeOH in $CH_2Cl_2$, mixed with 20 g of silica gel, and concentrated. The silica gel powder was packed and purified by ISCO silica gel flash chromatography (125 g silica column; 0-50% EtOAc in CH$_2$Cl$_2$) to afford 5-(3-bromo-4-fluoro-1H-pyrazol-1-yl)-3-chloropyridazine, as a white solid. LCMS calc.=278.93. found=278.82 (M+H)$^+$.

Step B: 5-(3-Bromo-4-fluoro-1H-pyrazol-1-yl)-3-methoxypyridazine

Triflic acid (245 µl, 2.76 mmol) was added dropwisely to a solution of 5-(3-bromo-4-fluoro-1H-pyrazol-1-yl)-3-chloropyridazine (383 mg, 1.380 mmol) in MeOH (9 mL) at 0° C. and the reaction mixture was heated at 50° C. for 7 h. All volatile was removed in vacuo. Toluene and triethylamine were added to neutralize residual acid, and the crude mixture was concentrated in vacuo and purified by flash chromatography (0-100% EtOAc in hexanes) to afford 5-(3-bromo-4-fluoro-1H-pyrazol-1-yl)-3-methoxypyridazine. LCMS calc.=274.98. found=274.86 (M+H)$^+$.

Intermediate 53

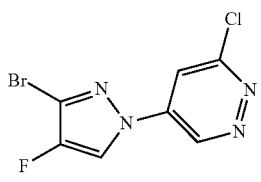 [SMILES: Fc1cn(-c2cnnc(Cl)c2)nc1Br]

5-(3-Bromo-4-fluoro-1H-pyrazol-1-yl)-3-chloropyridazine

To a solution of 3-bromo-4-fluoro-1H-pyrazole (100 mg, 0.606 mmol) in anhydrous DMF (1 mL) added potassium tert-butoxide (68 mg, 0.606 mmol) slowly at room temperature. The mixture was stirred at room temperature for 10 min, followed by the addition of 3,5-dichloropyridazine (90 mg, 0.606 mmol) in DMF (1 mL). The resulting mixture was stirred at 100° C. for 1 h. The mixture was cooled to room temperature, quenched with water (10 mL) and extracted with EtOAc (40 mL×3). The organic layer was collected and dried over Na$_2$SO$_4$. The solvent was removed in vacuo to give the crude product. This was purified by flash chromatography (ISCO Combiflash, 10 g, Biotage Si column, ~30 mL/min, 100% hexanes 5 min, gradient to 100% EtOAc in hexanes 15 min) to afford 5-(3-bromo-4-fluoro-1H-pyrazol-1-yl)-3-chloropyridazine. LCMS calc.=278.93. found=278.82 (M+H)$^+$.

Intermediate 54

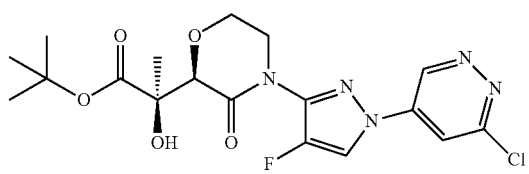

(R)-tert-Butyl 2-((R)-4-(1-(6-chloropyridazin-4-yl)-4-fluoro-1H-pyrazol-3-yl)-3-oxomorpholin-2-yl)-2-hydroxypropanoate 5-(3-Bromo-4-fluoro-1H-pyrazol-1-yl)-3-chloropyridazine (226 mg, 0.815 mmol), K$_3$PO$_4$ (312 mg, 1.468 mmol), CuI (46.6 mg, 0.245 mmol) and (1R,2R)—N$^1$,N$^2$-dimethylcyclohexane-1,2-diamine (0.113 mL, 0.408 mmol) were added successively to a solution of (R)-tert-butyl 2-hydroxy-2-((R)-3-oxomorpholin-2-yl)propanoate (200 mg, 0.815 mmol) in 1,4-dioxane (4 mL) at 25° C. and the reaction was stirred at 90° C. under N$_2$ overnight. After the mixture was filtered and washed with EtOAc (5 mL×3), the filtrate was collected and removed in vacuo to give the crude product. This was purified by flash chromatography (ISCO Combiflash, 24 g, Biotage Si column, ~60 mL/min, 100% hexanes 5 min, gradient to 100% EtOAc in hexanes 15 min) to afford (R)-tert-butyl 2-((R)-4-(1-(6-chloropyridazin-4-yl)-4-fluoro-1H-pyrazol-3-yl)-3-oxomorpholin-2-yl)-2-hydroxypropanoate. LCMS calc.=442.13. found=441.98 (M+H)$^+$.

Intermediate 55

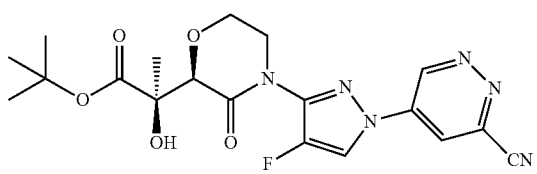

(R)-tert-Butyl 2-((R)-4-(1-(6-cyanopyridazin-4-yl)-4-fluoro-1H-pyrazol-3-yl)-3-oxomorpholin-2-yl)-2-hydroxypropanoate Zn (1.3 mg, 0.020 mmol), Zn(CN)$_2$ (21.3 mg, 0.181 mmol), Pd$_2$(dba)$_3$ (7.3 mg, 0.00792 mmol) and DPPF (35.1 mg, 0.063 mmol) were added successively to a solution of (R)-tert-butyl 2-((R)-4-(1-(6-chloropyridazin-4-yl)-4-fluoro-1H-pyrazol-3-yl)-3-oxomorpholin-2-yl)-2-hydroxypropanoate (50 mg, 0.113 mmol) in DMF (2 mL) at room temperature and the reaction was stirred at 120° C. under N$_2$ for 1 h. After the mixture was filtered and washed with EtOAc (5 mL×3), the filtrate was collected and removed in vacuo to give the crude product. This was purified by flash chromatography (ISCO Combiflash, 10 g, Biotage Si column, ~30 mL/min, 100% hexanes 5 min, gradient to 100% EtOAc in hexanes 15 min) to afford (R)-tert-butyl 2-((R)-4-(1-(6-cyanopyridazin-4-yl)-4-fluoro-1H-pyrazol-3-yl)-3-oxomorpholin-2-yl)-2-hydroxypropanoate. LCMS calc.=433.16. found=433.00 (M+H)$^+$.

Intermediate 56

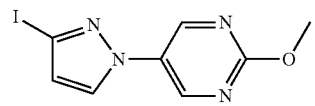

5-(3-Iodo-1H-pyrazol-1-yl)-2-methoxypyrimidine

A solution of 3-iodo-1H-pyrazole (0.7 g, 3.61 mmol), 2-methoxypyrimidine-4-boronic acid (0.722 g, 4.69 mmol), DMAP (1.763 g, 14.43 mmol), copper(II) acetate (0.655 g, 3.61 mmol), and cesium carbonate (2.94 g, 9.02 mmol) in 1,4-dioxane (18.0 mL) was heated at 80° C. overnight. The reaction was allowed to room temperature and filtered. The filtrate was diluted with EtOAc and water, and the separated aq. layer was extracted with EtOAc. The combined organics were dried over MgSO$_4$, filtered and concentrated. The residue was purified with flash chromatography (ISCO Combiflash, 40 g, 0-70% EtOAc in hexanes) to give 5-(3-iodo-1H-pyrazol-1-yl)-2-methoxypyrimidine, as a white solid. LCMS calc.=302.97. found=302.86 (M+H)$^+$. $^1$H NMR (500 MHz, CDCl$_3$): δ 8.82 (s, 2H); 7.66 (d, J=2.6 Hz, 1H); 6.68 (d, J=2.5 Hz, 1H); 4.07 (s, 3H).

Intermediate 57

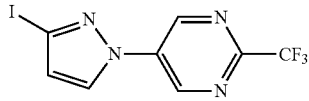 [SMILES: FC(F)(F)c1ncc(-n2ccc(I)n2)cn1]

5-(3-Iodo-1H-pyrazol-1-yl)-2-(trifluoromethyl)pyrimidine

A solution of 3-iodo-1H-pyrazole (0.7 g, 3.61 mmol), 2-trifluoromethylpyrimidine-4-boronic acid (0.722 g, 4.69 mmol), DMAP (1.763 g, 14.43 mmol), copper(II) acetate (0.655 g, 3.61 mmol), and cesium carbonate (2.94 g, 9.02 mmol) in 1,4-dioxane (18.0 mL) was heated at 80° C. overnight. The reaction was allowed to room temperature and filtered. The filtrate was diluted with EtOAc and water, and the separated aq. layer was extracted with EtOAc. The combined organics were dried over MgSO$_4$, filtered and concentrated. The residue was purified with flash chromatography (ISCO Combiflash, 40 g, 0-5% EtOAc in hexanes) to give 5-(3-iodo-1H-pyrazol-1-yl)-2-(trifluoromethyl)pyrimidine, as a white solid. LCMS calc.=340.94. found=340.88 (M+H)$^+$. $^1$H NMR (500 MHz, CDCl$_3$): δ 9.25 (s, 2H); 7.86 (d, J=2.5 Hz, 1H); 6.78 (d, J=2.7 Hz, 1H).

Intermediate 58

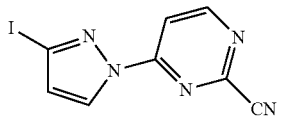 [SMILES: N#Cc1nccc(-n2ccc(I)n2)n1]

4-(3-Iodo-1H-pyrazol-1-yl)pyrimidine-2-carbonitrile

To a solution of 3-iodo-1H-pyrazole (298 mg, 1.536 mmol) in anhydrous DMSO (4 mL) added NaH (86 mg, 2.151 mmol) at 0° C. The mixture was stirred for 30 min at 0° C., followed by the addition of 4-chloropyrimidine-2-carbonitrile (214 mg, 1.536 mmol) in DMSO (1 mL). The resulting mixture was stirred at room temperature overnight. The mixture was quenched with water (10 mL) and extracted with EtOAc (40 mL×3). The organic layer was collected and dried over Na$_2$SO$_4$. The solvent was removed in vacuo to give the crude product. This was purified by flash chromatography (ISCO Combiflash, 10 g, Biotage Si column, ~30 mL/min, 100% hexanes 5 min, gradient to 100% EtOAc in hexanes 15 min) to afford 4-(3-iodo-1H-pyrazol-1-yl)pyrimidine-2-carbonitrile. LCMS calc.=297.95. found=297.92 (M+H)$^+$.

Intermediate 59

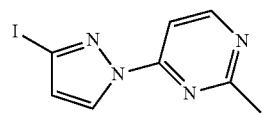

4-(3-Iodo-1H-pyrazol-1-yl)-2-methylpyrimidine

To a solution of 3-iodo-1H-pyrazole (500 mg, 2.58 mmol) in anhydrous DMSO (6 mL) was added NaH (155 mg, 3.87 mmol) at 0° C. The mixture was stirred for 30 min at 0° C., followed by the addition of 4-chloro-2-methylpyrimidine (331 mg, 2.58 mmol) in DMSO (2 mL). The resulting mixture was stirred at 90° C. overnight. The mixture was cooled to room temperature, quenched with water (10 mL) and extracted EtOAc (40 mL×3). The organic layer was collected and dried over Na$_2$SO$_4$. The solvent was removed in vacuo to give the crude product. This was purified by flash chromatography (ISCO Combiflash, 24 g, Biotage Si column, ~60 mL/min, 100% hexanes 5 min, gradient to 100% EtOAc in hexanes 15 min) to afford 4-(3-iodo-1H-pyrazol-1-yl)-2-methylpyrimidine. LCMS calc.=286.98. found=286.95 (M+H)$^+$.

Intermediate 60

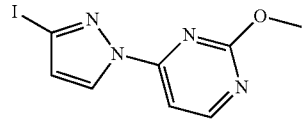

4-(3-Iodo-1H-pyrazol-1-yl)-2-methoxypyrimidine

To the stirred solution of 4-bromo-2-methoxypyrimidine (500 mg, 2.65 mmol) and 3-iodo-1H-pyrazole (518 mg, 2.67 mmol) in DMSO was added NaH (60% in oil, 132 mg, 3.31 mmol) in portion at 0° C. The mixture was stirred at room temperature for 30 min or until bubbling ceased, then warmed up to 90° C. and stirred at 90° C. for 4 h. The reaction mixture was cooled to room temperature, partitioned between EtOAc and water. The aqueous was extracted with EtOAc for three times. The organic phases were combined, dried over Na$_2$SO$_4$ and concentrated in vacuo to give the crude product. This was purified by flash chromatography (Isco CombiFlash, 80 g Silica gel column, 0-50% EtOAc in hexanes) to afford 4-(3-iodo-1H-pyrazol-1-yl)-2-methoxypyrimidine. LCMS calc.=302.97. found=302.99 (M+H)$^+$. $^1$H NMR (500 MHz, CDCl$_3$): δ 8.58

(d, J=1.5 Hz, 1H); 8.42 (d, J=2.0 Hz, 1H); 7.57 (d, J=1.5 Hz, 1H); 6.67 (d, J=2.0 Hz, 1H); 4.08 (s, 3H).

Intermediate 61

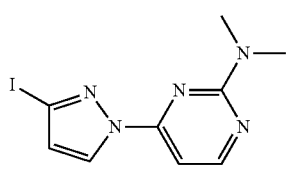

4-(3-Iodo-1H-pyrazol-1-yl)-N,N-dimethylpyrimidin-2-amine

NaH (119 mg, 60% in oil, 2.97 mmol) was added to a solution of 3-iodo-1H-pyrazole (480 mg, 2.48 mmol) in anhydrous DMF (10 mL) at 25° C. under $N_2$. The mixture was stirred for 10 min and 4-bromo-N,N-dimethylpyrimidin-2-amine (500 mg, 2.48 mmol) was added. The resulting mixture was stirred for another 2 h at 25° C. under $N_2$. The reaction mixture was then quenched with saturated aq. $NH_4Cl$ solution and extracted with EtOAc. The organic layer was washed with brine, dried ($Na_2SO_4$) and concentrated in vacuo to give the crude product. This was purified by flash chromatography (Isco Combiflash Rf, RediSep Silica 40 g, 30% EtOAc in hexanes, then 30-100% EtOAc in hexanes) to afford 4-(3-iodo-1H-pyrazol-1-yl)-N,N-dimethylpyrimidin-2-amine. LCMS calc.=314.99. found=315.99 $(M+H)^+$.

Intermediate 62

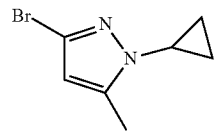

4-(3-Bromo-4-fluoro-1H-pyrazol-1-yl)-2-methoxypyrimidine

To a solution of 3-bromo-4-fluoro-1H-pyrazole (500 mg, 3.03 mmol) in anhydrous DMSO (6 mL) was added NaH (133 mg, 3.13 mmol) at 0° C. The mixture was stirred for 30 min at 0° C., followed by the addition of 4-chloro-2-methoxypyrimidine (438 mg, 3.03 mmol) in DMSO (2 mL). The resulting mixture was stirred at 90° C. overnight. The mixture was cooled to room temperature, quenched with water (10 mL) and extracted with EtOAc (40 mL×3). The organic layer was collected and dried over $Na_2SO_4$. The solvent was removed in vacuo to give the crude product. This was purified by flash chromatography (ISCO Combiflash, 24 g, Biotage Si column, ~60 mL/min, 100% hexanes 5 min, gradient to 100% EtOAc in hexanes 15 min) to afford 4-(3-bromo-4-fluoro-1H-pyrazol-1-yl)-2-methoxypyrimidine. LCMS calc.=274.98. found=274.90 $(M+H)^+$.

Intermediate 63

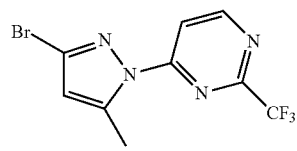 [SMILES: Cc1cc(Br)nn1-c1ccnc(C(F)(F)F)n1]

4-(3-bromo-5-methyl-1H-pyrazol-1-yl)-2-(trifluoromethyl)pyrimidine

To a solution of 3-bromo-5-methyl-1H-pyrazole (100 mg, 0.621 mmol) in anhydrous DMSO (2 mL) was added NaH (27.3 mg, 0.683 mmol) at 0° C. The mixture was stirred for 30 min at 0° C., followed by the addition of 4-chloro-2-(trifluoromethyl)pyrimidine (113 mg, 0.621 mmol) in DMSO (1 mL). The resulting mixture was stirred at room temperature overnight. The mixture was quenched with water (5 mL) and extracted EtOAc (10 mL×3). The organic layer was collected and dried over $Na_2SO_4$. The solvent was removed in vacuo to give the crude product. This was purified by flash chromatography (ISCO Combiflash, 10 g, Biotage Si column, ~30 mL/min, 100% hexanes 5 min, gradient to 100% EtOAc in hexanes 15 min) to afford 4-(3-bromo-5-methyl-1H-pyrazol-1-yl)-2-(trifluoromethyl)pyrimidine. LCMS calc.=308.98. found=308.91 $(M+H)^+$.

Intermediate 64

3-Bromo-1-cyclopropyl-5-methyl-1H-pyrazole

To a suspension of 3-bromo-5-methyl-1H-pyrazole (300 mg, 1.863 mmol) and cyclopropylboronic acid (320 mg, 3.73 mmol), $Na_2CO_3$ (395 mg, 3.73 mmol) in anhydrous dichloroethane (4 mL) added a suspensional solution of $Cu(OAc)_2$ (338 mg, 1.863 mmol) and 2,2'-bipyridine (291 mg, 1.863 mmol) in dichloroethane (4 mL). The resulting mixture was stirred at 70° C. under $N_2$ overnight. After the mixture was filtered through the Celite and washed with EtOAc (5 mL×3), the filtrate was collected and removed in vacuo to give the crude product. This was purified by flash chromatography (ISCO Combiflash, 10 g, Biotage Si column, ~30 mL/min, 100% hexanes 5 min, gradient to 100% EtOAc in hexanes 15 min) to afford 3-bromo-1-cyclopropyl-5-methyl-1H-pyrazole. LCMS calc.=203.00 (M+H). found=203.10 $(M+H)^+$.

Intermediate 65

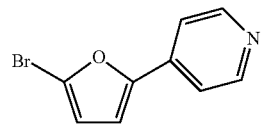 [SMILES: Brc1ccc(-c2ccncc2)o1]

4-(5-Bromofuran-2-yl)pyridine

Step A: 4-(Furan-2-yl)pyridine

A mixture of 2-furanylboronic acid MIDA ester (0.500 g, 2.242 mmol), 4-iodopyridine (0.460 g, 2.242 mmol), 2-dicyclohexylphosphino-2',6'-dimethoxybiphenyl (0.184 g, 0.448 mmol), palladium(II) acetate (0.101 g, 0.448 mmol) and potassium phosphate (0.952 g, 4.48 mmol) in 1,4-dioxane (18.7 mL) and water (3.7 mL) was degassed by bubbling with $N_2$ for 5 min. The reaction was heated at 60° C. overnight under $N_2$. After this time the reaction mixture was cooled to room temperature and filtered through a plug of silica. The filtrate was concentrated in vacuo to give the crude product. This was purified by flash chromatography (Isco Combiflash Rf, RediSep Silica 40 g, 40 mL/min, loaded using solid loading cartridge after dissolving in $CH_2Cl_2$, 100% hexanes for 2 min, gradient to 50% EtOAc in hexanes over 13 min, isocratic at 50% EtOAc in hexanes for 15 min) to afford 4-(furan-2-yl)pyridine, as a colorless solid. LCMS calc.=146.06. found=146.06 (M+H)$^+$. $^1$H NMR (500 MHz, $CHCl_3$-d): δ 8.60 (d, J=5.3 Hz, 2H); 7.55 (d, J=1.7 Hz, 1H); 7.52 (d, J=5.6 Hz, 2H); 6.88 (d, J=3.5 Hz, 1H); 6.53 (dd, J=3.4, 1.8 Hz, 1H).

Step B: 4-(5-Bromofuran-2-yl)pyridine

Bromine (0.5 M in acetic acid) (8.76 mL, 4.38 mmol) was added to a stirred solution of 4-(furan-2-yl)pyridine (0.1927 g, 1.328 mmol) in acetic acid (7.4 mL) and the reaction was stirred at 25° C. overnight. The reaction was diluted with satd aq. $NaHCO_3$ and extracted with EtOAc (3×). The combined extracts were dried ($Na_2SO_4$) and concentrated in vacuo to give the crude product. This was purified by flash chromatography (Isco Combiflash Rf, RediSep Silica 40 g, 40 mL/min, loaded using solid loading cartridge after dissolving in $CH_2Cl_2$, 100% hexanes for 2 min, gradient to 30% EtOAc in hexanes over 13 min, isocratic at 30% EtOAc in hexanes for 35 min) to afford 4-(5-bromofuran-2-yl)pyridine, as a colorless solid. LCMS calc.=225.97. found=225.99 (M+H)$^+$. $^1$H NMR (600 MHz, $CHCl_3$-d): δ 8.61 (s, 2H); 7.47 (d, J=4.9 Hz, 2H); 6.83 (d, J=3.5 Hz, 1H); 6.45 (d, J=3.5 Hz, 1H).

Intermediate 66

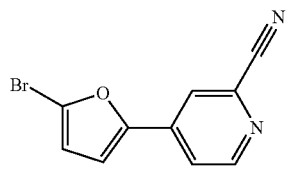 [SMILES: N#Cc1cc(-c2ccc(Br)o2)ccn1]

4-(5-Bromofuran-2-yl)picolinonitrile

Step A: 4-(Furan-2-yl)picolinonitrile

2-Furanylboronic acid MIDA ester (659 mg, 2.96 mmol), 4-iodo-2-cyanopyridine (680 mg, 2.96 mmol), potassium phosphate (1255 mg, 5.91 mmol), 2-dicyclohexylphosphino-2',6'-dimethoxybiphenyl (243 mg, 0.591 mmol), palladium(II) acetate (133 mg, 0.591 mmol), 1,4-dioxane (24.6 mL) and water (4.9 mL) were charged into a round bottom flask. $N_2$ was bubbled through the mixture for 2 min then the reaction was heated at 60° C. overnight under an $N_2$ atmosphere. The reaction was worked up with water/EtOAc. The combined extracts were dried over $Na_2SO_4$, filtered and evaporated in vacuo to afford a dark colored mixture. The resulting pot residue was purified by flash chromatography (Biotage SNAP Cartridge, silica gel, KP-Sil, 100 g cartridge, EtOAc/hexanes) to afford 4-(furan-2-yl)picolinonitrile, as a light orange solid. LCMS calc.=171.06. found=171.15 (M+H)$^+$.

Step B: 4-(5-bromofuran-2-yl)picolinonitrile 4-(Furan-2-yl)picolinonitrile (357.6 mg, 2.101 mmol), N-bromosuccinimide (411 mg, 2.312 mmol) and acetic acid (12 mL) were stirred at room temperature overnight. Volatiles were removed under reduced pressure. The resulting pot residue was worked up with aqueous sodium hydrogen carbonate/EtOAc. The combined extracts were dried over $Na_2SO_4$, filtered and evaporated in vacuo. The resulting crude mixture was purified by flash chromatography (Biotage SNAP Cartridge, silica gel, KP-Sil, 100 g cartridge, EtOAc/hexanes) to afford 4-(5-bromofuran-2-yl)picolinonitrile, as a pink solid. LCMS calc.=250.96. found=251.04 (M+H)$^+$.

Intermediate 67

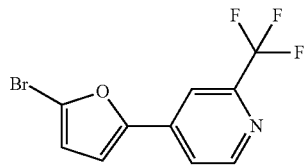 [SMILES: FC(F)(F)c1cc(-c2ccc(Br)o2)ccn1]

4-(5-Bromofuran-2-yl)-2-(trifluoromethyl)pyridine

Step A: 4-(Furan-2-yl)-2-(trifluoromethyl)pyridine

2-Furanylboronic acid MIDA ester (907.6 mg, 4.07 mmol), 4-iodo-2-(trifluoromethyl)pyridine (0.563 mL, 4.07 mmol), potassium phosphate (1728 mg, 8.14 mmol), 2-dicyclohexylphosphino-2',6'-dimethoxybiphenyl (334 mg, 0.814 mmol), palladium(II) acetate (183 mg, 0.814 mmol), 1,4-dioxane (34 mL) and water (6.80 mL) were sealed in a reaction vessel. $N_2$ was bubbled through the mixture for 2 min then the tube was sealed and heated at 60° C. overnight. The reaction mixture was then worked up with water/EtOAc. The combined extracts were dried over $Na_2SO_4$, filtered and evaporated in vacuo to afford a dark colored mixture. This was purified by flash chromatography (Biotage SNAP Cartridge, silica gel, KP-Sil, 100 g cartridge, EtOAc/hexanes) to afford 4-(furan-2-yl)-2-(trifluoromethyl)pyridine, as a dark colored oil. LCMS calc.=214.05. found=214.14 (M+H)$^+$.

Step B: 4-(5-Bromofuran-2-yl)-2-(trifluoromethyl)pyridine 4-(Furan-2-yl)-2-(trifluoromethyl)pyridine (695.6 mg, 3.26 mmol), N-bromosuccinimide (581 mg, 3.26 mmol) and acetic acid (18.6 mL) were stirred at room temperature overnight. Volatiles were removed under reduced pressure.

The pot residue was worked up with aqueous sodium hydrogen carbonate/EtOAc. The combined extracts were dried over Na₂SO₄, filtered and evaporated in vacuo. The resulting mixture was purified by flash chromatography (Biotage SNAP Cartridge, silica gel, KP-Sil, 100 g cartridge, EtOAc/hexanes) to afford 4-(5-bromofuran-2-yl)-2-(trifluoromethyl)pyridine, as a brown solid. LCMS calc.=293.96. found=294.02 (M+H)⁺.

Intermediate 68

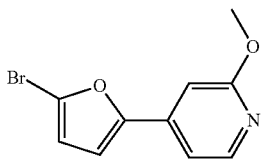

4-(5-Bromofuran-2-yl)-2-methoxypyridine

Step A: 4-(Furan-2-yl)-2-methoxypyridine

A mixture of 2-furanylboronic acid MIDA ester (500 mg, 2.242 mmol), 4-bromo-2-methoxypyridine (422 mg, 2.242 mmol), 2-dicyclohexylphosphino-2',6'-dimethoxybiphenyl (184 mg, 0.448 mmol), palladium(II) acetate (101 mg, 0.448 mmol) and potassium phosphate (952 mg, 4.48 mmol) in 1,4-dioxane (18.7 mL) and water (3.7 mL) in a microwave tube was degassed by bubbling with N₂ for 5 min. The vial was sealed and heated at 60° C. overnight. The reaction mixture was cooled to room temperature and filtered through a plug of silica. The filtrate was diluted with water and extracted with EtOAc. The organic layer was dried (Na₂SO₄) and concentrated in vacuo to give the crude product. This was purified by column chromatography (silica gel, EtOAc/hexanes gradient from 0-20%) to afford 4-(furan-2-yl)-2-methoxypyridine. LCMS calc.=176.07. found=176.13 (M+H)⁺. ¹H NMR (500 MHz, CDCl₃): δ 8.17 (d, J=5.4 Hz, 1H); 7.54 (s, 1H); 7.14 (d, J=5.4 Hz, 1H); 7.01 (s, 1H); 6.84 (d, J=3.4 Hz, 1H); 6.53 (dd, J=3.4, 1.69 Hz, 1H); 3.98 (s, 3H).

Step B: 4-(5-Bromofuran-2-yl)-2-methoxypyridine

To a solution of 4-(furan-2-yl)-2-methoxypyridine (152 mg, 0.868 mmol) in CHCl₃ (8.7 mL), was added bromine (45 μl, 0.868 mmol). The mixture was stirred at room temperature overnight. The reaction was concentrated in vacuo to afford the crude product. This was purified by column chromatography (silica gel, EtOAc/hexanes gradient from 0-10%) to afford 4-(5-bromofuran-2-yl)-2-methoxypyridine. LCMS calc.=253.98. found=254.05 (M+H)⁺. ¹H NMR (500 MHz, CDCl₃): δ 8.16 (d, J=5.4 Hz, 1H); 7.07 (dd, J=5.37, 1.6 Hz, 1H); 6.94 (s, 1H); 6.78 (d, J=3.4 Hz, 1H); 6.44 (d, J=3.4 Hz, 1H); 3.86 (s, 3H).

Intermediate 69

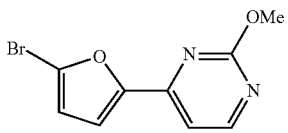 [SMILES: COc1nccc(-c2ccc(Br)o2)n1]

4-(5-Bromofuran-2-yl)-2-methoxypyrimidine

Step A: 4-(Furan-2-yl)-2-methoxypyrimidine

A mixture of 2-furanylboronic acid MIDA ester (0.500 g, 2.242 mmol), 4-bromo-2-methoxypyrimidine (0.424 g, 2.242 mmol), 2-dicyclohexylphosphino-2',6'-dimethoxybiphenyl (0.184 g, 0.448 mmol), palladium(II) acetate (0.101 g, 0.448 mmol) and potassium phosphate (0.952 g, 4.48 mmol) in 1,4-dioxane (18.69 mL) and water (3.74 mL) was degassed by bubbling with N₂ for 5 min. The reaction was heated at 60° C. overnight under N₂. After this time the reaction mixture was cooled to room temperature and filtered through a plug of silica. The filtrate was concentrated in vacuo to give the crude product. This was purified by flash chromatography (Isco Combiflash Rf, RediSep Silica 40 g, 40 mL/min, loaded using solid loading cartridge after dissolving in CH₂Cl₂, 100% hexanes for 2 min, gradient to 50% EtOAc in hexanes over 23 min, isocratic at 50% EtOAc in hexanes for 5 min) to afford 4-(furan-2-yl)-2-methoxypyrimidine, as a colorless solid. LCMS calc.=177.07. found=177.15 (M+H)⁺.

Step B: 4-(5-Bromofuran-2-yl)-2-methoxypyrimidine 4-(Furan-2-yl)-2-methoxypyrimidine (36.2 mg, 0.205 mmol), N-bromosuccinimide (43.9 mg, 0.247 mmol) and acetic acid (2 mL) were stirred at room temperature for 2 h. Volatiles were removed under reduced pressure. The pot residue was worked up with aqueous sodium hydrogen carbonate/EtOAc. The combined extracts were dried over Na₂SO₄, filtered and evaporated in vacuo to afford a dark colored mixture. The resulting mixture was purified by flash chromatography (Biotage SNAP Cartridge, silica gel, KP-Sil, 50 g cartridge, EtOAc/hexanes) to afford 4-(5-bromofuran-2-yl)-2-methoxypyrimidine, as a yellow solid. LCMS calc.=256.97. found=257.02 (M+H)⁺.

Intermediate 70

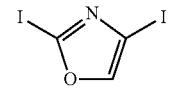

2,4-Diiodooxazole 1,3-Oxazole (1.00 mL, 14.90 mmol) was dissolved in a mixture of anhydrous THF (6.4 mL) and anhydrous DMPU (5.2 mL). The solution was cooled to −78° C. LiHMDS (32.80 mL, 1M in THF, 2.2 equiv) was added dropwise and the resulting reaction mixture was stirred at −78° C. for 1 h. After this time, solid iodine (7.60 g, 29.80 mmol) was added and the reaction mixture was stirred for an additional 30 min at −78° C. The cooling bath was then removed and the reaction mixture was left to warm to room temperature and stirred for 6 days under a low positive pressure of N₂. The reaction mixture was then poured into a mixture of aqueous Na₂S₂O₃ (10%, 100 mL) and Et₂O (100 mL). The organic layer was washed with brine (100 mL) and dried over MgSO₄. After filtration, the solvent was removed in vacuo. The residue was purified by flash chromatography (ISCO Combiflash, 40 g silica gel column, 0-20% EtOAc in hexanes) to afford 2,4-diiodooxazole, as a pale yellow solid which darkens over time. LCMS calc.=321.81. found=321.74 (M+H)⁺.

Intermediate 71

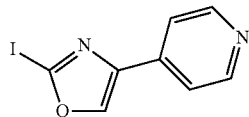 [SMILES: Ic1nc(-c2ccncc2)co1]

2-Iodo-4-(pyridin-4-yl)oxazole

To pyridin-4-ylboronic acid (148 mg, 1.20 mmol), 2,4-diiodooxazole (321 mg, 1.00 mmol), NaHCO₃ (aq, 1 M, 2.5 mL), and Pd(PPh₃)₂Cl₂ was added 1,4-dioxane. The reaction mixture was purged with N₂ in 1,4-dioxane and then heated to 85° C. for 3 h. The mixture was cooled down, passed through Celite, and rinsed with EtOAc. The organic layer was dried over MgSO₄ and concentrated. The crude product was purified by flash chromatography (ISCO Combiflash, 40 g silica gel column, 0-100% EtOAc in hexanes) to afford 2-iodo-4-(pyridin-4-yl)oxazole. LCMS calc.=272.94; found=272.95 (M+H)⁺. ¹H NMR (500 MHz, CDCl₃): δ 8.76 (d, J=5.0 Hz, 2H); 7.87 (d, J=5.0 Hz, 2H); 7.82 (s, 1H).

Intermediate 72

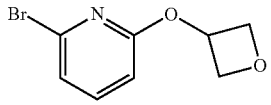 [SMILES: Brc1cccc(OC2COC2)n1]

2-Bromo-6-(oxetan-3-yloxy)pyridine

To 6-bromopyridin-2-ol (564 mg, 3.24 mmol), oxetan-3-ol and triphenylphosphine (1062 mg, 4.05 mmol) in THF (27 mL) was added DIAD (787 µl, 4.05 mmol). The reaction was heated at 50° C. for 1 h and concentrated in vacuo. The crude product was purified by flash chromatography (ISCO Combiflash, 0-20% EtOAc in hexanes) to afford 2-bromo-6-(oxetan-3-yloxy)pyridine. LCMS calc.=229.97. found=229.93 (M+H)⁺. ¹H NMR (500 MHz, CDCl₃): δ 7.48 (t, J=7.8 Hz, 1H); 7.11 (d, J=7.5 Hz, 1H), 6.77 (d, J=8.1 Hz, 1H); 5.63 (p, J=5.8 Hz, 1H); 5.01 (t, J=6.9 Hz, 2H); 4.75 (t, J=6.4 Hz, 2H).

Intermediate 73

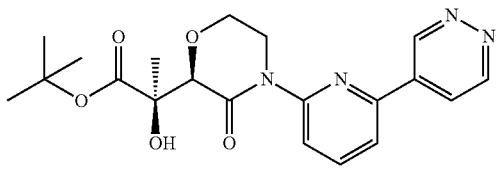

(R)-tert-Butyl 2-hydroxy-2-((R)-3-oxo-4-(6-(pyridazin-4-yl)pyridin-2-yl)morpholin-2-yl)propanoate Step A: (R)-tert-Butyl 2-hydroxy-2-((R)-4-(6-iodopyridin-2-yl)-3-oxomorpholin-2-yl)propanoate (R)-tert-Butyl 2-hydroxy-2-((R)-3-oxomorpholin-2-yl)propanoate (200 mg, 0.815 mmol), 2,6-diiodopyridine (270 mg, 0.815 mmol), trans-N,N'-dimethylcyclohexane-1,2-diamine (0.039 mL, 0.245 mmol), potassium phosphate (433 mg, 2.039 mmol), cuprous iodide (46.6 mg, 0.245 mmol) and 1,4-dioxane (3 mL) were sealed in a reaction vessel. N₂ was bubbled through the mixture for 2 min then the tube was sealed and heated at 66° C. for 4 h then allowed to cool to ambient overnight. The reaction crude was filtered into a stirred NH₄Cl (sat., aq)/ice mixture. The resulting mixture was partitioned between satd aq. NH₄Cl and EtOAc. The combined extracts were dried over Na₂SO₄, filtered and evaporated in vacuo. The resulting mixture was purified by flash chromatography (SiO₂, 100 g cartridge, EtOAc/hexanes) to afford (R)-tert-butyl 2-hydroxy-2-((R)-4-(6-iodopyridin-2-yl)-3-oxomorpholin-2-yl)propanoate, as an off-white solid. LCMS calc.=449.06. found=449.00 (M+H)⁺.

Step B: (R)-tert-Butyl 2-hydroxy-2-((R)-3-oxo-4-(6-(pyridazin-4-yl)pyridin-2-yl)morpholin-2-yl)propanoate (R)-tert-Butyl 2-hydroxy-2-((R)-4-(6-iodopyridin-2-yl)-3-oxomorpholin-2-yl)propanoate (213.3 mg, 0.476 mmol), 4-(4,4,5,5-tetramethyl-1,3,2-dioxaborolan-2-yl)pyridazine (147 mg, 0.714 mmol), dihydrogen dichlorobis(di-t-butylphosphinito-kp)palladate(2-) (23.88 mg, 0.048 mmol), Na₂CO₃ (2N) (1.5 mL) and THF (3 mL) were sealed in a reaction vessel and stirred in a 68° C. oil bath overnight. The reaction crude was worked up with water/EtOAc. The combined extracts were dried over Na₂SO₄, filtered and evaporated in vacuo. The resulting residue was purified by preparative HPLC (reversed phase, YMC-Pack ODS C-18 100×20 mm, MeCN/water (0% to 50% organic in 25 min, then to 100% in 5 min, 20 mL/min)) to afford (R)-tert-butyl 2-hydroxy-2-((R)-3-oxo-4-(6-(pyridazin-4-yl)pyridin-2-yl)morpholin-2-yl)propanoate, as an off-white solid. LCMS calc.=401.18. found=401.03 (M+H)⁺.

Intermediate 74

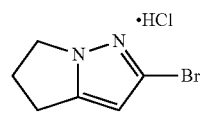

2-Bromo-5,6-dihydro-4H-pyrrolo[1,2-b]pyrazole hydrochloride

Step A: (S)-1-Nitrosopyrrolidine-2-carboxylic acid

A 2 L, three-neck, round-bottom flask (RBF) was made inert and was equipped with an overhead stirrer, temperature probe, 250 mL addition funnel, and nitrogen inlet located behind a blast shield. The RBF was charged with (S)-pyrrolidine-2-carboxylic acid (150.0 g, 1.0 eq), sodium nitrite (125.8 g, 1.823 mol, 1.4 equiv), and deionized water (375 mL, 2.5 vol). The reaction mixture was cooled in an ice/MeOH bath to =0° C. and concentrated HCl (150 mL, 1 vol) was charged to the addition funnel and added dropwise to the reactor over a period of 30 min while maintaining the internal reaction temperature below 10° C. Once the addition was complete, the mixture was stirred in the cold bath for 30 min, warmed slowly to ambient temperature, and stirred overnight (17 h). MTBE (500 mL, 3.3 vol) was charged to the reactor and the mixture was stirred for 30 min; the precipitated solids that formed overnight dissolved upon the addition of MTBE. The contents of the reactor were transferred to a separatory funnel and the two phases were separated. The aqueous phase (bottom layer) was extracted with MTBE (2×250 mL) and the combined organic extracts were washed with brine (300 mL), dried over $MgSO_4$, and filtered. The filtrates were concentrated under reduced pressure at <30° C. and under high vacuum for 3 days to afford (S)-1-nitrosopyrrolidine-2-carboxylic acid, as a white solid. The $^1H$ NMR and $^{13}C$ NMR were consistent with the assigned structure and showed a complex mixture of isomers, rotamers, and residual toluene, and exhibited the following properties: $^1H$ NMR (300 MHz, DMSO-$d_6$): δ 1.88-2.50 (m, 4.2H); 3.52 (m, 0.8H); 4.22-4.41 (m, 1.6H); 5.28 (dd, J=3.3, 8.7 Hz, 0.4H); 13.04 (bs, 1H). $^{13}C$ NMR (75 MHz, DMSO-$d_6$): δ 20.7, 22.7, 27.3, 28.3, 45.3, 49.6, 58.1, 61.6, 169.8, 172.0.

Step B: 5,6-Dihydro-4H-pyrrolo[1,2-c][1,2,3]oxadiazol-7-ium-3-olate

A 1 L, three-neck RBF was made inert and was equipped with an overhead stirrer, temperature probe, nitrogen inlet, and 250 mL addition funnel located behind a blast shield. The RBF was charged with intermediate (S)-1-nitrosopyrrolidine-2-carboxylic acid (141.7 g, 0.983 mol, 1.0 eq) and anhydrous toluene (290 mL, 2 vol). The reaction mixture was cooled to 0° C. by means of an ice/brine bath. TFAA (205 mL, 1.475 mol, 1.5 eq) was added dropwise into the reactor over a period of 70 min and once the addition was complete, the cold bath was removed; the reaction mixture was warmed to ambient temperature and stirred for 2 h. The deep red solution was transferred to a clean 1 L addition funnel attached to a 2 L, three-neck RBF equipped with an overhead stirrer, and temperature probe containing a mixture of $K_2CO_3$ (217.4 g, 1.573 mol, 1.6 eq), deionized water (215 mL, 1.5 vol), and dichloromethane (285 mL, 2 vol). The reactor was cooled to ≈0° C. by means of an ice/brine bath. The red reaction mixture was added dropwise via the addition funnel over a period of 1 h maintaining the internal reaction temperature<20° C. Once the addition was complete, the cold bath was removed; the reactor warmed to ambient temperature and the mixture stirred for 1 h. The contents of the reactor were transferred to a separatory funnel and the phases were separated. The top phase was the first desired organic phase containing product. The bottom phase was extracted with dichloromethane (300 mL) and following phase separation, the top organic phase was collected. The bottom aqueous phase was extracted once more with dichloromethane (300 mL) and the bottom organic phase was collected. All three organic extracts were combined and washed with water (300 mL). Following phase separation, the organic phase was concentrated under reduced pressure<30° C. to afford 210 g of a dark red oil. The crude product was purified through a plug of silica (600 g of silica slurried in heptane) and was eluted with 0.5 L of heptane, 2 L of heptane/ethyl acetate (7:3), 1 L of heptane/ethyl acetate (3:7), 2 L of heptane/ethyl acetate (1:9), and 2 L of ethyl acetate (500 mL fraction size). The product fractions ($R_f$=0.27, ethyl acetate, UV light and $KMnO_4$ staining) were collected and concentrated under reduced pressure at <30° C. to afford 5,6-dihydro-4H-pyrrolo[1,2-c][1,2,3]oxadiazol-7-ium-3-olate, as a red oil that solidified upon storing in the freezer overnight giving a brown solid. $^1H$ NMR (300 MHz, CDCl$_3$): δ 2.77-2.92 (m, 4H); 4.45 (t, J=7.5 Hz, 2H). $^{13}C$ NMR (75 MHz, CDCl$_3$): δ 21.4, 26.4, 51.0, 111.1, 165.5.

Step C: 2-(Tributylstannyl)-5,6-dihydro-4H-pyrrolo[1,2-b]pyrazole

Synthesis of Ethynyl Tributyltin Chloride

A 5 L, three-neck RBF was made inert and was equipped with an overhead stirrer, temperature probe, and nitrogen inlet. The RBF was charged with ethynyl magnesium chloride (0.5 M) in THF (2 L, 1.0 mol). The reaction mixture was cooled to 0-5° C. Tributyl tin chloride (181 mL, 0.667 mol) was added dropwise to the stirred reaction mixture over 15 min. The ice bath was removed and the contents stirred at ambient temperature for approximately 30 min. The reaction mixture was heated to 35° C. for approximately 1 h. For the reaction quench, a separate 12 L, three-neck RBF was equipped with a temperature probe and overhead stirrer and charged with a 15 wt % aqueous ammonium chloride solution (2000 mL, 10 vol). The quench reactor was cooled to 0-5° C. The reaction mixture was cooled to 20-25° C. and added slowly to the ammonium chloride quench solution. The reaction RBF and line were washed with THF (200 mL) and heptanes (400 mL). The layers were partitioned. The organic layer was washed with water (4×1 L). The organic was concentrated by rotary evaporation. Water was removed from the residue using azeotropic distillation with IPAc (2 L; 500 mL). The product was dried under vacuum (25-30 in Hg) at 20-25° C. to provide ethynyl tributyl tin chloride, as a dark oil that was used without further purification. $^1H$ NMR (300 MHz, CDCl$_3$) δ: 0.85-0.95 (t, J=7.3 Hz, 9H), 0.96-1.15 (m, 6H); 1.25-1.40 (m, 6H); 1.45-1.70 (m, 6H); 2.20 (s, 1H). $^{13}C$ NMR (75 MHz, CDCl$_3$): δ 11.1, 13.7, 27.1, 28.9, 88.9, 96.9.

2-(Tributylstannyl)-5,6-dihydro-4H-pyrrolo[1,2-b]pyrazole

A 1 L, three-neck RBF was made inert and equipped with an overhead stirrer, temperature probe, reflux condenser, and nitrogen inlet. The RBF was charged with intermediate 5,6-dihydro-4H-pyrrolo[1,2-c][1,2,3]oxadiazol-7-ium-3-olate (63.5 g, 0.503 mol) followed by m-xylene (317 mL, 5 vol). Ethynyl tributyltin chloride (196.7 g, 0.624 mol, 1.24 eq) was added in one portion and the mixture was heated to reflux (147° C.) and stirred for 42 h. The reaction mixture was cooled to ambient temperature. The crude reaction mixture was passed through a column of silica (1.35 kg of silica slurried in heptane); the product was eluted with 2 L of heptane/ethyl acetate (9:1) and 4 L of heptane/ethyl acetate (3:1; 500 mL fraction size). The product fractions ($R_f$=0.47, heptane/ethyl acetate (3:1), ceric ammonium sulfate staining) were collected and concentrated under reduced pressure at 25-35° C. to afford 2-(tributylstannyl)-5,6-dihydro-4H-pyrrolo[1,2-b]pyrazole, as a light yellow oil. $^1H$ NMR (300 MHz, DMSO-$d_6$): δ 0.86-1.57 (m, 27H); 2.53 (m, 2H); 2.77 (t, J=7.2 Hz, 2H); 4.04 (t, J=7.2 Hz, 2H), 5.96

(s, 1H). $^{13}$C NMR (75 MHz, DMSO-d$_6$): δ 9.7, 13.9, 22.2, 26.9, 27.0, 28.9, 47.0, 106.6, 145.9, 155.4.

Step D: 2-Bromo-5,6-dihydro-4H-pyrrolo[1,2-b]pyrazole

A 5 L, four-neck RBF was made inert and was equipped with an overhead stirrer, temperature probe, and nitrogen inlet. The RBF was charged with a solution of intermediate afford 2-(tributylstannyl)-5,6-dihydro-4H-pyrrolo[1,2-b]pyrazole (114.0 g, 0.287 mol) in anhydrous THF (2.0 L, 17.5 vol). N-Bromosuccinimide (51.1 g, 0.287 mol, 1.0 eq) was added in portions over two min and a gradual exotherm was observed following the addition (21→27° C.) and a cold bath was used to maintain the temperature<27° C. Once the exotherm subsided, the cold bath was removed and the reaction mixture was stirred at ambient temperature for 17 h. A 20 wt % aqueous NaCl solution (1 L) and ethyl acetate (0.6 L) were added to the reactor and the mixture was stirred for five min. The contents of the reactor were transferred to a separatory funnel and following phase separation, the aqueous phase (bottom layer) was extracted with ethyl acetate (0.6 L). Following phase separation, the combined organic extracts were transferred to a clean, 5 L, three-neck RBF and a 2 N aqueous solution of NaOH (1 L) was added in one portion. The biphasic mixture was stirred at ambient temperature for 30 min and transferred to a separatory funnel. The phases were separated and the organic phase was washed with brine (0.6 L) and phase-separated. The organic phase was dried over MgSO$_4$ and filtered and the filtrate was concentrated under reduced pressure to afford 136 g of an orange oil. The crude product was purified by column chromatography under vacuum (400 g of silica slurried in heptane) and the product was eluted with 3 L of heptane/ethyl acetate (7:3). The product fractions (R$_f$=0.50, heptane/ethyl acetate (1:1), KMnO$_4$ sulfate staining) were collected and concentrated under reduced pressure at 25-35° C. to afford 2-bromo-5,6-dihydro-4H-pyrrolo[1,2-b]pyrazole, as an off-white solid. $^1$H NMR (300 MHz, CDCl$_3$): δ 2.52-2.61 (m, 2H); 2.90 (t, 2H, J=7.5 Hz); 4.13 (t, J=7.5 Hz, 2H); 6.00 (s, 1H). $^{13}$C NMR (75 MHz, CDCl$_3$): δ 23.8, 25.7, 48.4, 102.1, 128.4, 147.6.

Step E: 2-Bromo-5,6-dihydro-4H-pyrrolo[1,2-b]pyrazole hydrochloride

A 250 mL, three-neck RBF equipped with an overhead stirrer, temperature probe, nitrogen inlet, and adaptor for HCl gas addition was charged with a solution of 2-bromo-5,6-dihydro-4H-pyrrolo[1,2-b]pyrazole (26.5 g, 0.142 mol) in MTBE (160 mL, 6 vol). The solution was cooled to ≈5° C. by means of an ice bath and HCl gas was bubbled directly into the solution for 15 min. The solution was stirred for an additional 30 min at ≈5° C. and the solids were filtered and washed with MTBE (2×30 mL). The solids were dried under high vacuum to afford 2-bromo-5,6-dihydro-4H-pyrrolo[1,2-b]pyrazole hydrochloride, of an off-white solid. MS: m/z=187 (M+H)$^+$. $^1$H NMR (300 MHz, DMSO-d$_6$): δ 2.52-2.61 (m, 2H); 2.90 (t, J=7.5 Hz, 2H); 4.13 (t, J=7.5 Hz, 2H); 6.00 (s, 1H). $^{13}$C NMR (75 MHz, DMSO-d$_6$): δ 22.9, 24.8, 48.0, 101.2, 126.2, 147.5.

Intermediate 75

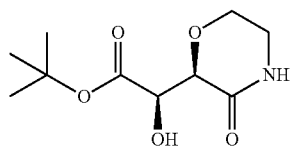 [SMILES: CC(C)(C)OC(=O)[C@H](O)[C@H]1OCCNC1=O]

(R)-tert-Butyl 2-hydroxy-2-((R)-3-oxomorpholin-2-yl)acetate

This compound was synthesized as in WO2010065717.

Intermediate 76

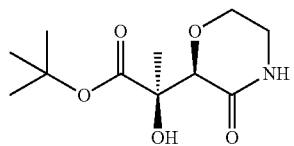

(R)-tert-Butyl 2-hydroxy-2-((R)-3-oxomorpholin-2-yl)propanoate

Step A: 2-((4-Methoxybenzyl)amino)ethanol

In a three neck flask equipped with a mechanical stirrer, anisaldehyde (30.8 mL, 253 mmol) is dissolved in EtOH (60 mL). Ethanolamine (18.36 mL, 304 mmol) is added to the mixture which is stirred at room temperature for 3 h. The reaction is cooled to −5° C. and sodium borohydride (10.52 g, 278 mmol) is added to the mixture in 7 portions keeping the temperature under 10° C. The reaction is warmed to room temperature overnight. The next day the reaction is quenched by slow addition of 1 M NaOH (25-30 mL). During the addition, the reaction becomes chunky. This is followed by addition of water (30 mL). CH$_2$Cl$_2$ is added to this mixture which is then transferred to separatory funnel and the layers are cut (slow phase cut). The aqueous is back extracted with CH$_2$Cl$_2$. The organics are then concentrated (still wet) and the resulting oil is then diluted with 2N HCl and further acidified with conc. HCl. The aqueous solution is washed twice with MTBE and then is basicified with 50 w % NaOH. The basic solution is then extracted twice with CH$_2$Cl$_2$. The combined organics are then treated with Na$_2$SO$_4$, filtered and concentrated to afford 2-((4-methoxybenzyl)amino)ethanol, as a yellow oil which was used directly without further purification. $^1$H NMR (500 MHz, CDCl$_3$): δ 7.23 (d; J=8.3 Hz; 2H); 6.86 (d; J=8.4 Hz; 2H); 3.73 (s; 2H); 3.80 (s; 3H); 3.64 (t; J=5.2 Hz; 2H); 2.78 (t; J=5.2 Hz; 2H).

Step B: (Z)-Methyl 4-((2-hydroxyethyl)(4-methoxybenzyl)amino)-3-methyl-4-oxobut-2-enoate and (Z)-Methyl 4-((2-hydroxyethyl)(4-methoxybenzyl)amino)-2-methyl-4-oxobut-2-enoate Citraconic anhydride (94 mL, 1071 mmol) was added to a pre-cooled 5-8° C. solution of MeOH (600 mL). The reaction is stirred over 4 days at 5-8° C. The MeOH was evaporated and the alkene isomers were used as a mixture for the next step (151.8 g, 527 mmol, 98% yield) and obtained as a clear oil. A portion of the mixture (22 g, 153 mmol), 2-((4-methoxybenzyl)amino)ethanol (30.4 g, 168 mmol) and DMAP (1.865 g, 15.26 mmol) are then dissolved in $CH_2Cl_2$ (220 mL). The mixture is cooled to ~2° C. and EDC (32.2 g, 168 mmol) is added to the mixture followed by DIPEA (26.7 mL, 153 mmol). After addition of all reagents the internal temperature was 0° C. and the mixture was allowed to warm to room temperature. After 6.5 h reaction had reached complete conversion. The reaction is diluted with 2 N HCl and the layers are cut. The organics are further washed with $NaHCO_3$ (5%) and brine and then dried with $Na_2SO_4$ and filtered. The crude amide (3:1 mixture of (Z)-methyl 4-((2-hydroxyethyl)(4-methoxybenzyl)amino)-3-methyl-4-oxobut-2-enoate and (Z)-methyl 4-((2-hydroxyethyl)(4-methoxybenzyl)amino)-2-methyl-4-oxobut-2-enoate, is obtained as a light yellow oil and used as is in the following step. LCMS calc.=308.15. found=307.70 $(M+H)^+$.

Step C: tert-Butyl 2-hydroxy-2-(4-(4-methoxybenzyl)-3-oxomorpholin-2-yl)propanoate Tert-Butyl hydroperoxide (39.9 mL, 220 mmol) is added to THF (150 mL). The solution is cooled to −45° C.). BuLi (88 mL of a 2.5 M solution in hexanes, 220 mmol) is added to the mixture bringing the reaction temperature to −12° C. To this stirring solution is added the mixture of alkene isomers of (Z)-methyl 4-((2-hydroxyethyl)(4-methoxybenzyl)amino)-3-methyl-4-oxobut-2-enoate and (Z)-methyl 4-((2-hydroxyethyl)(4-methoxybenzyl)amino)-2-methyl-4-oxobut-2-enoate (27 g, 88 mmol) in THF (150 mL) causing a slow temperature rise to −5° C. The temperature is gradually warmed to room temperature. After 4.5 h the reaction had reached complete conversion. The reaction is quenched by adding of sodium bisulfite (5%, 125 mL) and extracted with EtOAc (300 mL). The organics are washed with 0.5N NaOH (80 mL). The combined aqueous were washed with MTBE (250 mL). The aqueous was acidified with conc. HCl and extracted with MeTHF (350 mL). The aqueous was back-extracted with MeTHF (150 mL) and the combined MeTHF layers was then washed with 20% NaCl (200 mL) and concentrated. The resulting white solid racemic tert-butyl 2-hydroxy-2-(4-(4-methoxybenzyl)-3-oxomorpholin-2-yl)propanoate, is used directly in the next step. LCMS calc.=310.13. found=310.06 $(M+H)^+$.

Step D: tert-Butyl 2-hydroxy-2-(4-(4-methoxybenzyl)-3-oxomorpholin-2-yl)propanoate Racemic 2-hydroxy-2-(4-(4-methoxybenzyl)-3-oxomorpholin-2-yl)propanoic acid (3.6 g, 11.64 mmol) is added to THF (40 mL). 2-tert-butyl-1,3-diisopropylisourea (6.99 g, 34.9 mmol) is added and the mixture is heated to 60° C. After stirring for 3.5 h, the reaction had reached complete conversion. The mixture was diluted with MTBE, cooled and filtered. The filtrate is then concentrated and loaded on silica gel chromatography for purification using a 125 g column (10-70% EtOAc/Hex). Racemic tert-butyl 2-hydroxy-2-(4-(4-methoxybenzyl)-3-oxomorpholin-2-yl)propanoate (2.9 g, 7.94 mmol, 68.2% yield) is obtained as a clear oil. The two enantiomers could then be separated using SFC with the following conditions: IC (50×250 nm), 5 um, 15% $MeOH/CO_2$, 225 mL/min, 100 bar, 35° C., 230 nm, 14.4 g/50 mL 1:1 MeOH:MeCN, 1.5 mL/injection. The desired R,R-enantiomer was carried forward. $^1$H NMR (500 MHz, $CDCl_3$): δ 7.23 (d, J=8.3 Hz, 2H); 6.87 (d, J=8.4 Hz, 2H); 5.00 (s, 1H); 4.78 (d, J=14.5 Hz, 1H); 4.36 (d, J=14.5 Hz, 1H); 4.17 (s, 1H); 4.02 (d, J=11.8 Hz, 1H); 3.80 (s, 3H); 3.69-3.67 (m, 1H); 3.47 (td, J=11.4, 4.1 Hz, 1H); 3.05 (d, J=12.3 Hz, 1H); 1.54 (s, 3H); 1.48 (s, 9H).

Step E: (R)-tert-Butyl 2-hydroxy-2-((R)-3-oxomorpholin-2-yl)propanoate (R)-tert-Butyl 2-hydroxy-2-((R)-4-(4-methoxybenzyl)-3-oxomorpholin-2-yl)propanoate (2.9 g, 7.94 mmol) is added to MeCN (35 mL)/water (7 mL). CAN (17.40 g, 31.7 mmol) is added and the mixture left warming to room temperature. After 4 h, complete conversion of the starting material was observed and the reaction is diluted with $CH_2Cl_2$ (100 mL). The reaction is quenched by portionwise addition of excess solid $NaHCO_3$. This causes a change in color from orange to yellow. The heterogenous mixture is stirred for 30 min and then filtered over Solka-Floc® powdered cellulose. The filter cake was washed with $CH_2Cl_2$. The filtrate is then transferred to a separatory funnel where the organic layer is washed with 5% sodium bisulfite, then brine. The organic layer is then treated with $MgSO_4$, filtered and concentrated to afford the crude material. Pure (R)-tert-butyl 2-hydroxy-2-((R)-3-oxomorpholin-2-yl)propanoate is obtained from trituration with MTBE/hexanes as a white solid. $^1$H NMR ($CDCl_3$): δ 7.00 (s, 1H); 4.91 (s, 1H); 4.12 (s, 1H); 4.07 (d, J=11.9 Hz, 1H); 3.74-3.71 (m, 1H); 3.60-3.57 (m, 1H); 3.27 (d, J=12.2 Hz, 1H); 1.54 (s, 3H); 1.48 (s, 9H).

Example 1

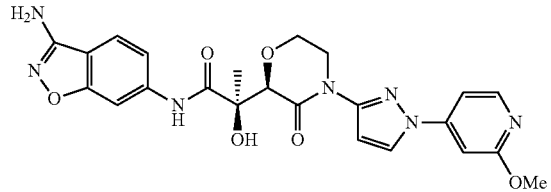

(2R)—N-(3-Amino-1,2-benzoxazol-6-yl)-2-hydroxy-2-[(2R)-4-[1-(2-methoxy-4-pyridyl)pyrazol-3-yl]-3-oxo-morpholin-2-yl]propanamide Step A. (2R)-2-Hydroxy-2-[(2R)-4-[1-(2-methoxy-4-pyridyl)pyrazol-3-yl]-3-oxo-morpholin-2-yl]propanoic acid A vial was charged with 4-(3-iodopyrazol-1-yl)-2-methoxy-pyridine (196 mg, 0.651 mmol), (R)-tert-butyl 2-hydroxy-2-((R)-3-oxomorpholin-2-yl)propanoate (133 mg, 0.542 mmol), CuI (31.0 mg, 0.163 mmol), potassium phosphate (207 mg, 0.976 mmol), trans-N,N-dimethylcyclohexane-1,2-diamine, and anhydrous toluene (3 mL). The vial was purged with nitrogen and screw-capped. The resulting reaction mixture was stirred in the sealed vial at 90° C. for 15 h. The reaction mixture was cooled and purified by flash chromatography (12 g, loaded with $CH_2Cl_2$, 7-50% EtOAc in hexanes) to give tert-butyl (2R)-2-hydroxy-2-[(2R)-4-[1-(2-methoxy-4-pyridyl)pyrazol-3-yl]-3-oxo-morpholin-2-yl]propanoate. LCMS calc.=419.19. found=419.12 $(M+H)^+$. This material was treated with a mixture of $CH_2Cl_2$ (3 mL) and TFA (2 mL) for 4 h. The insoluble material was collected by filtration. To remove excess TFA, the filtrate was concentrated, redissolved in CH$_2$Cl$_2$, concentrated again, redissolved in MeCN and 2N HCl in ether was added. This was concentrated in vacuo to afford (2R)-2-hydroxy-2-[(2R)-4-[1-(2-methoxy-4-pyridyl)pyrazol-3-yl]-3-oxo-morpholin-2-yl]propanoic acid. LCMS calc.=363.13. found=363.05 (M+H)$^+$.

Step B. (2R)—N-(3-Amino-1,2-benzoxazol-6-yl)-2-hydroxy-2-[(2R)-4-[1-(2-methoxy-4-pyridyl)pyrazol-3-yl]-3-oxo-morpholin-2-yl]propanamide A mixture of 1,2-benzoxazole-3,6-diamine (82 mg, 0.552 mmol), (2R)-2-hydroxy-2-[(2R)-4-[1-(2-methoxy-4-pyridyl)pyrazol-3-yl]-3-oxo-morpholin-2-yl]propanoic acid (200 mg, 0.552 mmol), HOAt (75 mg, 0.552 mmol), EDC hydrochloride (106 mg, 0.552 mmol) and NMP (2 mL) was stirred at room temperature for 24 h. HOAt (25 mg, 0.184 mmol) and EDC hydrochloride (35.3 mg, 0.184 mmol) were added, and reaction mixture was stirred at room temperature for another 24 h. HOAt (50 mg, 0.368 mmol) and EDC hydrochloride (70.7 mg, 0.368 mmol) were added, and reaction mixture was stirred at room temperature for another 24 h. The reaction mixture was diluted with DMSO and directly purified by reversed phase HPLC (YMC C18 column, gradient from 20% MeCN/80% water/0.1% ammonium formate, to 70% MeCN/30% water/0.1% ammonium formate). The product fraction was freeze-dried to afford (2R)—N-(3-amino-1,2-benzoxazol-6-yl)-2-hydroxy-2-[(2R)-4-[1-(2-methoxy-4-pyridyl)pyrazol-3-yl]-3-oxo-morpholin-2-yl]propanamide, as a white solid. LCMS calc.=494.18. found=494.06 (M+H)$^+$. $^1$H NMR (500 MHz, CD$_3$OD): δ 8.34 (d, J=2.7 Hz, 1H); 8.15 (d, J=5.8 Hz, 1H); 7.92 (d, J=1.4 Hz, 1H); 7.67 (d, J=8.6 Hz, 1H); 7.39 (m, 2H); 7.17 (d, J=1.7 Hz, 1H); 7.12 (d, J=2.6 Hz, 1H); 4.61 (s, 1H); 4.28 (m, 1H); 4.20 (m, 1H); 4.09 (m, 1H); 3.98-3.92 (m, 1H); 3.95 (s, 3H); 1.73 (s, 3H).

(FIXa IC50: 159.8 nM).

Example 2

(R)—N-(3-Aminoisoxazolo[4,5-b]pyridin-6-yl)-2-hydroxy-2-((R)-4-(1-(2-methoxypyridin-4-yl)-1H-pyrazol-3-yl)-3-oxomorpholin-2-yl)propanamide

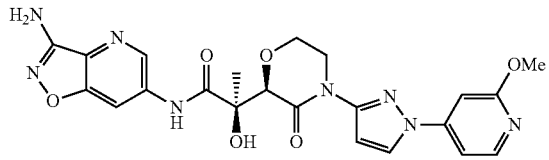

Step A: (R)—N-(3-(1,3-Dioxoisoindolin-2-yl)isoxazolo[4,5-b]pyridin-6-yl)-2-hydroxy-2-((R)-4-(1-(2-methoxypyridin-4-yl)-1H-pyrazol-3-yl)-3-oxomorpholin-2-yl)propanamide A mixture of thionyl chloride (519 μL, 7.14 mmol) and (R)-2-hydroxy-2-((R)-4-(1-(2-methoxypyridin-4-yl)-1H-pyrazol-3-yl)-3-oxomorpholin-2-yl)propanoic acid (34.2 mg, 0.086 mmol) was heated at 50° C. for 1 h. The reaction mixture was concentrated in vacuo. A solution of 2-(6-aminoisoxazolo[4,5-b]pyridin-3-yl)isoindoline-1,3-dione (20.0 mg, 0.071 mmol) in dry pyridine (714 μL) was added via cannula to the crude acid chloride and 4-dimethylaminopyridine (1.744 mg, 0.014 mmol). The mixture was stirred for 24 h at 25° C. The reaction mixture was concentrated in vacuo to give the crude product. This was purified by reversed-phase HPLC (C18, 20×100 mm, ~20 mL/min, gradient from 90% water in MeCN to 40% water in MeCN over 30 min, fractions containing desired product combined, lyophilized) to afford in order of elution desired product (R)—N-(3-(1,3-dioxoisoindolin-2-yl)isoxazolo[4,5-b]pyridin-6-yl)-2-hydroxy-2-((R)-4-(1-(2-methoxypyridin-4-yl)-1H-pyrazol-3-yl)-3-oxomorpholin-2-yl)propanamide, as a colorless solid. LCMS calc.=625.18. found=625.22 (M+H)$^+$.

Step B: (R)—N-(3-Aminoisoxazolo[4,5-b]pyridin-6-yl)-2-hydroxy-2-((R)-4-(1-(2-methoxypyridin-4-yl)-1H-pyrazol-3-yl)-3-oxomorpholin-2-yl)propanamide Hydrazine (2.6 μL, 0.083 mmol) was added to a solution of (R)—N-(3-(1,3-dioxoisoindolin-2-yl)isoxazolo[4,5-b]pyridin-6-yl)-2-hydroxy-2-((R)-4-(1-(2-methoxypyridin-4-yl)-1H-pyrazol-3-yl)-3-oxomorpholin-2-yl)propanamide (5.2 mg, 8.33 μmol) in CH$_2$Cl$_2$ (694 μL) and MeOH (694 μL) and the resulting mixture was stirred at 25° C. for 2 h. The reaction mixture was concentrated in vacuo to give the crude product. This was purified by reversed-phase HPLC (C18, 20×100 mm, ~20 mL/min, gradient from 100% water in MeCN to 60% water in MeCN over 25 min, gradient to 100% MeCN over 2 min, fractions containing desired product combined, lyophilized) to afford (R)—N-(3-Aminoisoxazolo[4,5-b]pyridin-6-yl)-2-hydroxy-2-((R)-4-(1-(2-methoxypyridin-4-yl)-1H-pyrazol-3-yl)-3-oxomorpholin-2-yl)propanamide, as a colorless solid. LCMS calc.=495.17. found=495.14 (M+H)$^+$. $^1$H NMR (600 MHz, Acetone-d$_6$): δ 9.76 (s, 1H); 8.80 (d, J=2.0 Hz, 1H); 8.46 (d, J=2.0 Hz, 1H); 8.42 (d, J=2.8 Hz, 1H); 8.18 (d, J=5.7 Hz, 1H); 7.41 (dd, J=5.8, 2.0 Hz, 1H); 7.15 (d, J=1.9 Hz, 1H); 7.12 (d, J=2.7 Hz, 1H); 5.76 (s, 2H); 5.43 (s, 1H); 4.57 (s, 1H); 4.29 (dt, J=11.7, 3.2 Hz, 1H); 4.21 (dt, J=12.6, 2.7 Hz, 1H); 4.10-4.03 (m, 1H); 4.03-3.97 (m, 1H); 3.92 (s, 3H); 1.70 (s, 3H).

Example 3

(R)—N-(3-Aminobenzo[d]isoxazol-6-yl)-2-(R)-4-(1-(6-cyanopyridazin-4-yl)-5-methyl-1H-pyrazol-3-yl)-3-oxomorpholin-2-yl)-2-hydroxypropanamide

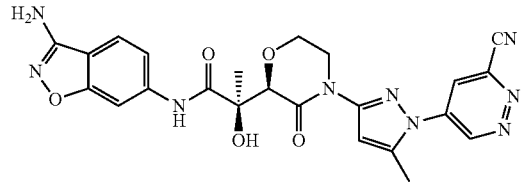

Step A: 5-(3-Bromo-5-methyl-1H-pyrazole-1-yl)-3-chloropyridazine

To a solution of 3-bromo-5-methylpyrazole (0.4 g, 2.48 mmol) in DMF (5 mL) at room temperature was added KOtBu (0.279 g, 2.48 mmol) in one portion. To this mixture was added a solution of 3,5-dichloropyridaine (0.37 g, 2.48 mmol) in DMF (5 mL). The reaction mixture was heated at 100° C. for 1 h. The reaction mixture was cooled to room temperature, diluted with EtOAc (50 mL), washed with satd aq. NaHCO₃ (10 mL) and water (100 mL), the aqueous layers were separated and extracted with EtOAc (3×50 mL). The combined organic layers were washed with water (100 mL), brine (100 mL), dried over Na₂SO₄, filtered and concentrated. The crude solid was purified by PTLC (50% EtOAc in hexanes) to afford 5-(3-bromo-5-methyl-1H-pyrazole-1-yl)-3-chloropyridazine, as a white solid. LCMS calc.=272.95. found=272.88 (M+H)⁺.

Step B: (R)-tert-Butyl 2-(R)-4-(1-(6-chloro-pyridazin-4-yl)-5-methyl-1H-pyrazol-3-yl)-3-oxo-morpholin-2-yl)-2-hydroxypropanoate Prepared by methods analogous to those described previously. LCMS calc.=438.15 found=438.98 (M+H)⁺.

Step C: (R)-tert-Butyl 2-(R)-4-(1-(6-cyano-pyridazin-4-yl)-5-methyl-1H-pyrazol-3-yl)-3-oxo-morpholin-2-yl)-2-hydroxypropanoate A mixture of (R)-tert-butyl 2-(R)-4-(1-(6-chloro-pyridazin-4-yl)-5-methyl-1H-pyrazol-3-yl)-3-oxomorpho-lin-2-yl)-2-hydroxypropanoate (0.099 g, 0.226 mmol), zinc cyanide (0.0425, 0.362 mmol), Pd₂(dba)₃ (0.0145 g, 0.016 mmol) and DPPF (0.0226 g, 0.041 mmol) in DMF (2 mL) was degassed and then heated at 100° C. for 0.5 h. The reaction mixture was cooled to room temperature, diluted with EtOAc (50 mL), washed with water (10 mL) and the aqueous layers were separated and extracted with EtOAc (3×50 mL). The combined organic layers were washed with water (100 mL), brine (100 mL), dried over Na₂SO₄, filtered and concentrated. The crude solid was purified by PTLC (50% EtOAc in hexanes) to afford (R)-tert-butyl 2-(R)-4-(1-(6-cyanopyridazin-4-yl)-5-methyl-1H-pyrazol-3-yl)-3-oxomorpholin-2-yl)-2-hydroxypropanoate. LCMS calc.=429.19. found=429.05 (M+H)⁺.

Step D: (R)-2-(R)-4-(1-(6-Cyanopyridazin-4-yl)-5-methyl-1H-pyrazol-3-yl)-3-oxomorpholin-2-yl)-2-hydroxypropanoic acid (R)-tert-Butyl 2-(R)-4-(1-(6-cyanopyridazin-4-yl)-5-methyl-1H-pyrazol-3-yl)-3-oxomorpholin-2-yl)-2-hydroxypropanoate (0.038 g, 0.089 mmol) was dissolved in CH₂Cl₂ (0.9 mL) and treated with TFA (1.8 mL). The reaction mixture was stirred at room temperature for 0.5 h and the solvents were removed. The crude residue was treated with 4 M HCl in 1,4-dioxane (2 mL) and concentrated and dried under high vacuum to afford the HCl salt. This was used without further purification. LCMS calc.=372.12. found=372.11 (M+H)⁺.

Step E: (R)—N-(3-Aminobenzo[d]isoxazol-6-yl)-2-(R)-4-(1-(6-cyanopyridazin-4-yl)-5-methyl-1H-pyra-zol-3-yl)-3-oxomorpholin-2-yl)-2-hydroxypropana-mide Prepared by methods analogous to those described previously. LCMS calc.=504.17 found=504.01 (M+H)⁺. ¹H NMR (500 MHz, DMSO-d₆): δ 9.87 (s, 1H); 9.820 (s, 1H); 8.56 (s, 1H); 7.98 (s, 1H); 7.69 (d, J=8.5 Hz, 1H); 7.53 (d, J=8.5 Hz, 1H); 7.01 (s, 1H); 6.30 (s, 2H); 6.12 (s, 1H); 4.57 (s, 1H); 4.07-4.20 (m, 2H); 3.84-3.95 (m, 2H); 3.16 (d, J=5.5 Hz, 1H); 2.640 (s, 3H); 1.60 (s, 3H).
(FIXa IC50: 68.37 nM)

Example 4

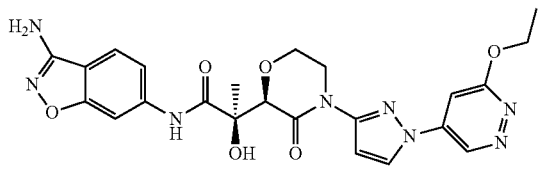

(R)—N-(3-Aminobenzo[d]isoxazol-6-yl)-2-(R)-4-(1-(6-ethoxypyridazin-4-yl)-1H-pyrazol-3-yl)-3-oxo-morpholin-2-yl)-2-hydroxypropanamide Step A:
3-Chloro-5-(3-iodo-1H-pyrazol-1-yl)pyridazine To a solution of 3-iodopyrazole (2.5 g, 12.89 mmol) in DMF (25 mL) at room temperature was added KOtBu (1.446 g, 12.89 mmol) in one portion. To this mixture was added a solution of 3,5-dichloropyridazine (1.92 g, 12.89 mmol) in DMF (25 mL). The reaction mixture was heated at 100° C. for 1 h. The reaction mixture was cooled to room temperature, diluted with EtOAc (50 mL), washed with satd aq. NaHCO₃ (10 mL) and water (100 mL), then the aqueous layers were separated and extracted with EtOAc (3×50 mL). The combined organic layers were washed with water (100 mL), brine (100 mL), dried over Na₂SO₄, filtered and concentrated. The crude solid was washed with CH₂Cl₂ and dried under vacuum, to afford 3-chloro-5-(3-iodo-1H-pyra-zol-1-yl)pyridazine. LCMS calc.=306.92. found=306.91 (M+H)⁺.

Step B:
3-Ethoxy-5-(3-iodo-1H-pyrazol-1-yl)pyridazine

To a suspension of 3-chloro-5-(3-iodo-1H-pyrazol-1-yl) pyridazine (0.5 g; 1.631 mmol) in EtOH (11 mL) was added triflic acid (0.375 mL, 4.23 mmol). The mixture was stirred at 50° C. for 6 h. The reaction mixture was cooled to room temperature and treated with of triethylamine (1.0 mL). The solvents were removed in vacuo and crude residue purified by silica gel chromatography (0-60% EtOAc in hexane) to afford 3-ethoxy-5-(3-iodo-1H-pyrazol-1-yl)pyridazine. LCMS calc.=316.99. found=316.84 (M+H)⁺.

Step C: (R)-tert-Butyl 2-(R)-4-(1-(6-ethoxy-pyridazin-4-yl)-1H-pyrazol-3-yl)-3-oxomorpholin-2-yl)-2-hydroxypropanoate Prepared by methods analogous to those described previously. LCMS calc.=432.20. found=434.01 (M+H)⁺.

Step D: (R)-2-(R)-4-(1-(6-Ethoxypyridazin-4-yl)-1H-pyrazol-3-yl)-3-oxomorpholin-2-yl)-2-hydroxy-propanoic acid (R)-tert-Butyl 2-(R)-4-(1-(6-ethoxypyridazin-4-yl)-1H-pyrazol-3-yl)-3-oxomorpholin-2-yl)-2-hydroxypropanoate (0.151 g 0.348 mmol) was dissolved in CH₂Cl₂ (1.8 mL) and treated with TFA (3.6 mL). The reaction mixture was stirred at room temperature for 0.5 h and the solvents were removed. The crude residue was treated with 4 M aq. HCl in 1,4-dioxane (2 mL) and concentrated and dried under high vacuum to afford (R)-2-(R)-4-(1-(6-ethoxypyridazin-4-yl)-1H-pyrazol-3-yl)-3-oxomorpholin-2-yl)-2-hydroxypropanoic acid, as the HCl salt. This was used without further purification. LCMS calc.=378.14. found=377.99 (M+H)+.

Step E: (R)—N-(3-Aminobenzo[d]isoxazol-6-yl)-2-(R)-4-(1-(6-ethoxypyridazin-4-yl)-1H-pyrazol-3-yl)-3-oxomorpholin-2-yl)-2-hydroxypropanamide Prepared by methods analogous to those described previously. LCMS calc.=509.19 found=508.97 (M+H)+.
(FIXa IC50: 23.17 nM)

Intermediate 77

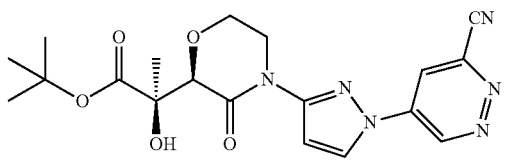

(R)-tert-Butyl 2-((R)-4-(1-(6-cyanopyridazin-4-yl)-1H-pyrazol-3-yl)-3-oxomorpholin-2-yl)-2-hydroxypropanoate A mixture of (R)-tert-butyl 2-((R)-4-(1-(6-chloropyridazin-4-yl)-1H-pyrazol-3-yl)-3-oxomorpholin-2-yl)-2-hydroxypropanoate (35 mg, 0.083 mmol), zinc cyanide (15 mg, 0.128 mmol), Pd$_2$(dba)$_3$ (5.6 mg, 6.12 μmol), DPPF (8.4 mg, 0.015 mmol) and zinc (3 mg, 0.046 mmol) in DMF (0.7 mL) was degassed by bubbling N$_2$ for 10 min. It was stirred in an oil-bath at 100° C. under N$_2$ for 0.5 h. It was diluted with water (5 mL), extracted with EtOAc (3×10 mL). The combined organic layers were washed with water (2×10 mL), brine (10 mL), dried over Na$_2$SO$_4$, filtered and concentrated. The residue was purified by ISCO (12 g, 0-40% EtOAc in hexane) to give (R)-tert-butyl 2-((R)-4-(1-(6-cyanopyridazin-4-yl)-1H-pyrazol-3-yl)-3-oxomorpholin-2-yl)-2-hydroxypropanoate, as a yellow solid. LCMS calc.=415.17. found=415.23 (M+H)+. $^1$H NMR (500 MHz, CDCl$_3$): δ 9.75-9.71 (m, 1H); 8.13-8.06 (m, 2H); 7.46 (t, J=2.9 Hz, 1H); 4.41-4.33 (m, 1H); 4.34-4.21 (m, 2H); 4.10-4.01 (m, 1H); 3.95 (td, J=11.4, 2.8 Hz, 1H); 1.62 (s, 3H); 1.48 (s, 9H).

Example 5

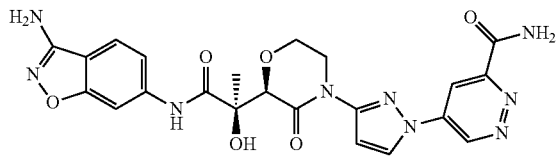

5-(3-((R)-2-((R)-1-((3-Aminobenzo[d]isoxazol-6-yl)amino)-2-hydroxy-1-oxopropan-2-yl)-3-oxomorpholino)-1H-pyrazol-1-yl)pyridazine-3-carboxamide (R)—N-(3-Aminobenzo[d]isoxazol-6-yl)-2-((R)-4-(1-(6-cyanopyridazin-4-yl)-1H-pyrazol-3-yl)-3-oxomorpholin-2-yl)-2-hydroxypropanamide (20 mg, 0.041 mmol) was treated with HCl (1 mL, 12.18 mmol) at room temperature for 6 h. It was concentrated and purified by HPLC (C18, MeCN/water with 0.1% TFA). The combined fractions of the desired product was concentrated under reduced pressure. A drop of DIEA was added to the residue and it was purified by ISCO to give 5-(3-((R)-2-((R)-1-((3-aminobenzo[d]isoxazol-6-yl)amino)-2-hydroxy-1-oxopropan-2-yl)-3-oxomorpholino)-1H-pyrazol-1-yl)pyridazine-3-carboxamide. LCMS calc.=508.17. found=507.94 (M+H)+.
(FIXa IC50: 20.22 nM)

Example 6

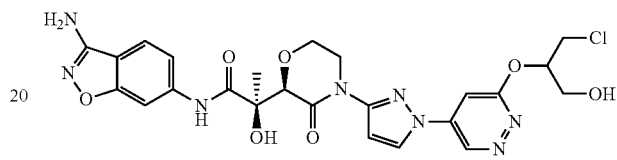

(2R)—N-(3-Aminobenzo[d]isoxazol-6-yl)-2-((2R)-4-(1-(6-((1-chloro-3-hydroxypropan-2-yl)oxy)pyridazin-4-yl)-1H-pyrazol-3-yl)-3-oxomorpholin-2-yl)-2-hydroxypropanamide To a suspension of HOAT (83 mg, 0.607 mmol), (R)-2-hydroxy-2-((R)-4-(1-(6-(oxetan-3-yloxy)pyridazin-4-yl)-1H-pyrazol-3-yl)-3-oxomorpholin-2-yl)propanoic acid (205 mg, 0.506 mmol) and ABI (106 mg, 0.708 mmol) in DMA (1.7 mL) was added EDC (194 mg, 1.011 mmol) at room temperature. It was stirred for 3 d. MeCN (5 mL) was added, then the mixture filtered through a syringe filter and purified by HPLC (C18, 20-50% MeCN in water with 0.1% TFA). The product fractions were collected, concentrated and DIEA (1 mL) was added. The mixture was dissolved in 10% MeOH in CH$_2$Cl$_2$ (10 mL), concentrated on an ISCO 10 g silica gel sampler and eluted by ISCO (Gold 24 g, 0-10% MeOH in CH$_2$Cl$_2$) to give (2R)—N-(3-Aminobenzo[d]isoxazol-6-yl)-2-((2R)-4-(1-(6-((1-chloro-3-hydroxypropan-2-yl)oxy)pyridazin-4-yl)-1H-pyrazol-3-yl)-3-oxomorpholin-2-yl)-2-hydroxypropanamide, as a slight yellow solid. LCMS calc.=573.16. found=572.96 (M+1). $^1$H NMR (500 MHz, DMSO-d$_6$): δ 9.84 (s, 1H); 8.66 (dd, J=11.2, 2.7 Hz, 2H); 7.99 (s, 1H); 7.69 (d, J=8.5 Hz, 1H); 7.54-7.51 (m, 1H); 7.22 (d, J=2.5 Hz, 1H); 7.16 (d, J=2.8 Hz, 1H); 6.31 (s, 2H); 6.16 (s, 1H); 5.35 (t, J=5.9 Hz, 1H); 4.58 (s, 1H); 4.48-4.43 (m, 1H); 4.42-4.37 (m, 2H); 4.23-4.17 (m, 1H); 4.11-4.05 (m, 1H); 3.98-3.93 (m, 1H); 3.89-3.84 (m, 1H); 3.70 (t, J=5.4 Hz, 2H); 1.61 (s, 3H).
(FIXa IC50: 974.9 nM)

Example 7

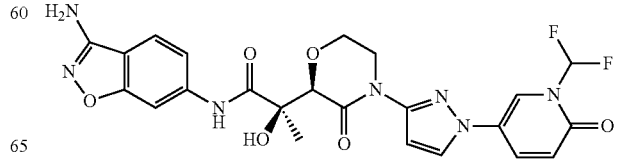

(R)—N-(3-Aminobenzo[d]isoxazol-6-yl)-2-((R)-4-(1-(1-(difluoromethyl)-6-oxo-1,6-dihydropyridin-3-yl)-1H-pyrazol-3-yl)-3-oxomorpholin-2-yl)-2-hydroxypropanamide Step A: (R)-tert-Butyl 2-((R)-4-(1-(1-(difluoromethyl)-6-oxo-1,6-dihydropyridin-3-yl)-1H-pyrazol-3-yl)-3-oxomorpholin-2-yl)-2-hydroxypropanoate According to Step C in the synthetic method for EXAMPLE 76, 1-(difluoromethyl)-5-(3-iodo-1H-pyrazol-1-yl)pyridin-2(1H)-one (0.15 g) and (R)-tert-butyl 2-hydroxy-2-((R)-3-oxomorpholin-2-yl)propanoate (0.13 g) were used instead of 5-bromo-1-difluoromethyl-1H-pyridin-2-one and 3-aminopyrazole to obtain (R)-tert-butyl 2-((R)-4-(1-(1-(difluoromethyl)-6-oxo-1,6-dihydropyridin-3-yl)-1H-pyrazol-3-yl)-3-oxomorpholin-2-yl)-2-hydroxypropanoate, as a colorless amorphous solid. LCMS 477 (M+Na)$^+$.

Step B: (R)-2-((R)-4-(1-(1-(Difluoromethyl)-6-oxo-1,6-dihydropyridin-3-yl)-1H-pyrazol-3-yl)-3-oxomorpholin-2-yl)-2-hydroxypropanoic acid According to Step F in the synthetic method for EXAMPLE 76, (R)-tert-butyl 2-((R)-4-(1-(1-(difluoromethyl)-6-oxo-1,6-dihydropyridin-3-yl)-1H-pyrazol-3-yl)-3-oxomorpholin-2-yl)-2-hydroxypropanoate (72 mg) was used instead of (R)-tert-butyl 2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetate to obtain (R)-2-((R)-4-(1-(1-(difluoromethyl)-6-oxo-1,6-dihydropyridin-3-yl)-1H-pyrazol-3-yl)-3-oxomorpholin-2-yl)-2-hydroxypropanoic acid, as a colorless solid. LCMS 399 (M+H)$^+$.

Step C: (R)—N-(3-Aminobenzo[d]isoxazol-6-yl)-2-((R)-4-(1-(1-(difluoromethyl)-6-oxo-1,6-dihydropyridin-3-yl)-1H-pyrazol-3-yl)-3-oxomorpholin-2-yl)-2-hydroxypropanamide According to Step G in the synthetic method for EXAMPLE 76, (R)-2-((R)-4-(1-(1-(difluoromethyl)-6-oxo-1,6-dihydropyridin-3-yl)-1H-pyrazol-3-yl)-3-oxomorpholin-2-yl)-2-hydroxypropanoic acid (90 mg) was used instead of (R)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetic acid to obtain (R)—N-(3-aminobenzo[d]isoxazol-6-yl)-2-((R)-4-(1-(1-(difluoromethyl)-6-oxo-1,6-dihydropyridin-3-yl)-1H-pyrazol-3-yl)-3-oxomorpholin-2-yl)-2-hydroxypropanamide, as a colorless solid. LCMS 530 (M+H)$^+$.

(FIXa IC50: 18.14 nM)

Example 8

(R)—N-(3-Aminobenzo[d]isoxazol-6-yl)-2-((R)-4-(1-(1-(difluoromethyl)-6-oxo-1,6-dihydropyridin-3-yl)-5-methyl-1H-pyrazol-3-yl)-3-oxomorpholin-2-yl)-2-hydroxypropanamide Step A: (R)-tert-Butyl 2-((R)-4-(1-(1-(difluoromethyl)-6-oxo-1,6-dihydropyridin-3-yl)-5-methyl-1H-pyrazol-3-yl)-3-oxomorpholin-2-yl)-2-hydroxypropanoate According to Step C in the synthetic method for EXAMPLE 76, 1-(difluoromethyl)-5-(3-iodo-5-methyl-1H-pyrazol-1-yl)pyridin-2(1H)-one (0.10 g) and (R)-tert-butyl 2-hydroxy-2-((R)-3-oxomorpholin-2-yl)propanoate (84 mg) were used instead of 5-bromo-1-difluoromethyl-1H-pyridin-2-one and 3-aminopyrazole to obtain (R)-tert-butyl 2-((R)-4-(1-(1-(difluoromethyl)-6-oxo-1,6-dihydropyridin-3-yl)-5-methyl-1H-pyrazol-3-yl)-3-oxomorpholin-2-yl)-2-hydroxypropanoate, as a colorless solid. LCMS 491 (M+Na)$^+$.

Step B: (R)-2-((R)-4-(1-(1-(Difluoromethyl)-6-oxo-1,6-dihydropyridin-3-yl)-5-methyl-1H-pyrazol-3-yl)-3-oxomorpholin-2-yl)-2-hydroxypropanoic acid According to Step F in the synthetic method for EXAMPLE 76, (R)-tert-butyl 2-((R)-4-(1-(1-(difluoromethyl)-6-oxo-1,6-dihydropyridin-3-yl)-5-methyl-1H-pyrazol-3-yl)-3-oxomorpholin-2-yl)-2-hydroxypropanoate (97 mg) was used instead of (R)-tert-butyl 2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetate to obtain (R)-2-((R)-4-(1-(1-(difluoromethyl)-6-oxo-1,6-dihydropyridin-3-yl)-5-methyl-1H-pyrazol-3-yl)-3-oxomorpholin-2-yl)-2-hydroxypropanoic acid, as a colorless solid. LCMS 413 (M+H)$^+$.

Step C: (R)—N-(3-Aminobenzo[d]isoxazol-6-yl)-2-((R)-4-(1-(1-(difluoromethyl)-6-oxo-1,6-dihydropyridin-3-yl)-5-methyl-1H-pyrazol-3-yl)-3-oxomorpholin-2-yl)-2-hydroxypropanamide According to Step G in the synthetic method for EXAMPLE 76, (R)-2-((R)-4-(1-(1-(difluoromethyl)-6-oxo-1,6-dihydropyridin-3-yl)-5-methyl-1H-pyrazol-3-yl)-3-oxomorpholin-2-yl)-2-hydroxypropanoic acid (70 mg) was used instead of (R)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetic acid to obtain (R)—N-(3-aminobenzo[d]isoxazol-6-yl)-2-((R)-4-(1-(1-(difluoromethyl)-6-oxo-1,6-dihydropyridin-3-yl)-5-methyl-1H-pyrazol-3-yl)-3-oxomorpholin-2-yl)-2-hydroxypropanamide, as a beige solid. LCMS 544 (M+H)$^+$.

Example 9

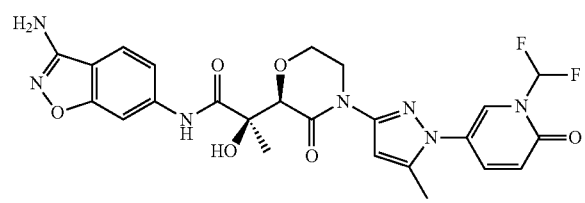 [SMILES: Cc1cc(N2CCO[C@H]([C@@](C)(O)C(=O)Nc3ccc4c(N)noc4c3)C2=O)nn1-c1ccc(=O)n(C(F)F)c1]

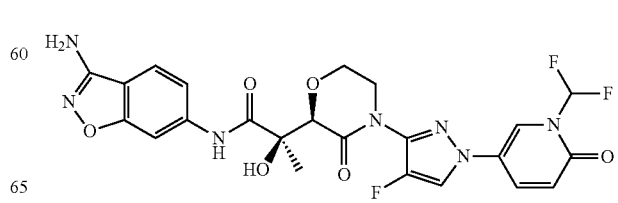

(R)—N-(3-Aminobenzo[d]isoxazol-6-yl)-2-((R)-4-(1-(1-(difluoromethyl)-6-oxo-1,6-dihydropyridin-3-yl)-4-fluoro-1H-pyrazol-3-yl)-3-oxomorpholin-2-yl)-2-hydroxypropanamide Step A: (R)-tert-Butyl 2-((R)-4-(1-(1-(difluoromethyl)-6-oxo-1,6-dihydropyridin-3-yl)-4-fluoro-1H-pyrazol-3-yl)-2-methyl-3-oxomorpholin-2-yl)-2-hydroxyacetate According to Step C in the synthetic method for EXAMPLE 76, 1-(difluoromethyl)-5-(4-fluoro-3-iodo-1H-pyrazol-1-yl)pyridin-2(1H)-one (50 mg) and (R)-tert-butyl 2-hydroxy-2-((R)-3-oxomorpholin-2-yl)propanoate (41 mg) were used instead of 5-bromo-1-difluoromethyl-1H-pyridin-2-one and 3-aminopyrazole to obtain (R)-tert-butyl 2-((R)-4-(1-(1-(difluoromethyl)-6-oxo-1,6-dihydropyridin-3-yl)-4-fluoro-1H-pyrazol-3-yl)-2-methyl-3-oxomorpholin-2-yl)-2-hydroxyacetate, as a yellow solid. $^1$H NMR (300 MHz, CDCl$_3$): δ 7.74-7.67 (2H, m), 7.70 (1H, t, J=60 Hz), 7.63 (1H, d, J=5 Hz), 6.70 (1H, d, J=11 Hz), 4.43 (1H, s), 4.37 (1H, s), 4.29-3.93 (3H, m), 3.85-3.78 (1H, m), 1.60 (3H, s), 1.51 (9H, s).

Step B: (R)-2-((R)-4-(1-(1-(Difluoromethyl)-6-oxo-1,6-dihydropyridin-3-yl)-4-fluoro-1H-pyrazol-3-yl)-2-methyl-3-oxomorpholin-2-yl)-2-hydroxyacetic acid According to Step F in the synthetic method for EXAMPLE 76, (R)-tert-butyl 2-((R)-4-(1-(1-(difluoromethyl)-6-oxo-1,6-dihydropyridin-3-yl)-4-fluoro-1H-pyrazol-3-yl)-2-methyl-3-oxomorpholin-2-yl)-2-hydroxyacetate (45 mg) was used instead of R)-tert-butyl 2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetate to obtain (R)-2-((R)-4-(1-(1-(difluoromethyl)-6-oxo-1,6-dihydropyridin-3-yl)-4-fluoro-1H-pyrazol-3-yl)-2-methyl-3-oxomorpholin-2-yl)-2-hydroxyacetic acid, as a pale yellow solid. LCMS 417 (M+H)$^+$.

Step C: (R)—N-(3-Aminobenzo[d]isoxazol-6-yl)-2-((R)-4-(1-(1-(difluoromethyl)-6-oxo-1,6-dihydropyridin-3-yl)-4-fluoro-1H-pyrazol-3-yl)-3-oxomorpholin-2-yl)-2-hydroxypropanamide According to Step G in the synthetic method for EXAMPLE 76, (R)-2-((R)-4-(1-(1-(difluoromethyl)-6-oxo-1,6-dihydropyridin-3-yl)-4-fluoro-1H-pyrazol-3-yl)-2-methyl-3-oxomorpholin-2-yl)-2-hydroxyacetic acid (40 mg) was used instead of (R)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetic acid to obtain (R)—N-(3-aminobenzo[d]isoxazol-6-yl)-2-((R)-4-(1-(1-(difluoromethyl)-6-oxo-1,6-dihydropyridin-3-yl)-4-fluoro-1H-pyrazol-3-yl)-3-oxomorpholin-2-yl)-2-hydroxypropanamide, as a colorless solid. LCMS 548 (M+H)$^+$.

Example 10

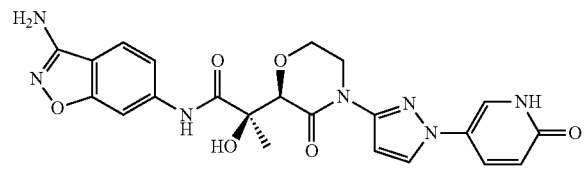 [SMILES: C[C@](O)(C(=O)Nc1ccc2c(N)noc2c1)[C@H]1OCCN(c2ccn(-c3ccc(=O)[nH]c3)n2)C1=O]

(R)—N-(3-Aminobenzo[d]isoxazol-6-yl)-2-hydroxy-2-((R)-3-oxo-4-(1-(6-oxo-1,6-dihydropyridin-3-yl)-1H-pyrazol-3-yl)morpholin-2-yl)propanamide Step A: (3-Iodo-1H-pyrazol-1-yl)methyl pivalate To a solution of 3-iodopyrazole (1.40 g) in THF (25 mL) was added NaH (0.32 g, 60% wt) at 0° C. After stirring for 10 min at 0° C., chloromethyl pivalate (1.14 g) was added to the reaction at the same temperature. The reaction mixture was stirred for 1 h at room temperature. It was diluted with sat. NaHCO$_3$ aq. and extracted with EtOAc (2 times). The combined organic layer was washed with brine, dried over Na$_2$SO$_4$, filtered and concentrated to give (3-iodo-1H-pyrazol-1-yl)methyl pivalate, as a brown oil, which was used in the next step without further purification. LCMS 331 (M+Na)$^+$. $^1$H NMR (300 MHz, CDCl$_3$): δ 7.48 (1H, d, J=2 Hz), 6.45 (1H, d, J=2 Hz), 5.97 (2H, s), 1.17 (9H, s).

Step B: (3-((R)-2-((R)-1-(tert-Butoxy)-2-hydroxy-1-oxopropan-2-yl)-3-oxomorpholino)-1H-pyrazol-1-yl)methyl pivalate According to Step C in the synthetic method for EXAMPLE 76, (3-iodo-1H-pyrazol-1-yl)methyl pivalate (1.4 g) and (R)-tert-butyl 2-hydroxy-2-((R)-3-oxomorpholin-2-yl)propanoate (1.0 g) were used instead of 5-bromo-1-difluoromethyl-1H-pyridin-2-one and 3-aminopyrazole to obtain (3-((R)-2-((R)-1-(tert-butoxy)-2-hydroxy-1-oxopropan-2-yl)-3-oxomorpholino)-1H-pyrazol-1-yl)methyl pivalate (1.1 g) as a colorless oil. LCMS 448 (M+Na)$^+$.

Step C: (R)-tert-Butyl 2-hydroxy-2-((R)-3-oxo-4-(1H-pyrazol-3-yl)morpholin-2-yl)propanoate To a solution of (3-((R)-2-((R)-1-(tert-butoxy)-2-hydroxy-1-oxopropan-2-yl)-3-oxomorpholino)-1H-pyrazol-1-yl)methyl pivalate (1.00 g) in MeOH (10 mL) was added NaOMe in MeOH (0.9 mL, 28% wt) at room temperature. The reaction mixture was stirred for 15 h at room temperature. It was diluted with water and extracted with EtOAc (3 times). The combined organic layer was washed with brine, dried over Na$_2$SO$_4$, filtered and concentrated in vacuo. The residue was purified by silica gel flash chromatography (eluent:Hexane:EtOAc=100:0~20:80) to give (R)-tert-butyl 2-hydroxy-2-((R)-3-oxo-4-(1H-pyrazol-3-yl)morpholin-2-yl)propanoate, as a colorless solid. LCMS 334 (M+Na)$^+$. $^1$H NMR (300 MHz, CDCl$_3$): δ 7.51 (1H, d, J=2 Hz), 6.83-6.57 (1H, m), 4.80 (1H, s), 4.28 (1H, s), 4.24-4.17 (1H, m), 4.06-3.83 (3H, m), 1.58 (3H, s), 1.42 (9H, s).

Step D: (R)-tert-Butyl 2-hydroxy-2-((R)-4-(1-(6-((4-methoxybenzyl)oxy)pyridin-3-yl)-1H-pyrazol-3-yl)-3-oxomorpholin-2-yl)propanoate According to Step C in the synthetic method for EXAMPLE 76, 5-iodo-2-((4-methoxybenzyl)oxy)pyridine (0.20 g) and (R)-tert-butyl 2-hydroxy-2-((R)-3-oxo-4-(1H-pyrazol-3-yl)morpholin-2-yl)propanoate (90 mg) were used instead of 5-bromo-1-difluoromethyl-1H-pyridin-2-one and 3-aminopyrazole to obtain (R)-tert-butyl 2-hydroxy-2-((R)-4-(1-(6-((4-methoxybenzyl)oxy)pyridin-3-yl)-1H-pyrazol-3-yl)-3-oxomorpholin-2-yl)propanoate, as a colorless oil. LCMS 525 (M+H)$^+$.

Step E: (R)-2-Hydroxy-2-((R)-3-oxo-4-(1-(6-oxo-1,6-dihydropyridin-3-yl)-1H-pyrazol-3-yl)morpholin-2-yl)propanoic acid According to Step F in the synthetic method for EXAMPLE 76, (R)-tert-butyl 2-hydroxy-2-((R)-4-(1-(6-((4-methoxybenzyl)oxy)pyridin-3-yl)-1H-pyrazol-3-yl)-3-oxomorpholin-2-yl)propanoate (0.11 g) was used instead of (R)-tert-butyl 2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetate to obtain (R)-2-hydroxy-2-((R)-3-oxo-4-(1-(6-oxo-1,6-dihydropyridin-3-yl)-1H-pyrazol-3-yl)morpholin-2-yl)propanoic acid, as a colorless solid. LCMS 349 (M+H)+.

Step F: (R)—N-(3-Aminobenzo[d]isoxazol-6-yl)-2-hydroxy-2-((R)-3-oxo-4-(1-(6-oxo-1,6-dihydropyridin-3-yl)-1H-pyrazol-3-yl)morpholin-2-yl)propanamide According to Step G in the synthetic method for EXAMPLE 76, (R)-2-hydroxy-2-((R)-3-oxo-4-(1-(6-oxo-1,6-dihydropyridin-3-yl)-1H-pyrazol-3-yl)morpholin-2-yl)propanoic acid (0.10 g) was used instead of (R)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetic acid to obtain (R)—N-(3-aminobenzo[d]isoxazol-6-yl)-2-hydroxy-2-((R)-3-oxo-4-(1-(6-oxo-1,6-dihydropyridin-3-yl)-1H-pyrazol-3-yl)morpholin-2-yl)propanamide, as a colorless solid. LCMS 480 (M+H)+.

Example 11

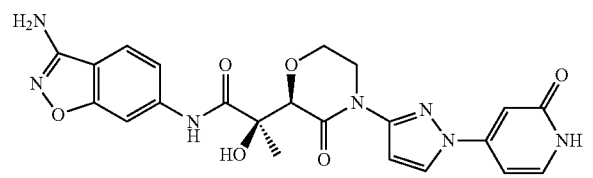 [SMILES: C[C@](O)(C(=O)Nc1ccc2c(N)noc2c1)[C@H]1OCCN(c2ccn(-c3cc[nH]c(=O)c3)n2)C1=O]

(R)—N-(3-Aminobenzo[d]isoxazol-6-yl)-2-hydroxy-2-((R)-3-oxo-4-(1-(2-oxo-1,2-dihydropyridin-4-yl)-1H-pyrazol-3-yl)morpholin-2-yl)propanamide Step A: (R)-tert-butyl 2-hydroxy-2-((R)-4-(1-(2-((4-methoxybenzyl)oxy)pyridin-4-yl)-1H-pyrazol-3-yl)-3-oxomorpholin-2-yl)propanoate According to Step C in the synthetic method for EXAMPLE 76, 4-iodo-2-((4-methoxybenzyl)oxy)pyridine (0.20 g) and (R)-tert-butyl 2-hydroxy-2-((R)-3-oxo-4-(1H-pyrazol-3-yl)morpholin-2-yl)propanoate (90 mg) were used instead of 5-bromo-1-difluoromethyl-1H-pyridin-2-one and 3-aminopyrazole to obtain (R)-tert-butyl 2-hydroxy-2-((R)-4-(1-(2-((4-methoxybenzyl)oxy)pyridin-4-yl)-1H-pyrazol-3-yl)-3-oxomorpholin-2-yl)propanoate, as a colorless solid. LCMS 525 (M+H)+.

Step B: (R)-2-Hydroxy-2-((R)-3-oxo-4-(1-(2-oxo-1,2-dihydropyridin-4-yl)-1H-pyrazol-3-yl)morpholin-2-yl)propanoic acid According to Step F in the synthetic method for EXAMPLE 76, (R)-tert-butyl 2-hydroxy-2-((R)-4-(1-(2-((4-methoxybenzyl)oxy)pyridin-4-yl)-1H-pyrazol-3-yl)-3-oxomorpholin-2-yl)propanoate (70 mg) was used instead of (R)-tert-butyl 2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetate to obtain (R)-2-hydroxy-2-((R)-3-oxo-4-(1-(2-oxo-1,2-dihydropyridin-4-yl)-1H-pyrazol-3-yl)morpholin-2-yl)propanoic acid, as a pale yellow solid. LCMS 349 (M+H)+.

Step C: (R)—N-(3-Aminobenzo[d]isoxazol-6-yl)-2-hydroxy-2-((R)-3-oxo-4-(1-(2-oxo-1,2-dihydropyridin-4-yl)-1H-pyrazol-3-yl)morpholin-2-yl)propanamide According to Step G in the synthetic method for EXAMPLE 76, (R)-2-hydroxy-2-((R)-3-oxo-4-(1-(2-oxo-1,2-dihydropyridin-4-yl)-1H-pyrazol-3-yl)morpholin-2-yl)propanoic acid (70 mg) was used instead of (R)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetic acid to obtain (R)—N-(3-aminobenzo[d]isoxazol-6-yl)-2-hydroxy-2-((R)-3-oxo-4-(1-(2-oxo-1,2-dihydropyridin-4-yl)-1H-pyrazol-3-yl)morpholin-2-yl)propanamide, as a pale brown solid. LCMS 480 (M+H)+.

Example 12

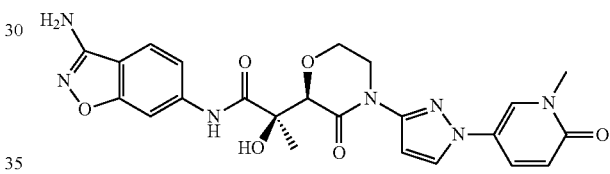

(R)—N-(3-Aminobenzo[d]isoxazol-6-yl)-2-hydroxy-2-((R)-4-(1-(1-methyl-6-oxo-1,6-dihydropyridin-3-yl)-1H-pyrazol-3-yl)-3-oxomorpholin-2-yl)propanamide Step A: (R)-tert-Butyl 2-hydroxy-2-((R)-4-(1-(1-methyl-6-oxo-1,6-dihydropyridin-3-yl)-1H-pyrazol-3-yl)-3-oxomorpholin-2-yl)propanoate According to Step C in the synthetic method for EXAMPLE 76, 5-iodo-1-methylpyridin-2(1H)-one (0.16 g) and (R)-tert-butyl 2-hydroxy-2-((R)-3-oxo-4-(1H-pyrazol-3-yl)morpholin-2-yl)propanoate (0.11 g) were used instead of 5-bromo-1-difluoromethyl-1H-pyridin-2-one and 3-aminopyrazole to obtain (R)-tert-butyl 2-hydroxy-2-((R)-4-(1-(1-methyl-6-oxo-1,6-dihydropyridin-3-yl)-1H-pyrazol-3-yl)-3-oxomorpholin-2-yl)propanoate, as a colorless solid. LCMS 419 (M+H)+.

Step B: (R)-2-Hydroxy-2-((R)-4-(1-(1-methyl-6-oxo-1,6-dihydropyridin-3-yl)-1H-pyrazol-3-yl)-3-oxomorpholin-2-yl)propanoic acid hydrochloride According to Step F in the synthetic method for EXAMPLE 76, (R)-tert-butyl 2-hydroxy-2-((R)-4-(1-(1-methyl-6-oxo-1,6-dihydropyridin-3-yl)-1H-pyrazol-3-yl)-3-oxomorpholin-2-yl)propanoate (0.13 g) was used instead of (R)-tert-butyl 2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetate to obtain (R)-2-hydroxy-2-

((R)-4-(1-(1-methyl-6-oxo-1,6-dihydropyridin-3-yl)-1H-pyrazol-3-yl)-3-oxomorpholin-2-yl)propanoic acid hydrochloride, as a colorless solid. LCMS 363 (M+H)⁺.

Step C: (R)—N-(3-Aminobenzo[d]isoxazol-6-yl)-2-hydroxy-2-((R)-4-(1-(1-methyl-6-oxo-1,6-dihydropyridin-3-yl)-1H-pyrazol-3-yl)-3-oxomorpholin-2-yl)propanamide According to Step F in the synthetic method for EXAMPLE 76, (R)-2-hydroxy-2-((R)-4-(1-(1-methyl-6-oxo-1,6-dihydropyridin-3-yl)-1H-pyrazol-3-yl)-3-oxomorpholin-2-yl)propanoic acid hydrochloride (0.12 g) was used instead of (R)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetic acid to obtain (R)—N-(3-aminobenzo[d]isoxazol-6-yl)-2-hydroxy-2-((R)-4-(1-(1-methyl-6-oxo-1,6-dihydropyridin-3-yl)-1H-pyrazol-3-yl)-3-oxomorpholin-2-yl)propanamide, as a colorless solid. LCMS 494 (M+H)⁺.

The following compounds (Table 1) were synthesized using methods analogous to those described for EXAMPLES 1, 2, 3, 4, and 7 from commercially available materials or intermediates whose syntheses are described above.

TABLE 1

| Example | R | LCMS (M + H)⁺ | Calc. (M + H)+ | FIXa IC50 (nM) |
|---|---|---|---|---|
| 13 | pyrazole-N-(4-fluorophenyl) | 481.08 | 481.16 | 677.9 |
| 14 | pyrazole-N-(4-methylsulfonylphenyl) | 541.07 | 541.15 | 13.16 |
| 15 | pyrazole-N-(4-carboxyphenyl) | 507.14 | 507.16 | 289.1 |
| 16 | pyrazole-N-(2-chloro-4-cyanophenyl) | 522.04 | 522.13 | 136.6 |
| 17 | 4-fluoro-pyrazole-N-(4-fluorophenyl) | 499.02 | 499.15 | 547.7 |
| 18 | pyrazole-N-(pyridin-4-yl) | 464.13 | 464.17 | |
| 19 | pyrazole-N-(2-methylpyridin-5-yl) | 478.30 | 478.18 | 71.93 |

TABLE 1-continued
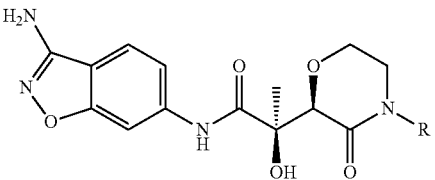
| Example | R | LCMS (M + H)+ | Calc. (M + H)+ | FIXa IC50 (nM) |
|---|---|---|---|---|
| 21 | 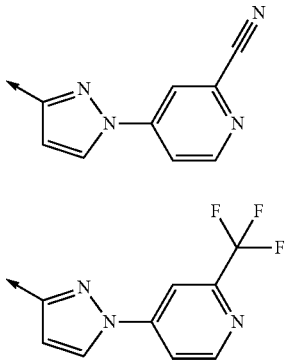 | 489.09 | 489.16 | 16.03 |
| 22 | 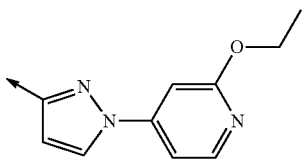 | 532.09 | 532.15 | 36.95 |
| 23 | 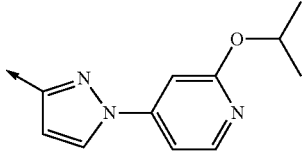 | 508.22 | 508.19 | 112.8 |
| 24 | 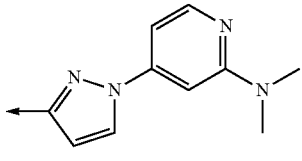 | 522.05 | 522.20 | 387.1 |
| 25 | 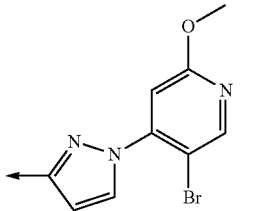 | 507.10 | 507.20 | 95.45 |
| 26 | 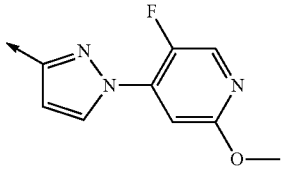 | 573.96 | 574.09 | 345.8 |
| 27 |  | 512.07 | 512.16 | 148 |

TABLE 1-continued
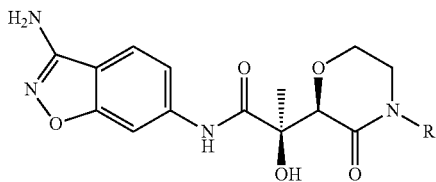
| Example | R | LCMS (M + H)+ | Calc. (M + H)+ | FIXa IC50 (nM) |
|---|---|---|---|---|
| 28 | 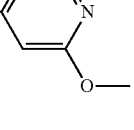 | 528.03 | 528.13 | 445.3 |
| 29 | 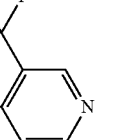 | 562.08 | 562.16 | 106 |
| 30 | 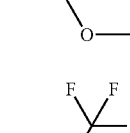 | 550.04 | 550.14 | 36.23 |
| 31 | 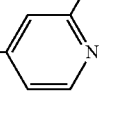 | 507.09 | 507.15 | 30.99 |
| 32 | 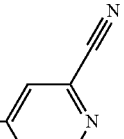 | 512.12 | 512.16 | |
| 33 | 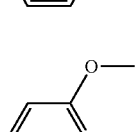 | 528.04 | 528.13 | 817 |
| 34 | 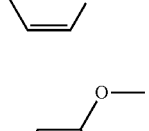 | 523.03 | 523.12 | 569.9 |

TABLE 1-continued
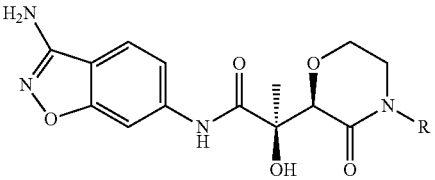
| Example | R | LCMS (M + H)+ | Calc. (M + H)+ | FIXa IC50 (nM) |
|---|---|---|---|---|
| 35 | 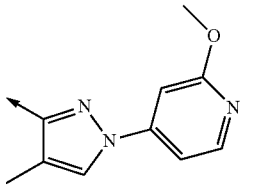 | 508.16 | 508.19 | 693.6 |
| 36 | 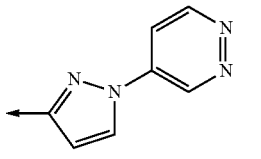 | 508.05 | 508.19 | 96.31 |
| 37 | 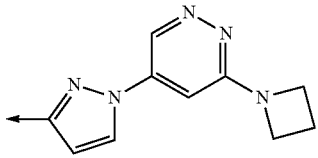 | 465.02 | 465.16 | 4.355 |
| 38 | 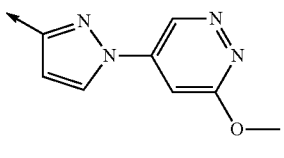 | 520.21 | 520.21 | 23.17 |
| 39 | 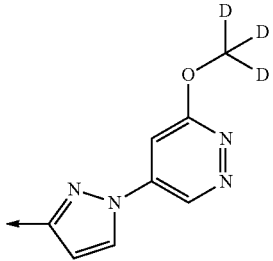 | 495.17 | 495.13 | 159.8 |
| 40 | 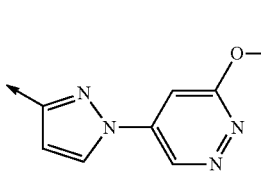 | 498.09 | 498.19 | 3.705 |
| 41 | | 523.20 | 523.04 | 57.84 |

TABLE 1-continued
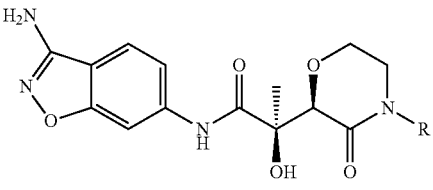
| Example | R | LCMS (M + H)+ | Calc. (M + H)+ | FIXa IC50 (nM) |
|---|---|---|---|---|
| 42 | 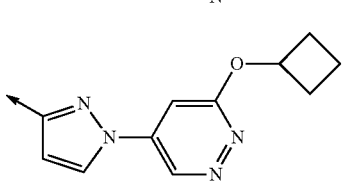 | 480.96 (M − tBu + H) | 480.15 | |
| 43 | 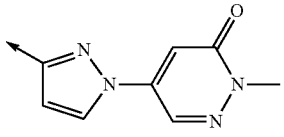 | 535.20 | 535.04 | 535.2 |
| 44 | 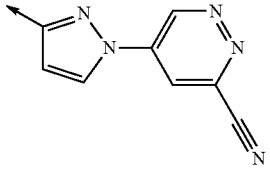 | 495.17 | 495.17 | 812.3 |
| 45 | 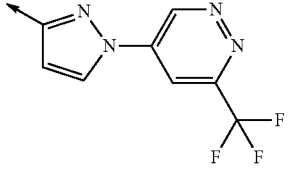 | 490.16 | 490.19 | 2.605 |
| 46 | 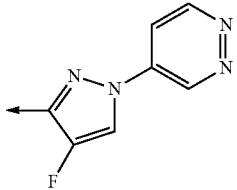 | 533.15 | 532.95 | 1.411 |
| 47 | 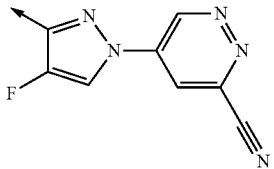 | 483.06 | 483.15 | 6.914 |
| 48 | 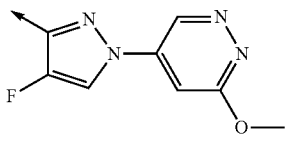 | 508.04 | 508.14 | 4.149 |
| 49 | | 513.06 | 513.16 | 6.478 |

TABLE 1-continued
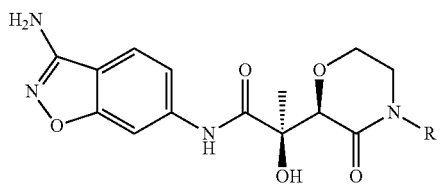
| Example | R | LCMS (M + H)+ | Calc. (M + H)+ | FIXa IC50 (nM) |
|---|---|---|---|---|
| 50 | | 551.22 | 551.14 | 1.886 |
| 51 | | 478.99 | 479.17 | 169.7 |
| 52 | | 508.14 | 508.20 | 101.7 |
| 53 | | 533.12 | 533.14 | 76.69 |
| 54 | | 490.07 | 490.15 | 145.4 |
| 55 | | 495.17 | 495.17 | 24.83 |
| 56 | | 495.01 | 495.17 | 84.54 |

TABLE 1-continued
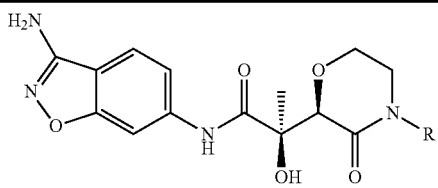
| Example | R | LCMS (M + H)+ | Calc. (M + H)+ | FIXa IC50 (nM) |
|---|---|---|---|---|
| 57 | [3-(trifluoromethyl)pyrimidin-4-yl-4-fluoropyrazole] | 551.11 | 551.13 | 63.69 |
| 58 | [2-methoxypyrimidin-4-yl-4-fluoropyrazole] | 513.19 | 513.16 | 32.03 |
| 59 | [2-(trifluoromethyl)pyrimidin-4-yl-5-methylpyrazole] | 547.15 | 547.16 | 72.81 |
| 60 | [5-(pyridin-4-yl)furan-2-yl] | 464.07 | 464.16 | |
| 61 | [5-(2-cyanopyridin-4-yl)furan-2-yl] | 489.10 | 489.14 | 93.03 |
| 62 | [5-(2-(trifluoromethyl)pyridin-4-yl)furan-2-yl] | 532.14 | 532.14 | 43.52 |
| 63 | [5-(2-methoxypyridin-4-yl)furan-2-yl] | 494.18 | 494.17 | 130.9 |
| 64 | [5-(2-methoxypyrimidin-4-yl)furan-2-yl] | 495.12 | 495.15 | 123.7 |

TABLE 1-continued

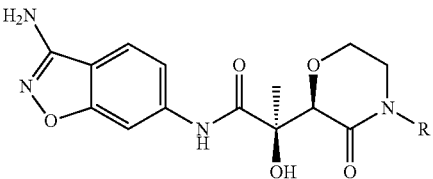

| Example | R | LCMS (M + H)+ | Calc. (M + H)+ | FIXa IC50 (nM) |
|---|---|---|---|---|
| 65 | 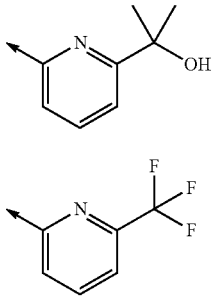 | 456.07 | 456.18 | 467.8 |
| 66 | 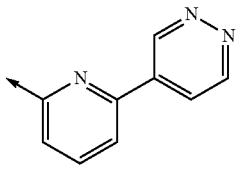 | 465.94 | 466.13 | |
| 67 | 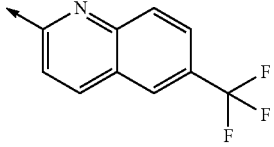 | 476.10 | 476.16 | 66.91 |
| 68 | 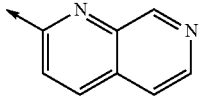 | 516.03 | 516.14 | 573.9 |
| 69 | 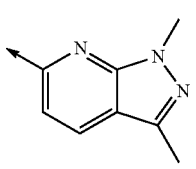 | 449.03 | 449.15 | 383.5 |
| 70 | 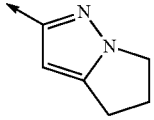 | 466.04 | 466.18 | 194.8 |
| 71 | | 427.06 | 427.17 | 368.4 |

Example 13

(R)—N-(3-aminobenzo[d]isoxazol-6-yl)-2-((R)-4-(1-(4-fluorophenyl)-1H-pyrazol-3-yl)-3-oxomorpholin-2-yl)-2-hydroxypropanamide, Example 14

(R)—N-(3-aminobenzo[d]isoxazol-6-yl)-2-hydroxy-2-((R)-4-(1-(4-(methylsulfonyl)phenyl)-1H-pyrazol-3-yl)-3-oxomorpholin-2-yl)propanamide, Example 15

4-(3-((R)-2-((R)-1-((3-aminobenzo[d]isoxazol-6-yl)amino)-2-hydroxy-1-oxopropan-2-yl)-3-oxomorpholino)-1H-pyrazol-1-yl)benzoic acid, Example 16

(R)—N-(3-aminobenzo[d]isoxazol-6-yl)-2-((R)-4-(1-(3-chloro-4-cyanophenyl)-1H-pyrazol-3-yl)-3-oxomorpholin-2-yl)-2-hydroxypropanamide, Example 17

(R)—N-(3-aminobenzo[d]isoxazol-6-yl)-2-((R)-4-(4-fluoro-1-(4-fluorophenyl)-1H-pyrazol-3-yl)-3-oxomorpholin-2-yl)-2-hydroxypropanamide, Example 18

(R)—N-(3-aminobenzo[d]isoxazol-6-yl)-2-hydroxy-2-((R)-3-oxo-4-(1-(pyridin-4-yl)-1H-pyrazol-3-yl)morpholin-2-yl)propanamide, Example 19

(R)—N-(3-aminobenzo[d]isoxazol-6-yl)-2-hydroxy-2-((R)-4-(1-(2-methylpyridin-4-yl)-1H-pyrazol-3-yl)-3-oxomorpholin-2-yl)propanamide, Example 21

(R)—N-(3-aminobenzo[d]isoxazol-6-yl)-2-((R)-4-(1-(2-cyanopyridin-4-yl)-1H-pyrazol-3-yl)-3-oxomorpholin-2-yl)-2-hydroxypropanamide, Example 22

(R)—N-(3-aminobenzo[d]isoxazol-6-yl)-2-hydroxy-2-((R)-3-oxo-4-(1-(2-(trifluoromethyl)pyridin-4-yl)-1H-pyrazol-3-yl)morpholin-2-yl)propanamide, Example 23

(R)—N-(3-aminobenzo[d]isoxazol-6-yl)-2-((R)-4-(1-(2-ethoxypyridin-4-yl)-1H-pyrazol-3-yl)-3-oxomorpholin-2-yl)-2-hydroxypropanamide, Example 24

(R)—N-(3-aminobenzo[d]isoxazol-6-yl)-2-hydroxy-2-((R)-4-(1-(2-isopropoxypyridin-4-yl)-1H-pyrazol-3-yl)-3-oxomorpholin-2-yl)propanamide, Example 25

(R)—N-(3-aminobenzo[d]isoxazol-6-yl)-2-((R)-4-(1-(2-(dimethylamino)pyridin-4-yl)-1H-pyrazol-3-yl)-3-oxomorpholin-2-yl)-2-hydroxypropanamide, Example 26

(R)—N-(3-aminobenzo[d]isoxazol-6-yl)-2-((R)-4-(1-(5-bromo-2-methoxypyridin-4-yl)-1H-pyrazol-3-yl)-3-oxomorpholin-2-yl)-2-hydroxypropanamide, Example 27

(R)—N-(3-aminobenzo[d]isoxazol-6-yl)-2-((R)-4-(1-(5-fluoro-2-methoxypyridin-4-yl)-1H-pyrazol-3-yl)-3-oxomorpholin-2-yl)-2-hydroxypropanamide, Example 28

(R)—N-(3-aminobenzo[d]isoxazol-6-yl)-2-((R)-4-(1-(5-chloro-2-methoxypyridin-4-yl)-1H-pyrazol-3-yl)-3-oxomorpholin-2-yl)-2-hydroxypropanamide, Example 29

(R)—N-(3-aminobenzo[d]isoxazol-6-yl)-2-hydroxy-2-((R)-4-(1-(2-methoxy-5-(trifluoromethyl)pyridin-4-yl)-1H-pyrazol-3-yl)-3-oxomorpholin-2-yl)propanamide, Example 30

(R)—N-(3-aminobenzo[d]isoxazol-6-yl)-2-((R)-4-(4-fluoro-1-(2-(trifluoromethyl)pyridin-4-yl)-1H-pyrazol-3-yl)-3-oxomorpholin-2-yl)-2-hydroxypropanamide, Example 31

(R)—N-(3-aminobenzo[d]isoxazol-6-yl)-2-((R)-4-(1-(2-cyanopyridin-4-yl)-4-fluoro-1H-pyrazol-3-yl)-3-oxomorpholin-2-yl)-2-hydroxypropanamide, Example 32

(R)—N-(3-aminobenzo[d]isoxazol-6-yl)-2-((R)-4-(4-fluoro-1-(2-methoxypyridin-4-yl)-1H-pyrazol-3-yl)-3-oxomorpholin-2-yl)-2-hydroxypropanamide, Example 33

(R)—N-(3-aminobenzo[d]isoxazol-6-yl)-2-((R)-4-(4-chloro-1-(2-methoxypyridin-4-yl)-1H-pyrazol-3-yl)-3-oxomorpholin-2-yl)-2-hydroxypropanamide, Example 34

(R)—N-(3-aminobenzo[d]isoxazol-6-yl)-2-((R)-4-(4-chloro-1-(2-cyanopyridin-4-yl)-1H-pyrazol-3-yl)-3-oxomorpholin-2-yl)-2-hydroxypropanamide, Example 35

(R)—N-(3-aminobenzo[d]isoxazol-6-yl)-2-hydroxy-2-((R)-4-(1-(2-methoxypyridin-4-yl)-4-methyl-1H-pyrazol-3-yl)-3-oxomorpholin-2-yl)propanamide, Example 36

(R)—N-(3-aminobenzo[d]isoxazol-6-yl)-2-hydroxy-2-((R)-4-(1-(2-methoxypyridin-4-yl)-5-methyl-1H-pyrazol-3-yl)-3-oxomorpholin-2-yl)propanamide, Example 37

(R)—N-(3-aminobenzo[d]isoxazol-6-yl)-2-hydroxy-2-((R)-3-oxo-4-(1-(pyridazin-4-yl)-1H-pyrazol-3-yl)morpholin-2-yl)propanamide, Example 38

(R)—N-(3-aminobenzo[d]isoxazol-6-yl)-2-((R)-4-(1-(6-(azetidin-1-yl)pyridazin-4-yl)-1H-pyrazol-3-yl)-3-oxomorpholin-2-yl)-2-hydroxypropanamide, Example 39

(R)—N-(3-aminobenzo[d]isoxazol-6-yl)-2-hydroxy-2-((R)-4-(1-(6-methoxypyridazin-4-yl)-1H-pyrazol-3-yl)-3-oxomorpholin-2-yl)propanamide,

Example 40

(2R)—N-(3-amino-1,2-benzoxazol-6-yl)-2-hydroxy-2-[(2R)-3-oxo-4-[1-[6-(trideuteriomethoxy)pyridazin-4-yl]pyrazol-3-yl]morpholin-2-yl]propanamide,

Example 41

(R)—N-(3-aminobenzo[d]isoxazol-6-yl)-2-hydroxy-2-((R)-4-(1-(6-isopropoxypyridazin-4-yl)-1H-pyrazol-3-yl)-3-oxomorpholin-2-yl)propanamide,

Example 42

(R)—N-(3-aminobenzo[d]isoxazol-6-yl)-2-((R)-4-(1-(6-(tert-butoxy)pyridazin-4-yl)-1H-pyrazol-3-yl)-3-oxomorpholin-2-yl)-2-hydroxypropanamide,

Example 43

(R)—N-(3-aminobenzo[d]isoxazol-6-yl)-2-((R)-4-(1-(6-cyclobutoxypyridazin-4-yl)-1H-pyrazol-3-yl)-3-oxomorpholin-2-yl)-2-hydroxypropanamide,

Example 44

(R)—N-(3-aminobenzo[d]isoxazol-6-yl)-2-hydroxy-2-((R)-4-(1-(1-methyl-6-oxo-1,6-dihydropyridazin-4-yl)-1H-pyrazol-3-yl)-3-oxomorpholin-2-yl)propanamide,

Example 45

(R)—N-(3-aminobenzo[d]isoxazol-6-yl)-2-((R)-4-(1-(6-cyanopyridazin-4-yl)-1H-pyrazol-3-yl)-3-oxomorpholin-2-yl)-2-hydroxypropanamide,

Example 46

(R)—N-(3-aminobenzo[d]isoxazol-6-yl)-2-hydroxy-2-((R)-3-oxo-4-(1-(6-(trifluoromethyl)pyridazin-4-yl)-1H-pyrazol-3-yl)morpholin-2-yl)propanamide,

Example 47

(R)—N-(3-aminobenzo[d]isoxazol-6-yl)-2-((R)-4-(4-fluoro-1-(pyridazin-4-yl)-1H-pyrazol-3-yl)-3-oxomorpholin-2-yl)-2-hydroxypropanamide,

Example 48

(R)—N-(3-aminobenzo[d]isoxazol-6-yl)-2-((R)-4-(1-(6-cyanopyridazin-4-yl)-4-fluoro-1H-pyrazol-3-yl)-3-oxomorpholin-2-yl)-2-hydroxypropanamide,

Example 49

(R)—N-(3-aminobenzo[d]isoxazol-6-yl)-2-((R)-4-(4-fluoro-1-(6-methoxypyridazin-4-yl)-1H-pyrazol-3-yl)-3-oxomorpholin-2-yl)-2-hydroxypropanamide,

Example 50

(R)—N-(3-aminobenzo[d]isoxazol-6-yl)-2-((R)-4-(4-fluoro-1-(6-(trifluoromethyl)pyridazin-4-yl)-1H-pyrazol-3-yl)-3-oxomorpholin-2-yl)-2-Hydroxypropanamide,

Example 51

(R)—N-(3-aminobenzo[d]isoxazol-6-yl)-2-hydroxy-2-((R)-4-(1-(2-methylpyrimidin-4-yl)-1H-pyrazol-3-yl)-3-oxomorpholin-2-yl)propanamide,

Example 52

(R)—N-(3-aminobenzo[d]isoxazol-6-yl)-2-((R)-4-(1-(2-(dimethylamino)pyrimidin-4-yl)-1H-pyrazol-3-yl)-3-oxomorpholin-2-yl)-2-Hydroxypropanamide,

Example 53

(R)—N-(3-aminobenzo[d]isoxazol-6-yl)-2-hydroxy-2-((R)-3-oxo-4-(1-(2-(trifluoromethyl)pyrimidin-4-yl)-1H-pyrazol-3-yl)morpholin-2-yl)propanamide,

Example 54

(R)—N-(3-aminobenzo[d]isoxazol-6-yl)-2-((R)-4-(1-(2-cyanopyrimidin-4-yl)-1H-pyrazol-3-yl)-3-oxomorpholin-2-yl)-2-hydroxypropanamide,

Example 55

(R)—N-(3-aminobenzo[d]isoxazol-6-yl)-2-hydroxy-2-((R)-4-(1-(2-methoxypyrimidin-4-yl)-1H-pyrazol-3-yl)-3-oxomorpholin-2-yl)propanamide,

Example 56

(R)—N-(3-aminobenzo[d]isoxazol-6-yl)-2-hydroxy-2-((R)-4-(1-(6-methoxypyrimidin-4-yl)-1H-pyrazol-3-yl)-3-oxomorpholin-2-yl)propanamide,

Example 57

(R)—N-(3-aminobenzo[d]isoxazol-6-yl)-2-((R)-4-(4-fluoro-1-(2-(trifluoromethyl)pyrimidin-4-yl)-1H-pyrazol-3-yl)-3-oxomorpholin-2-yl)-2-hydroxypropanamide,

Example 58

(R)—N-(3-aminobenzo[d]isoxazol-6-yl)-2-((R)-4-(4-fluoro-1-(2-methoxypyrimidin-4-yl)-1H-pyrazol-3-yl)-3-oxomorpholin-2-yl)-2-hydroxypropanamide,

Example 59

(R)—N-(3-aminobenzo[d]isoxazol-6-yl)-2-hydroxy-2-((R)-4-(5-methyl-1-(2-(trifluoromethyl)pyrimidin-4-yl)-1H-pyrazol-3-yl)-3-oxomorpholin-2-yl)propanamide,

Example 60

(R)—N-(3-aminobenzo[d]isoxazol-6-yl)-2-hydroxy-2-((R)-3-oxo-4-(5-(pyridin-4-yl)furan-2-yl)morpholin-2-yl)propanamide,

Example 61

(R)—N-(3-aminobenzo[d]isoxazol-6-yl)-2-((R)-4-(5-(2-cyanopyridin-4-yl)furan-2-yl)-3-oxomorpholin-2-yl)-2-hydroxypropanamide,

Example 62

(R)—N-(3-aminobenzo[d]isoxazol-6-yl)-2-hydroxy-2-((R)-3-oxo-4-(5-(2-(trifluoromethyl)pyridin-4-yl)furan-2-yl)morpholin-2-yl)propanamide,

Example 63

(R)—N-(3-aminobenzo[d]isoxazol-6-yl)-2-hydroxy-2-((R)-4-(5-(2-methoxypyridin-4-yl)furan-2-yl)-3-oxomorpholin-2-yl)propanamide,

Example 64

(R)—N-(3-aminobenzo[d]isoxazol-6-yl)-2-hydroxy-2-((R)-4-(5-(2-methoxypyrimidin-4-yl)furan-2-yl)-3-oxomorpholin-2-yl)propanamide,

Example 65

(R)—N-(3-aminobenzo[d]isoxazol-6-yl)-2-hydroxy-2-((R)-4-(6-(2-hydroxypropan-2-yl)pyridin-2-yl)-3-oxomorpholin-2-yl)propanamide,

Example 66

(R)—N-(3-aminobenzo[d]isoxazol-6-yl)-2-hydroxy-2-((R)-3-oxo-4-(6-(trifluoromethyl)pyridin-2-yl)morpholin-2-yl)propanamide,

Example 67

(R)—N-(3-aminobenzo[d]isoxazol-6-yl)-2-hydroxy-2-((R)-3-oxo-4-(6-(pyridazin-4-yl)pyridin-2-yl)morpholin-2-yl)propanamide,

Example 68

(R)—N-(3-aminobenzo[d]isoxazol-6-yl)-2-hydroxy-2-((R)-3-oxo-4-(6-(trifluoromethyl)quinolin-2-yl)morpholin-2-yl)propanamide,

Example 69

(R)-2-((R)-4-(1,7-naphthyridin-2-yl)-3-oxomorpholin-2-yl)-N-(3-aminobenzo[d]isoxazol-6-yl)-2-hydroxypropanamide,

Example 70

(R)—N-(3-aminobenzo[d]isoxazol-6-yl)-2-((R)-4-(1,3-dimethyl-1H-pyrazolo[3,4-b]pyridin-6-yl)-3-oxomorpholin-2-yl)-2-hydroxypropanamide,

Example 71

(R)—N-(3-aminobenzo[d]isoxazol-6-yl)-2-((R)-4-(5,6-dihydro-4H-pyrrolo[1,2-b]pyrazol-2-yl)-3-oxomorpholin-2-yl)-2-hydroxypropanamide,

Example 72

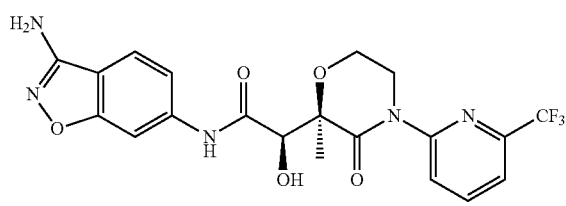

(R)—N-(3-Aminobenzo[d]isoxazol-6-yl)-2-hydroxy-2-((R)-2-methyl-3-oxo-4-(6-(trifluoromethyl)pyridin-2-yl)morpholin-2-yl)acetamide Step A: (R)-tert-Butyl 2-hydroxy-2-((R)-3-oxo-4-(6-(trifluoromethyl)pyridin-2-yl)morpholin-2-yl)acetate To (R)-tert-butyl 2-hydroxy-2-((R)-3-oxomorpholin-2-yl)acetate (2 g, 8.65 mmol), 2-bromo-6-(trifluoromethyl)pyridine (2.345 g, 10.38 mmol), (1R,2R)—N$^1$,N$^2$-dimethylcyclohexane-1,2-diamine (0.409 mL, 2.59 mmol), potassium phosphate tribasic (3.67 g, 17.30 mmol), and copper iodide (0.494 g, 2.59 mmol) was added 1,4-dioxane (86 mL). The reaction mixture was bubbled with N$_2$ for 5 min. The reaction vessel was then sealed and heated at 90° C. overnight. The reaction mixture was cooled to 25° C. and filtered through Celite using EtOAc as a rinse solvent. The filtrate was concentrated, diluted with EtOAc, washed with saturated NH$_4$Cl aqueous solution, water and brine. The layers were separated and the organic layer was concentrated and purified by ISCO (40 g silica gel column, 0-30% EtOAc in hexanes) to afford (R)-tert-butyl 2-hydroxy-2-((R)-3-oxo-4-(6-(trifluoromethyl)pyridin-2-yl)morpholin-2-yl)acetate, as a colorless oil. LCMS calc.=320.06. found=320.94 (M+H–C$_4$H$_9$)$^+$.

Step B: (R)-tert-Butyl 2-hydroxy-2-((R)-2-methyl-3-oxo-4-(6-(trifluoromethyl)pyridin-2-yl)morpholin-2-yl)acetate To (R)-tert-butyl 2-hydroxy-2-((R)-3-oxo-4-(6-(trifluoromethyl)pyridin-2-yl)morpholin-2-yl)acetate (300 mg, 0.797 mmol) in THF (3.9 mL) cooled to −78° C. was added 1.8 M LDA (1.1 mL, 1.993 mmol) in THF. The reaction was stirred at −78° C. for 30 min. Methyl iodide (75 μl, 1.196 mmol) was then added slowly to the reaction at −78° C. and the reaction was stirred for 1 h at −78° C. before slowly warmed to room temperature. The reaction was quenched with saturated NaHCO$_3$ aqueous solution. The aqueous layer was extracted with EtOAc (3×). The combined organic layers were washed with saturated NaHCO$_3$ aqueous solution and then brine, dried over MgSO$_4$ and filtered. The filtrate was concentrated in vacuo and the crude product was purified by ISCO (0-50% EtOAc in hexanes) to afford (R)-tert-butyl 2-hydroxy-2-((R)-2-methyl-3-oxo-4-(6-(trifluoromethyl)pyridin-2-yl)morpholin-2-yl)acetate, as a colorless oil. LCMS calc.=334.08. found=334.97 (M+H–C$_4$H$_9$)$^+$. $^1$H NMR (500 MHz, CDCl$_3$): δ 8.45 (d, J=8.2, 1 H); 7.89 (t, J=7.7 Hz, 1H); 7.50 (d, J=7.6 Hz, 1H); 4.45-4.32 (m, 2H); 4.24-4.11 (m, 1H); 4.10-3.95 (m, 2H); 3.77 (d, J=8.5 Hz, 1H); 1.67 (s, 3H); 1.56 (s, 9H).

Step C: (R)-2-Acetoxy-2-((R)-2-methyl-3-oxo-4-(6-(trifluoromethyl)pyridin-2-yl)morpholin-2-yl)acetic acid To (R)-tert-butyl 2-hydroxy-2-((R)-2-methyl-3-oxo-4-(6-(trifluoromethyl)pyridin-2-yl)morpholin-2-yl)acetate (42.7 mg, 0.109 mmol), pyridine (44 μl, 0.547 mmol) and DMAP (13.4 mg, 0.109 mmol) in CH$_2$Cl$_2$ (273 μl) was added acetic anhydride (52 μl, 0.547 mmol). The reaction was stirred at 25° C. overnight and concentrated and purified using ISCO CombiFlash® Rf (4 g, 0-30% EtOAc in hexanes) to yield a colorless oil, which was dissolve in CH$_2$Cl$_2$ (200 uL) and TFA (100 uL), and stirred at 25° C. for 3 h. To the reaction was added additional TFA (100 uL). After the reaction was complete the mixture was diluted with 1,4-dioxane:water (2:1) and purified by reverse-phase HPLC to afford (R)-2-acetoxy-2-((R)-2-methyl-3-oxo-4-(6-(trifluoromethyl)pyridin-2-yl)morpholin-2-yl)acetic acid. LCMS calc.=377.10. found=376.97 (M+H)⁺.

Step D: (R)—N-(3-Aminobenzo[d]isoxazol-6-yl)-2-hydroxy-2-((R)-2-methyl-3-oxo-4-(6-(trifluoromethyl)pyridin-2-yl)morpholin-2-yl)acetamide 1) To (R)-2-acetoxy-2-((R)-2-methyl-3-oxo-4-(6-(trifluoromethyl)pyridin-2-yl)morpholin-2-yl)acetic acid (24 mg, 0.064 mmol) in CH₂Cl₂ (638 μl) was added oxalyl chloride (17 μl, 0.191 mmol) followed by one drop of DMF. The reaction mixture was stirred at 25° C. for 1 h. To the reaction was added toluene and evaporated to dryness.

2) The crude product obtained in step 1 was dissolved in CH₂Cl₂ (638 μl) and cooled to 0° C. To the solution was added 2-(6-aminobenzo[d]isoxazol-3-yl)isoindoline-1,3-dione (35.6 mg, 0.128 mmol), pyridine (52 μl, 0.638 mmol) and DMAP (7.8 mg, 0.064 mmol), followed by MeCN (0.35 mL). The reaction was then warmed to 25° C. and stirred overnight. The reaction was diluted with EtOAc, washed with aq. NaHCO₃, water and brine. The organic layer was dried over MgSO₄ and filtered. The filtrate was concentrated to dryness.

3) The residue was dissolved in 7 N ammonia in MeOH and stirred at 25° C. for 6 h. The mixture was evaporated to dryness, acidified with 2 N TFA in DMSO and diluted with 2:1 1,4-dioxane/water. The solution was directly purified by reverse phase HPLC to afford (R)—N-(3-aminobenzo[d]isoxazol-6-yl)-2-hydroxy-2-((R)-2-methyl-3-oxo-4-(6-(trifluoromethyl)pyridin-2-yl)morpholin-2-yl)acetamide, as a white solid. LCMS calc.=466.13. found=465.98 (M+H)⁺. ¹H NMR (500 MHz, CDCl₃): δ 8.75 (s, 1H); 8.27 (d, J=8.4 Hz, 1H); 8.01 (s, 1H); 7.91 (t, J=8.0 Hz, 1H); 7.56-7.47 (m, 2H); 7.28 (m, 1H); 5.90 (br s, 3H); 4.59 (s, 1H); 4.28-4.14 (m, 4H); 1.81 (s, 3H).

(FIXa IC50: 12.92 nM)

Example 73

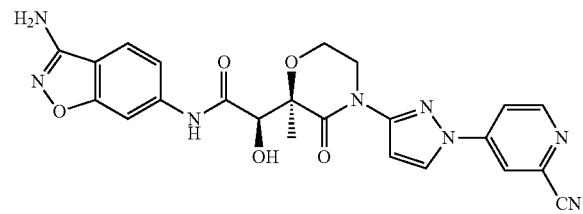

(R)—N-(3-Aminobenzo[d]isoxazol-6-yl)-2-((R)-4-(1-(2-cyanopyridin-4-yl)-1H-pyrazol-3-yl)-2-methyl-3-oxomorpholin-2-yl)-2-hydroxyacetamide Step A: (R)-tert-Butyl 2-hydroxy-2-((R)-4-(4-methoxybenzyl)-3-oxomorpholin-2-yl)acetate To (R)-tert-butyl 2-hydroxy-2-((R)-3-oxomorpholin-2-yl)acetate (10 g, 43.2 mmol) in DMF (108 mL) in a 1 L round bottom flask was added sodium hydride (1.730 g, 43.2 mmol) at 25° C. After stirring for 2 h, to the reaction vessel was added 4-methoxybenzyl chloride (5.87 mL, 43.2 mmol). The reaction was then stirred at 25° C. for 2 days. DMF was removed in vacuo. The residue was diluted with EtOAc, washed with sat. NH₄Cl (aq). The organic layer was dried over MgSO₄, filtered and concentrated. The crude product was loaded on ISCO silica gel column eluting with 0-30%-50% EtOAc in hexanes to afford (R)-tert-butyl 2-hydroxy-2-((R)-4-(4-methoxybenzyl)-3-oxomorpholin-2-yl)acetate. LCMS calc.=374.16. found=373.95 (M+Na)⁺.

Step B: (R)-tert-Butyl 2-hydroxy-2-((R)-4-(4-methoxybenzyl)-2-methyl-3-oxomorpholin-2-yl) acetate To (R)-tert-butyl 2-hydroxy-2-((R)-4-(4-methoxybenzyl)-3-oxomorpholin-2-yl)acetate in THF (42.7 mL) cooled to −78° C. was added 1.8 M LDA (11.86 mL, 21.34 mmol) in THF. The reaction was stirred at −78° C. for 2 h. Methyl iodide (0.641 mL, 10.24 mmol) was then added slowly to the reaction at −78° C. and the reaction was stirred at the same temperature for 1 h. The reaction was then slowly warmed to 25° C. and stirred overnight. To the reaction was added saturated bicarbonate (aq). The aqueous layer was extracted with EtOAc (3×). The combined organic layers were washed with saturated bicarbonate (aq) and then brine, dried over MgSO₄, filtered and the filtrate concentrated. The crude product was purified by ISCO (0-30-50% EtOAc in hexanes) to afford (R)-tert-Butyl 2-hydroxy-2-((R)-4-(4-methoxybenzyl)-2-methyl-3-oxomorpholin-2-yl)acetate. LCMS calc.=309.12. found=309.92 (M+H-C₄H₉).

Step C: (R)-tert-Butyl 2-hydroxy-2-((R)-2-methyl-3-oxomorpholin-2-yl)acetate

To a solution of (R)-tert-butyl 2-hydroxy-2-((R)-4-(4-methoxybenzyl)-2-methyl-3-oxomorpholin-2-yl)acetate (860 mg, 2.353 mmol) in MeCN (42.4 mL) and water (4.71 mL) was added ceric ammonium nitrate (2.58 g, 4.71 mmol) at 0° C. The reaction was warmed to 25° C. and stirred overnight. To the reaction was added ceric ammonium nitrate (2.58 g, 4.71 mmol) and the reaction was stirred at 25° C. for another 12 h. To the reaction was added saturated bicarbonate (aq) until the pH of the reaction mixture reached 4.5 to 5. The resulting suspension was filtered over Celite and the filter cake was washed with CH₂Cl₂, then with 5% MeOH in CH₂Cl₂. The combined organic phases were washed with brine, dried over MgSO₄, filtered and concentrated. The crude product was purified by ISCO (40 g silica gel column, 0-50-100% then 100% EtOAc in hexanes) to afford (R)-tert-butyl 2-hydroxy-2-((R)-2-methyl-3-oxomorpholin-2-yl)acetate, as a white solid. ¹H NMR (500 MHz, CDCl₃): δ 5.98, (s, 1H); 4.30 (d, J=8.6 Hz, 1H); 4.01 (d, J=12.0 Hz, 1H); 3.95-3.88 (m, 2H); 3.61-3.54 (m, 1H); 3.30 (dd, J=11.8, 4.0 Hz, 1H); 1.60 (s, 3H); 1.54 (s, 9H).

Step D: (R)-tert-Butyl 2-((R)-4-(1-(2-cyanopyridin-4-yl)-1H-pyrazol-3-yl)-2-methyl-3-oxomorpholin-2-yl)-2-hydroxyacetate To (R)-tert-butyl 2-hydroxy-2-((R)-2-methyl-3-oxomorpholin-2-yl)acetate (30 mg, 0.122 mmol), trans-N,N'-cyclohexyl-1,2-diamine (19.29 μl, 0.122 mmol), K₃PO₄ (51.9 mg, 0.245 mmol), copper iodide (23.3 mg, 0.122 mmol) was added 1,4-dioxane (1223 μl). The reaction mixture was purged with N₂ at 25° C. for 5 min. The reaction vessel was then sealed and heated at 90° C. for 3 h. The reaction was cooled to 25° C., diluted with hexanes, filter through Celite and concentrated. The crude product was purified by ISCO (0-100% EtOAc in hexanes) to afford (R)-tert-butyl 2-((R)-4-(1-(2-cyanopyridin-4-yl)-1H-pyrazol-3-yl)-2-methyl-3- oxomorpholin-2-yl)-2-hydroxyacetate. LCMS calc.= 414.17. found=414.13 (M+H)+.

Step E: (R)-2-((R)-4-(1-(2-Cyanopyridin-4-yl)-1H-pyrazol-3-yl)-2-methyl-3-oxomorpholin-2-yl)-2-hydroxyacetic acid A solution of (R)-tert-butyl 2-((R)-4-(1-(2-cyanopyridin-4-yl)-1H-pyrazol-3-yl)-2-methyl-3-oxomorpholin-2-yl)-2-hydroxyacetate (46 mg, 0.111 mmol) in CH$_2$Cl$_2$ (1 mL) and TFA (1 mL) was stirred at 25° C. for 1 h. The reaction was concentrated in vacuo. To the residue was added 2 N HCl in Et$_2$O. And the reaction was concentrated in vacuo. The process was repeated for three times to afford (R)-2-((R)-4-(1-(2-Cyanopyridin-4-yl)-1H-pyrazol-3-yl)-2-methyl-3-oxomorpholin-2-yl)-2-hydroxyacetic acid. LCMS calc.=358.11. found=358.04 (M+H)+.

Step F: (R)—N-(3-Aminobenzo[d]isoxazol-6-yl)-2-((R)-4-(1-(2-cyanopyridin-4-yl)-1H-pyrazol-3-yl)-2-methyl-3-oxomorpholin-2-yl)-2-hydroxyacetamide Benzo[d]isoxazole-3,6-diamine (35.1 mg, 0.235 mmol), (R)-2-((R)-4-(1-(2-cyanopyridin-4-yl)-1H-pyrazol-3-yl)-2-methyl-3-oxomorpholin-2-yl)-2-hydroxyacetic acid (42 mg, 0.118 mmol), EDC (45.1 mg, 0.235 mmol), HBOt (31.8 mg, 0.235 mmol) were stirred in DMF (735 µl) at 25° C. for 2 h. The reaction was acidified with 2 NTFA in DMSO, diluted with 2:1 1,4-dioxane:water and purified by reverse phase HPLC to afford (R)—N-(3-aminobenzo[d]isoxazol-6-yl)-2-((R)-4-(1-(2-cyanopyridin-4-yl)-1H-pyrazol-3-yl)-2-methyl-3-oxomorpholin-2-yl)-2-hydroxyacetamide. LCMS calc.=489.16. found=489.12 (M+H)+. $^1$H NMR (500 MHz, Acetone-d$_6$): δ 9.48 (s, 1H); 8.77 (d, J=5.6 Hz, 1H); 8.61 (dd, J=6.8, 2.8 Hz, 1H); 8.39 (s, 1H); 8.14-8.10 (m, 2H); 7.72 (d, J=8.5 Hz, 1H); 7.50 (d, J=8.6 Hz, 1H); 7.31-7.28 (m, 1H); 4.54 (s, 1H); 4.31-4.27 (m, 1H); 4.21 (d, J=5.6 Hz, 1H); 4.18-4.10 (m, 2H); 3.32 (brs, 3H); 1.69 (s, 3H).

(FIXa IC50: 66.1 nM)

Example 74

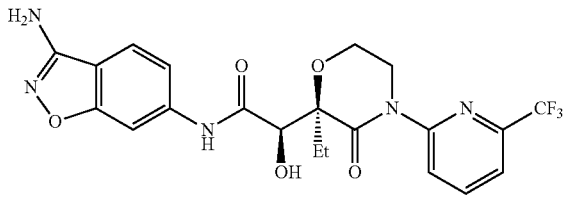

(R)—N-(3-Aminobenzo[d]isoxazol-6-yl)-2-((R)-2-ethyl-3-oxo-4-(6-(trifluoromethyl)pyridin-2-yl)morpholin-2-yl)-2-hydroxyacetamide Step A: (R)-tert-Butyl 2-((R)-2-ethyl-3-oxo-4-(6-(trifluoromethyl)pyridin-2-yl)morpholin-2-yl)-2-hydroxyacetate To (R)-tert-butyl 2-hydroxy-2-((R)-3-oxo-4-(6-(trifluoromethyl)pyridin-2-yl)morpholin-2-yl)acetate (300 mg, 0.797 mmol) in THF (4.0 mL) cooled to −78° C. was added 1.8 M LDA (1.1 mL, 1.993 mmol) in THF. The reaction was stirred at −78° C. for 30 min. Ethyl bromide (130 mg, 1.196 mmol) was then added slowly to the reaction at −78° C. and the reaction was stirred for 1 h at −78° C. before slowly warmed to room temperature. The reaction was quenched with saturated NaHCO$_3$ aqueous solution. The aqueous layer was extracted with EtOAc (3×). The combined organic layers were washed with saturated NaHCO$_3$ aqueous solution and then brine, dried over MgSO$_4$ and filtered. The filtrate was concentrated in vacuo and the crude product was purified by ISCO (0-30% EtOAc in hexanes) to afford (R)-tert-butyl 2-((R)-2-ethyl-3-oxo-4-(6-(trifluoromethyl)pyridin-2-yl)morpholin-2-yl)-2-hydroxyacetate, as a colorless oil. LCMS calc.=349.10. found=349.07 (M+H-C$_4$H$_9$)+. $^1$H NMR (500 MHz, CDCl$_3$): δ 8.52-8.41 (m, 1H); 7.89 (t, J=8.0 Hz, 1H); 7.50 (d, J=7.5 Hz, 1H); 4.40 (d, J=7.2 Hz, 1H); 4.34-4.25 (m, 1H); 4.20-4.03 (m, 3H); 4.04-3.93 (m, 1H); 2.16-2.04 (m, 2H); 1.52 (s, 9H); 1.03 (t, J=7.4 Hz, 3H).

Step B: (R)-2-Acetoxy-2-((R)-2-ethyl-3-oxo-4-(6-(trifluoromethyl)pyridin-2-yl)morpholin-2-yl)acetic acid To (R)-tert-butyl 2-((R)-2-ethyl-3-oxo-4-(6-(trifluoromethyl)pyridin-2-yl)morpholin-2-yl)-2-hydroxyacetate (55 mg, 0.136 mmol), pyridine (55 µl, 0.68 mmol) and DMAP (16.62 mg, 0.136 mmol) in CH$_2$Cl$_2$ (340 µl) was added acetic anhydride (64 µl, 0.68 mmol). The reaction was stirred at 25° C. overnight and concentrated and purified using ISCO CombiFlash Rf. The crude product was loaded onto 4 g silica gel column and eluted with 0-30% EtOAc in hexanes to yield a colorless oil, which was dissolved in (CH$_2$Cl$_2$, 300 uL) and TFA (30 uL), and stirred at 25° C. for 1 h. The volatiles were azeotropically removed with heptane to afford (R)-2-acetoxy-2-((R)-2-ethyl-3-oxo-4-(6-(trifluoromethyl)pyridin-2-yl)morpholin-2-yl)acetic acid. LCMS calc.=391.10. found=391.04 (M+H)+.

Step C: (R)—N-(3-Aminobenzo[d]isoxazol-6-yl)-2-((R)-2-ethyl-3-oxo-4-(6-(trifluoromethyl)pyridin-2-yl)morpholin-2-yl)-2-hydroxyacetamide 1) To (R)-2-acetoxy-2-((R)-2-ethyl-3-oxo-4-(6-(trifluoromethyl)pyridin-2-yl)morpholin-2-yl)acetic acid (46 mg, 0.064 mmol) in CH$_2$Cl$_2$ (1.2 mL) was added oxalyl chloride (62 µl, 0.707 mmol) followed by one drop of DMF. The reaction mixture was stirred at 25° C. for 1 h. To the reaction was added toluene and evaporated to dryness.

2) The crude product obtained in step 1 was dissolved in CH$_2$Cl$_2$ (1.2 mL) and cooled to 0° C. To the resulting solution was added 2-(6-aminobenzo[d]isoxazol-3-yl)isoindoline-1,3-dione (65.8 mg, 0.236 mmol), pyridine (95 µl, 1.179 mmol) and DMAP (14.4 mg, 0.118 mmol), followed by of MeCN (600 µL). The reaction was then warmed to 25° C. and stirred overnight. The reaction was diluted with EtOAc, washed with aq. NaHCO$_3$, water and brine. The organic layer was dried over MgSO$_4$ and filtered. The filtrate was concentrated to dryness.

3) To the residue in MeOH (1 mL) was added hydrazine (37 µl, 1.179 mmol) and the reaction was stirred at 25° C. for 1 h. The mixture was evaporated to dryness, acidified with 2N TFA in DMSO and diluted with 2:1 1,4-dioxane:water. The solution was directly purified by reversed phase HPLC to afford (R)—N-(3-aminobenzo[d]isoxazol-6-yl)-2-((R)-2-ethyl-3-oxo-4-(6-(trifluoromethyl)pyridin-2-yl)morpholin-2-yl)-2-hydroxyacetamide, as a white solid. LCMS calc.=480.14. found=479.97 (M+H)+. $^1$H NMR (500 MHz, CDCl$_3$): δ 8.68 (s, 1H); 8.31 (d, J=8.5 Hz, 1H); 7.98 (s, 1H); 7.90 (t, J=8.0 Hz, 1H); 7.53 (d, J=7.6 Hz, 1H); 7.48 (d, J=8.5

Hz, 1H); 7.26-7.28 (m, 1H), 4.55 (s, 1H); 4.40-4.70 (brs, 3H), 4.42-4.35 (m, 1H); 4.29-4.22 (m, 1H); 4.20-4.14 (m, 2H), 2.30-2.23 (m, 1H); 2.21-2.13 (m, 1H); 1.10 (t, J=7.4 Hz, 3H).

(FIXa IC50: 407.8 nM)

Example 75

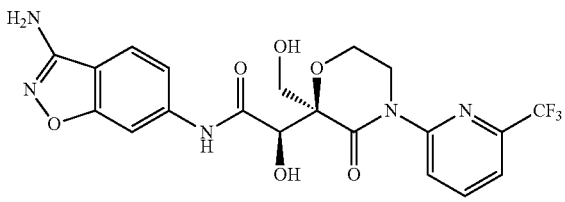 [SMILES: Nc1noc2cc(NC(=O)[C@H](O)[C@@]3(CO)OCCN(c4cccc(C(F)(F)F)n4)C3=O)ccc12]

(R)—N-(3-Aminobenzo[d]isoxazol-6-yl)-2-hydroxy-2-((R)-2-(hydroxymethyl)-3-oxo-4-(6-(trifluoromethyl)pyridin-2-yl)morpholin-2-yl)acetamide Step A: (R)-tert-Butyl 2-hydroxy-2-((R)-2-(hydroxymethyl)-3-oxo-4-(6-(trifluoromethyl)pyridin-2-yl)morpholin-2-yl)acetate 1) To a solution of 2,6-diphenylphenol (739 mg, 3.00 mmol) in $CH_2Cl_2$ (15 mL) was added 2M trimethylaluminum in hexanes (750 μl, 1.5 mmol) at 25° C. Methane gas evolved immediately. The resulting colorless solution was stirred 25° C. for 1 h to furnish a solution of MAPH in $CH_2Cl_2$.

2) To this 1.5 mmoL MAPH in $CH_2Cl_2$ was added a $CH_2Cl_2$ (0.2 mL) solution of 1,3,5-trioxane (40.5 mg, 0.450 mmol) at 0° C. The mixture was stirred at 0° C. for 0.5 h and then 25° C. for another 0.5 h. The product was used as a 0.1 M solution of $CH_2$=OMAPH complex in $CH_2Cl_2$ for the subsequent step without any further purification.

3) To (R)-tert-butyl 2-hydroxy-2-((R)-3-oxo-4-(6-(trifluoromethyl)pyridin-2-yl)morpholin-2-yl)acetate in THF (2.7 mL) cooled to −78° C. was added 1.8 M LDA in THF (1.1 mL, 1.966 mmol). The reaction was stirred at −78° C. then slowly warmed up to −10° C. over 45 min. $CH_2$=OMAPH solution from step 2 (8.0 mL, 0.797 mmol) was added and the reaction was stirred at −5~−10° C. for 30 min then warmed to 25° C. and stirred for 30 min. To the reaction mixture was added saturated aq. $NaHCO_3$. The aqueous layer was extracted with EtOAc for three times. The combined organic layers were washed with saturated aq. $NaHCO_3$ and brine, dried over $MgSO_4$, filtered and the filtrate concentrated. The crude product was purified by ISCO (0-100% EtOAc in hexanes) to afford (R)-tert-Butyl 2-hydroxy-2-((R)-2-(hydroxymethyl)-3-oxo-4-(6-(trifluoromethyl)pyridin-2-yl)morpholin-2-yl)acetate. LCMS calc.=429.12. found=428.86 $(M+Na)^+$.

Step B: (R)—N-(3-Aminobenzo[d]isoxazol-6-yl)-2-hydroxy-2-((R)-2-(hydroxymethyl)-3-oxo-4-(6-(trifluoromethyl)pyridin-2-yl)morpholin-2-yl)acetamide 1) To (R)-tert-butyl 2-hydroxy-2-((R)-2-(hydroxymethyl)-3-oxo-4-(6-(trifluoromethyl)pyridin-2-yl)morpholin-2-yl)acetate (9 mg, 0.021 mmol) in $CH_2Cl_2$ (207 μl) was added oxalyl chloride (11 μl, 0.124 mmol) followed by one drop of DMF. The reaction was stirred at 25° C. for 1 h. Toluene was added and the reaction mixture was evaporated to dryness.

2) To crude product from step 1 in $CH_2Cl_2$ (207 μl) at 0° C. was added 2-(6-aminobenzo[d]isoxazol-3-yl)isoindoline-1,3-dione (11.6 mg, 0.041 mmol), pyridine (17 μl, 0.207 mmol) and DMAP (2.5 mg, 0.021 mmol), followed by of MeCN (0.1 mL). The reaction was then warmed to 25° C. and stirred overnight. The reaction was diluted with EtOAc, washed with aq. $NaHCO_3$, water and brine. The organic layer was dried over $MgSO_4$ and filtered. The filtrate was concentrated to dryness.

3) The product of step 2 was dissolved in MeOH (0.5 mL), hydrazine (13 μl, 0.414 mmol) was added and the resulting mixture was stirred at 25° C. for 40 min. More hydrazine (13 μl) was added and the reaction was stirred for another 20 min. The mixture was evaporated to dryness, acidified with 2N TFA in DMSO and diluted with 2:1 1,4-dioxane:water. The solution was directly purified by reversed phase HPLC to afford (R)—N-(3-Aminobenzo[d]isoxazol-6-yl)-2-hydroxy-2-((R)-2-(hydroxymethyl)-3-oxo-4-(6-(trifluoromethyl)pyridin-2-yl)morpholin-2-yl)acetamide, as a white solid. LCMS calc.=482.13. found=481.97 $(M+H)^+$. $^1H$ NMR (500 MHz, $CDCl_3$): δ 9.03 (s, 1H); 8.39 (d, J=8.5 Hz, 1H); 8.05 (s, 1H); 7.94 (t, J=7.6 Hz, 1H); 7.57-7.48 (m, 2H); 7.31 (m, 1H); 4.95 (s, 1H); 4.43-4.19 (m, 5H); 3.99 (m, 1H); 3.77 (m, 1H); 3.17 (brs, 3H).

Example 76

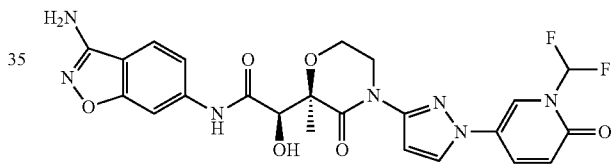

(R)—N-(3-Aminobenzo[d]isoxazol-6-yl)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetamide Step A: (R)-tert-Butyl 2-hydroxy-2-((R)-4-(4-methoxybenzyl)-2-methyl-3-oxomorpholin-2-yl)acetate To a solution of diisopropylamine (8.29 mL) in THF (40 mL) was added 2.6 M n-butyl lithium (20.0 mL) at −78° C., and stirred 10 min, warmed to 0° C. and stirred for 15 min, then cooled back to −78° C. A solution of (R)-tert-butyl 2-hydroxy-2-((R)-3-oxomorpholin-2-yl)acetate (8.29 g, WO2010065717) in THF (80 mL) was added via cannula to the cold LDA solution. The resulting reaction mixture was stirred at −78° C. for 2 h, and then methyliodide (3.67 mL) was added via syringe. This solution was slowly warmed to room temperature and stirred overnight. To this mixture was added sat. $NaHCO_3$, and extracted with $CH_2Cl_2$ (×3). The combined organic layer was washed with sat. $NaHCO_3$, and brine, dried over $Na_2SO_4$, filtered and concentrated in vacuo. The residue was purified by silica gel flash chromatography (eluent: Hexane:EtOAc=90:10~50:50) to give (R)-tert-butyl 2-hydroxy-2-((R)-4-(4-methoxybenzyl)-2-methyl-3-oxomorpholin-2-yl)acetate, as a colorless solid.

LCMS 388 (M+Na)⁺. ¹H NMR (300 MHz, CDCl₃): δ 7.22 (2H, d, J=9 Hz), 6.86 (2H, d, J=9 Hz), 4.70-4.60 (1H, m), 4.51 (1H, d, J=14 Hz), 4.32 (1H, d, J=9 Hz), 3.96-3.77 (6H, m), 3.42-3.31 (1H, m), 3.04 (1H, dt, J=12, 3 Hz), 1.60 (3H, s), 1.51 (9H, s).

Step B: (R)-tert-Butyl 2-hydroxy-2-((R)-2-methyl-3-oxomorpholin-2-yl)acetate To a solution of (R)-tert-butyl 2-hydroxy-2-((R)-4-(4-methoxybenzyl)-2-methyl-3-oxomorpholin-2-yl)acetate (3.90 g) in acetonitrile (150 mL) and water (20 mL) was added ceric ammonium nitrate (11.7 g) at 0° C. The reaction mixture was stirred for 14 h and for 3 h at 50° C. Sat. NaHCO₃ was added until the pH of the reaction mixture reached 4 to 5. The resulting suspension was filtered over Celite and the filter cake was washed with CH₂Cl₂ and then 5% MeOH in CH₂Cl₂. The combined organic phase was washed with brine, dried over Na₂SO₄, filtered and concentrated in vacuo. The residue was triturated with CH₂Cl₂ to give (R)-tert-butyl 2-hydroxy-2-((R)-2-methyl-3-oxomorpholin-2-yl)acetate as a colorless solid. LCMS 268 (M+Na)⁺. ¹H NMR (300 MHz, CDCl₃): δ 6.12 (1H, br s), 4.27 (1H, d, J=9 Hz), 4.02-3.83 (3H, m), 3.61-3.50 (1H, m), 3.31-3.22 (1H, m), 1.58 (3H, s), 1.51 (9H, s).

Step C: 5-(3-Amino-1H-pyrazol-1-yl)-1-(difluoromethyl)pyridin-2(1H)-one

To a solution of CuI (4.43 g) in DMSO (150 mL) was added trans-N,N'-dimethylcyclohexane-1,2-diamine (7.3 mL) under N₂. The mixture was degassed under vacuum, filled with N₂, and it was stirred for 10 min. Then, to the reaction was added 5-bromo-1-difluoromethyl-1H-pyridin-2-one (5.20 g, *Organic Letters* (2006), 8(17), 3805-3808.), 3-aminopyrazole (1.93 g) and K₃PO₄ (9.86 g), and it was degassed. The reaction mixture was stirred for 2 h at 80° C. After cooling to room temperature, it was diluted with 1% NH₃ aq. and extracted with EtOAc (4 times). The combined organic layer was washed with brine, dried over Na₂SO₄, filtered and concentrated in vacuo. The residue was purified by silica gel flash chromatography (eluent:Hexane:EtOAc=60:40~30:70) to give 5-(3-amino-1H-pyrazol-1-yl)-1-(difluoromethyl)pyridin-2(1H)-one, as a yellow solid. LCMS 227 (M+H)⁺. ¹H NMR (300 MHz, CDCl₃): δ 7.73-7.67 (2H, m), 7.70 (1H, t, J=60 Hz), 7.48-7.45 (1H, m), 6.68-6.61 (1H, m), 5.84 (1H, d, J=2 Hz), 3.82 (2H, s).

Step D: 1-(Difluoromethyl)-5-(3-iodo-1H-pyrazol-1-yl)pyridin-2(1H)-one

To a solution of 5-(3-amino-1H-pyrazol-1-yl)-1-(difluoromethyl)pyridin-2(1H)-one (1.15 g) in MeCN (30 mL) was added concentrated H₂SO₄ (0.68 mL) and NaNO₂ (0.70 g) in water (3 mL) at 0° C. After stirring for 10 min at 0° C., KI (3.38 g) in water (4 mL) was added to the reaction at the same temperature. The reaction mixture was stirred for 1 h at room temperature and for 20 min at 40° C. It was diluted with water and extracted with EtOAc. The organic layer was washed with sat. Na₂S₂O₃ aq., sat. NaHCO₃ aq. and brine, dried over Na₂SO₄, filtered and concentrated. The residue was purified by silica gel flash chromatography (eluent: Hexane:EtOAc=90:10~50:50) to give 1-(difluoromethyl)-5-(3-iodo-1H-pyrazol-1-yl)pyridin-2(1H)-one, as colorless solid. LCMS 338 (M+H)⁺. ¹H NMR (400 MHz, CDCl₃): δ 7.81 (1H, d, J=3 Hz), 7.75 (1H, dd, J=10, 3 Hz), 7.69 (1H, t, J=60 Hz), 7.56-7.53 (1H, m), 6.68 (1H, d, J=10 Hz), 6.63 (1H, d, J=3 Hz).

Step E: (R)-tert-Butyl 2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetate According to Step C above, 1-(difluoromethyl)-5-(3-iodo-1H-pyrazol-1-yl)pyridin-2(1H)-one (0.59 g) and (R)-tert-butyl 2-hydroxy-2-((R)-2-methyl-3-oxomorpholin-2-yl) acetate (0.43 g) were used instead of 5-bromo-1-difluoromethyl-1H-pyridin-2-one and 3-aminopyrazole to obtain (R)-tert-butyl 2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetate, as a brown powder. LCMS 477 (M+Na)⁺.

Step F: (R)-2-((R)-4-(1-(1-(Difluoromethyl)-6-oxo-1,6-dihydropyridin-3-yl)-1H-pyrazol-3-yl)-2-methyl-3-oxomorpholin-2-yl)-2-hydroxyacetic acid A solution of (R)-tert-butyl 2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetate (68.3 mg) in 4M HCl-dioxane (2 mL) was stirred for 1 h at room temperature and for 2 h at 40° C. The organic solvent was evaporated under reduced pressure to afford the desired (R)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetic acid, as a colorless solid, which was used in the next step without further purification. LCMS 399 (M+H)⁺. ¹H NMR (300 MHz, DMSO-d₆): δ 8.36 (1H, d, J=2 Hz), 8.16-8.11 (2H, m), 7.91 (1H, t, J=60 Hz), 7.00-6.96 (1H, m), 6.75-6.69 (1H, m), 4.22 (1H, s), 4.19-4.11 (1H, m), 4.03-3.86 (3H, m), 1.51 (3H, s).

Step G: (R)—N-(3-Aminobenzo[d]isoxazol-6-yl)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetamide To a suspension of (R)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetic acid (58.0 mg), HOAt (19.8 mg) and 1,2-benzisoxazole-3,6-diamine (65.2 mg) in DMF (2 mL) was added WSC HCl (1-(3-dimethylaminopropyl)-3-ethylcarbodiimide hydrochloride, 83.7 mg) at room temperature. The reaction mixture was stirred for 16 h at room temperature. It was diluted with water and extracted with EtOAc. The organic layer was washed with 1N HCl aq., sat. NaHCO₃ aq. and brine, dried over Na₂SO₄, filtered and concentrated. The residue was purified by silica gel flash chromatography (eluent:Hexane:EtOAc=50:50~0:100) to give (R)—N-(3-aminobenzo[d]isoxazol-6-yl)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetamide, as a colorless solid. LCMS 530 (M+H)⁺. ¹H NMR (300 MHz, DMSO-d₆): δ 9.92 (1H, s), 8.39 (1H, d, J=3 Hz), 8.18-8.11 (2H, m), 8.00 (1H, d, J=1 Hz), 7.92 (1H, t, J=60 Hz), 7.69 (1H, d, J=9 Hz), 7.54 (1H, dd, J=9, 1 Hz), 7.01 (1H, d, J=3 Hz), 6.73 (1H, d, J=10 Hz), 6.46 (1H, s), 6.33 (2H, s), 4.39 (1H, s), 4.26-4.16 (1H, m), 4.06-3.92 (3H, m), 1.56 (3H, s).

(FIXa IC50: 11.09 nM)

Example 77

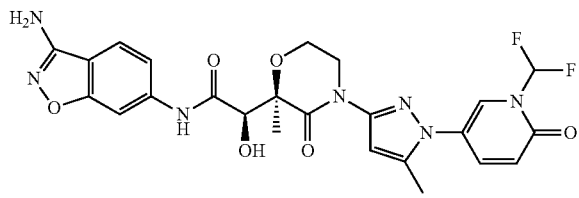

(R)—N-(3-Aminobenzo[d]isoxazol-6-yl)-2-((R)-4-(1-(1-(difluoromethyl)-6-oxo-1,6-dihydropyridin-3-yl)-5-methyl-1H-pyrazol-3-yl)-2-methyl-3-oxomorpholin-2-yl)-2-hydroxyacetamide

Step A: 1-(Difluoromethyl)-5-(3-iodo-5-methyl-1H-pyrazol-1-yl)pyridin-2(1H)-one According to Step C in the synthetic method for EXAMPLE 76, 3-iodo-5-methylpyrazole (1.71 g) was used instead of 3-aminopyrazole to obtain 1-(difluoromethyl)-5-(3-iodo-5-methyl-1H-pyrazol-1-yl)pyridin-2(1H)-one, as a colorless solid. LCMS 352 $(M+H)^+$.

Step B: (R)-tert-Butyl 2-((R)-4-(1-(1-(difluoromethyl)-6-oxo-1,6-dihydropyridin-3-yl)-5-methyl-1H-pyrazol-3-yl)-2-methyl-3-oxomorpholin-2-yl)-2-hydroxyacetate According to Step C in the synthetic method for EXAMPLE 76, 1-(difluoromethyl)-5-(3-iodo-5-methyl-1H-pyrazol-1-yl)pyridin-2(1H)-one (0.40 g) and (R)-tert-butyl 2-hydroxy-2-((R)-2-methyl-3-oxomorpholin-2-yl)acetate (0.28 g) were used instead of 5-bromo-1-difluoromethyl-1H-pyridin-2-one and 3-aminopyrazole to obtain (R)-tert-butyl 2-((R)-4-(1-(1-(difluoromethyl)-6-oxo-1,6-dihydropyridin-3-yl)-5-methyl-1H-pyrazol-3-yl)-2-methyl-3-oxomorpholin-2-yl)-2-hydroxyacetate, as a colorless solid. LCMS 491 $(M+Na)^+$.

Step C: (R)-2-((R)-4-(1-(1-(Difluoromethyl)-6-oxo-1,6-dihydropyridin-3-yl)-5-methyl-1H-pyrazol-3-yl)-2-methyl-3-oxomorpholin-2-yl)-2-hydroxyacetic acid According to Step F in the synthetic method for EXAMPLE 76, (R)-tert-butyl 2-((R)-4-(1-(1-(difluoromethyl)-6-oxo-1,6-dihydropyridin-3-yl)-5-methyl-1H-pyrazol-3-yl)-2-methyl-3-oxomorpholin-2-yl)-2-hydroxyacetate (0.15 g) was used instead of (R)-tert-butyl 2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetate to obtain (R)-2-((R)-4-(1-(1-(difluoromethyl)-6-oxo-1,6-dihydropyridin-3-yl)-5-methyl-1H-pyrazol-3-yl)-2-methyl-3-oxomorpholin-2-yl)-2-hydroxyacetic acid, as a colorless solid. LCMS 413 $(M+H)^+$.

Step D: (R)—N-(3-Aminobenzo[d]isoxazol-6-yl)-2-((R)-4-(1-(1-(difluoromethyl)-6-oxo-1,6-dihydropyridin-3-yl)-5-methyl-1H-pyrazol-3-yl)-2-methyl-3-oxomorpholin-2-yl)-2-hydroxyacetamide According to Step G in the synthetic method for EXAMPLE 76, (R)-2-((R)-4-(1-(1-(difluoromethyl)-6-oxo-1,6-dihydropyridin-3-yl)-5-methyl-1H-pyrazol-3-yl)-2-methyl-3-oxomorpholin-2-yl)-2-hydroxyacetic acid (0.15 g) was used instead of (R)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetic acid to obtain (R)—N-(3-aminobenzo[d]isoxazol-6-yl)-2-((R)-4-(1-(1-(difluoromethyl)-6-oxo-1,6-dihydropyridin-3-yl)-5-methyl-1H-pyrazol-3-yl)-2-methyl-3-oxomorpholin-2-yl)-2-hydroxyacetamide, as a colorless solid. LCMS 544 $(M+H)^+$. (FIXa IC50: 26.49 nM)

Example 78

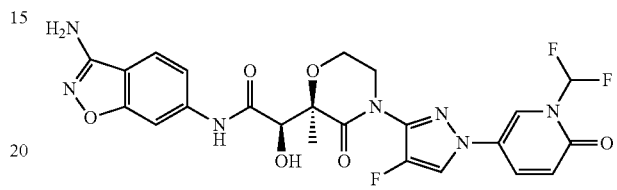

(R)—N-(3-Aminobenzo[d]isoxazol-6-yl)-2-((R)-4-(1-(1-(difluoromethyl)-6-oxo-1,6-dihydropyridin-3-yl)-4-fluoro-1H-pyrazol-3-yl)-2-methyl-3-oxomorpholin-2-yl)-2-hydroxyacetamide

Step A: 4-Fluoro-1H-pyrazol-3-amine

A solution of 3-aminopyrazole (5.86 g) in MeCN (117 mL) and diisopropylethylamine (18.43 ml) was added Selectfluor (24.98 g) at 0° C., and it was stirred for 20 h at 100° C. Then the reaction mixture was filtered with Celite. The filtrate was concentrated in vacuo and purified by column chromatography on NH—SiO$_2$ (heptane/EtOAc=½ to EtOAc) to give 4-fluoro-1H-pyrazol-3-amine, as a brown solid. LCMS 102 $(M+H)^+$. $^1$H NMR (300 MHz, DMSO-d$_6$): δ 11.29 (1H, s), 7.47 (1H, s), 4.58 (2H, s).

Step B: 5-(3-Amino-4-fluoro-1H-pyrazol-1-)-1-(difluoromethyl)pyridin-2(1H)-one According to Step C in the synthetic method for EXAMPLE 76, 4-fluoro-1H-pyrazol-3-amine (0.35 g) was used instead of 3-aminopyrazole to obtain 5-(3-amino-4-fluoro-1H-pyrazol-1-yl)-1-(difluoromethyl)pyridin-2(1H)-one, as a colorless solid. LCMS 245 $(M+H)^+$.

Step C: 1-(Difluoromethyl)-5-(4-fluoro-3-iodo-1H-pyrazol-1-yl)pyridin-2(1H)-one According to Step D in the synthetic method for EXAMPLE 76, 5-(3-amino-4-fluoro-1H-pyrazol-1-yl)-1-(difluoromethyl)pyridin-2(1H)-one, was used instead of 5-(3-amino-1H-pyrazol-1-yl)-1-(difluoromethyl)pyridin-2(1H)-one to obtain 1-(difluoromethyl)-5-(4-fluoro-3-iodo-1H-pyrazol-1-yl)pyridin-2(1H)-one, as a colorless solid. LCMS 356 $(M+H)^+$.

Step D: (R)-tert-Butyl 2-((R)-4-(1-(1-(difluoromethyl)-6-oxo-1,6-dihydropyridin-3-yl)-4-fluoro-1H-pyrazol-3-yl)-3-oxomorpholin-2-yl)-2-hydroxypropanoate According to Step C in the synthetic method for EXAMPLE 76, 1-(difluoromethyl)-5-(4-fluoro-3-iodo-1H- pyrazol-1-yl)pyridin-2(1H)-one (70 mg) and (R)-tert-butyl 2-hydroxy-2-((R)-2-methyl-3-oxomorpholin-2-yl)acetate (58 mg) were used instead of 5-bromo-1-difluoromethyl-1H-pyridin-2-one and 3-aminopyrazole to obtain (R)-tert-butyl 2-((R)-4-(1-(1-(difluoromethyl)-6-oxo-1,6-dihydropyridin-3-yl)-4-fluoro-1H-pyrazol-3-yl)-3-oxomorpholin-2-yl)-2-hydroxypropanoate, as a colorless oil. $^1$H NMR (300 MHz, CDCl$_3$): δ 7.75-7.68 (2H, m), 7.70 (1H, t, J=60 Hz), 7.65-7.61 (1H, m), 6.69 (1H, d, J=11 Hz), 4.42-4.36 (1H, m), 4.21-3.99 (3H, m), 3.82-3.75 (1H, m), 3.74-3.68 (1H, m), 1.71-1.67 (3H, m), 1.57-1.52 (9H, m).

Step E: (R)-2-((R)-4-(1-(1-(Difluoromethyl)-6-oxo-1,6-dihydropyridin-3-yl)-4-fluoro-1H-pyrazol-3-yl)-3-oxomorpholin-2-yl)-2-hydroxypropanoic acid According to Step F in the synthetic method for EXAMPLE 76, (R)-tert-butyl 2-((R)-4-(1-(1-(difluoromethyl)-6-oxo-1,6-dihydropyridin-3-yl)-4-fluoro-1H-pyrazol-3-yl)-3-oxomorpholin-2-yl)-2-hydroxypropanoate (45 mg) was used instead of (R)-tert-butyl 2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetate to obtain (R)-2-((R)-4-(1-(1-(difluoromethyl)-6-oxo-1,6-dihydropyridin-3-yl)-4-fluoro-1H-pyrazol-3-yl)-3-oxomorpholin-2-yl)-2-hydroxypropanoic acid, as a colorless amorphous solid. LCMS 417 (M+H)$^+$.

Step F: (R)—N-(3-Aminobenzo[d]isoxazol-6-yl)-2-((R)-4-(1-(1-(difluoromethyl)-6-oxo-1,6-dihydropyridin-3-yl)-4-fluoro-1H-pyrazol-3-yl)-2-methyl-3-oxomorpholin-2-yl)-2-hydroxyacetamide According to Step G in the synthetic method for EXAMPLE 76, (R)-2-((R)-4-(1-(1-(difluoromethyl)-6-oxo-1,6-dihydropyridin-3-yl)-4-fluoro-1H-pyrazol-3-yl)-3-oxomorpholin-2-yl)-2-hydroxypropanoic acid (40 mg) was used instead of (R)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetic acid to obtain (R)—N-(3-aminobenzo[d]isoxazol-6-yl)-2-((R)-4-(1-(1-(difluoromethyl)-6-oxo-1,6-dihydropyridin-3-yl)-4-fluoro-1H-pyrazol-3-yl)-2-methyl-3-oxomorpholin-2-yl)-2-hydroxyacetamide, as a colorless solid. LCMS 548 (M+H)$^+$. (FIXa IC50: 25.62 nM)

The following compounds (Table 2) were synthesized using methods analogous to those described for EXAMPLES 72, 73 and 76 from commercially available materials or intermediates whose syntheses are described above.

TABLE 2

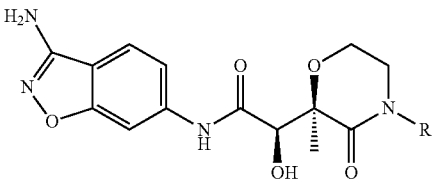

| Example | R | LCMS (M + H)$^+$ | Calc. (M + H)+ | FIXa IC50 (nM) |
|---|---|---|---|---|
| 79 | pyrazole-phenyl-F | 481.11 | 481.16 | 169.7 |
| 80 | pyrazole-phenyl-CN | 488.09 | 488.16 | 25.31 |
| 81 | pyrazole-phenyl-C(O)OMe | 521.00 | 521.17 | 417.7 |
| 82 | pyrazole-phenyl-C(O)OH | 507.06 | 507.15 | 32.75 |
| 83 | pyrazole-phenyl-Cl | 496.92 | 497.13 | 351.6 |
| 84 | pyrazole-phenyl-S(O)$_2$Me | 541.10 | 541.14 | 13.16 |
| 85 | pyrazole-3-pyridyl | 464.01 | 464.16 | 278.9 |
| 86 | pyrazole-pyridyl-CF$_3$ | 531.92 | 532.15 | 414.3 |
| 87 | pyrazole-pyridyl-CF$_3$ | 532.16 | 532.15 | 227.9 |
| 88 | pyrazole-pyridyl-CN | 489.19 | 489.16 | 950.4 |
| 89 | pyrazole-4-pyridyl | 464.03 | 464.16 | 1062 |

TABLE 2-continued
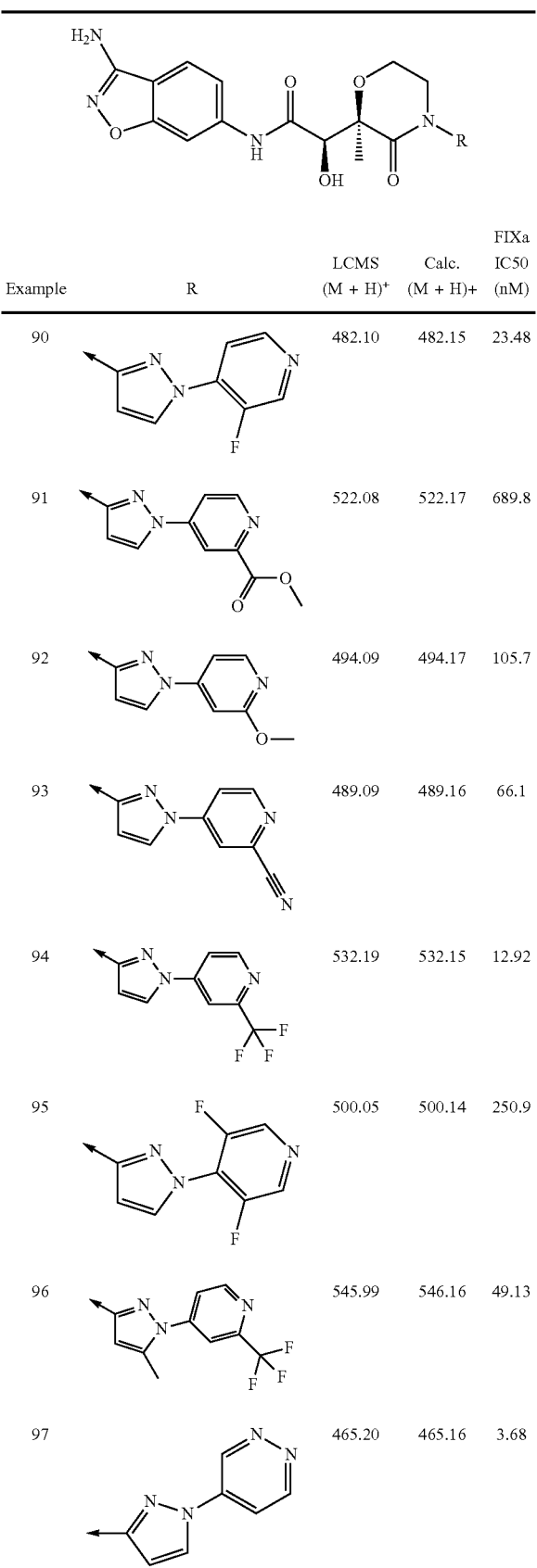
| Example | R | LCMS (M + H)+ | Calc. (M + H)+ | FIXa IC50 (nM) |
|---|---|---|---|---|
| 90 | | 482.10 | 482.15 | 23.48 |
| 91 | | 522.08 | 522.17 | 689.8 |
| 92 | | 494.09 | 494.17 | 105.7 |
| 93 | | 489.09 | 489.16 | 66.1 |
| 94 | | 532.19 | 532.15 | 12.92 |
| 95 | | 500.05 | 500.14 | 250.9 |
| 96 | | 545.99 | 546.16 | 49.13 |
| 97 | | 465.20 | 465.16 | 3.68 |
TABLE 2-continued
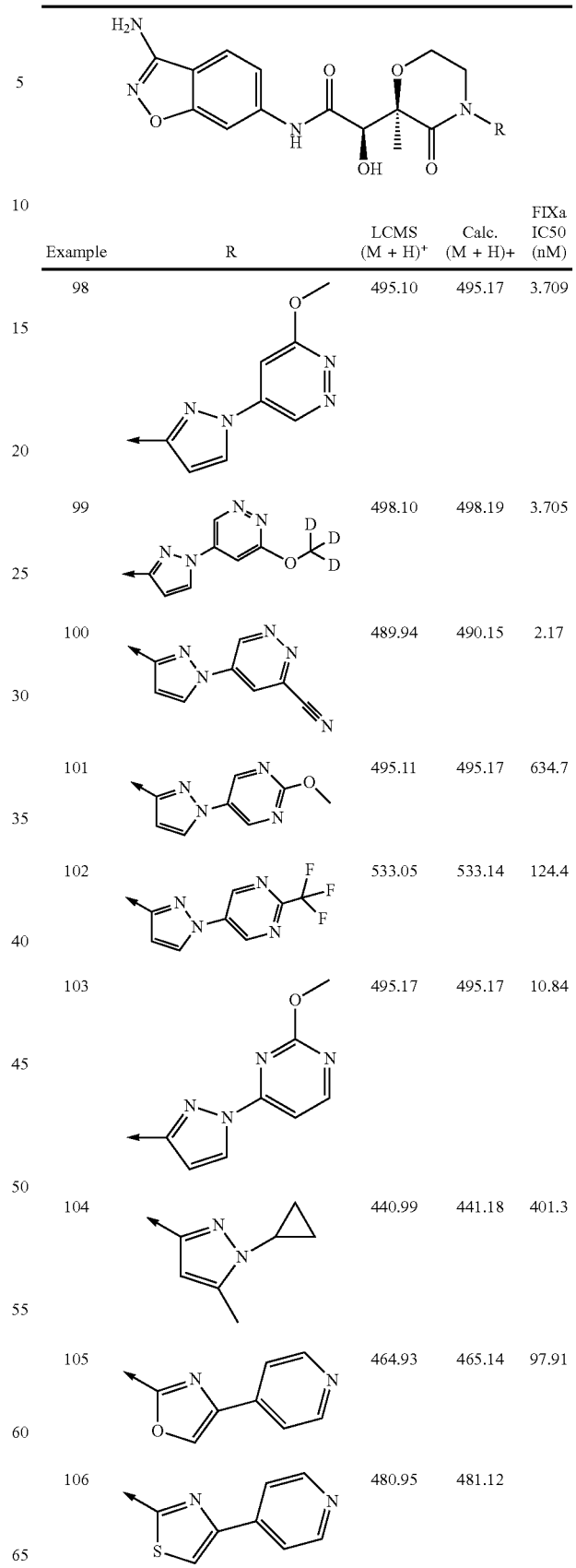
| Example | R | LCMS (M + H)+ | Calc. (M + H)+ | FIXa IC50 (nM) |
|---|---|---|---|---|
| 98 | | 495.10 | 495.17 | 3.709 |
| 99 | | 498.10 | 498.19 | 3.705 |
| 100 | | 489.94 | 490.15 | 2.17 |
| 101 | | 495.11 | 495.17 | 634.7 |
| 102 | | 533.05 | 533.14 | 124.4 |
| 103 | | 495.17 | 495.17 | 10.84 |
| 104 | | 440.99 | 441.18 | 401.3 |
| 105 | | 464.93 | 465.14 | 97.91 |
| 106 | | 480.95 | 481.12 | |

TABLE 2-continued

[Structure: (R)-2-hydroxy-N-(3-aminobenzo[d]isoxazol-6-yl)-2-((R)-2-methyl-3-oxomorpholin-2-yl)acetamide with R group on morpholine N]

| Example | R | LCMS (M + H)+ | Calc. (M + H)+ | FIXa IC50 (nM) |
|---|---|---|---|---|
| 107 | [2-(pyridin-4-yl)thiazol-4-yl] | 480.95 | 481.12 | |
| 108 | [6-(tetrahydropyran-4-yloxy)pyridin-2-yl] | 498.11 | 498.19 | 369.9 |
| 109 | [6-(4-trifluoromethoxyphenyl)pyridin-2-yl] | 557.97 | 558.16 | 379.7 |
| 110 | [6-(4-carboxyphenyl)pyridin-2-yl] | 517.95 | 518.17 | 455.2 |
| 111 | [6-(2-carboxy-4-trifluoromethylphenyl)pyridin-2-yl] | 585.92 | 586.15 | 972.1 |
| 112 | [6-(pyridazin-4-yl)pyridin-2-yl] | 476.05 | 476.16 | 41.6 |
| 113 | [6-(2-trifluoromethylpyrimidin-5-yl)pyridin-2-yl] | 544.01 | 544.16 | 463.8 |
| 114 | [6-(isoxazol-4-yl)pyridin-2-yl] | 464.90 | 465.15 | 45.29 |
| 115 | [6-(3-methylisoxazol-4-yl)pyridin-2-yl] | 479.00 | 479.17 | 68.2 |
| 116 | [6-(3,5-dimethylisoxazol-4-yl)pyridin-2-yl] | 492.94 | 493.18 | 93.53 |
| 117 | [1,7-naphthyridin-2-yl] | 449.02 | 449.15 | 544.2 |
| 118 | [6-(trifluoromethyl)-1,7-naphthyridin-2-yl] | 517.01 | 517.14 | 101.4 |

Example 79

(R)—N-(3-aminobenzo[d]isoxazol-6-yl)-2-((R)-4-(1-(4-fluorophenyl)-1H-pyrazol-3-yl)-2-methyl-3-oxomorpholin-2-yl)-2-hydroxyacetamide,

Example 80

(R)—N-(3-aminobenzo[d]isoxazol-6-yl)-2-((R)-4-(1-(4-cyanophenyl)-1H-pyrazol-3-yl)-2-methyl-3-oxomorpholin-2-yl)-2-hydroxyacetamide,

Example 81 methyl 4-(3-((R)-2-((R)-2-((3-aminobenzo[d]isoxazol-6-yl)amino)-1-hydroxy-2-oxoethyl)-2-methyl-3-oxomorpholino)-1H-pyrazol-1-yl)benzoate,

Example 82

4-(3-((R)-2-((R)-2-((3-aminobenzo[d]isoxazol-6-yl)amino)-1-hydroxy-2-oxoethyl)-2-methyl-3-oxomorpholino)-1H-pyrazol-1-yl)benzoic acid,

Example 83

(R)—N-(3-aminobenzo[d]isoxazol-6-yl)-2-((R)-4-(1-(4-chlorophenyl)-1H-pyrazol-3-yl)-2-methyl-3-oxomorpholin-2-yl)-2-hydroxyacetamide, Example 84

(R)—N-(3-aminobenzo[d]isoxazol-6-yl)-2-hydroxy-2-((R)-2-methyl-4-(1-(4-(methylsulfonyl)phenyl)-1H-pyrazol-3-yl)-3-oxomorpholin-2-yl)acetamide, Example 85

(R)—N-(3-aminobenzo[d]isoxazol-6-yl)-2-hydroxy-2-((R)-2-methyl-3-oxo-4-(1-(pyridin-3-yl)-1H-pyrazol-3-yl)morpholin-2-yl)acetamide, Example 86

(R)—N-(3-aminobenzo[d]isoxazol-6-yl)-2-hydroxy-2-((R)-2-methyl-3-oxo-4-(1-(6-(trifluoromethyl)pyridin-3-yl)-1H-pyrazol-3-yl)morpholin-2-yl)acetamide, Example 87

(R)—N-(3-aminobenzo[d]isoxazol-6-yl)-2-hydroxy-2-((R)-2-methyl-3-oxo-4-(1-(5-(trifluoromethyl)pyridin-3-yl)-1H-pyrazol-3-yl)morpholin-2-yl)acetamide, Example 88

(R)—N-(3-aminobenzo[d]isoxazol-6-yl)-2-((R)-4-(1-(5-cyanopyridin-3-yl)-1H-pyrazol-3-yl)-2-methyl-3-oxo-morpholin-2-yl)-2-hydroxyacetamide, Example 89

(R)—N-(3-aminobenzo[d]isoxazol-6-yl)-2-hydroxy-2-((R)-2-methyl-3-oxo-4-(1-(pyridin-4-yl)-1H-pyrazol-3-yl)morpholin-2-yl)acetamide, Example 90

(R)—N-(3-aminobenzo[d]isoxazol-6-yl)-2-((R)-4-(1-(3-fluoropyridin-4-yl)-1H-pyrazol-3-yl)-2-methyl-3-oxo-morpholin-2-yl)-2-hydroxyacetamide, Example 91 methyl 4-(3-((R)-2-((R)-2-((3-aminobenzo[d]isoxazol-6-yl)amino)-1-hydroxy-2-oxoethyl)-2-methyl-3-oxomorpholino)-1H-pyrazol-1-yl)picolinate, Example 92

(R)—N-(3-aminobenzo[d]isoxazol-6-yl)-2-hydroxy-2-((R)-4-(1-(2-methoxypyridin-4-yl)-1H-pyrazol-3-yl)-2-methyl-3-oxomorpholin-2-yl)acetamide, Example 93

(R)—N-(3-aminobenzo[d]isoxazol-6-yl)-2-hydroxy-2-((R)-4-(1-(2-cyanopyridin-4-yl)-1H-pyrazol-3-yl)-2-methyl-3-oxo-morpholin-2-yl)-2-hydroxyacetamide, Example 94

(R)—N-(3-aminobenzo[d]isoxazol-6-yl)-2-hydroxy-2-((R)-2-methyl-3-oxo-4-(1-(2-(trifluoromethyl)pyridin-4-yl)-1H-pyrazol-3-yl)morpholin-2-yl)acetamide, Example 95

(R)—N-(3-aminobenzo[d]isoxazol-6-yl)-2-((R)-4-(1-(3,5-difluoropyridin-4-yl)-1H-pyrazol-3-yl)-2-methyl-3-oxo-morpholin-2-yl)-2-hydroxyacetamide, Example 96

(R)—N-(3-aminobenzo[d]isoxazol-6-yl)-2-hydroxy-2-((R)-2-methyl-4-(5-methyl-1-(2-(trifluoromethyl)pyridin-4-yl)-1H-pyrazol-3-yl)-3-oxomorpholin-2-yl)acetamide, Example 97

(R)—N-(3-aminobenzo[d]isoxazol-6-yl)-2-hydroxy-2-((R)-2-methyl-3-oxo-4-(1-(pyridazin-4-yl)-1H-pyrazol-3-yl)morpholin-2-yl)acetamide, Example 98

(R)—N-(3-aminobenzo[d]isoxazol-6-yl)-2-hydroxy-2-((R)-4-(1-(6-methoxypyridazin-4-yl)-1H-pyrazol-3-yl)-2-methyl-3-oxomorpholin-2-yl)acetamide, Example 99

(2R)—N-(3-amino-1,2-benzoxazol-6-yl)-2-hydroxy-2-[(2R)-2-methyl-3-oxo-4-[1-[6-(trideuteriomethoxy)pyridazin-4-yl]pyrazol-3-yl]morpholin-2-yl]acetamide, Example 100

(R)—N-(3-aminobenzo[d]isoxazol-6-yl)-2-((R)-4-(1-(6-cyanopyridazin-4-yl)-1H-pyrazol-3-yl)-2-methyl-3-oxo-morpholin-2-yl)-2-hydroxyacetamide, Example 101

(R)—N-(3-aminobenzo[d]isoxazol-6-yl)-2-hydroxy-2-((R)-4-(1-(2-methoxypyrimidin-5-yl)-1H-pyrazol-3-yl)-2-methyl-3-oxomorpholin-2-yl)acetamide, Example 102

(R)—N-(3-aminobenzo[d]isoxazol-6-yl)-2-hydroxy-2-((R)-2-methyl-3-oxo-4-(1-(2-(trifluoromethyl)pyrimidin-5-yl)-1H-pyrazol-3-yl)morpholin-2-yl)acetamide, Example 103

(R)—N-(3-aminobenzo[d]isoxazol-6-yl)-2-hydroxy-2-((R)-4-(1-(2-methoxypyrimidin-4-yl)-1H-pyrazol-3-yl)-2-methyl-3-oxomorpholin-2-yl)acetamide,

Example 104

(R)—N-(3-aminobenzo[d]isoxazol-6-yl)-2-((R)-4-(1-cyclopropyl-5-methyl-1H-pyrazol-3-yl)-2-methyl-3-oxomorpholin-2-yl)-2-hydroxyacetamide,

Example 105

(R)—N-(3-aminobenzo[d]isoxazol-6-yl)-2-hydroxy-2-((R)-2-methyl-3-oxo-4-(4-(pyridin-4-yl)oxazol-2-yl)morpholin-2-yl)acetamide,

Example 106

(R)—N-(3-aminobenzo[d]isoxazol-6-yl)-2-hydroxy-2-((R)-2-methyl-3-oxo-4-(4-(pyridin-4-yl)thiazol-2-yl)morpholin-2-yl)acetamide,

Example 107

(R)—N-(3-aminobenzo[d]isoxazol-6-yl)-2-hydroxy-2-((R)-2-methyl-3-oxo-4-(2-(pyridin-4-yl)thiazol-4-yl)morpholin-2-yl)acetamide,

Example 108

(R)—N-(3-aminobenzo[d]isoxazol-6-yl)-2-hydroxy-2-((R)-2-methyl-3-oxo-4-(6-((tetrahydro-2H-pyran-4-yl)oxy)pyridin-2-yl)morpholin-2-yl)acetamide,

Example 109

(R)—N-(3-aminobenzo[d]isoxazol-6-yl)-2-hydroxy-2-((R)-2-methyl-3-oxo-4-(6-(4-(trifluoromethoxy)phenyl)pyridin-2-yl)morpholin-2-yl)acetamide,

Example 110

4-(6-((R)-2-((R)-2-((3-aminobenzo[d]isoxazol-6-yl)amino)-1-hydroxy-2-oxoethyl)-2-methyl-3-oxomorpholino)pyridin-2-yl)benzoic acid,

Example 111

2-(6-((R)-2-((R)-2-((3-aminobenzo[d]isoxazol-6-yl)amino)-1-hydroxy-2-oxoethyl)-2-methyl-3-oxomorpholino)pyridin-2-yl)-5-(trifluoromethyl)benzoic acid,

Example 112

(R)—N-(3-aminobenzo[d]isoxazol-6-yl)-2-hydroxy-2-((R)-2-methyl-3-oxo-4-(6-(pyridazin-4-yl)pyridin-2-yl)morpholin-2-yl)acetamide,

Example 113

(R)—N-(3-aminobenzo[d]isoxazol-6-yl)-2-hydroxy-2-((R)-2-methyl-3-oxo-4-(6-(2-(trifluoromethyl)pyrimidin-5-yl)pyridin-2-yl)morpholin-2-yl)acetamide,

Example 114

(R)—N-(3-aminobenzo[d]isoxazol-6-yl)-2-hydroxy-2-((R)-4-(6-(isoxazol-4-yl)pyridin-2-yl)-2-methyl-3-oxomorpholin-2-yl)acetamide,

Example 115

(R)—N-(3-aminobenzo[d]isoxazol-6-yl)-2-hydroxy-2-((R)-2-methyl-4-(6-(3-methylisoxazol-4-yl)pyridin-2-yl)-3-oxomorpholin-2-yl)acetamide,

Example 116

(R)—N-(3-aminobenzo[d]isoxazol-6-yl)-2-((R)-4-(6-(3,5-dimethylisoxazol-4-yl)pyridin-2-yl)-2-methyl-3-oxomorpholin-2-yl)-2-hydroxyacetamide,

Example 117

(R)—N-(3-aminobenzo[d]isoxazol-6-yl)-2-hydroxy-2-((R)-2-methyl-4-(1,7-naphthyridin-2-yl)-3-oxomorpholin-2-yl)acetamide,

Example 118

(R)—N-(3-aminobenzo[d]isoxazol-6-yl)-2-hydroxy-2-((R)-2-methyl-3-oxo-4-(6-(trifluoromethyl)-1,7-naphthyridin-2-yl)morpholin-2-yl)acetamide.

The following compounds (Table 3) were synthesized using methods analogous to those described for EXAMPLES 1, 2, 3, 4, and 7 from commercially available materials or intermediates whose syntheses are described above.

TABLE 3

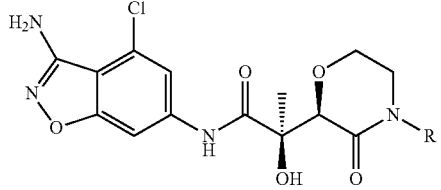

| Example | R | LCMS (M + H)+ | Calc. (M + H)+ | FIXa IC50 (nM) |
|---|---|---|---|---|
| 119 | ![pyrazole-pyridin-4-yl] | 498.00 | 498.13 | 224.3 |
| 120 | ![pyrazole-pyridine-CF3] | 566.11 | 566.11 | 1049 |

TABLE 3-continued

[Structure: H2N-substituted chlorobenzo[d]isoxazole linked via NH-C(=O)-C(CH3)(OH) to morpholinone with N-R substituent]

| Example | R | LCMS (M + H)+ | Calc. (M + H)+ | FIXa IC50 (nM) |
|---|---|---|---|---|
| 121 | [pyrazole-pyridine with CF3 and F] | 584.03 | 584.10 | 193.5 |
| 122 | [pyrazole-pyridazine] | 499.16 | 499.12 | 129 |
| 123 | [F-pyrazole-pyridazine] | 517.11 | 517.87 | 21.75 |
| 124 | [F-pyrazole-cyanopyridazine] | 541.91 | 542.10 | 158.4 |
| 125 | [F-pyrazole-methoxypyridazine] | 546.99 | 547.13 | 45.02 |
| 126 | [F-pyrazole-CF3-pyridazine] | 585.24 | 585.10 | 31.58 |

Example 119

(R)—N-(3-amino-4-chlorobenzo[d]isoxazol-6-yl)-2-hydroxy-2-((R)-3-oxo-4-(1-(pyridin-4-yl)-1H-pyrazol-3-yl)morpholin-2-yl)propanamide, Example 120

(R)—N-(3-amino-4-chlorobenzo[d]isoxazol-6-yl)-2-hydroxy-2-((R)-3-oxo-4-(1-(2-(trifluoromethyl)pyridin-4-yl)-1H-pyrazol-3-yl)morpholin-2-yl)propanamide, Example 121

(R)—N-(3-amino-4-chlorobenzo[d]isoxazol-6-yl)-2-((R)-4-(4-fluoro-1-(2-(trifluoromethyl)pyridin-4-yl)-1H-pyrazol-3-yl)-3-oxomorpholin-2-yl)-2-hydroxypropanamide, Example 122

(R)—N-(3-amino-4-chlorobenzo[d]isoxazol-6-yl)-2-hydroxy-2-((R)-3-oxo-4-(1-(pyridazin-4-yl)-1H-pyrazol-3-yl)morpholin-2-yl)propanamide, Example 123

(R)—N-(3-amino-4-chlorobenzo[d]isoxazol-6-yl)-2-((R)-4-(4-fluoro-1-(pyridazin-4-yl)-1H-pyrazol-3-yl)-3-oxomorpholin-2-yl)-2-hydroxypropanamide, Example 124

(R)—N-(3-amino-4-chlorobenzo[d]isoxazol-6-yl)-2-((R)-4-(1-(6-cyanopyridazin-4-yl)-4-fluoro-1H-pyrazol-3-yl)-3-oxomorpholin-2-yl)-2-hydroxypropanamide, Example 125

(R)—N-(3-amino-4-chlorobenzo[d]isoxazol-6-yl)-2-((R)-4-(4-fluoro-1-(6-methoxypyridazin-4-yl)-1H-pyrazol-3-yl)-3-oxomorpholin-2-yl)-2-hydroxypropanamide, Example 126

(R)—N-(3-amino-4-chlorobenzo[d]isoxazol-6-yl)-2-((R)-4-(4-fluoro-1-(6-(trifluoromethyl)pyridazin-4-yl)-1H-pyrazol-3-yl)-3-oxomorpholin-2-yl)-2-hydroxypropanamide.

The following compounds (Table 4) were synthesized using methods analogous to those described for EXAMPLES 72, 73 and 76 from commercially available materials or intermediates whose syntheses are described above.

TABLE 4

[Structure: H2N-substituted chlorobenzo[d]isoxazole linked via NH-C(=O)-C(CH3)(OH) to morpholinone with N-R substituent, with methyl at alpha carbon]

| Example | R | LCMS (M + H)+ | Calc. (M + H)+ | FIXa IC50 (nM) |
|---|---|---|---|---|
| 127 | [pyrazole-phenyl-SO2CH3] | 575.08 | 575.10 | 746 |
| 128 | [pyrazole-pyridine] | 498.00 | 498.13 | 224.3 |

Example 127

(R)—N-(3-amino-4-chlorobenzo[d]isoxazol-6-yl)-2-hydroxy-2-((R)-2-methyl-4-(1-(4-(methylsulfonyl)phenyl)-1H-pyrazol-3-yl)-3-oxomorpholin-2-yl)acetamide, Example 128

(R)—N-(3-amino-4-chlorobenzo[d]isoxazol-6-yl)-2-hydroxy-2-((R)-2-methyl-3-oxo-4-(1-(pyridin-4-yl)-1H-pyrazol-3-yl)morpholin-2-yl)acetamide.

The following compounds (Table 5) were synthesized using methods analogous to those described for EXAMPLES 1, 2, 3, 4, and 7 from commercially available materials or intermediates whose syntheses are described above.

TABLE 5
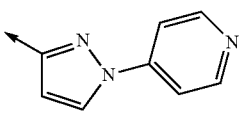
| Example | R | LCMS (M + H)+ | Calc. (M + H)+ | FIXa IC50 (nM) |
|---|---|---|---|---|
| 129 | 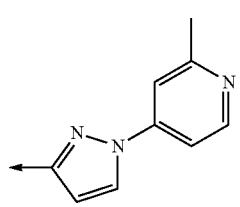 | 482.18 | 482.44 | 49.79 |
| 130 | 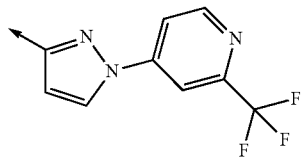 | 496.25 | 496.17 | 211.2 |
| 131 | 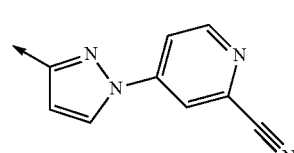 | 550.14 | 550.43 | 95.16 |
| 132 | 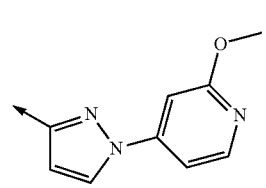 | 507.15 | 507.45 | 117.4 |
| 133 | 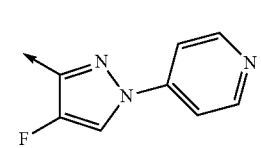 | 512.00 | 512.16 | 275.3 |
| 134 | 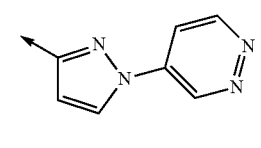 | 500.14 | 500.43 | 55.18 |
| 135 | 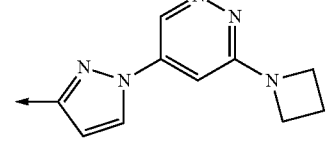 | 483.15 | 483.42 | 10.19 |
| 136 |  | 538.24 | 538.20 | 53.24 |

TABLE 5-continued

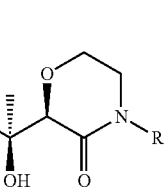

| Example | R | LCMS (M + H)+ | Calc. (M + H)+ | FIXa IC50 (nM) |
|---|---|---|---|---|
| 137 | 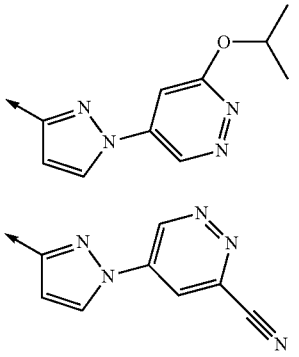 | 541.20 | 541.04 | 190.4 |
| 138 | 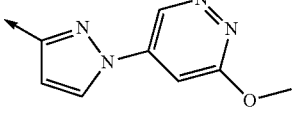 | 508.15 | 507.99 | 7.105 |
| 139 | 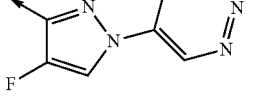 | 513.16 | 512.95 | 13.99 |
| 140 | 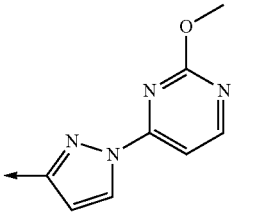 | 501.14 | 501.04 | 5.605 |
| 141 | | 513.20 | 513.16 | 106.8 |

Example 129

(R)—N-(3-amino-4-fluorobenzo[d]isoxazol-6-yl)-2-hydroxy-2-((R)-3-oxo-4-(1-(pyridin-4-yl)-1H-pyrazol-3-yl)morpholin-2-yl)propanamide, Example 130

(R)—N-(3-amino-4-fluorobenzo[d]isoxazol-6-yl)-2-hydroxy-2-((R)-4-(1-(2-methylpyridin-4-yl)-1H-pyrazol-3-yl)-3-oxomorpholin-2-yl)propanamide, Example 131

(R)—N-(3-amino-4-fluorobenzo[d]isoxazol-6-yl)-2-hydroxy-2-((R)-3-oxo-4-(1-(2-(trifluoromethyl)pyridin-4-yl)-1H-pyrazol-3-yl)morpholin-2-yl)propanamide, Example 132

(R)—N-(3-amino-4-fluorobenzo[d]isoxazol-6-yl)-2-((R)-4-(1-(2-cyanopyridin-4-yl)-1H-pyrazol-3-yl)-3-oxomorpholin-2-yl)-2-hydroxypropanamide, Example 133

(R)—N-(3-amino-4-fluorobenzo[d]isoxazol-6-yl)-2-hydroxy-2-((R)-4-(1-(2-methoxypyridin-4-yl)-1H-pyrazol-3-yl)-3-oxomorpholin-2-yl)propanamide, Example 134

(R)—N-(3-amino-4-fluorobenzo[d]isoxazol-6-yl)-2-((R)-4-(4-fluoro-1-(pyridin-4-yl)-1H-pyrazol-3-yl)-3-oxomorpholin-2-yl)-2-hydroxypropanamide,

Example 135

(R)—N-(3-amino-4-fluorobenzo[d]isoxazol-6-yl)-2-hydroxy-2-((R)-3-oxo-4-(1-(pyridazin-4-yl)-1H-pyrazol-3-yl)morpholin-2-yl)propanamide,

Example 136

(R)—N-(3-amino-4-fluorobenzo[d]isoxazol-6-yl)-2-((R)-4-(1-(6-(azetidin-1-yl)pyridazin-4-yl)-1H-pyrazol-3-yl)-3-oxomorpholin-2-yl)-2-hydroxypropanamide,

Example 137

(R)—N-(3-amino-4-fluorobenzo[d]isoxazol-6-yl)-2-hydroxy-2-((R)-4-(1-(6-isopropoxypyridazin-4-yl)-1H-pyrazol-3-yl)-3-oxomorpholin-2-yl)propanamide,

Example 138

(R)—N-(3-amino-4-fluorobenzo[d]isoxazol-6-yl)-2-((R)-4-(1-(6-cyanopyridazin-4-yl)-1H-pyrazol-3-yl)-3-oxomorpholin-2-yl)-2-hydroxypropanamide,

Example 139

(R)—N-(3-amino-4-fluorobenzo[d]isoxazol-6-yl)-2-hydroxy-2-((R)-4-(1-(6-methoxypyridazin-4-yl)-1H-pyrazol-3-yl)-3-oxomorpholin-2-yl)propanamide,

Example 140

(R)—N-(3-amino-4-fluorobenzo[d]isoxazol-6-yl)-2-((R)-4-(4-fluoro-1-(pyridazin-4-yl)-1H-pyrazol-3-yl)-3-oxomorpholin-2-yl)-2-hydroxypropanamide,

Example 141

(R)—N-(3-amino-4-fluorobenzo[d]isoxazol-6-yl)-2-hydroxy-2-((R)-4-(1-(2-methoxypyrimidin-4-yl)-1H-pyrazol-3-yl)-3-oxomorpholin-2-yl)propanamide.

The following compounds (Table 6) were synthesized using methods analogous to those described for EXAMPLES 72, 73 and 76 from commercially available materials or intermediates whose syntheses are described above.

TABLE 6

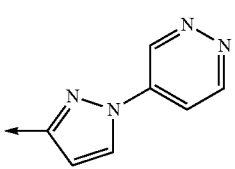

| Example | R | LCMS (M + H)+ | Calc. (M + H)+ | FIXa IC50 (nM) |
|---|---|---|---|---|
| 142 | 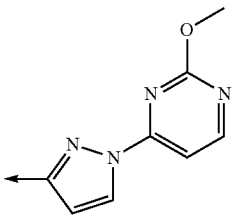 | 483.30 | 483.15 | 6.273 |
| 143 | 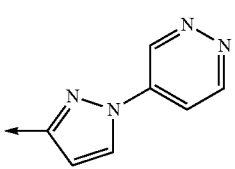 | 513.17 | 513.16 | 22.07 |

Example 142

(R)—N-(3-amino-4-fluorobenzo[d]isoxazol-6-yl)-2-hydroxy-2-((R)-2-methyl-3-oxo-4-(1-(pyridazin-4-yl)-1H-pyrazol-3-yl)morpholin-2-yl)acetamide,

Example 143

(R)—N-(3-amino-4-fluorobenzo[d]isoxazol-6-yl)-2-hydroxy-2-((R)-4-(1-(2-methoxypyrimidin-4-yl)-1H-pyrazol-3-yl)-2-methyl-3-oxomorpholin-2-yl)acetamide.

The following compounds (Table 7) were synthesized using methods analogous to those described for EXAMPLES 1, 2, 3, 4 and 7 from commercially available materials or intermediates whose syntheses are described above.

TABLE 7

| Ex | | LCMS (M + H)+ | Calc. (M + H)+ | FIXa IC50 (nM) |
|---|---|---|---|---|
| 144 | 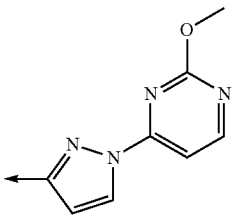 | 465.15 | 465.16 | 457.9 |

TABLE 7-continued

| Ex | | LCMS (M + H)+ | Calc. (M + H)+ | FIXa IC50 (nM) |
|---|---|---|---|---|
| 145 | (structure) | 525.01 | 525.16 | 1098 |
| 146 | (structure) | 496.11 | 496.14 | 28.09 |

Example 144

(R)—N-(3-aminoisoxazolo[4,5-b]pyridin-6-yl)-2-hydroxy-2-((R)-3-oxo-4-(1-(pyridin-4-yl)-1H-pyrazol-3-yl)morpholin-2-yl)propanamide,

Example 145

(R)—N-(3-chloro-2-methyl-1H-indol-5-yl)-2-hydroxy-2-((R)-4-(1-(2-methoxypyridin-4-yl)-1H-pyrazol-3-yl)-3-oxomorpholin-2-yl)propanamide,

Example 146

(R)—N-(3-chloro-2-methyl-1H-indol-5-yl)-2-hydroxy-2-((R)-3-oxo-4-(1-(pyridazin-4-yl)-1H-pyrazol-3-yl)morpholin-2-yl)propanamide.

The following compounds (Table 8) were synthesized using methods analogous to those described for EXAMPLES 72, 73 and 76 from commercially available materials or intermediates whose syntheses are described above.

Example 147

(R)—N-(4-aminoquinazolin-7-yl)-2-hydroxy-2-((R)-2-methyl-3-oxo-4-(1-(pyridin-4-yl)-1H-pyrazol-3-yl)morpholin-2-yl)acetamide

Example 148

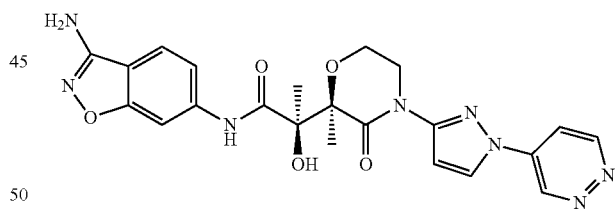

TABLE 8

| Example | | LCMS (M + H)+ | Calc. (M + H)+ |
|---|---|---|---|
| 147 | (structure) | 475.14 | 475.18 |

(R)—N-(3-Aminobenzo[d]isoxazol-6-yl)-2-hydroxy-2-((R)-2-methyl-3-oxo-4-(1-(pyridazin-4-yl)-1H-pyrazol-3-yl)morpholin-2-yl)propanamide Step A: (R)-tert-Butyl 2-hydroxy-2-((R)-4-(4-methoxybenzyl)-2-methyl-3-oxomorpholin-2-yl) propanoate To the stirred solution of (R)-tert-butyl 2-hydroxy-2-((R)-4-(4-methoxybenzyl)-3-oxomorpholin-2-yl)propanoate (5.1 g, 13.96 mmol) in anhydrous THF (70 mL) was added LDA (2.0 M in THF, 19.54 mL, 39.1 mL) at −78° C. under $N_2$. The mixture was stirred at −78° C. for 60 min, followed by addition of MeI (2.62 mL, 41.9 mmol) at −78° C. The mixture was slowly warmed up to room temperature, and stirred at room temperature overnight. The reaction was quenched by addition of satd. $NH_4Cl$, and the mixture was partitioned between EtOAc and water. The aqueous was extracted with EtOAc three times. The organic phases were combined, dried over $MgSO_4$, filtered, concentrated in vacuo and purified by flash chromatography (Isco Combi-Flash, 120 g Silica gel column, 0-60% EtOAc in hexanes) to afford (R)-tert-butyl 2-hydroxy-2-((R)-4-(4-methoxybenzyl)-2-methyl-3-oxomorpholin-2-yl)propanoate, as a colorless oil. LCMS calc.=380.21. found=380.15 $(M+H)^+$. $^1H$ NMR (500 MHz, $CDCl_3$): δ 7.25 (d, J=8.5 Hz, 2H); 6.89 (d, J=8.5 Hz, 2H); 5.29 (s, 1H); 4.88 (d, J=14.5 Hz, 1H); 4.27 (d, J=15.0 Hz, 1H); 3.88-3.80 (m, 2H); 3.82 (s, 3H), 3.43-3.38 (m, 1H); 3.06-3.02 (m, 1H); 1.62 (s, 3H); 1.51 br (s, 12H).

Step B: (R)-tert-Butyl 2-hydroxy-2-((R)-2-methyl-3-oxomorpholin-2-yl)propanoate

To a stirred solution of (R)-tert-butyl 2-hydroxy-2-((R)-4-(4-methoxybenzyl)-2-methyl-3-oxomorpholin-2-yl)propanoate (2.6 g, 6.85 mmol) in MeCN (61.7 mL) and water (6.85 mL) was added CAN (15.03 g, 27.4 mmol) at 0° C. The resulting mixture was stirred at 0° C. for 30 min, then slowly warmed to room temperature and stirred at room temperature for 6 h. To the mixture was added satd. $NaHCO_3$ until pH was adjusted to 4.5-5.0. The resulting suspension was extracted with EtOAc, followed by extraction with 5% MeOH in $CH_2Cl_2$. The organic phases were combined, dried over $MgSO_4$, filtered, and concentrated in vacuo to give the crude product, which was purified by flash chromatography (Isco CombiFlash, 80 g Silica gel column, 0-100% EtOAc in hexanes) to afford (R)-tert-butyl 2-hydroxy-2-((R)-2-methyl-3-oxomorpholin-2-yl)propanoate, as a brown oil. LCMS calc.=260.15. found=260.09 $(M+H)^+$.

Step C: (R)-tert-Butyl 2-hydroxy-2-((R)-2-methyl-3-oxo-4-(1-(pyridazin-4-yl)-1H-pyrazol-3-yl)morpholin-2-yl)propanoate To a vial was added (R)-tert-butyl 2-hydroxy-2-((R)-2-methyl-3-oxomorpholin-2-yl)propanoate (150 mg, 0.578 mmol), 4-(3-iodo-1H-pyrazol-1-yl)pyridazine (189 mg, 0.694 mmol), cesium carbonate (565 mg, 1.735 mmol) and CuI (110 mg, 0.578 mmol). The vial was sealed and degassed, followed by addition of anhydrous 1,4-dioxane and trans-$N^1,N^2$-dimethylcyclohexane-1,2-diamine (0.182 mL, 1.16 mmol). The vial was degassed and flushed with $N_2$ three times, and then warmed up to 60° C. The mixture was stirred at 60° C. under $N_2$ for 15 h. The mixture was cooled to room temperature, diluted with EtOAc and filtered through a pad of celite, then washed with EtOAc and $CH_2Cl_2$. The filtrate was concentrated in vacuo and the resulting crude product was purified by flash chromatography (Isco CombiFlash, 40 g silica gel column, 0-50% acetone in $CH_2Cl_2$) to afford (R)-tert-butyl 2-hydroxy-2-((R)-2-methyl-3-oxo-4-(1-(pyridazin-4-yl)-1H-pyrazol-3-yl)morpholin-2-yl)propanoate, as brownish solid. LCMS calc.=404.19. found=404.14 $(M+H)^+$.

Step D: (R)-2-Hydroxy-2-((R)-2-methyl-3-oxo-4-(1-(pyridazin-4-yl)-1H-pyrazol-3-yl)morpholin-2-yl) propanoic acid To a stirred solution of (R)-tert-butyl 2-hydroxy-2-((R)-2-methyl-3-oxo-4-(1-(pyridazin-4-yl)-1H-pyrazol-3-yl)morpholin-2-yl)propanoate (108 mg, 0.268 mmol) in 4N HCl in 1,4-dioxane (5 mL) was added one drop of water. The mixture was stirred at room temperature overnight. The mixture was concentrated in vacuo afford (R)-2-hydroxy-2-((R)-2-methyl-3-oxo-4-(1-(pyridazin-4-yl)-1H-pyrazol-3-yl)morpholin-2-yl)propanoic acid the HCl salt in quantitative yield. LCMS calc.=348.13. found=348.09 $(M+H)^+$.

Step E: (R)—N-(3-aminobenzo[d]isoxazol-6-yl)-2-hydroxy-2-((R)-2-methyl-3-oxo-4-(1-(pyridazin-4-yl)-1H-pyrazol-3-yl)morpholin-2-yl)propanamide To a stirred solution of (R)-2-hydroxy-2-((R)-2-methyl-3-oxo-4-(1-(pyridazin-4-yl)-1H-pyrazol-3-yl)morpholin-2-yl)propanoic acid (50 mg, 0.130 mmol) in anhydrous DMA (1 mL) was added HOAt (26.6 mg, 0.195 mmol), benzo[d]isoxazole-3,6-diamine (33 mg, 0.221 mmol) and EDC (40.0 mg, 0.208 mmol). After stirring for 2-5 min, DIEA (0.045 mL, 0.261 mmol) was added, and the mixture was stirred at room temperature overnight. The mixture was diluted with 1,4-dioxane and water, neutralized with TFA (44.6 mg, 0.391 mmol), and purified by reversed HPLC (Waters Sunfire, 19×100 mm, 5 uM, MeCN-water with formic acid as eluting solvent) to afford (R)—N-(3-aminobenzo[d]isoxazol-6-yl)-2-hydroxy-2-((R)-2-methyl-3-oxo-4-(1-(pyridazin-4-yl)-1H-pyrazol-3-yl)morpholin-2-yl)propanamide, as an off-white solid. LCMS calc.=479.18. found=479.21 $(M+H)^+$.

(FIXa IC50: 62.63 nM)

The following compounds (Table 9) were synthesized using methods analogous to those described for EXAMPLE 148 from commercially available materials or intermediates whose syntheses are described above.

TABLE 9

| Example | LCMS (M + H)+ | Calc. (M + H)+ | FIXa IC50 (nM) |
|---|---|---|---|
| 149 | 509.12 | 509.19 | 92.36 |

Example 149

(R)—N-(3-aminobenzo[d]isoxazol-6-yl)-2-hydroxy-2-((R)-4-(1-(6-methoxypyridazin-4-yl)-1H-pyrazol-3-yl)-2-methyl-3-oxomorpholin-2-yl)propanamide.

The following compounds (Table 10) were synthesized using methods analogous to those described for EXAMPLES 1, 2, 3, 4, 7, 72, 73 and 76 from commercially available materials or intermediates whose syntheses are described above.

Example 150

(R)—N-(4-(aminomethyl)phenyl)-2-hydroxy-2-((R)-3-oxo-4-(1-(pyridin-4-yl)-1H-pyrazol-3-yl)morpholin-2-yl)propanamide, Example 151

(R)—N-(4-(aminomethyl)-3-fluorophenyl)-2-hydroxy-2-((R)-3-oxo-4-(1-(pyridin-4-yl)-1H-pyrazol-3-yl)morpholin-2-yl)propanamide,

TABLE 10

| Ex | LCMS (M + H)+ | Calc. (M + H)+ | FIXa IC50 (nM) |
|---|---|---|---|
| 150 | 420.16 [M − NH$_2$]+ | 420.17 [M − NH$_2$]+ | 66.17 |
| 151 | 438.18 [M − NH$^2$]+ | 438.16 [M − NH$^2$]+ | 69.96 |
| 152 | 420.16 [M − NH$_2$]+ | 420.17 [M − NH$_2$]+ | 9.685 |
| 153 | 438.27 [M − NH$_2$]+ | 438.16 [M − NH$_2$]+ | 12.65 |

Example 152

(R)—N-(4-(aminomethyl)phenyl)-2-hydroxy-2-((R)-2-methyl-3-oxo-4-(1-(pyridin-4-yl)-1H-pyrazol-3-yl)morpholin-2-yl)acetamide,

Example 153

(R)—N-(4-(aminomethyl)-3-fluorophenyl)-2-hydroxy-2-((R)-2-methyl-3-oxo-4-(1-(pyridin-4-yl)-1H-pyrazol-3-yl)morpholin-2-yl)acetamide,

Intermediates 78 and 79

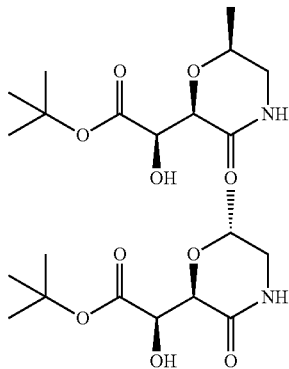

(R)-tert-Butyl 2-hydroxy-2-((2R,6S)-6-methyl-3-oxomorpholin-2-yl)acetate and (R)-tert-Butyl 2-hydroxy-2-((2R,6R)-6-methyl-3-oxomorpholin-2-yl)acetate

Step A: 1-((4-Methoxybenzyl)amino)propan-2-ol

1-Amino-2-propanol (1.00 mL, 13.31 mmol) was added to a stirred solution of p-anisaldehyde (1.70 mL, 13.98 mmol) in absolute EtOH (18.0 mL) at 25° C. and the reaction mixture was stirred overnight. The reaction mixture was cooled to 0° C., sodium borohydride (0.756 g, 19.97 mmol) was added and the reaction mixture was warmed to room temperature and stirred for 7 h. The reaction mixture was diluted with EtOAc and water and the organic layer was separated, washed with brine, dried ($Na_2SO_4$) and concentrated in vacuo to give the crude product. This was purified by flash chromatography (Isco Combiflash Rf, RediSep Silica 80 g, 60 mL/min, loaded using solid loading cartridge after dissolving in $CH_2Cl_2$, 100% $CH_2Cl_2$ for 2 min, gradient to 10% (2M $NH_3$ in MeOH) in $CH_2Cl_2$ over 25 min, isocratic at 10% (2M $NH_3$ in MeOH) in $CH_2Cl_2$ for 23 min) to afford 1-((4-methoxybenzyl)amino)propan-2-ol, as a colorless oil. LCMS calc.=196.13. found=196.21 $(M+H)^+$. $^1H$ NMR (600 MHz, $CH_3CN-d_3$): δ 7.23 (d, J=8.3 Hz, 2H); 6.86 (d, J=8.5 Hz, 2H); 3.75 (s, 3H); 3.71-3.62 (m, 3H); 2.54 (dd, J=11.9, 3.7 Hz, 1H); 2.35 (dd, J=11.9, 8.5 Hz, 1H); 1.94-1.91 (m, 1H); 1.04 (d, J=6.2 Hz, 3H).

Step B: 2-Chloro-N-(4-methoxybenzyl)propan-1-amine

Thionyl chloride (1.72 mL, 23.63 mmol) was added to a stirred solution of 1-((4-methoxybenzyl)amino)propan-2-ol (2.3072 g, 11.82 mmol) in dry 1,2-dichloroethane (59.1 mL) and the resulting solution was heated at 60° C. for 4 h. After this time the mixture was concentrated in vacuo to give the crude product as an HCl salt. This was partitioned between MTBE and satd aq. $NaHCO_3$. The aqueous layer was extracted with MTBE (2×). The combined organic layers were dried ($Na_2SO_4$) and concentrated in vacuo to give crude 2-chloro-N-(4-methoxybenzyl)propan-1-amine, as a free base. This was used in the next step without any further purification. LCMS calc.=214.10. found=214.17 $(M+H)^+$. $^1H$ NMR (600 MHz, $CH_3CN-d_3$): δ 7.55 (d, J=8.4 Hz, 2H); 6.95 (d, J=8.5 Hz, 2H); 4.65-4.58 (m, 1H); 4.21-4.02 (m, 3H); 3.80 (s, 3H); 3.23-3.16 (m, 1H); 3.05-2.98 (m, 1H); 1.52 (d, J=6.7 Hz, 3H).

Step C: (2R,3R)-2,3-Diacetoxy-4-((2-chloropropyl)(4-methoxybenzyl)amino)-4-oxobutanoic acid A solution of 2-chloro-N-(4-methoxybenzyl)propan-1-amine (2.53 g, 11.84 mmol) in dry THF (59.2 mL) was added a to stirred solution of (+)-diacetyl-L-tartaric anhydride (2.61 g, 12.08 mmol) in dry THF (59.2 mL) at 0° C. under $N_2$ and the reaction was stirred at 4° C. overnight (reaction was transferred to refrigerator for overnight portion, no stirring). The reaction was concentrated in vacuo to afford crude (2R,3R)-2,3-diacetoxy-4-((2-chloropropyl)(4-methoxybenzyl)amino)-4-oxobutanoic acid, which was carried forward without any further purification. LCMS calc.=430.13. found=430.06 $(M+H)^+$.

Step D: (2R,3R)-1-(tert-Butoxy)-4-((2-chloropropyl)(4-methoxybenzyl)amino)-1,4-dioxobutane-2,3-diyl diacetate 2-tert-Butyl-1,3-diisopropylisourea (8.73 mL, 37.3 mmol) was added to a stirred solution of (2R,3R)-2,3-diacetoxy-4-((2-chloropropyl)(4-methoxybenzyl)amino)-4-oxobutanoic acid (5.09 g, 11.84 mmol) in dry THF (118 mL) and the mixture was heated at 60° C. under a reflux condenser under $N_2$. After 4 h another 1.05 eq of 2-tert-butyl-1,3-diisopropylisourea was added and the reaction was heated at 60° C. for 1 h. The reaction mixture was concentrated in vacuo to give the crude product. This was purified by flash chromatography (Isco Combiflash Rf, RediSep Silica 80 g, 60 mL/min, loaded using solid loading cartridge after dissolving in $CH_2Cl_2$, 100% hexanes for 3 min, gradient to 50% EtOAc in hexanes over 24 min, isocratic at 50% EtOAc in hexanes for 23 min) to afford (2R,3R)-1-(tert-butoxy)-4-((2-chloropropyl)(4-methoxybenzyl)amino)-1,4-dioxobutane-2,3-diyl diacetate, as a colorless oil. LCMS calc.=486.19. found=486.18 $(M+H)^+$.

Step E: (2R,3R)-tert-Butyl 4-((2-chloropropyl)(4-methoxybenzyl)amino)-2,3-dihydroxy-4-oxobutanoate Potassium cyanide (0.293 g, 4.49 mmol) was added to a stirred solution of (2R,3R)-1-(tert-butoxy)-4-((2-chloropropyl)(4-methoxybenzyl)amino)-1,4-dioxobutane-2,3-diyl diacetate (4.20 g, 8.64 mmol) in MeOH (86 mL) at 0° C. under $N_2$. The resulting mixture was stirred at 0° C. for 4 h. The reaction mixture was diluted with water and extracted with MTBE (3×). The combined extracts were dried ($Na_2SO_4$) and concentrated in vacuo to afford (2R,3R)-tert-butyl 4-((2-chloropropyl)(4-methoxybenzyl)amino)-2,3-dihydroxy-4-oxobutanoate, as a colorless oil. This was carried forward with no further purification. LCMS calc.=402.17. found=402.17 $(M+H)^+$.

Step F: (R)-tert-Butyl 2-hydroxy-2-((2R,6S)-4-(4-methoxybenzyl)-6-methyl-3-oxomorpholin-2-yl)acetate and (R)-tert-Butyl 2-hydroxy-2-((2R,6R)-4-(4-methoxybenzyl)-6-methyl-3-oxomorpholin-2-yl)acetate Benzyltrimethylammonium hydroxide (40 wt % in MeOH) (9.50 mL, 20.90 mmol) was added to a stirred mixture of (2R,3R)-tert-butyl 4-((2-chloropropyl)(4-methoxybenzyl)amino)-2,3-dihydroxy-4-oxobutanoate (4.20 g, 10.45 mmol), CH$_2$Cl$_2$ (85 mL) and water (19.7 mL) at 25° C. and the mixture was stirred for 4 h. The mixture was diluted with water and extracted with CH$_2$Cl$_2$ (3×). The combined extracts were dried (Na$_2$SO$_4$) and concentrated in vacuo to give the crude product. This was purified by flash chromatography (Isco Combiflash Rf, Gold RediSep Silica 80 g, 60 mL/min, loaded using solid loading cartridge after dissolving in CH$_2$Cl$_2$, 100% toluene for 3 min, gradient to 50% EtOAc in toluene over 42 min, isocratic at 50% EtOAc in toluene for 5 min) to afford a mixture of desired product diastereoisomers. This was purified by chiral SFC (AS, 20×250 mm, 20% 2:1 MeOH:MeCN/CO$_2$, 35° C.) to afford the two diastereoisomers in order of elution (R)-tert-butyl 2-hydroxy-2-((2R,6S)-4-(4-methoxybenzyl)-6-methyl-3-oxomorpholin-2-yl)acetate and (R)-tert-butyl 2-hydroxy-2-((2R,6R)-4-(4-methoxybenzyl)-6-methyl-3-oxomorpholin-2-yl)acetate, as colorless solids. Diastereoisomer 1: LCMS calc.=366.19. found=366.20 (M+H)$^+$. $^1$H NMR (600 MHz, CHCl$_3$-d): δ 7.20 (d, J=8.4 Hz, 2H); 6.84 (d, J=8.5 Hz, 2H); 4.71 (s, 1H); 4.62 (d, J=14.6 Hz, 1H); 4.52 (d, J=2.1 Hz, 1H); 4.47 (d, J=14.6 Hz, 1H); 3.88-3.84 (m, 1H); 3.78 (s, 3H); 3.15 (t, J=11.3 Hz, 1H); 2.98-2.91 (m, 1H); 1.48 (s, 9H); 1.14 (d, J=6.2 Hz, 3H). Diastereoisomer 2: LCMS calc.=366.19. found=366.20 (M+H)$^+$. $^1$H NMR (600 MHz, CHCl$_3$-d): δ 7.20 (d, J=8.4 Hz, 2H); 6.85 (d, J=8.5 Hz, 2H); 4.81 (d, J=2.3 Hz, 1H); 4.65 (d, J=14.6 Hz, 1H); 4.60 (d, J=2.4 Hz, 1H); 4.51 (d, J=14.7 Hz, 1H); 4.49-4.45 (m, 1H); 3.78 (s, 3H); 3.19-3.09 (m, 1H); 3.05 (dd, J=12.3, 8.7 Hz, 1H); 1.49 (s, 9H); 1.07 (d, J=6.3 Hz, 3H).

Step G: (R)-tert-Butyl 2-hydroxy-2-((2R,6S)-6-methyl-3-oxomorpholin-2-yl)acetate Ceric ammonium nitrate (2.272 g, 4.14 mmol) was added to a stirred solution of (R)-tert-butyl 2-hydroxy-2-((2R,6S)-4-(4-methoxybenzyl)-6-methyl-3-oxomorpholin-2-yl)acetate (0.3786 g, 1.036 mmol) in MeCN (13.3 mL) and water (1.5 mL) at 0° C. The reaction was warmed to room temperature and stirred for 5 h. The reaction was diluted with satd aq. NaHCO$_3$ and the resulting precipitate was collected by filtration and washed with CH$_2$Cl$_2$. The organic layer of the filtrate was separated and the aqueous layer was further extracted with CH$_2$Cl$_2$ (2×). The combined organic extracts were dried (Na$_2$SO$_4$) and concentrated in vacuo to give the crude product. This was left on the high vacuum pump for 3 days during which time the 4-MeO-benzaldehyde byproduct was removed to afford the desired product (R)-tert-butyl 2-hydroxy-2-((2R,6S)-6-methyl-3-oxomorpholin-2-yl)acetate, as a colorless solid. LCMS calc.=246.13. found=246.20 (M+H)$^+$. $^1$H NMR (500 MHz, CHCl$_3$-d): δ 7.20 (s, 1H); 4.64 (d, J=7.6 Hz, 1H); 4.48 (d, J=2.1 Hz, 1H); 3.98-3.83 (m, 1H); 3.41 (d, J=12.2 Hz, 1H); 3.33-3.15 (m, 2H); 1.50 (s, 9H); 1.23 (d, J=6.2 Hz, 3H).

Step H: (R)-tert-Butyl 2-hydroxy-2-((2R,6R)-6-methyl-3-oxomorpholin-2-yl)acetate Ceric ammonium nitrate (1.479 g, 2.70 mmol) was added to a stirred solution of (R)-tert-butyl 2-hydroxy-2-((2R,6R)-4-(4-methoxybenzyl)-6-methyl-3-oxomorpholin-2-yl)acetate (0.2465 g, 0.675 mmol) in MeCN (8.7 mL) and water (0.96 mL) at 0° C. The reaction was warmed to room temperature and stirred for 5 h. The reaction was diluted with satd aq. NaHCO$_3$ and the resulting precipitate was collected by filtration and washed with CH$_2$Cl$_2$. The organic layer of the filtrate was separated and the aqueous layer was further extracted with CH$_2$Cl$_2$ (2×). The combined organic extracts were dried (Na$_2$SO$_4$) and concentrated in vacuo to give the crude product. This was left on the high vacuum pump for 3 days during which time the 4-MeO-benzaldehyde byproduct was removed to afford the desired product (R)-tert-butyl 2-hydroxy-2-((2R,6R)-6-methyl-3-oxomorpholin-2-yl)acetate, as a colorless solid. LCMS calc.=246.13. found=246.20 (M+H)$^+$. $^1$H NMR (500 MHz, CHCl$_3$-d): δ 7.45 (s, 1H); 4.72 (s, 1H); 4.56 (d, J=2.3 Hz, 1H); 4.49 (d, J=9.8 Hz, 1H); 3.55 (s, 1H); 3.39-3.32 (m, 1H); 3.22-3.04 (m, 1H); 1.51 (s, 9H); 1.18 (d, J=6.3 Hz, 3H).

Example 154

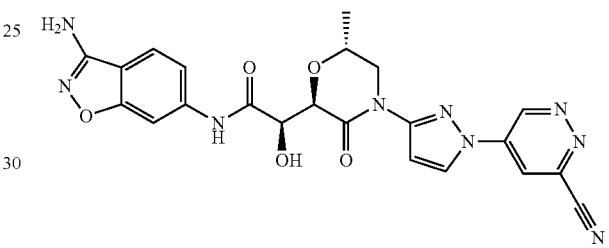

(R)—N-(3-Aminobenzo[d]isoxazol-6-yl)-2-((2R,6R)-4-(1-(6-cyanopyridazin-4-yl)-1H-pyrazol-3-yl)-6-methyl-3-oxomorpholin-2-yl)-2-hydroxyacetamide Step A: (R)-tert-Butyl 2-hydroxy-2-((2R,6R)-6-methyl-3-oxomorpholin-2-yl)acetate Ceric ammonium nitrate (1500 mg, 2.74 mmol) was added to a stirred solution of (R)-tert-butyl 2-hydroxy-2-((2R,6R)-4-(4-methoxybenzyl)-6-methyl-3-oxomorpholin-2-yl)acetate (250 mg, 0.684 mmol) in MeCN (6.2 mL) and water (0.68 mL) at 0° C. The reaction was warmed to room temperature and stirred for 5 h. The reaction was diluted with satd aq. NaHCO$_3$ and the resulting precipitate was collected by filtration and washed with CH$_2$Cl$_2$. The organic layer of the filtrate was separated and the aqueous layer was back extracted with CH$_2$Cl$_2$ (2×). The combined organic extracts were dried (Na$_2$SO$_4$) and concentrated in vacuo to afford (R)-tert-butyl 2-hydroxy-2-((2R,6R)-6-methyl-3-oxomorpholin-2-yl)acetate. LCMS calc.=246.13. found=246.13 (M+H)$^+$.

Step B: (R)-tert-Butyl 2-((2R,6R)-4-(1-(6-chloropyridazin-4-yl)-1H-pyrazol-3-yl)-6-methyl-3-oxomorpholin-2-yl)-2-hydroxyacetate (R)-tert-Butyl 2-hydroxy-2-((2R,6R)-6-methyl-3-oxomorpholin-2-yl)acetate (36.5 mg, 0.149 mmol), 3-chloro-5-(3-iodo-1H-pyrazol-1-yl)pyridazine (68.4 mg, 0.223 mmol), trans-N,N'-dimethylcyclohexane-1,2-diamine (0.023 mL, 0.149 mmol), potassium phosphate (63.2 mg, 0.298 mmol), cuprous iodide (28.3 mg, 0.149 mmol) and 1,4-dioxane (1.5 mL) were sealed in a reaction vessel. N₂ was bubbled through the mixture for 2 min then the tube was heated at 80° C. overnight. The reaction crude was filtered into a stirred satd aq. NH₄Cl/ice mixture. The resulting mixture was partitioned between satd aq. NH₄Cl and EtOAc. The combined extracts were dried over Na₂SO₄, filtered and evaporated in vacuo. The pot residue was purified by flash chromatography (SiO₂, 12 g cartridge, EtOAc/hexanes) to afford (R)-tert-butyl 2-((2R,6R)-4-(1-(6-chloropyridazin-4-yl)-1H-pyrazol-3-yl)-6-methyl-3-oxomorpholin-2-yl)-2-hydroxyacetate, as a yellow solid. LCMS calc.=424.14. found=424.00 (M+H)⁺.

Step C: (R)-tert-Butyl 2-((2R,6R)-4-(1-(6-cyano-pyridazin-4-yl)-1H-pyrazol-3-yl)-6-methyl-3-oxo-morpholin-2-yl)-2-hydroxyacetate (R)-tert-Butyl 2-((2R,6R)-4-(1-(6-chloropyridazin-4-yl)-1H-pyrazol-3-yl)-6-methyl-3-oxomorpholin-2-yl)-2-hydroxyacetate (34.3 mg, 0.081 mmol), 1,1'-bis(diphenylphosphino)ferrocene (7.63 mg, 0.014 mmol), tris(dibenzylideneacetone)dipalladium(0) (3.71 mg, 4.05 μmol) and zinc cyanide (9.50 mg, 0.081 mmol) were stirred in DMF (0.81 mL) at 100° C. for 2 h. The reaction crude was purified by preparative HPLC (reversed phase, YMC-Pack Pro C-18, 100×20 mm, MeCN/water) to afford (R)-tert-butyl 2-((2R,6R)-4-(1-(6-cyanopyridazin-4-yl)-1H-pyrazol-3-yl)-6-methyl-3-oxomorpholin-2-yl)-2-hydroxyacetate, as a light tan solid. LCMS calc.=415.17. found=415.09 (M+H)⁺.

Step D: (R)-2-((2R,6R)-4-(1-(6-Cyanopyridazin-4-yl)-1H-pyrazol-3-yl)-6-methyl-3-oxomorpholin-2-yl)-2-hydroxyacetic acid hydrochloride (R)-tert-Butyl 2-((2R,6R)-4-(1-(6-cyanopyridazin-4-yl)-1H-pyrazol-3-yl)-6-methyl-3-oxomorpholin-2-yl)-2-hydroxyacetate (14.5 mg, 0.035 mmol), trifluoroacetic acid (0.3 mL, 0.035 mmol) and CH₂Cl₂ (2 mL) were stirred at room temperature for 2 h. Volatiles were removed under reduced pressure. The pot residue was stirred in hydrochloric acid (0.3 mL of a 4 M solution in 1,4-dioxane, 1.200 mmol) at room temperature for 1 h. Volatiles were removed in vacuo. The resulting yellow oil was chased with toluene (3×5 mL) and evaporated in vacuo to afford (R)-2-((2R,6R)-4-(1-(6-Cyanopyridazin-4-yl)-1H-pyrazol-3-yl)-6-methyl-3-oxomorpholin-2-yl)-2-hydroxyacetic acid hydrochloride, as a yellow glass. LCMS (free acid) calc.=359.11. found=359.06 (M+H)⁺.

Step E: (R)—N-(3-Aminobenzo[d]isoxazol-6-yl)-2-((2R,6R)-4-(1-(6-cyanopyridazin-4-yl)-1H-pyrazol-3-yl)-6-methyl-3-oxomorpholin-2-yl)-2-hydroxyac-etamide (R)-2-((2R,6R)-4-(1-(6-Cyanopyridazin-4-yl)-1H-pyrazol-3-yl)-6-methyl-3-oxomorpholin-2-yl)-2-hydroxyacetic acid hydrochloride (13.8 mg, 0.035 mmol), 1-hydroxy-7-azabenzotriazole (9.5 mg, 0.070 mmol), 1-(3-dimethylaminopropyl)-3-ethylcarbodiimide hydrochloride (13.4 mg, 0.070 mmol) and benzo[d]isoxazole-3,6-diamine (10.4 mg, 0.070 mmol) were stirred in NMP (1.5 mL) at room temperature over the weekend. The reaction crude was purified by preparative HPLC (reversed phase, YMC-Pack ODS C-18, 100×20 mm, MeCN/water (0% to 40% organic in 25 min, then to 100% in 5 min, 20 mL/min)) to afford (R)—N-(3-aminobenzo[d]isoxazol-6-yl)-2-((2R,6R)-4-(1-(6-cyanopyridazin-4-yl)-1H-pyrazol-3-yl)-6-methyl-3-oxomor-pholin-2-yl)-2-hydroxyacetamide, as a white solid. LCMS calc.=490.16. found=489.99 (M+H)⁺. ¹H NMR (500 MHz, DMSO-d₆): δ 10.17 (s, 1H); 10.03 (s, 1H); 8.83 (s, 1H); 8.74 (s, 1H); 8.00 (s, 1H); 7.69 (d, J=8.6 Hz, 1H); 7.59 (d, J=8.6 Hz, 1H); 7.28 (s, 1H); 6.30 (s, 2H); 4.79 (s, 1H); 4.72 (s, 1H); 4.31 (s, 1H); 4.29 (s, 1H); 4.04-3.98 (m, 1H); 3.67-3.61 (m, 1H); 1.19 (d, J=5.9 Hz, 3H).

(FIXa IC50: 1.978 nM)

Example 155

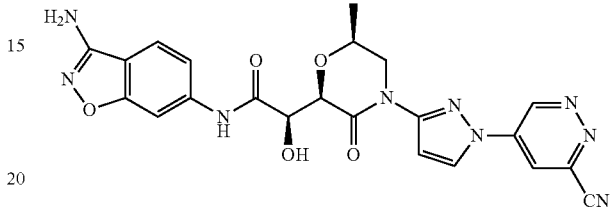

(R)—N-(3-Aminobenzo[d]isoxazol-6-yl)-2-((2R,6S)-4-(1-(6-cyanopyridazin-4-yl)-1H-pyrazol-3-yl)-6-methyl-3-oxomorpholin-2-yl)-2-hydroxyacetamide Step A: (R)-tert-Butyl 2-((2R,6S)-4-(1-(6-chloro-pyridazin-4-yl)-1H-pyrazol-3-yl)-6-methyl-3-oxo-morpholin-2-yl)-2-hydroxyacetate Copper(I) iodide (10.5 mg, 0.055 mmol), potassium phosphate tribasic (78 mg, 0.367 mmol) and trans-N,N-dimethylcyclohexane-1,2-diamine (9 μl, 0.055 mmol) were added successively to a stirred solution of (R)-tert-butyl 2-hydroxy-2-((2R,6S)-6-methyl-3-oxomorpholin-2-yl)acetate (45 mg, 0.183 mmol) and 3-chloro-5-(3-iodo-1H-pyrazol-1-yl)pyridazine (61.9 mg, 0.202 mmol) in dry 1,4-dioxane (1.8 mL) at room temperature under N₂. N₂ was bubbled through the mixture for 5 min then the tube was sealed and heated at 80° C. overnight. The reaction was filtered through a plug of silica. The filtrate was diluted with water and extracted with EtOAc. The organic layer was dried (Na₂SO₄) and concentrated in vacuo to give the crude product. This was purified by flash chromatography (EtOAc/Hex gradient from 0-100%) to afford (R)-tert-butyl 2-((2R,6S)-4-(1-(6-chloropyridazin-4-yl)-1H-pyrazol-3-yl)-6-methyl-3-oxomorpholin-2-yl)-2-hydroxyacetate. LCMS calc.=424.14. found=424.03 (M+H)⁺. ¹H NMR (500 MHz, CDCl₃): δ 9.52 (d, J=2.4 Hz, 1H); 8.04 (d, J=2.9 Hz, 1H); 7.77 (d, J=2.3 Hz, 1H); 7.45 (d, J=2.8 Hz, 1H); 4.75 (dd, J=7.6, 2.1 Hz, 1H); 4.69-4.66 (m, 1H); 4.24 (dd, J=12.7, 2.6 Hz, 1H); 4.15-4.08 (m, 1H); 3.70 (dd, J=12.7, 10.8 Hz, 1H); 3.24 (d, J=7.7 Hz, 1H); 1.54 (s, 9H); 1.41 (d, J=6.2 Hz, 3H).

Step B: (R)-tert-Butyl 2-((2R,6S)-4-(1-(6-cyano-pyridazin-4-yl)-1H-pyrazol-3-yl)-6-methyl-3-oxo-morpholin-2-yl)-2-hydroxyacetate A mixture of (R)-tert-butyl 2-((2R,6S)-4-(1-(6-chloro-pyridazin-4-yl)-1H-pyrazol-3-yl)-6-methyl-3-oxomorpholin-2-yl)-2-hydroxyacetate (19.2 mg, 0.045 mmol), zinc cyanide (8.2 mg, 0.070 mmol), tris(dibenzylideneacetone)dipalladium(0) (2.9 mg, 3.17 μmol), 1,1'-bis(diphenylphosphino)ferrocene (4.27 mg, 7.70 μmol) and zinc (1.9 mg, 0.029 mmol) in dry DMF (450 μl) in a microwave tube was degassed by bubbling with N₂ for 10 min. The tube was capped and heated at 100° C. for 3 h. The mixture was diluted with water and extracted with EtOAc. The organic layer was dried (Na$_2$SO$_4$) and concentrated in vacuo to give the crude product. This was purified by flash chromatography (EtOAc/hexanes gradient from 0-100%) to afford (R)-tert-butyl 2-((2R,6S)-4-(1-(6-cyanopyridazin-4-yl)-1H-pyrazol-3-yl)-6-methyl-3-oxomorpholin-2-yl)-2-hydroxyacetate. LCMS calc.=415.17. found=415.10 (M+H)$^+$. $^1$H NMR (500 MHz, CDCl$_3$): δ 9.72 (d, J=2.5 Hz, 1H); 8.12 (d, J=2.6 Hz, 2H); 7.47 (d, J=2.8 Hz, 1H); 4.74 (d, J=5.9 Hz, 1H); 4.67 (s, 1H); 4.22 (d, J=12.7 Hz, 1H); 4.15-4.10 (m, 1H); 3.75-3.65 (m, 1H); 3.29 (d, J=7.1 Hz, 1H); 1.54 (s, 9H); 1.41 (d, J=6.2 Hz, 3H).

Step C: (R)-2-((2R,6S)-4-(1-(6-Cyanopyridazin-4-yl)-1H-pyrazol-3-yl)-6-methyl-3-oxomorpholin-2-yl)-2-hydroxyacetic acid (R)-tert-Butyl 2-((2R,6S)-4-(1-(6-cyanopyridazin-4-yl)-1H-pyrazol-3-yl)-6-methyl-3-oxomorpholin-2-yl)-2-hydroxyacetate (10.7 mg, 0.026 mmol) in a mixture of CH$_2$Cl$_2$ (129 µl) and TFA (129 µl) was stirred at room temperature for 4 h. The mixture was concentrated in vacuo. The residue was redissolved in 2 M HCl in 1,4-dioxane. The was concentrated in vacuo to afford (R)-2-((2R,6S)-4-(1-(6-cyanopyridazin-4-yl)-1H-pyrazol-3-yl)-6-methyl-3-oxomorpholin-2-yl)-2-hydroxyacetic acid. LCMS calc.=359.11. found=359.05 (M+H)$^+$.

Step D: (R)—N-(3-Aminobenzo[d]isoxazol-6-yl)-2-((2R,6S)-4-(1-(6-cyanopyridazin-4-yl)-1H-pyrazol-3-yl)-6-methyl-3-oxomorpholin-2-yl)-2-hydroxyacetamide (R)-2-((2R,6S)-4-(1-(6-Cyanopyridazin-4-yl)-1H-pyrazol-3-yl)-6-methyl-3-oxomorpholin-2-yl)-2-hydroxyacetic acid (9.2 mg, 0.026 mmol), benzo[d]isoxazole-3,6-diamine (7.7 mg, 0.051 mmol), EDC (9.8 mg, 0.051 mmol), 1-hydroxy-7-azabenzotriazole (7.0 mg, 0.051 mmol) and NMP (257 µl) were stirred at room temperature overnight. The reaction mixture was diluted with DMSO and purified by preparative reversed phase HPLC (C-18, eluting with MeCN/water) to give (R)—N-(3-aminobenzo[d]isoxazol-6-yl)-2-((2R,6S)-4-(1-(6-cyanopyridazin-4-yl)-1H-pyrazol-3-yl)-6-methyl-3-oxomorpholin-2-yl)-2-hydroxyacetamide. LCMS calc.=490.16. found=490.07 (M+H)$^+$. $^1$H NMR (500 MHz, CDCl$_3$): δ 10.03 (d, J=9.4 Hz, 2H); 8.84 (d, J=2.9 Hz, 1H); 8.75 (d, J=2.6 Hz, 1H); 8.03 (s, 1H); 7.69 (d, J=8.6 Hz, 1H); 7.61-7.57 (m, 1H); 7.29 (d, J=2.8 Hz, 1H); 6.40 (s, 1H); 6.32 (s, 2H); 4.83 (d, J=1.8 Hz, 1H); 4.68 (s, 1H); 4.27-4.23 (m, 1H); 4.18 (dd, J=10.7, 6.5 Hz, 1H); 3.62-3.56 (m, 1H); 1.24 (d, J=6.1 Hz, 3H).
(FIXa IC50: 1.958 nM)

Intermediate 80

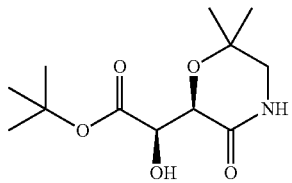 [SMILES: CC(C)(C)OC(=O)[C@H](O)[C@H]1OC(C)(C)CNC1=O]

(R)-tert-Butyl 2-((R)-6,6-dimethyl-3-oxomorpholin-2-yl)-2-hydroxyacetate

Step A: N-(4-Methoxybenzyl)-2-methylprop-2-en-1-amine

2-Methylallylamine (1.28 mL, 14.06 mmol) was added to a stirred solution of p-anisaldehyde (1.71 mL, 14.06 mmol) in absolute EtOH (19.1 mL) at 25° C. and the reaction mixture was stirred overnight. The reaction mixture was cooled to 0° C., sodium borohydride (0.798 g, 21.09 mmol) was added and the reaction mixture was warmed to room temperature and stirred for 7 h. The reaction mixture was diluted with EtOAc and water and the organic layer was separated, washed with brine, dried (Na$_2$SO$_4$) and concentrated in vacuo to give the crude product. This was purified by flash chromatography (Isco Combiflash Rf, RediSep Silica 80 g, 60 mL/min, loaded using solid loading cartridge after dissolving in CH$_2$Cl$_2$, 100% CH$_2$Cl$_2$ for 2 min, gradient to 10% (2M NH$_3$ in MeOH) in CH$_2$Cl$_2$ over 25 min, isocratic at 10% (2M NH$_3$ in MeOH) in CH$_2$Cl$_2$ for 23 min) to afford N-(4-methoxybenzyl)-2-methylprop-2-en-1-amine, as a colorless oil. LCMS calc.=192.14. found=192.22 (M+H)$^+$. $^1$H NMR (500 MHz, CHCl$_3$-d): δ 6.75 (d, J=8.3 Hz, 2H); 6.37 (d, J=8.4 Hz, 2H); 4.40 (s, 1H); 4.36 (s, 1H); 3.30 (s, 3H); 3.20 (s, 2H); 2.69 (s, 2H); 1.27 (s, 3H).

Step B: (2R,3R)-2,3-Diacetoxy-4-((4-methoxybenzyl)(2-methylallyl)amino)-4-oxobutanoic acid A solution of N-(4-methoxybenzyl)-2-methylprop-2-en-1-amine (2.26 g, 11.82 mmol) in dry THF (59.1 mL) was added a to stirred solution of (+)-diacetyl-l-tartaric anhydride (2.61 g, 12.05 mmol) in dry THF (59.1 mL) at 0° C. under N$_2$ and the reaction was stirred at 4° C. overnight (reaction was transferred to refrigerator for overnight portion, no stirring). The reaction was concentrated in vacuo to afford (2R,3R)-2,3-diacetoxy-4-((4-methoxybenzyl)(2-methylallyl)amino)-4-oxobutanoic acid, which was carried forward without any further purification. LCMS calc.=408.17. found=408.14 (M+H)$^+$.

Step C: (2R,3R)-1-Methoxy-4-((4-methoxybenzyl)(2-methylallyl)amino)-1,4-dioxobutane-2,3-diyl diacetate (Trimethylsilyl)diazomethane (2M in Et$_2$O) (1.96 mL, 3.93 mmol) was added to a stirred solution of (2R,3R)-2,3-diacetoxy-4-((4-methoxybenzyl)(2-methylallyl)amino)-4-oxobutanoic acid (1.00 g, 2.455 mmol) in MeOH (2.5 mL) and CH$_2$Cl$_2$ (22.1 mL) at room temperature and the resulting solution was stirred for 1 h. After this time the reaction mixture was concentrated in vacuo to afford the crude methyl ester. This was purified by flash chromatography (Isco Combiflash Rf, RediSep Silica 40 g, 40 mL/min, loaded using solid loading cartridge after dissolving in CH$_2$Cl$_2$, 100% hexanes for 2 min, gradient to 50% EtOAc in hexanes over 13 min, isocratic at 50% EtOAc in hexanes for 15 min) to afford (2R,3R)-1-methoxy-4-((4-methoxybenzyl)(2-methylallyl)amino)-1,4-dioxobutane-2,3-diyl diacetate, as a colorless oil. LCMS calc.=422.18. found=422.16 (M+H)$^+$.

Step D: (2R,3R)-Methyl 2,3-dihydroxy-4-((4-methoxybenzyl)(2-methylallyl)amino)-4-oxobutanoate Potassium cyanide (0.076 g, 1.172 mmol) was added to a stirred solution of (2R,3R)-1-methoxy-4-((4-methoxybenzyl)(2-methylallyl)amino)-1,4-dioxobutane-2,3-diyl diacetate (0.95 g, 2.254 mmol) in MeOH (22.5 mL) at 0° C. under N₂. The resulting mixture was stirred at 0° C. for 4 h. Solid NaHCO₃ (0.197 g, 2.344 mmol) was added and the reaction mixture was diluted with water and extracted with MTBE (3×). The combined extracts were dried (Na₂SO₄) and concentrated in vacuo to afford (2R,3R)-methyl 2,3-dihydroxy-4-((4-methoxybenzyl)(2-methylallyl)amino)-4-oxobutanoate, as a colorless oil. This was carried forward with no further purification. LCMS calc.=338.16. found=338.18 (M+H)⁺.

Step E: (R)-Methyl 2-hydroxy-2-((R)-4-(4-methoxybenzyl)-6,6-dimethyl-3-oxomorpholin-2-yl)acetate Mercuric acetate (0.670 g, 2.101 mmol) was added to solution of (2R,3R)-methyl 2,3-dihydroxy-4-((4-methoxybenzyl)(2-methylallyl)amino)-4-oxobutanoate (0.4726 g, 1.401 mmol) in water (7.0 mL) and THF (7.0 mL) at 25° C. and the reaction was stirred for 3 days. After this time sodium borohydride (0.085 g, 2.241 mmol) was added and the reaction was stirred at 25° C. overnight. After this time another 1.6 eq sodium borohydride was added and the reaction was stirred for 6 h. The reaction was diluted with water and extracted with MTBE (3×). The combined extracts were dried (Na₂SO₄) and concentrated in vacuo to give the crude product. This was purified by flash chromatography (Isco Combiflash Rf, RediSep Silica 40 g, 40 mL/min, loaded using solid loading cartridge after dissolving in CH₂Cl₂, 100% hexanes for 2 min, gradient to 100% EtOAc over 22 min, isocratic at 100% EtOAc for 6 min) to afford (R)-methyl 2-hydroxy-2-((R)-4-(4-methoxybenzyl)-6,6-dimethyl-3-oxomorpholin-2-yl)acetate, as a colorless oil. LCMS calc.=338.16. found=338.13 (M+H)⁺. ¹H NMR (600 MHz, CHCl₃-d): δ 7.19 (d, J=8.4 Hz, 2H); 6.84 (d, J=8.4 Hz, 2H); 4.77 (s, 1H); 4.67 (d, J=14.5 Hz, 1H); 4.49 (d, J=2.2 Hz, 1H); 4.42 (d, J=14.5 Hz, 1H); 3.77 (s, 6H); 3.29 (d, J=12.2 Hz, 1H); 2.78 (d, J=12.2 Hz, 1H); 1.16 (s, 6H).

Step F: (R)-2-Hydroxy-2-((R)-4-(4-methoxybenzyl)-6,6-dimethyl-3-oxomorpholin-2-yl)acetic acid 1N Lithium hydroxide (578 μL, 0.578 mmol) was added to a stirred solution of (R)-methyl 2-hydroxy-2-((R)-4-(4-methoxybenzyl)-6,6-dimethyl-3-oxomorpholin-2-yl)acetate (97.5 mg, 0.289 mmol) in 1,4-dioxane (5.4 mL) and water (1.3 mL) and the mixture was stirred at 25° C. for 2 h. The reaction was acidified with 1N aq. HCl (1.0 mL) then extracted with MTBE (3×). The combined extracts were dried (Na₂SO₄) and concentrated in vacuo to afford (R)-2-hydroxy-2-((R)-4-(4-methoxybenzyl)-6,6-dimethyl-3-oxomorpholin-2-yl)acetic acid, as a colorless solid. LCMS calc.=324.14. found=324.13 (M+H)⁺. ¹H NMR (500 MHz, CHCl₃-d): δ 7.19 (d, J=8.3 Hz, 2H); 6.85 (d, J=8.4 Hz, 2H); 5.12 (s, 1H); 4.84 (d, J=2.2 Hz, 1H); 4.71 (d, J=14.4 Hz, 1H); 4.61 (d, J=2.2 Hz, 1H); 4.39 (d, J=14.5 Hz, 1H); 3.78 (s, 3H); 3.33 (d, J=12.3 Hz, 1H); 2.81 (d, J=12.3 Hz, 1H); 1.18 (s, 3H).

Step G: (R)-tert-Butyl 2-hydroxy-2-((R)-4-(4-methoxybenzyl)-6,6-dimethyl-3-oxomorpholin-2-yl)acetate 2-tert-Butyl-1,3-diisopropylisourea (222 μL, 0.950 mmol) was added to a stirred solution of (R)-2-hydroxy-2-((R)-4-(4-methoxybenzyl)-6,6-dimethyl-3-oxomorpholin-2-yl)acetic acid (102.4 mg, 0.317 mmol) in dry THF (921 μL) and the mixture was heated at 60° C. in a sealed vial under N₂. After 4 h the reaction mixture was diluted with MTBE and cooled with an ice bath. The urea precipitate was collected by filtration and the filtrate was concentrated in vacuo to give the crude product. This was purified by flash chromatography (Isco Combiflash Rf, RediSep Silica 12 g, 30 mL/min, loaded as a solution in CH₂Cl₂, 100% hexanes for 1 min, gradient to 50% EtOAc in hexanes over 11 min, isocratic at 50% EtOAc in hexanes for 4 min) to afford (R)-tert-butyl 2-hydroxy-2-((R)-4-(4-methoxybenzyl)-6,6-dimethyl-3-oxomorpholin-2-yl)acetate, as a colorless oil. LCMS calc.=380.21. found=380.15 (M+H)⁺. ¹H NMR (600 MHz, CHCl₃-d): δ 7.20 (d, J=8.4 Hz, 2H); 6.84 (d, J=8.5 Hz, 2H); 4.72 (d, J=14.5 Hz, 1H); 4.67 (d, J=6.7 Hz, 1H); 4.48 (d, J=2.1 Hz, 1H); 4.37 (d, J=14.5 Hz, 1H); 3.77 (s, 3H); 3.29 (d, J=12.1 Hz, 1H); 3.24 (d, J=8.1 Hz, 1H); 2.78 (d, J=12.1 Hz, 1H); 1.46 (s, 9H); 1.14 (s, 6H).

Step H: (R)-tert-Butyl 2-((R)-6,6-dimethyl-3-oxomorpholin-2-yl)-2-hydroxyacetate Ceric ammonium nitrate (556 mg, 1.014 mmol) was added to a stirred solution of (R)-tert-butyl 2-hydroxy-2-((R)-4-(4-methoxybenzyl)-6,6-dimethyl-3-oxomorpholin-2-yl)acetate (96.2 mg, 0.254 mmol) in MeCN (3.3 mL) and water (0.36 mL) at 0° C. The reaction was warmed to room temperature and stirred for 5 h. The reaction was diluted with satd aq. NaHCO₃ and the resulting precipitate was collected by filtration and washed with CH₂Cl₂. The organic layer of the filtrate was separated and the aqueous layer was further extracted with CH₂Cl₂ (2×). The combined organic extracts were dried (Na₂SO₄) and concentrated in vacuo to give the crude product. This was left on the high vacuum pump for 3 days during which time the 4-MeO-benzaldehyde byproduct was removed to afford (R)-tert-Butyl 2-((R)-6,6-dimethyl-3-oxomorpholin-2-yl)-2-hydroxyacetate, as a colorless solid. LCMS calc.=260.15. found=260.20 (M+H)⁺. ¹H NMR (500 MHz, CHCl₃-d): δ 7.28 (s, 1H); 4.59 (d, J=7.5 Hz, 1H); 4.41 (d, J=5.8 Hz, 1H); 3.44-3.35 (m, 2H); 3.01 (dd, J=12.1, 5.1 Hz, 1H); 1.46 (s, 9H); 1.32 (s, 3H); 1.22 (s, 3H).

Example 156

(R)—N-(3-Aminobenzo[d]isoxazol-6-yl)-2-((R)-4-(1-(6-cyanopyridazin-4-yl)-1H-pyrazol-3-yl)-6,6-dimethyl-3-oxomorpholin-2-yl)-2-hydroxyacetamide

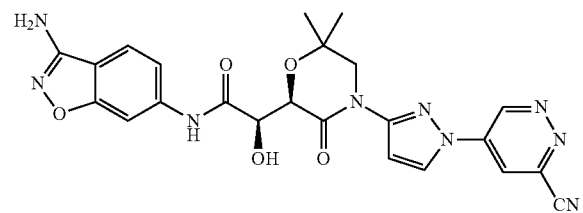 [SMILES: CC1(C)CN(c2ccn(-c3cnnc(C#N)c3)n2)C(=O)[C@@H]([C@@H](O)C(=O)Nc2ccc3c(N)noc3c2)O1]

Step A: (R)-tert-Butyl 2-((R)-4-(1-(6-chloropyridazin-4-yl)-1H-pyrazol-3-yl)-6,6-dimethyl-3-oxomorpholin-2-yl)-2-hydroxyacetate Copper(I) iodide (6.6 mg, 0.035 mmol), potassium phosphate tribasic (49.1 mg, 0.231 mmol) and trans-N,N-dimethylcyclohexane-1,2-diamine (5.5 μL, 0.035 mmol) were added successively to a stirred solution of (R)-tert-butyl 2-((R)-6,6-dimethyl-3-oxomorpholin-2-yl)-2-hydroxyacetate (30.0 mg, 0.116 mmol) and 3-chloro-5-(3-iodo-1H-pyrazol-1-yl)pyridazine (53.2 mg, 0.174 mmol) in dry 1,4-dioxane (1.2 mL) at room temperature under $N_2$. $N_2$ was bubbled through the mixture for 5 min then the tube was sealed and heated at 80° C. overnight. The reaction mixture was filtered through a plug of silica and the filtrate was concentrated in vacuo to give the crude product. This was purified by flash chromatography (Isco Combiflash Rf, RediSep Silica 12 g, 30 mL/min, loaded using solid loading cartridge after dissolving in $CH_2Cl_2$, 100% hexanes for 2 min, gradient to 50% EtOAc in hexanes over 23 min, isocratic at 50% EtOAc in hexanes for 5 min) to afford (R)-tert-butyl 2-((R)-4-(1-(6-chloropyridazin-4-yl)-1H-pyrazol-3-yl)-6,6-dimethyl-3-oxomorpholin-2-yl)-2-hydroxyacetate, as a colorless solid. LCMS calc.=438.15. found=438.06 (M+H)$^+$. $^1$H NMR (600 MHz, CHCl$_3$-d): δ 9.49 (d, J=2.4 Hz, 1H); 8.03 (d, J=2.9 Hz, 1H); 7.74 (d, J=2.3 Hz, 1H); 7.43 (d, J=2.8 Hz, 1H); 4.70-4.65 (m, 1H); 4.63 (d, J=15.4 Hz, 1H); 4.11 (d, J=12.7 Hz, 1H); 3.80 (d, J=12.2 Hz, 1H); 3.25 (d, J=7.8 Hz, 1H); 1.50 (s, 9H); 1.40 (s, 3H); 1.39 (s, 3H).

Step B: (R)-tert-Butyl 2-((R)-4-(1-(6-cyanopyridazin-4-yl)-1H-pyrazol-3-yl)-6,6-dimethyl-3-oxomorpholin-2-yl)-2-hydroxyacetate A mixture of (R)-tert-butyl 2-((R)-4-(1-(6-chloropyridazin-4-yl)-1H-pyrazol-3-yl)-6,6-dimethyl-3-oxomorpholin-2-yl)-2-hydroxyacetate (28.0 mg, 0.064 mmol), zinc cyanide (11.6 mg, 0.098 mmol), tris(dibenzylideneacetone)dipalladium(0) (4.1 mg, 4.48 μmol), 1,1'-bis(diphenylphosphino)ferrocene (6.0 mg, 10.87 μmol) and zinc (2.6 mg, 0.041 mmol) in dry DMF (0.64 mL) in a microwave tube was degassed by bubbling with $N_2$ for 10 min. The tube was capped and heated at 100° C. for 1 h. The reaction mixture was diluted with water (20 mL) and extracted with EtOAc (3×20 mL). The combined extracts were dried ($Na_2SO_4$) and concentrated in vacuo to give the crude product. This was purified by flash chromatography (Isco Combiflash Rf, RediSep Silica 12 g, 30 mL/min, loaded using solid loading cartridge after dissolving in $CH_2Cl_2$, 100% hexanes for 2 min, gradient to 50% EtOAc in hexanes over 23 min, isocratic at 50% EtOAc in hexanes for 5 min) to afford (R)-tert-butyl 2-((R)-4-(1-(6-cyanopyridazin-4-yl)-1H-pyrazol-3-yl)-6,6-dimethyl-3-oxomorpholin-2-yl)-2-hydroxyacetate, as a colorless glass. LCMS calc.=429.19. found=429.03 (M+H)$^+$.

Step C: (R)-2-((R)-4-(1-(6-Cyanopyridazin-4-yl)-1H-pyrazol-3-yl)-6,6-dimethyl-3-oxomorpholin-2-yl)-2-hydroxyacetic acid A solution of (R)-tert-butyl 2-((R)-4-(1-(6-cyanopyridazin-4-yl)-1H-pyrazol-3-yl)-6,6-dimethyl-3-oxomorpholin-2-yl)-2-hydroxyacetate (18.8 mg, 0.044 mmol) in TFA (0.22 mL) and dry $CH_2Cl_2$ (0.22 mL) was stirred at 25° C. under $N_2$ for 1 h. The mixture was concentrated in vacuo to give the crude product. This was dissolved in 2N HCl in 1,4-dioxane then concentrated in vacuo to afford (R)-2-((R)-4-(1-(6-cyanopyridazin-4-yl)-1H-pyrazol-3-yl)-6,6-dimethyl-3-oxomorpholin-2-yl)-2-hydroxyacetic acid, as a colorless solid. LCMS calc.=373.13. found=373.04 (M+H)$^+$.

Step D: (R)—N-(3-Aminobenzo[d]isoxazol-6-yl)-2-((R)-4-(1-(6-cyanopyridazin-4-yl)-1H-pyrazol-3-yl)-6,6-dimethyl-3-oxomorpholin-2-yl)-2-hydroxyacetamide $N^1$-((Ethylimino)methylene)-$N^3,N^3$-dimethylpropane-1,3-diamine hydrochloride (16.9 mg, 0.088 mmol), (R)-2-((R)-4-(1-(6-cyanopyridazin-4-yl)-1H-pyrazol-3-yl)-6,6-dimethyl-3-oxomorpholin-2-yl)-2-hydroxyacetic acid (18.0 mg, 0.044 mmol), benzo[d]isoxazole-3,6-diamine (13.1 mg, 0.088 mmol), and 1-hydroxy-7-azabenzotriazole (12.0 mg, 0.088 mmol) were stirred at 25° C. in dry N-methyl-2-pyrrolidinone (275 μL) for 3 days. The reaction mixture was directly purified by reversed-phase HPLC (C18, 20×100 mm, ~20 mL/min, gradient from 100% water to 60% water in MeCN over 25 min, gradient to 100% MeCN over 2 min, fractions containing desired product combined, lyophilized) to afford desired product (R)—N-(3-aminobenzo[d]isoxazol-6-yl)-2-((R)-4-(1-(6-cyanopyridazin-4-yl)-1H-pyrazol-3-yl)-6,6-dimethyl-3-oxomorpholin-2-yl)-2-hydroxyacetamide, as a colorless solid. LCMS calc.=504.17. found=504.09 (M+H)$^+$. $^1$H NMR (600 MHz, Acetone-d$_6$): δ 9.99 (s, 1H); 9.52 (s, 1H); 8.71 (s, 1H); 8.56 (s, 1H); 8.11 (s, 1H); 7.70 (d, J=8.5 Hz, 1H); 7.52 (d, J=8.8 Hz, 1H); 7.38 (s, 1H); 5.67 (s, 2H); 4.88 (s, 1H); 4.80 (s, 1H); 4.30 (d, J=12.8 Hz, 1H); 3.91 (d, J=12.7 Hz, 1H); 1.39 (s, 3H); 1.36 (s, 3H).

(FIXa IC50: 1.683 nM)

The following compounds (Table 11) were synthesized using methods analogous to those described for EXAMPLE 154, 155 AND 156 from commercially available materials or intermediates whose syntheses are described above.

TABLE 11

| Ex | | LCMS (M + H)$^+$ | Calc. (M + H)+ | FIXa IC50 (nM) |
| --- | --- | --- | --- | --- |
| 157 | [structure] | 465.12 | 465.16 | 1.345 |

TABLE 11-continued

| Ex | | LCMS (M + H)+ | Calc. (M + H)+ | FIXa IC50 (nM) |
|---|---|---|---|---|
| 158 | | 482.98 | 483.15 | 4.402 |
| 159 | | 495.04 | 495.17 | 2.257 |
| 160 | | 465.06 | 465.16 | 2.274 |
| 161 | | 483.07 | 483.15 | 32.3 |
| 162 | | 495.12 | 495.17 | 2.611 |
| 163 | | 464.08 | 464.17 | 11.27 |
| 164 | | 489.15 | 489.16 | 5.68 |

TABLE 11-continued
| Ex | | LCMS (M + H)+ | Calc. (M + H)+ | FIXa IC50 (nM) |
|---|---|---|---|---|
| 165 | 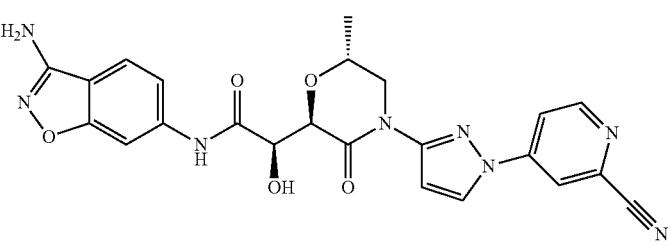 [SMILES: C[C@@H]1CN(c2ccn(-c3ccnc(C#N)c3)n2)C(=O)[C@@H]([C@@H](O)C(=O)Nc2ccc3c(N)noc3c2)O1] | 489.16 | 489.16 | 1.978 |
| 166 | 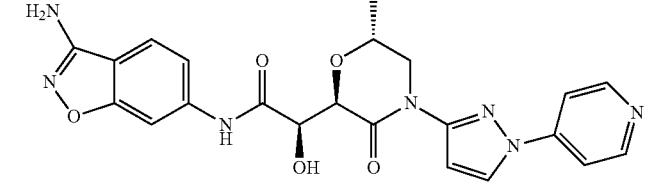 [SMILES: CC1(C)CN(c2ccn(-c3ccnnc3)n2)C(=O)[C@@H]([C@@H](O)C(=O)Nc2ccc3c(N)noc3c2)O1] | 464.18 | 464.17 | 3.365 |
| 167 | 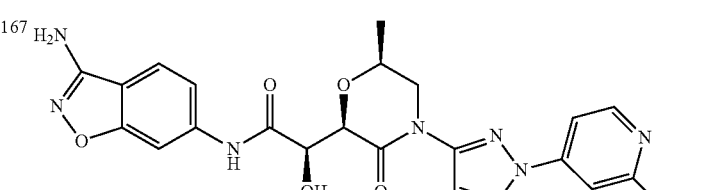 | 494.16 | 494.18 | 17.84 |
| 168 | 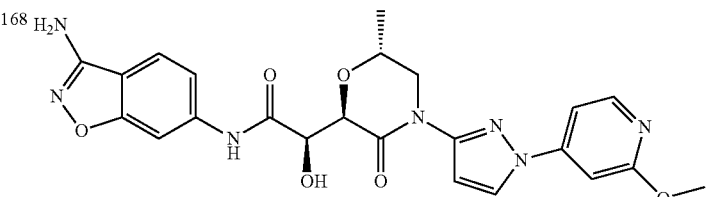 | 494.17 | 494.18 | 5.848 |
| 169 | 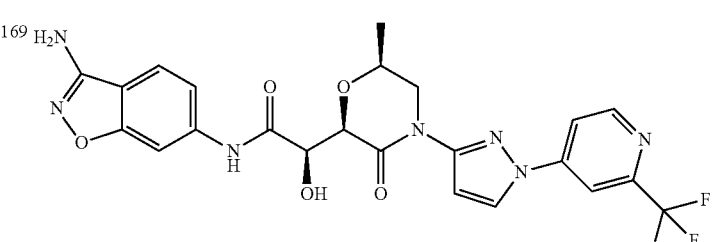 | 532.15 | 532.16 | 8.995 |
| 170 | 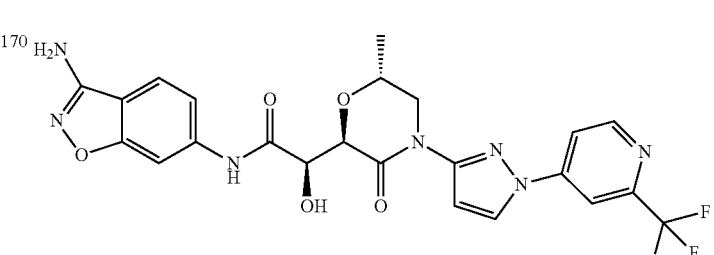 | 532.16 | 532.16 | 2.415 |

TABLE 11-continued

| Ex | LCMS (M + H)+ | Calc. (M + H)+ | FIXa IC50 (nM) |
|---|---|---|---|
| 171 | 508.07 | 508.19 | 20.92 |
| 172 | 479.10 | 479.18 | 1.805 |
| 173 | 497.02 | 497.17 | 21.1 |
| 174 | 509.08 | 509.19 | 2.77 |

Example 157

(R)—N-(3-aminobenzo[d]isoxazol-6-yl)-2-hydroxy-2-((2R,6R)-6-methyl-3-oxo-4-(1-(pyridazin-4-yl)-1H-pyrazol-3-yl)morpholin-2-yl)acetamide,

Example 158

(R)—N-(3-aminobenzo[d]isoxazol-6-yl)-2-((2R,6R)-4-(4-fluoro-1-(pyridazin-4-yl)-1H-pyrazol-3-yl)-6-methyl-3-oxomorpholin-2-yl)-2-hydroxyacetamide,

Example 159

(R)—N-(3-aminobenzo[d]isoxazol-6-yl)-2-hydroxy-2-((2R,6R)-4-(1-(6-methoxypyridazin-4-yl)-1H-pyrazol-3-yl)-6-methyl-3-oxomorpholin-2-yl)acetamide,

Example 160

(R)—N-(3-aminobenzo[d]isoxazol-6-yl)-2-hydroxy-2-((2R,6S)-6-methyl-3-oxo-4-(1-(pyridazin-4-yl)-1H-pyrazol-3-yl)morpholin-2-yl)acetamide,

Example 161

(R)—N-(3-aminobenzo[d]isoxazol-6-yl)-2-((2R,6S)-4-(4-fluoro-1-(pyridazin-4-yl)-1H-pyrazol-3-yl)-6-methyl-3-oxomorpholin-2-yl)-2-hydroxyacetamide,

Example 162

(R)—N-(3-aminobenzo[d]isoxazol-6-yl)-2-hydroxy-2-((2R,6S)-4-(1-(6-methoxypyridazin-4-yl)-1H-pyrazol-3-yl)-6-methyl-3-oxomorpholin-2-yl)acetamide,

Example 163

(R)—N-(3-aminobenzo[d]isoxazol-6-yl)-2-hydroxy-2-((2R,6S)-6-methyl-3-oxo-4-(1-(pyridin-4-yl)-1H-pyrazol-3-yl)morpholin-2-yl)acetamide,

Example 164

(R)—N-(3-aminobenzo[d]isoxazol-6-yl)-2-((2R,6S)-4-(1-(2-cyanopyridin-4-yl)-1H-pyrazol-3-yl)-6-methyl-3-oxomorpholin-2-yl)-2-hydroxyacetamide,

Example 165

(R)—N-(3-aminobenzo[d]isoxazol-6-yl)-2-((2R,6R)-4-(1-(2-cyanopyridin-4-yl)-1H-pyrazol-3-yl)-6-methyl-3-oxomorpholin-2-yl)-2-hydroxyacetamide,

Example 166

(R)—N-(3-aminobenzo[d]isoxazol-6-yl)-2-hydroxy-2-((2R,6R)-6-methyl-3-oxo-4-(1-(pyridin-4-yl)-1H-pyrazol-3-yl)morpholin-2-yl)acetamide,

Example 167

(R)—N-(3-aminobenzo[d]isoxazol-6-yl)-2-hydroxy-2-((2R,6S)-4-(1-(2-methoxypyridin-4-yl)-1H-pyrazol-3-yl)-6-methyl-3-oxomorpholin-2-yl)acetamide,

Example 168

(R)—N-(3-aminobenzo[d]isoxazol-6-yl)-2-hydroxy-2-((2R,6R)-4-(1-(2-methoxypyridin-4-yl)-1H-pyrazol-3-yl)-6-methyl-3-oxomorpholin-2-yl)acetamide,

Example 169

(R)—N-(3-aminobenzo[d]isoxazol-6-yl)-2-hydroxy-2-((2R,6S)-6-methyl-3-oxo-4-(1-(2-(trifluoromethyl)pyridin-4-yl)-1H-pyrazol-3-yl)morpholin-2-yl)acetamide,

Example 170

(R)—N-(3-aminobenzo[d]isoxazol-6-yl)-2-hydroxy-2-((2R,6R)-6-methyl-3-oxo-4-(1-(2-(trifluoromethyl)pyridin-4-yl)-1H-pyrazol-3-yl)morpholin-2-yl)acetamide,

Example 171

(R)—N-(3-aminobenzo[d]isoxazol-6-yl)-2-hydroxy-2-((R)-4-(1-(2-methoxypyridin-4-yl)-1H-pyrazol-3-yl)-6,6-dimethyl-3-oxomorpholin-2-yl)acetamide,

Example 172

(R)—N-(3-aminobenzo[d]isoxazol-6-yl)-2-((R)-6,6-dimethyl-3-oxo-4-(1-(pyridazin-4-yl)-1H-pyrazol-3-yl)morpholin-2-yl)-2-hydroxyacetamide,

Example 173

(R)—N-(3-aminobenzo[d]isoxazol-6-yl)-2-((R)-4-(4-fluoro-1-(pyridazin-4-yl)-1H-pyrazol-3-yl)-6,6-dimethyl-3-oxomorpholin-2-yl)-2-hydroxyacetamide, or

Example 174

(R)—N-(3-aminobenzo[d]isoxazol-6-yl)-2-hydroxy-2-((R)-4-(1-(6-methoxypyridazin-4-yl)-1H-pyrazol-3-yl)-6,6-dimethyl-3-oxomorpholin-2-yl)acetamide.

Determination of Inhibitory Activity Against Factor IXa

Formation of a clot to stem bleeding at a site of blood vessel injury involves the coordinated activity of a group of plasma proteins that initiate and propagate fibrin formation and subsequently protect fibrin from premature degradation. Factor IX is a key component of the plasma system that forms a fibrin clot at a site of vascular injury. The activity of Factor IXa is measured by monitoring the cleavage of the fluorescent peptide, $CH_3SO_2$-D-CHG-Gly-Arg-AFC.AcOH ("CHG" is cyclohexyl-glycine and "AFC" is trifluoro aminomethyl coumarin). Factor IXa cleaves the amide bond between Arg and AFC, thereby releasing the AFC fluorophore. The free AFC can be detected with a fluorescence detector at an excitation wavelength of 405 nM and emission wavelength of 510 nM.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

Compounds of the Formula (I) can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor IXa inhibitors can also be co-administered with suitable anticoagulants, including, but not limited to, other Factor IXa inhibitors, thrombin inhibitors, thrombin receptor antagonists, factor VIIa inhibitors, factor Xa inhibitors, factor XIa inhibitors, factor XIIa inhibitors, adenosine diphosphate antiplatelet agents (e.g., P2Y12 antagonists), fibrinogen receptor antagonists (e.g., to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor IXa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, eplerenone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methyl-propyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor IXa inhibitors of the invention in combination with other suitable anti-platelet agents, anticoagulation agents, or thrombolytic agents may be the same as those doses of Factor IXa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds in preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

What is claimed is:
1. A compound of formula I

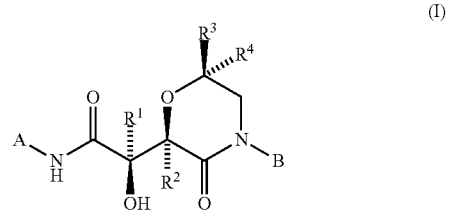

or a pharmaceutically acceptable salt thereof, wherein
$R^1$ is H or $C_{1-6}$ alkyl, $R^2$, is H or $C_{1-6}$ alkyl or $CH_2OH$, $R^3$ is H or $C_{1-6}$ alkyl, and $R^4$ is H or $C_{1-6}$ alkyl, provided that when $R^1$, $R^2$, and $R^3$ are H, $R^4$ is $C_{1-6}$ alkyl, and when $R^1$, $R^2$, and $R^4$ are H, then $R^3$ is $C_{1-6}$ alkyl, and when $R^1$, $R^3$, and $R^4$ are H, $R^2$ is $C_{1-6}$ alkyl or —$CH_2OH$, and when $R^2$, $R^3$, and $R^4$ are H, then $R^1$ is $C_{1-6}$ alkyl;

A is
1) a 9-10 membered bicyclic heterocycle having 1-3 heteroatoms independently selected from N, S and O, which 9-10 membered bicyclic heterocycle is unsubstituted or substituted with $R^5$, unsubstituted or substituted with $R^6$, and unsubstituted or substituted with $NH_2$, or
2) a 6-9 membered monocyclic or bicyclic carbocyclic ring system unsubstituted or substituted with $R^5$, unsubstituted or substituted with $R^6$, and unsubstituted or substituted with —$CH_2NH_2$;

$R^5$ is halogen;
$R^6$ is $C_{1-6}$alkyl;
B is
1) a 5- or 6-membered monocyclic heterocycle having 1 or 2 heteroatoms independently selected from N, S or O, which is unsubstituted or substituted on a carbon or nitrogen atom with $R^7$, unsubstituted or substituted on a carbon or nitrogen atom with $R^8$, and unsubstituted or substituted on a carbon or nitrogen atom with $R^9$, or
2) an 8- or 9-membered fused bicyclic heterocycle having 1, 2 or 3 nitrogen atoms which is unsubstituted or substituted on a carbon or nitrogen atom with $R^7$, and unsubstituted or substituted on a carbon or nitrogen atom with $R^8$;

$R^7$ is $CF_3$, $C_{1-6}$alkyl, $C_{1-6}$alkanol, $C_{3-8}$carbocycle, aryl,

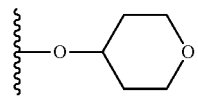

or a 5- or 6-membered heterocycle having 1 or 2 nitrogen atoms and zero or 1 oxygen atom, which heterocycle or $C_{3-8}$carbocycle or aryl is unsubstituted or mono-, di-, tri- or tetra-substituted with a group independently selected from $R^{10}$, $R^{11}$, $R^{12}$, $R^{13}$, and $R^{15}$;

$R^8$ is $C_{1-6}$alkyl;
$R^9$ is halogen;
$R^{10}$ is $CF_3$, CN, $C(O)NH_2$, $OCD_3$, $OC_{1-6}$alkyl, $OCH(CH_2Cl)(CH_2OH)$,
—$OC_{3-8}$cycloalkyl, or

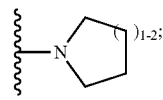

$R^{11}$ is halogen, $C_{1-6}$alkyl, $CF_3$, $CHF_2$, CN, or COOH;
$R^{12}$ is $CF_3$, COOH, $C(O)OC_{1-6}$alkyl, CN, halogen, $OCF_3$, =O, or $SO_2C_{1-6}$alkyl;
$R^{13}$ is $C_{1-6}$alkyl, $C(O)OC_{1-6}$alkyl, CN, $CF_3$, $OC_{1-6}$alkyl, $N(C_{1-6}alkyl)_2$, $OC_{1-6}$alkyl, or $OCHF_2$; and
$R^{15}$ is halogen, $CF_3$, $CHF_2$, $C_{1-6}$alkyl, CN, or COOH.

2. A compound of formula I

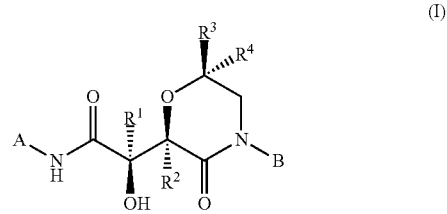

(I)

or a pharmaceutically acceptable salt thereof, wherein
$R^1$ is H or $C_{1-6}$ alkyl, $R^2$, is H or $C_{1-6}$ alkyl or $CH_2OH$, $R^3$ is H or $C_{1-6}$ alkyl, and $R^4$ is H or $C_{1-6}$ alkyl, provided that when $R^1$, $R^2$, and $R^3$ are H, $R^4$ is $C_{1-6}$ alkyl, and when $R^1$, $R^2$, and $R^4$ are H, then $R^3$ is $C_{1-6}$ alkyl, and when $R^1$, $R^3$, and $R^4$ are H, $R^2$ is $C_{1-6}$ alkyl or —$CH_2OH$, and when $R^2$, $R^3$, and $R^4$ are H, then $R^1$ is $C_{1-6}$ alkyl;

A is

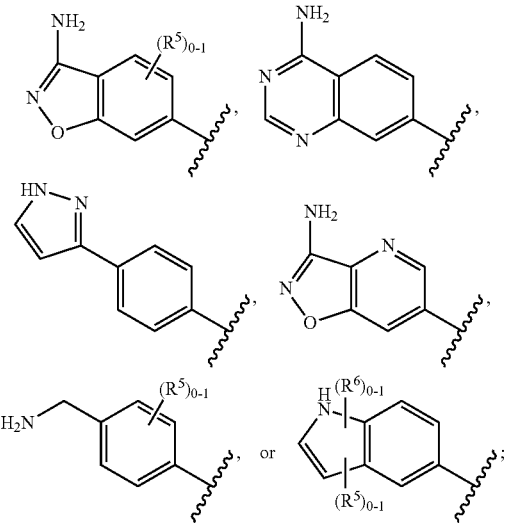

$R^5$ is halogen;
$R^6$ is $C_{1-6}$alkyl;
B is

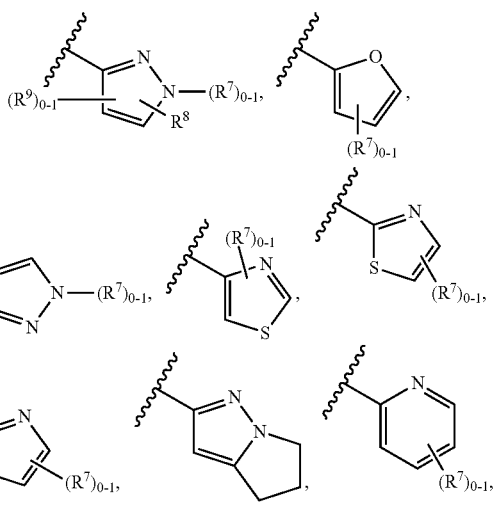

-continued

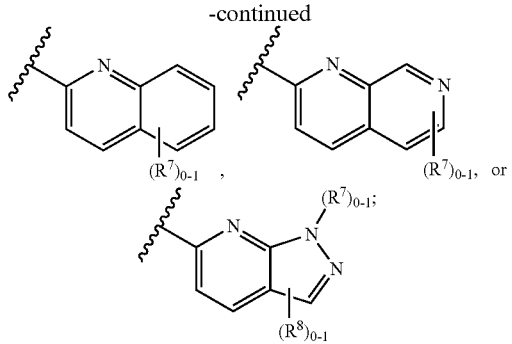

R[7] is CF$_3$, C$_{1-6}$alkyl, C$_{1-6}$alkanol, or C$_{3-8}$carbocycle,

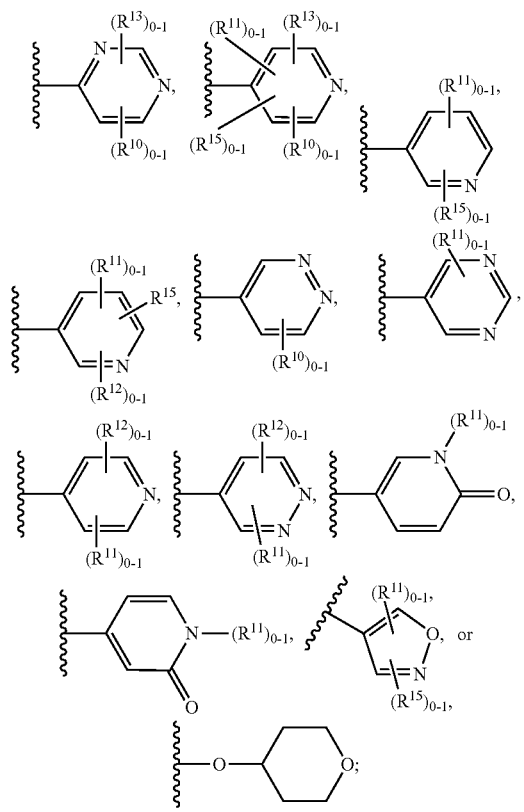

R[8] is C$_{1-6}$alkyl;
R[9] is halogen;
R[10] is CF$_3$, CN, C(O)NH$_2$, OD$_3$, OC$_{1-6}$alkyl, OCH(CH$_2$Cl)(CH$_2$OH), —OC$_{3-8}$cycloalkyl, or

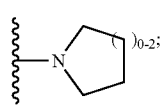

R[11] is halogen, C$_{1-6}$alkyl, CF$_3$, CHF$_2$, CN, or COOH;
R[12] is CF$_3$, COOH, C(O)OC$_{1-6}$alkyl, CN, halogen, OCF$_3$, =O, or SO$_2$C$_{1-6}$alkyl;
R[13] is C$_{1-6}$alkyl, C(O)OC$_{1-6}$alkyl, CN, CF$_3$, OC$_{1-6}$alkyl, N(C$_{1-6}$alkyl)$_2$, OC$_{1-6}$alkyl, or OCHF$_2$; and
R[15] is halogen, CF$_3$, CHF$_2$, C$_{1-6}$alkyl, CN, or COOH.

3. A compound of claim 2, or a pharmaceutically acceptable salt thereof, wherein A is

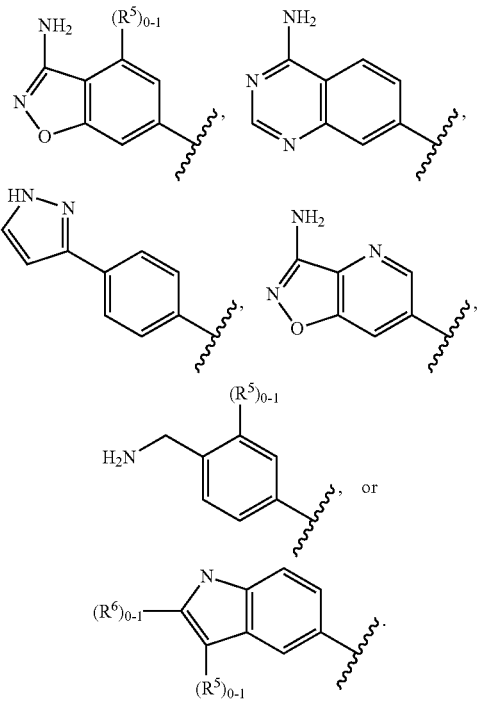

4. A compound of claim 2, or a pharmaceutically acceptable salt thereof, wherein B is

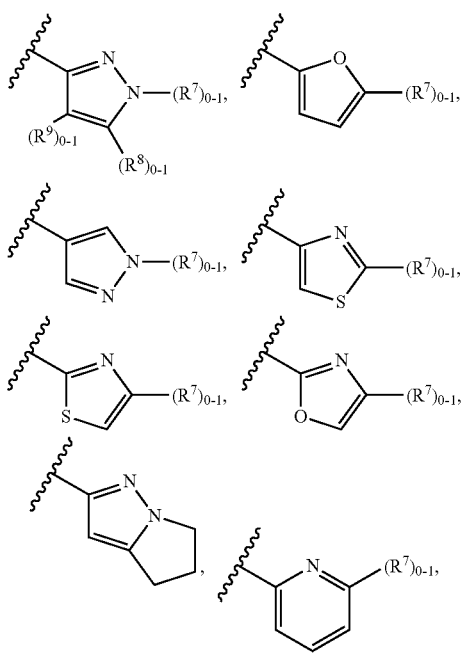

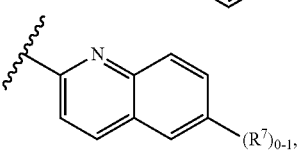

-continued

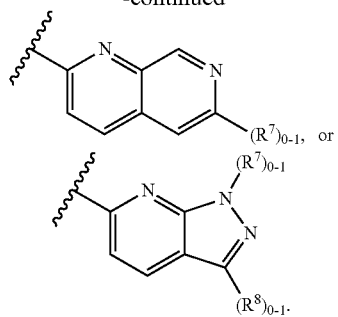

5. A compound of claim 2, or a pharmaceutically acceptable salt thereof, wherein $R^7$ is $CF_3$, $CH_3$, $C(CH_3)_2OH$, cyclopropyl,

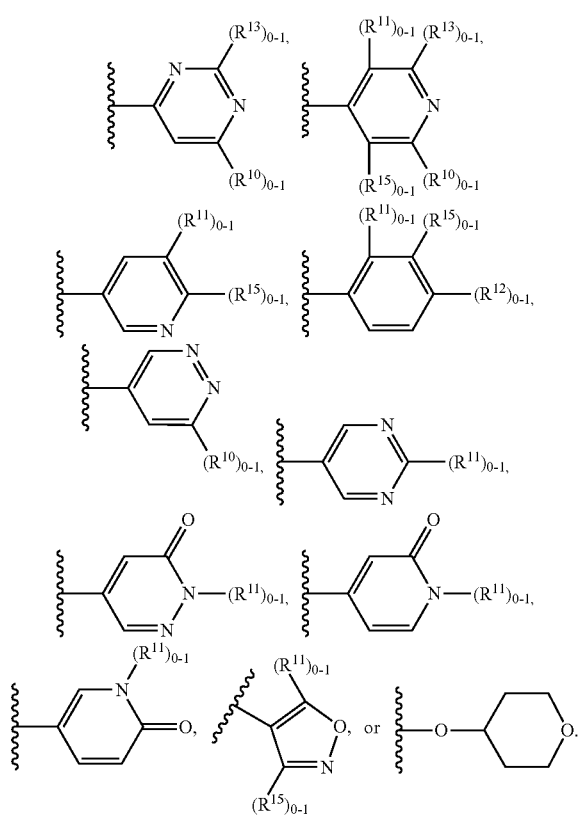

6. A compound of claim 2, or a pharmaceutically acceptable salt thereof, wherein
$R^5$ is Cl, or F;
$R^6$ is $CH_3$;
$R^8$ is $CH_3$;
$R^9$ is F;
$R^{10}$ is $CF_3$, CN, $C(O)NH_2$, $OCH_2CH_3$, $OD_3$, $OCH_3$, $OC(CH_3)_3$, $OCH(CH_3)_2$, $OCH(CH_2Cl)(CH_2OH)$,

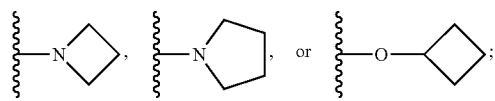

$R^{11}$ is F, Cl, Br, $CH_3$, $CF_3$, $CHF_2$, CN, COOH;
$R^{12}$ is $CF_3$, COOH, $C(O)OCH_3$, CN, F, Cl, $OCF_3$, $SO_2CH_3$;
$R^{13}$ is $CH_3$, $C(O)OCH_3$, CN, $CF_3$, $OCH_3$, $N(CH_3)_2$, $OCH_2CH_3$, $OCH(CH_3)_2$, $OCHF_2$;
$R^{15}$ is F, Cl, Br, $CF_3$, $CHF_2$, $CH_3$, CN, COOH.

7. A compound of claim 2, or a pharmaceutically acceptable salt thereof, wherein
$R^1$ is H or $CH_3$, $R^2$ is H, $CH_3$, $CH_2CH_3$, or $CH_2OH$, $R^3$ is H or $CH_3$, and $R^4$ is H or $CH_3$, provided that at least one of the group of $R^1$, $R^2$, $R^3$, and $R^4$ is $CH_3$ or, when $R^1$, $R^3$ and $R^4$ are H, then $R^2$ is $CH_3$, $CH_2CH_3$, or $CH_2OH$;
A is

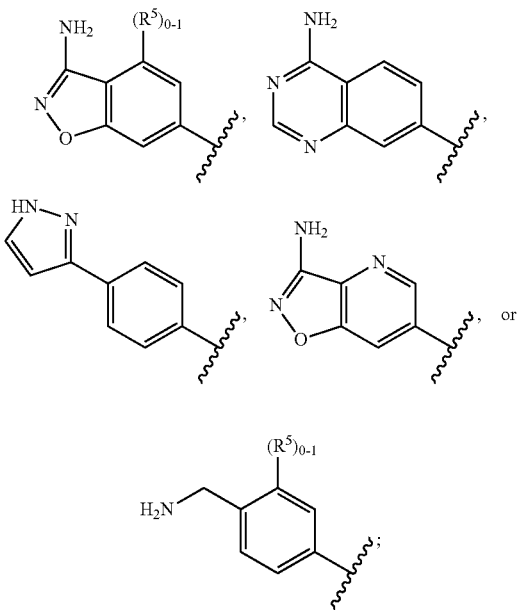

$R^5$ is Cl, or F;
$R^6$ is $CH_3$;
B is

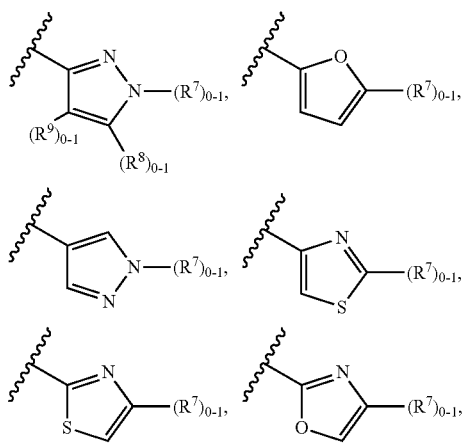

-continued

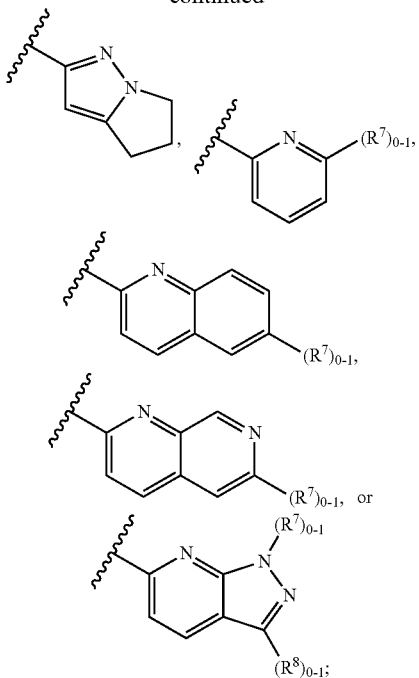

R⁷ is $CF_3$, $CH_3$, $C(CH_3)_2OH$, cyclopropyl,

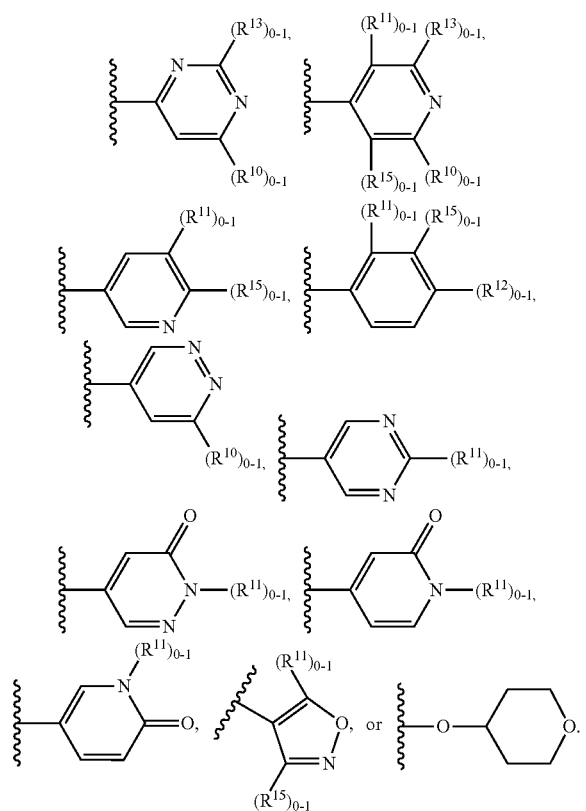

$R^8$ is $CH_3$;
$R^9$ is F;
$R^{10}$ is $CF_3$, CN, $C(O)NH_2$, $OCH_2CH_3$, $OCD_3$, $OCH_3$, $OC(CH_3)_3$, $OCH(CH_3)_2$, $OCH(CH_2Cl)(CH_2OH)$

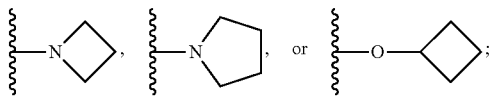

$R^{11}$ is F, Cl, Br, $CH_3$, $CF_3$, $CHF_2$, CN, COOH;
$R^{12}$ is $CF_3$, COOH, $C(O)OCH_3$, CN, F, Cl, $OCF_3$, $SO_2CH_3$;
$R^{13}$ is $CH_3$, $C(O)OCH_3$, CN, $CF_3$, $OCH_3$, $N(CH_3)_2$, $OCH_2CH_3$, $OCH(CH_3)_2$, $OCHF_2$; and
$R^{15}$ is F, Cl, Br, $CF_3$, $CHF_2$, $CH_3$, CN, COOH.

8. A compound of claim 2, or a pharmaceutically acceptable salt thereof, wherein $R^1$ and $R^2$ are H, and $R^3$ and $R^4$ are $CH_3$.

9. A compound of claim 2, or a pharmaceutically acceptable salt thereof, wherein $R^1$, $R^2$ and $R^3$ are H, and $R^4$ is $CH_3$.

10. A compound of claim 2, or a pharmaceutically acceptable salt thereof, wherein $R^2$, $R^3$ and $R^4$ are H, and $R^1$ is $CH_3$.

11. A compound of claim 2, or a pharmaceutically acceptable salt thereof, wherein $R^1$, $R^3$ and $R^4$ are H, and $R^2$ is $CH_3$.

12. A compound of claim 2, or a pharmaceutically acceptable salt thereof, wherein $R^1$ and $R^2$ are $CH_3$, and $R^3$ and $R^4$ are H.

13. A compound of claim 2, or a pharmaceutically acceptable salt thereof, wherein $R^1$, $R^3$ and $R^4$ are H, and $R^2$ is $CH_2OH$.

14. A compound of claim 2, or a pharmaceutically acceptable salt thereof, wherein $R^1$, $R^3$ and $R^4$ are H, and $R^2$ is $CH_2CH_3$.

15. A compound of claim 2, or a pharmaceutically acceptable salt thereof, which is
(2R)—N-(3-Amino-1,2-benzoxazol-6-yl)-2-hydroxy-2-[(2R)-4-[1-(2-methoxy-4-pyridyl)pyrazol-3-yl]-3-oxomorpholin-2-yl]propanamide,
(R)—N-(3-Aminoisoxazolo[4,5-b]pyridin-6-yl)-2-hydroxy-2-((R)-4-(1-(2-methoxypyridin-4-yl)-1H-pyrazol-3-yl)-3-oxomorpholin-2-yl)propanamide,
(R)—N-(3-Aminobenzo[d]isoxazol-6-yl)-2-(R)-4-(1-(6-cyanopyridazin-4-yl)-5-methyl-1H-pyrazol-3-yl)-3-oxomorpholin-2-yl)-2-hydroxypropanamide,
(R)—N-(3-Aminobenzo[d]isoxazol-6-yl)-2-(R)-4-(1-(6-ethoxypyridazin-4-yl)-1H-pyrazol-3-yl)-3-oxomorpholin-2-yl)-2-hydroxypropanamide,
5-(3-((R)-2-((R)-1-((3-Aminobenzo[d]isoxazol-6-yl)amino)-2-hydroxy-1-oxopropan-2-yl)-3-oxomorpholino)-1H-pyrazol-1-yl)pyridazine-3-carboxamide,
(2R)—N-(3-Aminobenzo[d]isoxazol-6-yl)-2-((2R)-4-(1-(6-((1-chloro-3-hydroxypropan-2-yl)oxy)pyridazin-4-yl)-1H-pyrazol-3-yl)-3-oxomorpholin-2-yl)-2-hydroxypropanamide,
(R)—N-(3-Aminobenzo[d]isoxazol-6-yl)-2-((R)-4-(1-(1-(difluoromethyl)-6-oxo-1,6-dihydropyridin-3-yl)-1H-pyrazol-3-yl)-3-oxomorpholin-2-yl)-2-hydroxypropanamide,
(R)—N-(3-Aminobenzo[d]isoxazol-6-yl)-2-((R)-4-(1-(1-(difluoromethyl)-6-oxo-1,6-dihydropyridin-3-yl)-5-methyl-1H-pyrazol-3-yl)-3-oxomorpholin-2-yl)-2-hydroxypropanamide,
(R)—N-(3-Aminobenzo[d]isoxazol-6-yl)-2-((R)-4-(1-(1-(difluoromethyl)-6-oxo-1,6-dihydropyridin-3-yl)-4-fluoro-1H-pyrazol-3-yl)-3-oxomorpholin-2-yl)-2-hydroxypropanamide, (R)—N-(3-Aminobenzo[d]isoxazol-6-yl)-2-hydroxy-2-((R)-3-oxo-4-(1-(6-oxo-1,6-dihydropyridin-3-yl)-1H-pyrazol-3-yl)morpholin-2-yl)propanamide,
(R)—N-(3-Aminobenzo[d]isoxazol-6-yl)-2-hydroxy-2-((R)-3-oxo-4-(1-(2-oxo-1,2-dihydropyridin-4-yl)-1H-pyrazol-3-yl)morpholin-2-yl)propanamide,
(R)—N-(3-Aminobenzo[d]isoxazol-6-yl)-2-hydroxy-2-((R)-4-(1-(1-methyl-6-oxo-1,6-dihydropyridin-3-yl)-1H-pyrazol-3-yl)-3-oxomorpholin-2-yl)propanamide,
(R)—N-(3-aminobenzo[d]isoxazol-6-yl)-2-((R)-4-(1-(4-fluorophenyl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-4-(1-(4-(methylsulfonyl)phenyl)-1H-pyrazol-3-yl)-3-oxomorpholin-2-yl)propanamide,
4-(3-((R)-2-((R)-1-(((3-aminobenzo[d]isoxazol-6-yl)amino)-2-hydroxy-1-oxopropan-2-yl)-3-oxomorpholino)-1H-pyrazol-1-yl)benzoic acid,
(R)—N-(3-aminobenzo[d]isoxazol-6-yl)-2-((R)-4-(1-(3-chloro-4-cyanophenyl)-1H-pyrazol-3-yl)-3-oxomorpholin-2-yl)-2-hydroxypropanamide,
(R)—N-(3-aminobenzo[d]isoxazol-6-yl)-2-((R)-4-(4-fluoro-1-(4-fluorophenyl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-3-oxo-4-(1-(pyridin-4-yl)-1H-pyrazol-3-yl)morpholin-2-yl)propanamide,
(R)—N-(3-aminobenzo[d]isoxazol-6-yl)-2-hydroxy-2-((R)-4-(1-(2-methylpyridin-4-yl)-1H-pyrazol-3-yl)-3-oxomorpholin-2-yl)propanamide,
(R)—N-(3-aminobenzo[d]isoxazol-6-yl)-2-((R)-4-(1-(2-cyanopyridin-4-yl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-3-oxo-4-(1-(2-(trifluoromethyl)pyridin-4-yl)-1H-pyrazol-3-yl)morpholin-2-yl)propanamide,
(R)—N-(3-aminobenzo[d]isoxazol-6-yl)-2-((R)-4-(1-(2-ethoxypyridin-4-yl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-4-(1-(2-isopropoxypyridin-4-yl)-1H-pyrazol-3-yl)-3-oxomorpholin-2-yl)propanamide,
(R)—N-(3-aminobenzo[d]isoxazol-6-yl)-2-((R)-4-(1-(2-(dimethylamino)pyridin-4-yl)-1H-pyrazol-3-yl)-3-oxomorpholin-2-yl)-2-hydroxypropanamide,
(R)—N-(3-aminobenzo[d]isoxazol-6-yl)-2-((R)-4-(1-(5-bromo-2-methoxypyridin-4-yl)-1H-pyrazol-3-yl)-3-oxomorpholin-2-yl)-2-hydroxypropanamide,
(R)—N-(3-aminobenzo[d]isoxazol-6-yl)-2-((R)-4-(1-(5-fluoro-2-methoxypyridin-4-yl)-1H-pyrazol-3-yl)-3-oxomorpholin-2-yl)-2-hydroxypropanamide,
(R)—N-(3-aminobenzo[d]isoxazol-6-yl)-2-((R)-4-(1-(5-chloro-2-methoxypyridin-4-yl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-4-(1-(2-methoxy-5-(trifluoromethyl)pyridin-4-yl)-1H-pyrazol-3-yl)-3-oxomorpholin-2-yl)propanamide,
(R)—N-(3-aminobenzo[d]isoxazol-6-yl)-2-((R)-4-(4-fluoro-1-(2-(trifluoromethyl)pyridin-4-yl)-1H-pyrazol-3-yl)-3-oxomorpholin-2-yl)-2-hydroxypropanamide,
(R)—N-(3-aminobenzo[d]isoxazol-6-yl)-2-((R)-4-(1-(2-cyanopyridin-4-yl)-4-fluoro-1H-pyrazol-3-yl)-3-oxomorpholin-2-yl)-2-hydroxypropanamide,
(R)—N-(3-aminobenzo[d]isoxazol-6-yl)-2-((R)-4-(4-fluoro-1-(2-methoxypyridin-4-yl)-1H-pyrazol-3-yl)-3-oxomorpholin-2-yl)-2-hydroxypropanamide,
(R)—N-(3-aminobenzo[d]isoxazol-6-yl)-2-((R)-4-(4-chloro-1-(2-methoxypyridin-4-yl)-1H-pyrazol-3-yl)-3-oxomorpholin-2-yl)-2-hydroxypropanamide,
(R)—N-(3-aminobenzo[d]isoxazol-6-yl)-2-((R)-4-(4-chloro-1-(2-cyanopyridin-4-yl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-4-(1-(2-methoxypyridin-4-yl)-4-methyl-1H-pyrazol-3-yl)-3-oxomorpholin-2-yl)propanamide,
(R)—N-(3-aminobenzo[d]isoxazol-6-yl)-2-hydroxy-2-((R)-4-(1-(2-methoxypyridin-4-yl)-5-methyl-1H-pyrazol-3-yl)-3-oxomorpholin-2-yl)propanamide,
(R)—N-(3-aminobenzo[d]isoxazol-6-yl)-2-hydroxy-2-((R)-3-oxo-4-(1-(pyridazin-4-yl)-1H-pyrazol-3-yl)morpholin-2-yl)propanamide,
(R)—N-(3-aminobenzo[d]isoxazol-6-yl)-2-((R)-4-(1-(6-(azetidin-1-yl)pyridazin-4-yl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-4-(1-(6-methoxypyridazin-4-yl)-1H-pyrazol-3-yl)-3-oxomorpholin-2-yl)propanamide,
(2R)—N-(3-amino-1,2-benzoxazol-6-yl)-2-hydroxy-2-[(2R)-3-oxo-4-[1-[6-(trideuteriomethoxy)pyridazin-4-yl]pyrazol-3-yl]morpholin-2-yl]propanamide,
(R)—N-(3-aminobenzo[d]isoxazol-6-yl)-2-hydroxy-2-((R)-4-(1-(6-isopropoxypyridazin-4-yl)-1H-pyrazol-3-yl)-3-oxomorpholin-2-yl)propanamide,
(R)—N-(3-aminobenzo[d]isoxazol-6-yl)-2-((R)-4-(1-(6-(tert-butoxy)pyridazin-4-yl)-1H-pyrazol-3-yl)-3-oxomorpholin-2-yl)-2-hydroxypropanamide,
(R)—N-(3-aminobenzo[d]isoxazol-6-yl)-2-((R)-4-(1-(6-cyclobutoxypyridazin-4-yl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-4-(1-(1-methyl-6-oxo-1,6-dihydropyridazin-4-yl)-1H-pyrazol-3-yl)-3-oxomorpholin-2-yl)propanamide,
(R)—N-(3-aminobenzo[d]isoxazol-6-yl)-2-((R)-4-(1-(6-cyanopyridazin-4-yl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-3-oxo-4-(1-(6-(trifluoromethyl)pyridazin-4-yl)-1H-pyrazol-3-yl)morpholin-2-yl)propanamide,
(R)—N-(3-aminobenzo[d]isoxazol-6-yl)-2-((R)-4-(4-fluoro-1-(pyridazin-4-yl)-1H-pyrazol-3-yl)-3-oxomorpholin-2-yl)-2-hydroxypropanamide,
(R)—N-(3-aminobenzo[d]isoxazol-6-yl)-2-((R)-4-(1-(6-cyanopyridazin-4-yl)-4-fluoro-1H-pyrazol-3-yl)-3-oxomorpholin-2-yl)-2-hydroxypropanamide,
(R)—N-(3-aminobenzo[d]isoxazol-6-yl)-2-((R)-4-(4-fluoro-1-(6-methoxypyridazin-4-yl)-1H-pyrazol-3-yl)-3-oxomorpholin-2-yl)-2-hydroxypropanamide,
(R)—N-(3-aminobenzo[d]isoxazol-6-yl)-2-((R)-4-(4-fluoro-1-(6-(trifluoromethyl)pyridazin-4-yl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-4-(1-(2-methylpyrimidin-4-yl)-1H-pyrazol-3-yl)-3-oxomorpholin-2-yl)propanamide,
(R)—N-(3-aminobenzo[d]isoxazol-6-yl)-2-((R)-4-(1-(2-(dimethylamino)pyrimidin-4-yl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-3-oxo-4-(1-(2-(trifluoromethyl)pyrimidin-4-yl)-1H-pyrazol-3-yl)morpholin-2-yl)propanamide, (R)—N-(3-aminobenzo[d]isoxazol-6-yl)-2-((R)-4-(1-(2-cyanopyrimidin-4-yl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-4-(1-(2-methoxypyrimidin-4-yl)-1H-pyrazol-3-yl)-3-oxomorpholin-2-yl)propanamide,
(R)—N-(3-aminobenzo[d]isoxazol-6-yl)-2-hydroxy-2-((R)-4-(1-(6-methoxypyrimidin-4-yl)-1H-pyrazol-3-yl)-3-oxomorpholin-2-yl)propanamide,
(R)—N-(3-aminobenzo[d]isoxazol-6-yl)-2-((R)-4-(4-fluoro-1-(2-(trifluoromethyl)pyrimidin-4-yl)-1H-pyrazol-3-yl)-3-oxomorpholin-2-yl)-2-hydroxypropanamide,
(R)—N-(3-aminobenzo[d]isoxazol-6-yl)-2-((R)-4-(4-fluoro-1-(2-methoxypyrimidin-4-yl)-1H-pyrazol-3-yl)-3-oxomorpholin-2-yl)-2-hydroxypropanamide,
(R)—N-(3-aminobenzo[d]isoxazol-6-yl)-2-hydroxy-2-((R)-4-(5-methyl-1-(2-(trifluoromethyl)pyrimidin-4-yl)-1H-pyrazol-3-yl)-3-oxomorpholin-2-yl)propanamide,
(R)—N-(3-aminobenzo[d]isoxazol-6-yl)-2-hydroxy-2-((R)-3-oxo-4-(5-(pyridin-4-yl)furan-2-yl)morpholin-2-yl)propanamide,
(R)—N-(3-aminobenzo[d]isoxazol-6-yl)-2-((R)-4-(5-(2-cyanopyridin-4-yl)furan-2-yl)-3-oxomorpholin-2-yl)-2-hydroxypropanamide,
(R)—N-(3-aminobenzo[d]isoxazol-6-yl)-2-hydroxy-2-((R)-3-oxo-4-(5-(2-(trifluoromethyl)pyridin-4-yl)furan-2-yl)morpholin-2-yl)propanamide,
(R)—N-(3-aminobenzo[d]isoxazol-6-yl)-2-hydroxy-2-((R)-4-(5-(2-methoxypyridin-4-yl)furan-2-yl)-3-oxomorpholin-2-yl)propanamide,
(R)—N-(3-aminobenzo[d]isoxazol-6-yl)-2-hydroxy-2-((R)-4-(5-(2-methoxypyrimidin-4-yl)furan-2-yl)-3-oxomorpholin-2-yl)propanamide,
(R)—N-(3-aminobenzo[d]isoxazol-6-yl)-2-hydroxy-2-((R)-4-(6-(2-hydroxypropan-2-yl)pyridin-2-yl)-3-oxomorpholin-2-yl)propanamide,
(R)—N-(3-aminobenzo[d]isoxazol-6-yl)-2-hydroxy-2-((R)-3-oxo-4-(6-(trifluoromethyl)pyridin-2-yl)morpholin-2-yl)propanamide,
(R)—N-(3-aminobenzo[d]isoxazol-6-yl)-2-hydroxy-2-((R)-3-oxo-4-(6-(pyridazin-4-yl)pyridin-2-yl)morpholin-2-yl)propanamide,
(R)—N-(3-aminobenzo[d]isoxazol-6-yl)-2-hydroxy-2-((R)-3-oxo-4-(6-(trifluoromethyl)quinolin-2-yl)morpholin-2-yl)propanamide,
(R)-2-((R)-4-(1,7-naphthyridin-2-yl)-3-oxomorpholin-2-yl)-N-(3-aminobenzo[d]isoxazol-6-yl)-2-hydroxypropanamide,
(R)—N-(3-aminobenzo[d]isoxazol-6-yl)-2-((R)-4-(1,3-dimethyl-1H-pyrazolo[3,4-b]pyridin-6-yl)-3-oxomorpholin-2-yl)-2-hydroxypropanamide,
(R)—N-(3-aminobenzo[d]isoxazol-6-yl)-2-((R)-4-(5,6-dihydro-4H-pyrrlo[1,2-b]pyrazol-2-yl)-3-oxomorpholin-2-yl)-2-hydroxypropanamide,
(R)—N-(3-Aminobenzo[d]isoxazol-6-yl)-2-hydroxy-2-((R)-2-methyl-3-oxo-4-(6-(trifluoromethyl)pyridin-2-yl)morpholin-2-yl)acetamide,
(R)—N-(3-Aminobenzo[d]isoxazol-6-yl)-2-((R)-4-(1-(2-cyanopyridin-4-yl)-1H-pyrazol-3-yl)-2-methyl-3-oxomorpholin-2-yl)-2-hydroxyacetamide,
(R)—N-(3-Aminobenzo[d]isoxazol-6-yl)-2-((R)-2-ethyl-3-oxo-4-(6-(trifluoromethyl)pyridin-2-yl)morpholin-2-yl)-2-hydroxyacetamide,
(R)—N-(3-Aminobenzo[d]isoxazol-6-yl)-2-hydroxy-2-((R)-2-(hydroxymethyl)-3-oxo-4-(6-(trifluoromethyl)pyridin-2-yl)morpholin-2-yl)acetamide,
(R)—N-(3-Aminobenzo[d]isoxazol-6-yl)-2-((R)-4-(1-(1-(difluoromethyl)-6-oxo-1,6-dihydropyridin-3-yl)-1H-pyrazol-3-yl)-2-methyl-3-oxomorpholin-2-yl)-2-hydroxyacetamide,
(R)—N-(3-Aminobenzo[d]isoxazol-6-yl)-2-((R)-4-(1-(1-(difluoromethyl)-6-oxo-1,6-dihydropyridin-3-yl)-5-methyl-1H-pyrazol-3-yl)-2-methyl-3-oxomorpholin-2-yl)-2-hydroxyacetamide,
(R)—N-(3-Aminobenzo[d]isoxazol-6-yl)-2-((R)-4-(1-(1-(difluoromethyl)-6-oxo-1,6-dihydropyridin-3-yl)-4-fluoro-1H-pyrazol-3-yl)-2-methyl-3-oxomorpholin-2-yl)-2-hydroxyacetamide,
(R)—N-(3-aminobenzo[d]isoxazol-6-yl)-2-((R)-4-(1-(4-fluorophenyl)-1H-pyrazol-3-yl)-2-methyl-3-oxomorpholin-2-yl)-2-hydroxyacetamide,
(R)—N-(3-aminobenzo[d]isoxazol-6-yl)-2-((R)-4-(1-(4-cyanophenyl)-1H-pyrazol-3-yl)-2-methyl-3-oxomorpholin-2-yl)-2-hydroxyacetamide,
methyl 4-(3-((R)-2-((R)-2-((3-aminobenzo[d]isoxazol-6-yl)amino)-1-hydroxy-2-oxoethyl)-2-methyl-3-oxomorpholino)-1H-pyrazol-1-yl)benzoate,
4-(3-((R)-2-((R)-2-((3-aminobenzo[d]isoxazol-6-yl)amino)-1-hydroxy-2-oxoethyl)-2-methyl-3-oxomorpholino)-1H-pyrazol-1-yl)benzoic acid,
(R)—N-(3-aminobenzo[d]isoxazol-6-yl)-2-((R)-4-(1-(4-chlorophenyl)-1H-pyrazol-3-yl)-2-methyl-3-oxomorpholin-2-yl)-2-hydroxyacetamide,
(R)—N-(3-aminobenzo[d]isoxazol-6-yl)-2-hydroxy-2-((R)-2-methyl-4-(1-(4-(methylsulfonyl)phenyl)-1H-pyrazol-3-yl)-3-oxomorpholin-2-yl)acetamide,
(R)—N-(3-aminobenzo[d]isoxazol-6-yl)-2-hydroxy-2-((R)-2-methyl-3-oxo-4-(1-(pyridin-3-yl)-1H-pyrazol-3-yl)morpholin-2-yl)acetamide,
(R)—N-(3-aminobenzo[d]isoxazol-6-yl)-2-hydroxy-2-((R)-2-methyl-3-oxo-4-(1-(6-(trifluoromethyl)pyridin-3-yl)-1H-pyrazol-3-yl)morpholin-2-yl)acetamide,
(R)—N-(3-aminobenzo[d]isoxazol-6-yl)-2-hydroxy-2-((R)-2-methyl-3-oxo-4-(1-(5-(trifluoromethyl)pyridin-3-yl)-1H-pyrazol-3-yl)morpholin-2-yl)acetamide,
(R)—N-(3-aminobenzo[d]isoxazol-6-yl)-2-((R)-4-(1-(5-cyanopyridin-3-yl)-1H-pyrazol-3-yl)-2-methyl-3-oxomorpholin-2-yl)-2-hydroxyacetamide,
(R)—N-(3-aminobenzo[d]isoxazol-6-yl)-2-hydroxy-2-((R)-2-methyl-3-oxo-4-(1-(pyridin-4-yl)-1H-pyrazol-3-yl)morpholin-2-yl)acetamide,
(R)—N-(3-aminobenzo[d]isoxazol-6-yl)-2-((R)-4-(1-(3-fluoropyridin-4-yl)-1H-pyrazol-3-yl)-2-methyl-3-oxomorpholin-2-yl)-2-hydroxyacetamide,
methyl 4-(3-((R)-2-((R)-2-((3-aminobenzo[d]isoxazol-6-yl)amino)-1-hydroxy-2-oxoethyl)-2-methyl-3-oxomorpholino)-1H-pyrazol-1-yl)picolinate,
(R)—N-(3-aminobenzo[d]isoxazol-6-yl)-2-hydroxy-2-((R)-4-(1-(2-methoxypyridin-4-yl)-1H-pyrazol-3-yl)-2-methyl-3-oxomorpholin-2-yl)acetamide,
(R)—N-(3-aminobenzo[d]isoxazol-6-yl)-2-((R)-4-(1-(2-cyanopyridin-4-yl)-1H-pyrazol-3-yl)-2-methyl-3-oxomorpholin-2-yl)-2-hydroxyacetamide,
(R)—N-(3-aminobenzo[d]isoxazol-6-yl)-2-hydroxy-2-((R)-2-methyl-3-oxo-4-(1-(2-(trifluoromethyl)pyridin-4-yl)-1H-pyrazol-3-yl)morpholin-2-yl)acetamide,
(R)—N-(3-aminobenzo[d]isoxazol-6-yl)-2-hydroxy-2-((R)-4-(1-(3,5-difluoropyridin-4-yl)-1H-pyrazol-3-yl)-2-methyl-3-oxomorpholin-2-yl)-2-hydroxyacetamide, (R)—N-(3-aminobenzo[d]isoxazol-6-yl)-2-hydroxy-2-((R)-2-methyl-4-(5-methyl-1-(2-(trifluoromethyl)pyridin-4-yl)-1H-pyrazol-3-yl)-3-oxomorpholin-2-yl)acetamide, (R)—N-(3-aminobenzo[d]isoxazol-6-yl)-2-hydroxy-2-((R)-2-methyl-3-oxo-4-(1-(pyridazin-4-yl)-1 H-pyrazol-3-yl)morpholin-2-yl)acetamide, (R)—N-(3-aminobenzo[d]isoxazol-6-yl)-2-hydroxy-2-((R)-4-(1-(6-methoxypyridazin-4-yl)-1H-pyrazol-3-yl)-2-methyl-3-oxomorpholin-2-yl)acetamide, (2R)—N-(3-amino-1,2-benzoxazol-6-yl)-2-hydroxy-2-[(2R)-2-methyl-3-oxo-4-[1-[6-(trideuteriomethoxy)pyridazin-4-yl]pyrazol-3-yl]morpholin-2-yl]acetamide, (R)—N-(3-aminobenzo[d]isoxazol-6-yl)-2-((R)-4-(1-(6-cyanopyridazin-4-yl)-1H-pyrazol-3-yl)-2-methyl-3-oxomorpholin-2-yl)-2-hydroxyacetamide, (R)—N-(3-aminobenzo[d]isoxazol-6-yl)-2-hydroxy-2-((R)-4-(1-(2-methoxypyrimidin-5-yl)-1H-pyrazol-3-yl)-2-methyl-3-oxomorpholin-2-yl)acetamide, (R)—N-(3-aminobenzo[d]isoxazol-6-yl)-2-hydroxy-2-((R)-2-methyl-3-oxo-4-(1-(2-(trifluoromethyl)pyrimidin-5-yl)-1H-pyrazol-3-yl)morpholin-2-yl)acetamide, (R)—N-(3-aminobenzo[d]isoxazol-6-yl)-2-hydroxy-2-((R)-4-(1-(2-methoxypyrimidin-4-yl)-1H-pyrazol-3-yl)-2-methyl-3-oxomorpholin-2-yl)acetamide, (R)—N-(3-aminobenzo[d]isoxazol-6-yl)-2-((R)-4-(1-cyclopropyl-5-methyl-1H-pyrazol-3-yl)-2-methyl-3-oxomorpholin-2-yl)-2-hydroxyacetamide, (R)—N-(3-aminobenzo[d]isoxazol-6-yl)-2-hydroxy-2-((R)-2-methyl-3-oxo-4-(4-(pyridin-4-yl)oxazol-2-yl)morpholin-2-yl)acetamide, (R)—N-(3-aminobenzo[d]isoxazol-6-yl)-2-hydroxy-2-((R)-2-methyl-3-oxo-4-(4-(pyridin-4-yl)thiazol-2-yl)morpholin-2-yl)acetamide, (R)—N-(3-aminobenzo[d]isoxazol-6-yl)-2-hydroxy-2-((R)-2-methyl-3-oxo-4-(2-(pyridin-4-yl)thiazol-4-yl)morpholin-2-yl)acetamide, (R)—N-(3-aminobenzo[d]isoxazol-6-yl)-2-hydroxy-2-((R)-2-methyl-3-oxo-4-(6-((tetrahydro-2H-pyran-4-yl)oxy)pyridin-2-yl)morpholin-2-yl)acetamide, (R)—N-(3-aminobenzo[d]isoxazol-6-yl)-2-hydroxy-2-((R)-2-methyl-3-oxo-4-(6-(4-(trifluoromethoxy)phenyl)pyridin-2-yl)morpholin-2-yl)acetamide, 4-(6-((R)-2-((R)-2-((3-aminobenzo[d]isoxazol-6-yl)amino)-1-hydroxy-2-oxoethyl)-2-methyl-3-oxomorpholino)pyridin-2-yl)benzoic acid, 2-(6-((R)-2-((R)-2-((3-aminobenzo[d]isoxazol-6-yl)amino)-1-hydroxy-2-oxoethyl)-2-methyl-3-oxomorpholino)pyridin-2-yl)-5-(trifluoromethyl)benzoic acid, (R)—N-(3-aminobenzo[d]isoxazol-6-yl)-2-hydroxy-2-((R)-2-methyl-3-oxo-4-(6-(pyridazin-4-yl)pyridin-2-yl)morpholin-2-yl)acetamide, (R)—N-(3-aminobenzo[d]isoxazol-6-yl)-2-hydroxy-2-((R)-2-methyl-3-oxo-4-(6-(2-(trifluoromethyl)pyrimidin-5-yl)pyridin-2-yl)morpholin-2-yl)acetamide, (R)—N-(3-aminobenzo[d]isoxazol-6-yl)-2-hydroxy-2-((R)-4-(6-(isoxazol-4-yl)pyridin-2-yl)-2-methyl-3-oxomorpholin-2-yl)acetamide, (R)—N-(3-aminobenzo[d]isoxazol-6-yl)-2-hydroxy-2-((R)-2-methyl-4-(6-(3-methylisoxazol-4-yl)pyridin-2-yl)-3-oxomorpholin-2-yl)acetamide, (R)—N-(3-aminobenzo[d]isoxazol-6-yl)-2-((R)-4-(6-(3,5-dimethylisoxazol-4-yl)pyridin-2-yl)-2-methyl-3-oxomorpholin-2-yl)-2-hydroxyacetamide, (R)—N-(3-aminobenzo[d]isoxazol-6-yl)-2-hydroxy-2-((R)-2-methyl-4-(1,7-naphthyridin-2-yl)-3-oxomorpholin-2-yl)acetamide, (R)—N-(3-aminobenzo[d]isoxazol-6-yl)-2-hydroxy-2-((R)-2-methyl-3-oxo-4-(6-(trifluoromethyl)-1,7-naphthyridin-2-yl)morpholin-2-yl)acetamide, (R)—N-(3-amino-4-chlorobenzo[d]isoxazol-6-yl)-2-hydroxy-2-((R)-3-oxo-4-(1-(pyridin-4-yl)-1H-pyrazol-3-yl)morpholin-2-yl)propanamide, (R)—N-(3-amino-4-chlorobenzo[d]isoxazol-6-yl)-2-hydroxy-2-((R)-3-oxo-4-(1-(2-(trifluoromethyl)pyridin-4-yl)-1H-pyrazol-3-yl)morpholin-2-yl)propanamide, (R)—N-(3-amino-4-chlorobenzo[d]isoxazol-6-yl)-2-((R)-4-(4-fluoro-1-(2-(trifluoromethyl)pyridin-4-yl)-1H-pyrazol-3-yl)-3-oxomorpholin-2-yl)-2-hydroxypropanamide, (R)—N-(3-amino-4-chlorobenzo[d]isoxazol-6-yl)-2-hydroxy-2-((R)-3-oxo-4-(1-(pyridazin-4-yl)-1H-pyrazol-3-yl)morpholin-2-yl)propanamide, (R)—N-(3-amino-4-chlorobenzo[d]isoxazol-6-yl)-2-((R)-4-(4-fluoro-1-(pyridazin-4-yl)-1H-pyrazol-3-yl)-3-oxomorpholin-2-yl)-2-hydroxypropanamide, (R)—N-(3-amino-4-chlorobenzo[d]isoxazol-6-yl)-2-((R)-4-(1-(6-cyanopyridazin-4-yl)-4-fluoro-1H-pyrazol-3-yl)-3-oxomorpholin-2-yl)-2-hydroxypropanamide, (R)—N-(3-amino-4-chlorobenzo[d]isoxazol-6-yl)-2-((R)-4-(4-fluoro-1-(6-methoxypyridazin-4-yl)-1H-pyrazol-3-yl)-3-oxomorpholin-2-yl)-2-hydroxypropanamide, (R)—N-(3-amino-4-chlorobenzo[d]isoxazol-6-yl)-2-((R)-4-(4-fluoro-1-(6-(trifluoromethyl)pyridazin-4-yl)-1H-pyrazol-3-yl)-3-oxomorpholin-2-yl)-2-hydroxypropanamide, (R)—N-(3-amino-4-chlorobenzo[d]isoxazol-6-yl)-2-hydroxy-2-((R)-2-methyl-4-(1-(4-(methylsulfonyl)phenyl)-1H-pyrazol-3-yl)-3-oxomorpholin-2-yl)acetamide, (R)—N-(3-amino-4-chlorobenzo[d]isoxazol-6-yl)-2-hydroxy-2-((R)-2-methyl-3-oxo-4-(1-(pyridin-4-yl)-1H-pyrazol-3-yl)morpholin-2-yl)acetamide, (R)—N-(3-amino-4-fluorobenzo[d]isoxazol-6-yl)-2-hydroxy-2-((R)-3-oxo-4-(1-(pyridin-4-yl)-1H-pyrazol-3-yl)morpholin-2-yl)propanamide, (R)—N-(3-amino-4-fluorobenzo[d]isoxazol-6-yl)-2-hydroxy-2-((R)-4-(1-(2-methylpyridin-4-yl)-1H-pyrazol-3-yl)-3-oxomorpholin-2-yl)propanamide, (R)—N-(3-amino-4-fluorobenzo[d]isoxazol-6-yl)-2-hydroxy-2-((R)-3-oxo-4-(1-(2-(trifluoromethyl)pyridin-4-yl)-1H-pyrazol-3-yl)morpholin-2-yl)propanamide, (R)—N-(3-amino-4-fluorobenzo[d]isoxazol-6-yl)-2-((R)-4-(1-(2-cyanopyridin-4-yl)-1H-pyrazol-3-yl)-3-oxomorpholin-2-yl)-2-hydroxypropanamide, (R)—N-(3-amino-4-fluorobenzo[d]isoxazol-6-yl)-2-hydroxy-2-((R)-4-(1-(2-methoxypyridin-4-yl)-1H-pyrazol-3-yl)-3-oxomorpholin-2-yl)propanamide, (R)—N-(3-amino-4-fluorobenzo[d]isoxazol-6-yl)-2-((R)-4-(4-fluoro-1-(pyridin-4-yl)-1H-pyrazol-3-yl)-3-oxomorpholin-2-yl)-2-hydroxypropanamide, (R)—N-(3-amino-4-fluorobenzo[d]isoxazol-6-yl)-2-hydroxy-2-((R)-3-oxo-4-(-(pyridazin-4-yl)-1H-pyrazol-3-yl)morpholin-2-yl)propanamide, (R)—N-(3-amino-4-fluorobenzo[d]isoxazol-6-yl)-2-((R)-4-(1-(6-(azetidin-1-yl)pyridazin-4-yl)-1H-pyrazol-3-yl)-3-oxomorpholin-2-yl)-2-hydroxypropanamide, (R)—N-(3-amino-4-fluorobenzo[d]isoxazol-6-yl)-2-hydroxy-2-((R)-4-(1-(6-isopropoxypyridazin-4-yl)-1H-pyrazol-3-yl)-3-oxomorpholin-2-yl)propanamide,
(R)—N-(3-amino-4-fluorobenzo[d]isoxazol-6-yl)-2-((R)-4-(1-(6-cyanopyridazin-4-yl)-1H-pyrazol-3-yl)-3-oxomorpholin-2-yl)-2-hydroxypropanamide,
(R)—N-(3-amino-4-fluorobenzo[d]isoxazol-6-yl)-2-hydroxy-2-((R)-4-(1-(6-methoxypyridazin-4-yl)-1H-pyrazol-3-yl)-3-oxomorpholin-2-yl)propanamide,
(R)—N-(3-amino-4-fluorobenzo[d]isoxazol-6-yl)-2-((R)-4-(4-fluoro-1-(pyridazin-4-yl)-1H-pyrazol-3-yl)-3-oxomorpholin-2-yl)-2-hydroxypropanamide,
(R)—N-(3-amino-4-fluorobenzo[d]isoxazol-6-yl)-2-hydroxy-2-((R)-4-(1-(2-methoxypyrimidin-4-yl)-1H-pyrazol-3-yl)-3-oxomorpholin-2-yl)propanamide,
(R)—N-(3-amino-4-fluorobenzo[d]isoxazol-6-yl)-2-hydroxy-2-((R)-2-methyl-3-oxo-4-(1-(pyridazin-4-yl)-1H-pyrazol-3-yl)morpholin-2-yl)acetamide,
(R)—N-(3-amino-4-fluorobenzo[d]isoxazol-6-yl)-2-hydroxy-2-((R)-4-(1-(2-methoxypyrimidin-4-yl)-1H-pyrazol-3-yl)-2-methyl-3-oxomorpholin-2-yl)acetamide,
(R)—N-(3-aminoisoxazolo[4,5-b]pyridin-6-yl)-2-hydroxy-2-((R)-3-oxo-4-(1-(pyridin-4-yl)-1H-pyrazol-3-yl)morpholin-2-yl)propanamide,
(R)—N-(3-chloro-2-methyl-1H-indol-5-yl)-2-hydroxy-2-((R)-4-(1-(2-methoxypyridin-4-yl)-1H-pyrazol-3-yl)-3-oxomorpholin-2-yl)propanamide,
(R)—N-(3-chloro-2-methyl-1H-indol-5-yl)-2-hydroxy-2-((R)-3-oxo-4-(1-(pyridazin-4-yl)-1H-pyrazol-3-yl)morpholin-2-yl)propanamide,
(R)—N-(4-aminoquinazolin-7-yl)-2-hydroxy-2-((R)-2-methyl-3-oxo-4-(1-(pyridin-4-yl)-1H-pyrazol-3-yl)morpholin-2-yl)acetamide,
(R)—N-(3-Aminobenzo[d]isoxazol-6-yl)-2-hydroxy-2-((R)-2-methyl-3-oxo-4-(1-(pyridazin-4-yl)-1H-pyrazol-3-yl)morpholin-2-yl)propanamide,
(R)—N-(3-aminobenzo[d]isoxazol-6-yl)-2-hydroxy-2-((R)-4-(1-(6-methoxypyridazin-4-yl)-1H-pyrazol-3-yl)-2-methyl-3-oxomorpholin-2-yl)propanamide,
(R)—N-(4-(aminomethyl)phenyl)-2-hydroxy-2-((R)-3-oxo-4-(1-(pyridin-4-yl)-1H-pyrazol-3-yl)morpholin-2-yl)propanamide,
(R)—N-(4-(aminomethyl)-3-fluorophenyl)-2-hydroxy-2-((R)-3-oxo-4-(1-(pyridin-4-yl)-1H-pyrazol-3-yl)morpholin-2-yl)propanamide,
(R)—N-(4-(aminomethyl)phenyl)-2-hydroxy-2-((R)-2-methyl-3-oxo-4-(1-(pyridin-4-yl)-1H-pyrazol-3-yl)morpholin-2-yl)acetamide,
(R)—N-(4-(aminomethyl)-3-fluorophenyl)-2-hydroxy-2-((R)-2-methyl-3-oxo-4-(1-(pyridin-4-yl)-1H-pyrazol-3-yl)morpholin-2-yl)acetamide,
(R)—N-(3-Aminobenzo[d]isoxazol-6-yl)-2-((2R,6R)-4-(1-(6-cyanopyridazin-4-yl)-1H-pyrazol-3-yl)-6-methyl-3-oxomorpholin-2-yl)-2-hydroxyacetamide,
(R)—N-(3-Aminobenzo[d]isoxazol-6-yl)-2-((2R,6S)-4-(1-(6-cyanopyridazin-4-yl)-1H-pyrazol-3-yl)-6-methyl-3-oxomorpholin-2-yl)-2-hydroxyacetamide,
(R)—N-(3-Aminobenzo[d]isoxazol-6-yl)-2-((R)-4-(1-(6-cyanopyridazin-4-yl)-1H-pyrazol-3-yl)-6,6-dimethyl-3-oxomorpholin-2-yl)-2-hydroxyacetamide,
(R)—N-(3-aminobenzo[d]isoxazol-6-yl)-2-hydroxy-2-((2R,6R)-6-methyl-3-oxo-4-(1-(pyridazin-4-yl)-1H-pyrazol-3-yl)morpholin-2-yl)acetamide,
(R)—N-(3-aminobenzo[d]isoxazol-6-yl)-2-((2R,6R)-4-(4-fluoro-1-(pyridazin-4-yl)-1H-pyrazol-3-yl)-6-methyl-3-oxomorpholin-2-yl)-2-hydroxyacetamide,
(R)—N-(3-aminobenzo[d]isoxazol-6-yl)-2-hydroxy-2-((2R,6R)-4-(1-(6-methoxypyridazin-4-yl)-1H-pyrazol-3-yl)-6-methyl-3-oxomorpholin-2-yl)acetamide,
(R)—N-(3-aminobenzo[d]isoxazol-6-yl)-2-hydroxy-2-((2R,6 S)-6-methyl-3-oxo-4-(1-(pyridazin-4-yl)-1H-pyrazol-3-yl)morpholin-2-yl)acetamide,
(R)—N-(3-aminobenzo[d]isoxazol-6-yl)-2-((2R,6 S)-4-(4-fluoro-1-(pyridazin-4-yl)-1H-pyrazol-3-yl)-6-methyl-3-oxomorpholin-2-yl)-2-hydroxyacetamide,
(R)—N-(3-aminobenzo[d]isoxazol-6-yl)-2-hydroxy-2-((2R,6 S)-4-(1-(6-methoxypyridazin-4-yl)-1H-pyrazol-3-yl)-6-methyl-3-oxomorpholin-2-yl)acetamide,
(R)—N-(3-aminobenzo[d]isoxazol-6-yl)-2-hydroxy-2-((2R,6 S)-6-methyl-3-oxo-4-(1-(pyridin-4-yl)-1H-pyrazol-3-yl)morpholin-2-yl)acetamide,
(R)—N-(3-aminobenzo[d]isoxazol-6-yl)-2-((2R,6S)-4-(1-(2-cyanopyridin-4-yl)-1H-pyrazol-3-yl)-6-methyl-3-oxomorpholin-2-yl)-2-hydroxyacetamide,
(R)—N-(3-aminobenzo[d]isoxazol-6-yl)-2-((2R,6R)-4-(1-(2-cyanopyridin-4-yl)-1H-pyrazol-3-yl)-6-methyl-3-oxomorpholin-2-yl)-2-hydroxyacetamide,
(R)—N-(3-aminobenzo[d]isoxazol-6-yl)-2-hydroxy-2-((2R,6R)-6-methyl-3-oxo-4-(1-(pyridin-4-yl)-1H-pyrazol-3-yl)morpholin-2-yl)acetamide,
(R)—N-(3-aminobenzo[d]isoxazol-6-yl)-2-hydroxy-2-((2R,6 S)-4-(1-(2-methoxypyridin-4-yl)-1H-pyrazol-3-yl)-6-methyl-3-oxomorpholin-2-yl)acetamide,
(R)—N-(3-aminobenzo[d]isoxazol-6-yl)-2-hydroxy-2-((2R,6R)-4-(1-(2-methoxypyridin-4-yl)-1H-pyrazol-3-yl)-6-methyl-3-oxomorpholin-2-yl)acetamide,
(R)—N-(3-aminobenzo[d]isoxazol-6-yl)-2-hydroxy-2-((2R,6S)-6-methyl-3-oxo-4-(1-(2-(trifluoromethyl)pyridin-4-yl)-1H-pyrazol-3-yl)morpholin-2-yl)acetamide,
(R)—N-(3-aminobenzo[d]isoxazol-6-yl)-2-hydroxy-2-((2R,6R)-6-methyl-3-oxo-4-(1-(2-(trifluoromethyl)pyridin-4-yl)-1H-pyrazol-3-yl)morpholin-2-yl)acetamide,
(R)—N-(3-aminobenzo[d]isoxazol-6-yl)-2-hydroxy-2-((R)-4-(1-(2-methoxypyridin-4-yl)-1H-pyrazol-3-yl)-6,6-dimethyl-3-oxomorpholin-2-yl)acetamide,
(R)—N-(3-aminobenzo[d]isoxazol-6-yl)-2-((R)-6,6-dimethyl-3-oxo-4-(1-(pyridazin-4-yl)-1H-pyrazol-3-yl)morpholin-2-yl)-2-hydroxyacetamide,
(R)—N-(3-aminobenzo[d]isoxazol-6-yl)-2-((R)-4-(4-fluoro-1-(pyridazin-4-yl)-1H-pyrazol-3-yl)-6,6-dimethyl-3-oxomorpholin-2-yl)-2-hydroxyacetamide, or
(R)—N-(3-aminobenzo[d]isoxazol-6-yl)-2-hydroxy-2-((R)-4-(1-(6-methoxypyridazin-4-yl)-1H-pyrazol-3-yl)-6,6-dimethyl-3-oxomorpholin-2-yl)acetamide.

16. A composition for inhibiting thrombus formation in blood comprising a compound of claim 2 and a pharmaceutically acceptable carrier.

* * * * *